United States Patent
Donahue et al.

(10) Patent No.: US 10,421,999 B2
(45) Date of Patent: Sep. 24, 2019

(54) TARGETED SEQUENCING AND UID FILTERING

(71) Applicant: Roche Molecular Systems, Inc., Pleasanton, CA (US)

(72) Inventors: William Donahue, Quincy, MA (US); Francois Vigneault, Beverly, MA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 382 days.

(21) Appl. No.: 14/910,237

(22) PCT Filed: Feb. 11, 2015

(86) PCT No.: PCT/EP2015/052723
§ 371 (c)(1),
(2) Date: Feb. 4, 2016

(87) PCT Pub. No.: WO2015/121236
PCT Pub. Date: Aug. 20, 2015

(65) Prior Publication Data
US 2016/0201124 A1    Jul. 14, 2016

Related U.S. Application Data

(60) Provisional application No. 61/938,227, filed on Feb. 11, 2014, provisional application No. 62/031,405, filed on Jul. 31, 2014.

(51) Int. Cl.
| | |
|---|---|
| *C12Q 1/6853* | (2018.01) |
| *C12Q 1/6874* | (2018.01) |
| *C12Q 1/6806* | (2018.01) |
| *C12Q 1/6855* | (2018.01) |
| *C12Q 1/686* | (2018.01) |
| *C12N 15/10* | (2006.01) |

(52) U.S. Cl.
CPC ....... *C12Q 1/6874* (2013.01); *C12N 15/1096* (2013.01); *C12Q 1/6806* (2013.01); *C12Q 1/686* (2013.01); *C12Q 1/6853* (2013.01); *C12Q 1/6855* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,965,443 A | 10/1999 | Reznikoff et al. | |
| 6,437,109 B1 | 8/2002 | Reznikoff et al. | |
| 7,083,980 B2 | 8/2006 | Reznikoff et al. | |
| 7,608,434 B2 | 10/2009 | Reznikoff et al. | |
| 9,238,671 B2 | 1/2016 | Goryshin et al. | |
| 9,315,863 B2 | 4/2016 | Nadeau | |
| 9,546,399 B2 | 1/2017 | Amorese et al. | |
| 9,708,657 B2 | 7/2017 | Asbury et al. | |
| 2005/0266439 A1* | 12/2005 | Hjorleifsdottir | |
| 2006/0073511 A1 | 4/2006 | Jones et al. | |
| 2007/0020640 A1 | 1/2007 | McCloskey et al. | |
| 2008/0242555 A1 | 10/2008 | Shen et al. | |
| 2012/0115145 A1 | 5/2012 | Fu | |
| 2012/0289414 A1 | 11/2012 | Mitra et al. | |
| 2013/0231253 A1 | 9/2013 | Amorese et al. | |
| 2013/0303461 A1 | 11/2013 | Iafrate et al. | |
| 2014/0193860 A1 | 7/2014 | Bevilacqua et al. | |
| 2015/0119261 A1 | 4/2015 | Richard | |
| 2015/0211050 A1 | 7/2015 | Lafrate et al. | |

FOREIGN PATENT DOCUMENTS

| | | |
|---|---|---|
| CN | 105658812 | 6/2016 |
| WO | 2009148560 A2 | 12/2009 |
| WO | 2012048341 A1 | 4/2012 |
| WO | 2012042242 A2 | 10/2012 |
| WO | 2013130512 A2 | 9/2013 |
| WO | 2013181170 A1 | 12/2013 |
| WO | PCTEP2015052723 | 7/2015 |

OTHER PUBLICATIONS

Alon, Shahar, et al., Barcoding bias in high-throughput multiplex sequencing of miRNA, Genome Research, 2011, 1506-1511.
Fu, Glenn K., et al., Molecular indexing enables quantitative targeted RNA sequencing and reveals poor efficiencies in standard library preparations, PNAS, 2014, 1901-1896, 111(5).
Hashimoshony, Tamar, et al.,, CEL-Seq: Single -Cell RNA-Seq by Multiplexed Linear Amplification, Cell Reports 2, 2012, 666-673, 2.
Hashimshony, Tamar, CEL-Seq Protocol, Supplemental Information Document, 2012, 1-9.
Head, Steven R., et al.,, Library construction for next-generation sequencing:Overviews and challenges, BioTechniques, 2014, 61-77, 56.
Heger, Monica, Roche Acquires AbVitro's Sample Prep Tech to Integrate with Genie and PacBio Systems, genomeweb, 2014, 1-2.
Islam, Saiful, et al.,, Highly multiplexed and strand-specific single-cell RNA 5' end sequencing, Nature Protocol, 2012, 813-828, 7 (5).
Illumina, "An Introduction to Next-Generation Sequencing Technology", Illumina_Sequencing_Introduction, (2011), pp. 1-5, N/A.
International Search Report and Written Opinion dated Jul. 22, 2015 in corresponding PCT/EP2015/052723 filed on Feb. 2015, pp. 1-16.
Batzer et al, 1991, "Enhanced evolutionary PCR using oligonucleotides with inosine at the 3'-terminus", Nucleic Acids Research, 19(18):5081.
Croucher NJ, Fookes MC, Perkins TT, Turner DJ, Marguerat SB, Keane T, Quial MA, He M, Assefa S, Bahler J, Kingsley RA, Parkhill J, Bentley SD, Dougan G, Thompon NR. A simple method for directional transcriptome sequencing using illumine technology, Nucleic Acids Res, Dec. 2009; 37(22): e148. (Year:2009).
Gupta et al, 2005, "Synthesis and surface engineering of iron oxide nanoparticles for biomedical applications", Biomaterials, 26:3995-4021.

(Continued)

*Primary Examiner* — Christopher M Gross
(74) *Attorney, Agent, or Firm* — Olga Kay

(57) ABSTRACT

Provided herein are methods, compositions, and kits for targeted sequencing of polynucleotides with high accuracy and low amplification and sequencing errors.

7 Claims, 69 Drawing Sheets

Specification includes a Sequence Listing.

(56) References Cited

OTHER PUBLICATIONS

International Search Report and written opinion dated Oct. 18, 2017 in corresponding PCT application No. PCT/US2017/041748 filed on Jul. 12, 2017.

Jabara et al, "Swanstrom R. Accurate sampling and deep sequencing of the HIV-1 potease gene using a Primer ID". Proc Natl Acad Sci U S A. Dec. 13, 2011; 108(50):20166-71. Epub Nov. 30, 2011 (year: 2011).

Jabara et al. Supplemental Information. (2011, PNAS, 108(50):20166-71: pp. 1-9). (year:2011).

Kim et al, 2008, "Multifunctional Uniform Nanoparticles Composed of a Magnetite Nanocrystal Core and a Mesoporous Silica Shell for Magnetic Resonance and Fluorescence Imaging and for Drug Delivery", Angewandte Chemie International Edition, 48:8438-8441.

Liu et al, 2010, "Shape Evolution and Tunable Properties of Monodisperse Magnetite Crystals Synthesized by a Facile Surfactant-Free Hydrothermal Method", European Journal of Inorganic Chemistry, 4499-4505.

Meyer et al, A high-coverage genome sequence from an archaic Denisovan individual. Science. Oct. 12, 2012; 338(6104):222-6. Epub Aug. 30, 2012. (year:2012).

Meyer et al. A(2012, Supplemental Information, Science 338(6104):222-6. pp. 1-146). (year:2012).

Narayanan et al, Enhanced Bio-Coompatibility of Ferrofluids of Self-Assembled Superparamagnetic Iron Oxide-Silica core-Shell Nanoparticles, Journal of Nanoscience and Nanotechnology, 2011, pp. 1958-1967, vol. 11.

Ohtsuka et al, 1985, "An Alternative Approach to Deoxyoligonucleotides as Hybridization Probes by Insertion of Deoxylnosine at Ambiguous Codon Positions", The Journal of Biological Chemistry, 260(5):2605-2608.

Tormanen et al, Extension product capture improves genomic sequencing and DNase I footprinting by ligation-mediated PCR, Nucleic Acids Research, 1992, pp. 5487-5488, vol. 20, No. 20.

* cited by examiner

| Panel | Amplicons | On Target % |
|---|---|---|
| CS-350* | 346 | 92.20% |
| Tex-1 | 336 | 97.10% |
| CS-30* | 30 | 94.20% |
| CS-23 | 23 | 99.20% |
| Other #1 | 207 | 90% |
| Other #2 | 220 | 93% |

Fig. 4

| | | Group 1 | | Group 2 | | |
|---|---|---|---|---|---|---|
| | | Fixed per probe concentration | | Fixed global concentration | | |
| | | Final Concentration* | | RESULT | Final Concentration* | | RESULT |
| Panel size | Amplicons | global | per probe | Products? | global | per probe | Products? |
| Full | 346 | 86.5 nM | 250 pM | NO | 480 nM | 1.38 nM | Yes, faint |
| Half | 173 | 43.2 nM | 250 pM | NO | 480 nM | 2.77 nM | Yes, faint |
| Quarter | 86 | 21.5 nM | 250 pM | Yes, faint | 480 nM | 5.58 nM | Yes, strong |
| Small | 24 | 6.0 nM | 250 pM | Yes, faint | 480 nM | 20 nM | Yes, strong |

* Refers to primer concentrations at both gPE and PE2

*Fig. 8*

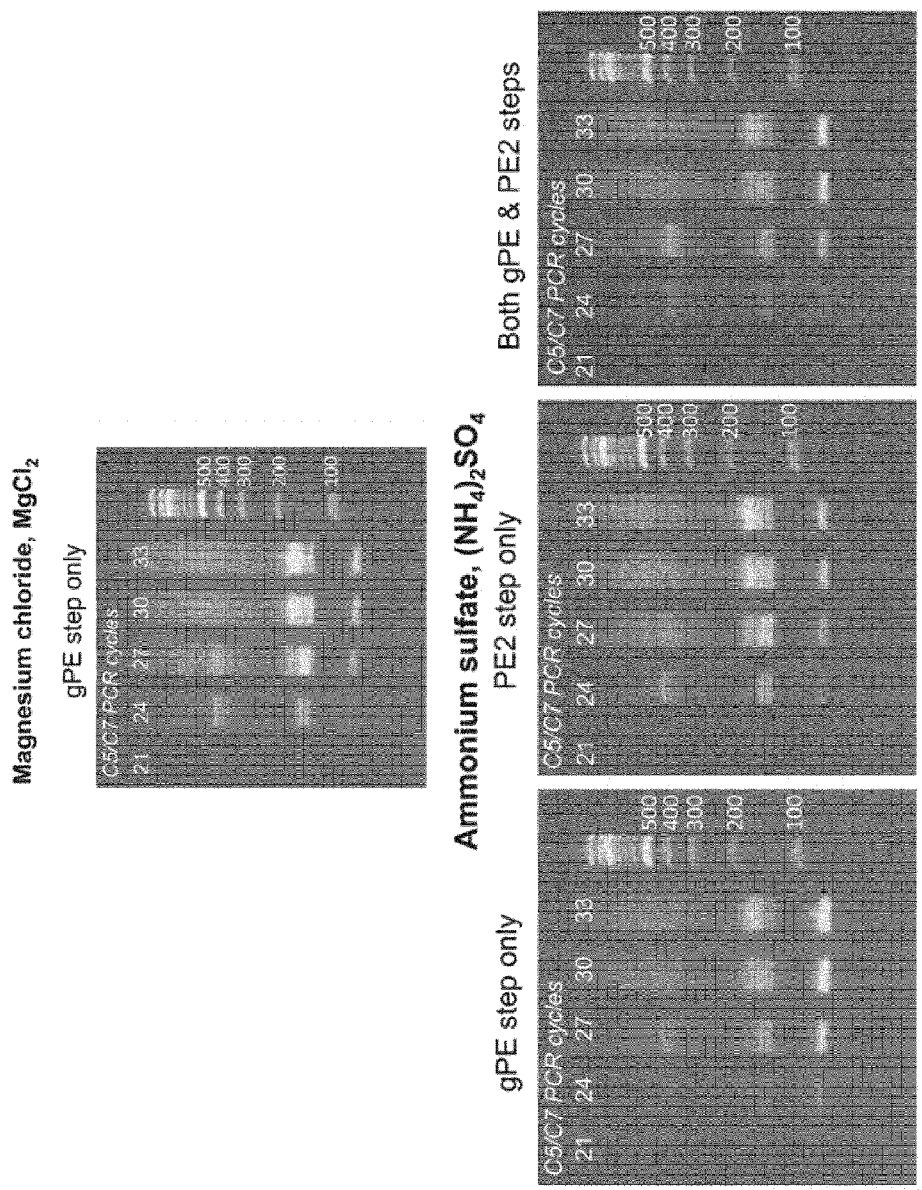
Fig. 9 (Cnt'd)

| Disease | Gene | Exons | Probe sets | Primerless Exons |
|---|---|---|---|---|
| Alpha-Thalassemia | HBA1 | 3 | 3 | SMN1_04 |
| Alpha-Thalassemia | HBA2 | 3 | 2 | HBB_03 |
| Beta-Thalassemia | HBB | 3 | 3 | ASPA_06 |
| Bloom's syndrome | BLM | 22 | 24 | DLD_01-01 |
| Canavan disease | ASPA | 6 | 6 | DLD_05 |
| Cystic Fibrosis | CFTR | 27 | 31 | DLD_14 |
| Dihydrolipoamide dehydrogenase deficiency | DLD | 14 | 12 | BLM_03-02 |
| Familial dysautonomia | IKBKAP | 37 | 39 | BLM_16 |
| Fanconi anemia type C | FANCC | 15 | 16 | BLM_22 |
| Fragile X syndrome (non-ngs) | FMR1 | 17 | 17 | MCOLN1_03 |
| Gaucher disease | GBA | 11 | 12 | HEXA_14 |
| Glycogen storage disease type 1a | G6PC | 5 | 6 | POMGNT1_06 |
| Joubert syndrome 2 | TMEM237 | 13 | 13 | PCDH15_33 |
| Krabbe disease | GALC | 17 | 18 | CFTR_04 |
| Maple syrup urine disease type 1B | BCKDHB | 10 | 11 | CFTR_08-01 |
| Mucolipidosis IV | MCOLN1 | 14 | 13 | CFTR_14-01 |
| Muscle-eye-brain disease (Walker-Warburg Syndrome) | POMGNT1 | 22 | 22 | |
| Niemann Pick disease type A/B | SMPD1 | 6 | 11 | |
| Pompe disease | GAA | 20 | 22 | |
| Spinal muscular atrophy | SMN1 | 9 | 8 | |
| Tay-Sachs disease | HEXA | 14 | 17 | |
| Usher syndrome type 1F | PCDH15 | 33 | 35 | |
| Usher syndrome type 3 | CLRN1 | 3 | 5 | |
| 22 | 23 | 324 | 346 | |

*Fig. 13*

| panel | # amplicons | mean read depth per amplicon | on target specificity | Uniformity of Coverage (100x cap) |
|---|---|---|---|---|
| CS_350_panel | 346 | 1339 | 92.69% | 89.88% |
| Tex_01_panel | 336 | 1404 | 97.20% | 95.54% |
| Tex_02_panel | 326 | 1403 | 97.11% | 92.94% |
| Tex_03_panel | 316 | 1412 | 97.78% | 94.62% |
| Tex_04_panel | 335 | 1378 | 95.42% | 91.94% |
| Tex_07_panel | 303 | 1415 | 97.92% | 93.73% |
| Tex_09_panel | 332 | 1333 | 92.31% | 88.86% |
| Tex_10_panel | 295 | 1414 | 97.85% | 88.81% |

*Fig. 15B*

- Tighten melt temp range: 60 – 68°C; optimal 64°C
- Loosen length: 21 – 32 nt; optimal 25 nt
- Avoid high GC at 3' end: ≤ 3 GC in last 5 nt
- % GC: 30 – 70%; optimal 50%
- Amplicon length: 225 – 300 bp

*Fig. 25*

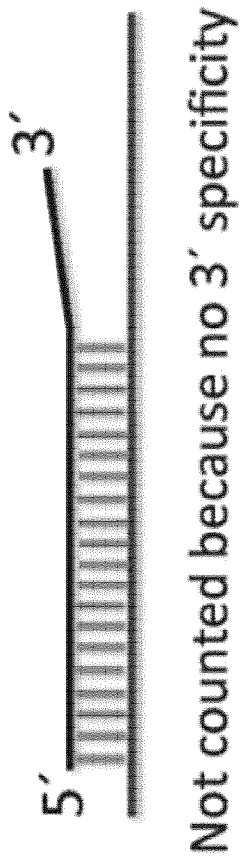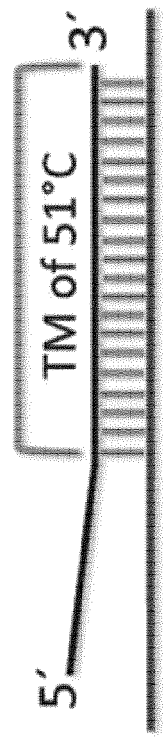
Fig. 26

*Fig. 27*

Missed Calls in Blood

| Missed_by_WB | Position | Notes | Mutation |
|---|---|---|---|
| IKBKAP_28_-1_f_0: | 140 | Only 1 UID in WB sample | C->G |
| IKBKAP_01-02_-1_o_8: | 62 | Only 6 UIDs in WB | C->G |
| GAA_05_1_o_9: | 196 | 71% GC content | CCCGCCCGCCGCCCGCCGC->CCCGCCCGCCGCCCGCCGCCCGCCGC |
| GAA_02-02_1_o_3: | 103 | Only 4 UIDs in WB | A->G |
| GAA_18_1_f_0: | 91 | Only 1 UIDs in WB | G->A |
| Missed_by_WB3x | Position | Notes | Mutation |
| IKBKAP_01-02_-1_o_8: | 62 | Only 4 UIDs in WB3x | C->G |
| GAA_05_1_o_9: | 196 | 71% GC content | CCCGCCCGCCGCCCGCCGC->CCCGCCCGCCGCCCGCCGCCCGCCGC |
| GAA_02-02_1_o_3: | 103 | Only 3 UIDs in WB3x | A->G |
| GAA_18_1_f_0: | 91 | Only 8 UIDs in WB3x | G->A |

SNP Calls in Blood not in gDNA

| Called_by_WB_not_gDNA | Position | Notes | Mutation |
|---|---|---|---|
| CFTR_10_1_f_7: | 20 | repetitive region | ATGTGTGTGTGTGTGTGTGTGTGT |
| BCKDHB_01-01_1_f_0: | 157 | 14 UIDs for WB and high GC at 71.2% | C->G |
| Called_by_WB3x_not_gDNA | | | |
| CFTR_10_1_f_7: | 20 | repetitive region | ATGTGTGTGTGTGTGTGTGTGTGT |
| CFTR_10_1_f_7: | 39 | repetitive region | TG->TGCG |
| SMPD1_01-02_1_o_0: | 177 | SAM tools pile up issue | GCCAGCACCAG->GCCAG |
| BLM_10_1_f_8: | 75 | Only 5 UIDs/gDNA, 10 UIDs/WB3x | A->T |
| BLM_05_1_f_3: | 145 | 10 UIDs for WB3x and low GC at 35% | C->G |

*Fig. 32*

| No. | Expected Numbers | | Actual Numbers | |
| --- | --- | --- | --- | --- |
| | Sequences | % of Run | Total Sequences | % of Run |
| BC_05 | 115,000 | 0.75 | 175,120 | 0.95 |
| BC_11 | 200,000 | 1.30 | 249,559 | 1.35 |
| BC_17 | 200,000 | 1.30 | 439,386 | 2.38 |
| BC_01 | 400,000 | 2.59 | 415,986 | 2.25 |
| BC_02 | 400,000 | 2.59 | 381,609 | 2.07 |
| BC_03 | 400,000 | 2.59 | 279,127 | 1.51 |
| BC_04 | 400,000 | 2.59 | 518,732 | 2.81 |
| BC_08 | 500,000 | 3.24 | 641,863 | 3.48 |
| BC_10 | 500,000 | 3.24 | 602,764 | 3.27 |
| BC_14 | 500,000 | 3.24 | 630,015 | 3.41 |
| BC_16 | 500,000 | 3.24 | 618,677 | 3.35 |
| BC_06 | 500,000 | 3.24 | 661,402 | 3.58 |
| BC_21 | 500,000 | 3.24 | 611,911 | 3.32 |
| BC_36 | 500,000 | 3.24 | 732,291 | 3.97 |
| BC_39 | 500,000 | 3.24 | 600,183 | 3.25 |
| BC_26 | 500,000 | 3.24 | 578,438 | 3.13 |
| BC_29 | 500,000 | 3.24 | 637,069 | 3.45 |
| BC_19 | 500,000 | 3.24 | 612,868 | 3.32 |
| BC_31 | 500,000 | 3.24 | 660,459 | 3.58 |
| BC_34 | 500,000 | 3.24 | 509,304 | 2.76 |
| BC_30 | 500,000 | 3.24 | 489,322 | 2.65 |
| BC_32 | 500,000 | 3.24 | 546,824 | 2.96 |
| BC_33 | 500,000 | 3.24 | 497,437 | 2.70 |
| BC_35 | 500,000 | 3.24 | 547,810 | 2.97 |
| BC_43 | 800,000 | 5.19 | 932,081 | 5.05 |
| BC_44 | 800,000 | 5.19 | 1,052,359 | 5.70 |
| BC_45 | 800,000 | 5.19 | 998,955 | 5.41 |
| BC_46 | 800,000 | 5.19 | 1,100,682 | 5.96 |
| BC_47 | 800,000 | 5.19 | 914,388 | 4.96 |
| BC_48 | 800,000 | 5.19 | 815,854 | 4.42 |
| Total | 15,415,000 | 100.00 | 18,452,475 | 100.00 |

Fig. 39

| Quality Metrics Summary | |
|---|---|
| On Target Specificity[1] | 97.1% |
| Uniformity of Coverage[2] | >90% |
| SNP Accuracy[3] | 99.98% |

1- Mapped reads on targeted/Total mapped reads
2- Coverage uniformity—bases covered at >20% of the mean coverage.
3- Total correct base calls/Total base calls

*Fig. 46*

```
GBA_allele2       ACTACCTTTGTCTCTAGATACCCCTGATTCACCGAGCCCTGCAGTTGGCCCAGCGTCCCG  60
Reference_genome  ACTACCTTTGTCTCTAGATACCCCTGATTCACCGAGCCCTGCAGTTGGCCCAGCGTCCCG  60
GBA_allele1       ACTACCTTTGTCTCTAGATACCCCTGATTCACCGAGCCCTGCAGTTGGCCCAGCGTCCCG  60
                  ************************************************************

GBA_allele2       TTTCACTCCTTGCCACCCCCTGGACATCACCACTTGCTCAAGACCAATGAGCCGGTGA  120
Reference_genome  TTTCACTCCTTGCCAGCCCCTGGACATCACCACTTGCTCAAGACCAATCCAGCCGGTGA  120
GBA_allele1       TTTCACTCCTTGCCACCCCCTGGACATCACCACTGGCTCAAGACCAAGGGAGCCGGGGA  120
                  ***************  ****************  ***********    ****  **

GBA_allele2       ATGGGAGGGGGTCACTCAAGGGACACAGCCCCGGAGACATCTACCACCAGAGCCCAGAT  180
Reference_genome  ATGGGAGGGGTCACTCAAGGGACACAGCCACACTTACCACCAGACCAGACCTGGGCCAGAT  180
GBA_allele1       ATGGGAAGGGGGCCACTCAAGGGACACAGCCACACTTACCACCAGAGACCTGGGCCAGAT  180
                  ******  ****                 ***  ******** ***********

GBA_allele2       ACTTTGTGAAGTAAGGATCAGCAGGATGT  211
Reference_genome  ACTTTGTGAAGTAAGGATCAGCAGGATGT  211
GBA_allele1       ACATTGTGAAGTAAGGATCAGCAGGATGT  211
                  ** **************************
```

*Fig. 57*

TARGETED SEQUENCING AND UID FILTERING

SEQUENCE LISTING

The instant application contains a Sequence Listing which has been submitted electronically in ASCII format and is hereby incorporated by reference in it entirety. Said ASCII copy, created on Feb. 6, 2015, is named 32510-US2_SL.text and is 37,693 bytes in size.

BACKGROUND

Many current next-generation sequencing (NGS) technologies use a form of sequencing by synthesis (SBS). NGS technologies have the ability to massively parallel sequence millions of DNA templates. To attain high-throughput, many millions of single stranded templates are arrayed across a chip and the sequence of each template is independently read. Second-generation NGS platforms clonally amplify DNA templates on a solid support followed by cyclic sequencing. Third-generation NGS platforms employ single molecule PCR-free protocols and cycle-free chemistry (Schadt et al., Hum Mol Genet., 19(R2):R227-40, (2010)).

Major limitations of NGS methods and other high-throughput sequencing methods include sequencing and amplification error and bias. Due to error and bias associated with amplification and sequencing, these sequencing technologies deviate from the ideal uniform distribution of reads and can impair many scientific and medical applications. For clinical applications, labs must verify the accuracy of a mutation or a single nucleotide polymorphism (SNP) call before reporting to a patient. Typically sequence verification is done by making a Sanger library of the target after obtaining the sequences and "Sanger qualifying" the next-generation sequencing (NGS) results. To overcome the higher error rate of NGS platforms compared to traditional Sanger sequencing a high level of redundancy or sequence coverage is required to accurately call bases. A 30-50× coverage is typically required for accurate base calling, although this can vary based on the accuracy of the sequencing platform, variant detection methods, and the material being sequenced (Koboldt D C et al., Brief Bioinform., 11:484-98 (2010)). In general, all second-generation platforms produce data of a similar accuracy (98-99.5%), relying upon adequate sequence depth e.g., coverage) to make higher accuracy base calls.

Sequencing bias can manifest as coverage bias (deviation from a uniform distribution of reads) and error bias (deviations from uniform mismatch, insertion, and deletion rates). Current sequencing technologies are limited because the chemistries used in high-throughput sequencing methods are inherently biased. Some nucleotide sequences are read more frequently than other sequences, and have an inherent error rate. Depending on many factors, including the sequencing platform used, read errors (most of which are misidentified bases due to low quality base calls) can occur anywhere in the range of one error per 100-2000 bases. While coverage bias is an important sequencing metric, variations in sequence accuracy are also important.

Another major limitation is PCR amplification bias, because conditions during library construction of nucleotide templates for sequencing can significantly influence sequencing bias. PCR amplification for library construction has been shown to be a source of sequencing data error (Keohavong P et al., PNAS 86:9253-9257 (1989); Cariello et al., Nucleic Acids Res., 19:4193-4198 (1991); Cline et al., Nucleic Acids Res., 24:3546-3551 (1996)). Library construction methods can affect evenness of coverage. For example, PCR amplification is also a known source of under coverage of GC-extreme regions during library construction (Aird et al., Genome Biol., 12:R18 (2011); Oyola et al., BMC Genomics, 13:1; 22 (2012); Benjamini et al., Nucleic Acids Res., 40:e72 (2012)). Similar biases may also be introduced during bridge PCR for cluster amplification and on some NGS platforms strand-specific errors can lead to coverage biases by impairing aligner performance (Nakamura et al., Nucleic Acids Res., 39:e90 (2011)). Other platforms that utilizing a terminator-free chemistry can be limited in their ability to accurately sequence long homopolymers, and can also be sensitive to coverage biases introduced by emulsion PCR in library construction (Rothberg et al., Nature, 475:348-352 (2011); Margulies et al., Nature 2005, 437:376-380 (2005); Huse et al., Genome Biol., 8:R143 (2007); Merriman et al., Electrophoresis, 33:3397-3417 (2012)).

SUMMARY

In one aspect, a method of generating a library of polynucleotides comprising: (a) generating a first complement sequence (CS) of a target polynucleotide from a sample using a first primer, the first primer comprising a target specific sequence; (b) attaching to the first CS an adaptor comprising a first primer binding sequence (PBS) or portion thereof, thereby forming a modified complement sequence (MCS); (c) extending a second primer hybridized to the MCS, thereby forming a second CS, wherein the second primer comprises: (i) a target specific region, and (ii) a second PBS; and (d) amplifying the second CS using primers that hybridize to the first PBS and second PBS respectively, wherein the first or the second primer comprises a unique identification (UID) sequence is provided.

In some embodiments, the first primer comprises the UID.

In some embodiments, the second primer comprises the UID.

In one aspect, a method of generating a library of polynucleotides comprising: (a) extending target specific first primer hybridized to a target polynucleotide to form a first CS; (b) attaching an adaptor to the first CS to form an MCS; (c) extending a second primer hybridized to the MCS to form a second CS; and (d) amplifying the second CS; wherein (a) or (c) do not comprise exponential amplification, and wherein the first or the second primer comprises a UID is provided.

In some embodiments, the first primer comprises the UID.

In some embodiments, the second primer comprises the UID.

In one aspect, a method of generating a library of polynucleotides comprising: (a) generating a first CS, or modified form thereof (MCS), from a target polynucleotide; (b) generating a second CS from a polynucleotide comprising the sequence of the first CS; wherein the second CS is generated by a non-exponential amplification reaction; and (c) amplifying the second CS; wherein the first CS or the second CS comprises a UID is provided.

In some embodiments, the first CS comprises the UID.

In some embodiments, the second CS comprises the UID.

In one aspect, a method of accurately determining the sequence of a target polynucleotide comprising: (a) generating a second CS from a first CS, or modified form thereof (MCS), generated from a target polynucleotide; wherein the first CS, second CS, or MCS comprises a UID, and wherein the first and second CSs are each individually generated by (i) a primer extension reaction, or (ii) a linear amplification reaction; (b) amplifying the second CS; (c) sequencing at least one of the amplified second CSs; (d) aligning at least two sequences containing the same UID from (c); and (e) determining a consensus sequence based on (d), wherein the consensus sequence accurately represents the target polynucleotide sequence is provided.

In some embodiments, the first CS comprises the UID.

In some embodiments, the second CS comprises the UID.

In some embodiments, (a) comprises generating the first CS by hybridizing the first primer to the target polynucleotide and extending the hybridized first primer.

In some embodiments, (a) comprises generating the first CS by extending a first primer hybridized to the target polynucleotide.

In some embodiments, the first primer is hybridized to the target polynucleotide via a target specific sequence.

In some embodiments, (a) comprises performing a primer extension reaction or a reverse transcription reaction.

In some embodiments, (a) comprises a primer extension reaction.

In some embodiments, the target polynucleotide is DNA.

In some embodiments, (a) is performed using a DNA polymerase.

In some embodiments, (a) comprises a reverse transcription reaction.

In some embodiments, the target polynucleotide is RNA.

In some embodiments, (a) is performed using a reverse transcriptase.

In some embodiments, the adaptor comprises a first PBS.

In some embodiments, the MCS comprises the first PBS.

In some embodiments, the second primer comprises a target specific region.

In some embodiments, the second primer comprises a second PBS.

In some embodiments, the first CS comprises a first PBS.

In some embodiments, the method further comprises attaching an adaptor to the first CS to form the MCS.

In some embodiments, the adaptor comprises a first PBS.

In some embodiments, the polynucleotide comprising the sequence of the first CS is the MCS.

In some embodiments, the MCS comprises a first PBS

In some embodiments, the MCS comprises a first PBS.

In some embodiments, the attaching is performed after (a).

In some embodiments, the attaching is performed before (b).

In some embodiments, generating the second CS comprises extending a second primer hybridized to the first CS.

In some embodiments, generating the second CS comprises extending a second primer hybridized to the MCS.

In some embodiments, the second primer comprises a target specific region.

In some embodiments, the second primer comprises a second PBS.

In some embodiments, the second CS is generated from the first CS.

In some embodiments, the first CS comprises a first PBS.

In some embodiments, the second CS is generated from the MCS.

In some embodiments, the MCS is generated via attaching an adaptor to the first CS to form the MCS.

In some embodiments, the MCS comprises a first PBS.

In some embodiments, generating the second CS comprises extending a second primer hybridized to the first CS.

In some embodiments, the generating the second CS comprises extending a second primer hybridized to the MCS.

In some embodiments, the second primer comprises a target specific region.

In some embodiments, the second primer comprises a second PBS.

In some embodiments, the first primer comprises a universal ligation sequence (ULS).

In some embodiments, the adaptor comprises a single stranded region comprising a sequence complementary to the ULS.

In some embodiments, the sequence complementary to the ULS is at the 5' end of the single stranded region of the adaptor.

In some embodiments, the first primer further comprises a phosphorylated 5' end.

In some embodiments, the method comprises generating the phosphorylated 5' end prior to attaching the adapter.

In some embodiments, the first primer further comprises a first portion of a partial primer binding site, wherein the complete primer binding site comprises two portions.

In some embodiments, the adapter comprises the second portion of the partial primer binding site.

In some embodiments, the complete primer binding site is formed by the attaching of the adapter to the first CS.

In some embodiments, the second primer further comprises a universal priming sequence (UPS).

In some embodiments, the adapter further comprises a UPS.

In some embodiments, the adapter comprises a single stranded polynucleotide.

In some embodiments, the method further comprises extending the first primer hybridized to the adaptor, wherein the extended portion of the first primer comprises a region complementary to the adaptor or a portion thereof.

In some embodiments, the adapter comprises a double stranded polynucleotide.

In some embodiments, the adapter further comprises an overhang region.

In some embodiments, the overhang region comprises a sequence complementary to a portion of the first CS.

In some embodiments, the portion of the first CS complementary to the overhang region of the adaptor is an end of the first CS.

In some embodiments, the adapter further comprises a region not complementary to the first CS.

In some embodiments, the adapter further comprises a sample barcode (SBC) sequence.

In some embodiments, the adapter further comprises an SBC sequence.

In some embodiments, the region not complementary to the first CS comprises the SBC sequence.

In some embodiments, the adapter further comprises an affinity molecule or capture sequence.

In some embodiments, the adapter comprises an affinity molecule, wherein the affinity molecule is biotin.

In some embodiments, the MCS further comprises an affinity molecule or capture sequence.

In some embodiments, the MCS comprises an affinity molecule, wherein the affinity molecule is biotin.

In some embodiments, the method comprises binding the affinity molecule or capture sequence to a solid surface.

In some embodiments, the solid surface is a bead.

In some embodiments, the method comprises separating the target polynucleotide or a non-target polynucleotide from the bound MCS.

In some embodiments, the sequence complementary to a portion of the first CS is 5' to the SBC.

In some embodiments, the sequence complementary to a portion of the first CS is 3' or 5' to the UPS.

In some embodiments, the MCS comprises the adapter.

In some embodiments, the MCS comprises a single strand of the double stranded adapter.

In some embodiments, the MCS comprises a UPS.

In some embodiments, the first PBS of the MCS comprises the UPS.

In some embodiments, the first PBS of the MCS does not comprise the UPS.

In some embodiments, the second primer comprises a UPS.

In some embodiments, the second PBS of the second primer comprises the UPS.

In some embodiments, the second PBS of the second primer does not comprise the UPS.

In some embodiments, the MCS comprises a first UPS and the second primer comprises a second UPS.

In some embodiments, the first PBS of the MCS comprises the first UPS.

In some embodiments, the second PBS of the second primer comprises the second UPS.

In some embodiments, the second CS comprises the first PBS, the MCS, the second PBS, the target sequence, compliments thereof, or any combination thereof.

In some embodiments, the second CS comprises a sequence complementary to the first PBS.

In some embodiments, the second CS comprises a sequence complementary to the MCS.

In some embodiments, the second CS comprises the second PBS.

In some embodiments, the second CS comprises the target sequence.

In some embodiments, the second CS comprises the UPS.

In some embodiments, the second CS comprises a sequence complementary to the first UPS.

In some embodiments, the second CS comprises the second UPS.

In some embodiments, the second CS is generated from a non-exponential amplification reaction.

In some embodiments, the second CS is generated from a single second primer.

In some embodiments, the second CS is generated from a primer extension reaction.

In some embodiments, the second CS is generated from a linear amplification reaction.

In some embodiments, the amplification reaction comprises a single round of amplification.

In some embodiments, the amplification reaction comprises two or more rounds of amplification.

In some embodiments, the amplification reaction comprises 10 or more rounds of amplification.

In some embodiments, the second CS is generated before an exponential amplification reaction is performed.

In some embodiments, the target polynucleotide comprises a plurality of target polynucleotides.

In some embodiments, each of the target polynucleotides of the plurality comprises different sequences.

In some embodiments, each of the target polynucleotides of the plurality comprises the same sequence.

In some embodiments, the first primer comprises a plurality of first primers each comprising a target specific region.

In some embodiments, the target specific region of each of the plurality of first primers is different.

In some embodiments, the target specific region of each of the plurality of first primers is the same.

In some embodiments, the second primer comprises a plurality of second primers, each comprising a sequence complementary to a target specific region.

In some embodiments, the target specific region of each of the plurality of first primers is different.

In some embodiments, the target specific region of each of the plurality of first primers is the same.

In some embodiments, the first primer hybridizes to the 3' end, the 5' end, or an internal region of the target polynucleotide.

In some embodiments, the second primer hybridizes to the 3' end, the 5' end, or an internal region of the first CS or MCS.

In some embodiments, the first CS comprises a plurality of first CSs

In some embodiments, each of the first CSs of the plurality comprises different sequences.

In some embodiments, each of the first CSs of the plurality comprises the same sequence.

In some embodiments, the adapter comprises a plurality of adapters.

In some embodiments, each of the adapters of the plurality comprises different sequences.

In some embodiments, each of the adapters of the plurality comprises the same sequence.

In some embodiments, the MCS comprises a plurality of MCSs.

In some embodiments, each of the MCSs of the plurality comprises different sequences.

In some embodiments, each of the MCSs of the plurality comprises the same sequence.

In some embodiments, the second CS comprises a plurality of second CSs.

In some embodiments, each of the second CSs of the plurality comprises different sequences.

In some embodiments, each of the second CSs of the plurality comprises the same sequence.

In some embodiments, the UID is unique for each first primer.

In some embodiments, the UID is not unique for each first primer.

In some embodiments, each first primer comprises the same UPS, the same first PBS, or both.

In some embodiments, each first CS comprises the same UPS the same first PBS, or both.

In some embodiments, each adapter comprises the same UPS the same first PBS, the same SBC or a combination thereof.

In some embodiments, each MCS comprises the same UPS the same first PBS, the same SBC or a combination thereof.

In some embodiments, each second primer comprises the same UPS, the same second PBS, or both.

In some embodiments, each second CS comprises the same UPS, the same first UPS, the same second UPS, the same SBC, the same first PBS, the same second PBS, or a combination thereof.

In some embodiments, each adapter comprises a different UPS, a different first PBS, a different SBC, or a combination thereof.

In some embodiments, each MCS comprises a different UPS, a different first PBS, a different SBC, or a combination thereof.

In some embodiments, each first primer of a first plurality of first primers is extended simultaneously, is extended in the same reaction chamber, is hybridized to a target polynucleotide simultaneously, or is hybridized to a target polynucleotide in the same reaction chamber.

In some embodiments, each first CS or MCS of a first plurality of first CSs or MCSs is generated simultaneously, is generated in the same reaction chamber, is amplified simultaneously, or is amplified in the same reaction chamber.

In some embodiments, each second primer of a first plurality of second primer is extended simultaneously, is extended in the same reaction chamber, is hybridized to a first CS or MCS simultaneously, or is hybridized to a first CS or MCS in the same reaction chamber.

In some embodiments, each second CS of a first plurality of second CSs is generated simultaneously, is generated in the same reaction chamber, is amplified simultaneously, or is amplified in the same reaction chamber.

In some embodiments, the sample is a biological sample.

In some embodiments, the sample is a biological sample from a subject.

In some embodiments, the subject is a subject with a disease or condition.

In some embodiments, the subject is a subject without a disease or condition.

In some embodiments, the subject is an animal

In some embodiments, the animal is a human.

In some embodiments, the sample is a blood sample.

In some embodiments, the target polynucleotide is isolated from the sample.

In some embodiments, the target polynucleotide is amplified directly from the sample.

In some embodiments, the sample comprises a plurality of samples comprising a first sample and a second sample.

In some embodiments, the plurality of samples comprises at least 3, 4 5, 10, 20, 30, 40, 50, 60, 70, 80, 90 or 100 or more samples.

In some embodiments, the plurality of samples comprises at least about 100, 200, 300, 400, 500, 600, 700, 800, 900 or 1000 or more samples.

In some embodiments, the plurality of samples comprises at least about 1000, 2000, 3000, 4000, 5000, 6000, 7000, 8000 samples, 9000, or 10,000 samples, or 100,000 samples, or 1,000,000 or more samples.

In some embodiments, the plurality of samples comprises at least about 10,000 samples.

In some embodiments, the first sample is from a first subject and the second sample is from a second subject.

In some embodiments, the first subject is a subject with a disease or condition.

In some embodiments, the second subject is a subject without a disease or condition.

In some embodiments, each first primer of the first plurality of first primers is contacted to the first sample and each first primer of a second plurality of first primers is contacted to the second sample.

In some embodiments, each first primer of the second plurality of first primers is extended simultaneously, is extended in the same reaction chamber, is hybridized to a target polynucleotide simultaneously, or is hybridized to a target polynucleotide in the same reaction chamber.

In some embodiments, the first plurality of first primers and the second plurality of first primers are extended simultaneously or are hybridized to a target polynucleotide simultaneously.

In some embodiments, each second primer of the first plurality of second primers is contacted to the first sample and each second primer of the second plurality of second primers is contacted to the second sample.

In some embodiments, each second primer of a second plurality of second primers is extended simultaneously, is extended in the same reaction chamber, is hybridized to a target polynucleotide simultaneously, or is hybridized to a target polynucleotide in the same reaction chamber.

In some embodiments, the first plurality of second primers and the second plurality second primers are extended simultaneously, are extended in the same reaction chamber, are hybridized to a first CS or MCS simultaneously, or are hybridized to a first CS or MCS in the same reaction chamber.

In some embodiments, each first CS or MCS of the first plurality of first CSs or MCSs generated from a target polynucleotide in the first sample and each first CS or MCS of a second plurality of first CSs or MCSs is generated from a target polynucleotide in the second sample.

In some embodiments, each first CS or MCS of the second plurality of first CSs or the second MCSs is generated simultaneously, is generated in the same reaction chamber, is amplified simultaneously, or is amplified in the same reaction chamber.

In some embodiments, the first plurality of first CSs and the second plurality of first CSs are generated simultaneously, are generated in the same reaction chamber, are amplified simultaneously, or are amplified in the same reaction chamber.

In some embodiments, each second CS of the first plurality of second CSs generated from a target polynucleotide in the first sample and each second CS of a second plurality of second CSs is generated from a target polynucleotide in the second sample.

In some embodiments, each second CS of the second plurality of second CSs is generated simultaneously, is generated in the same reaction chamber, is amplified simultaneously, or is amplified in the same reaction chamber.

In some embodiments, the first plurality of second CSs and the second plurality of second CSs are generated simultaneously, are generated in the same reaction chamber, are amplified simultaneously, or are amplified in the same reaction chamber.

In some embodiments, the method further comprises combining the first sample and the second sample.

In some embodiments, the combining is done after generating the first plurality of first CSs or MCSs.

In some embodiments, one or more of the target polynucleotides or plurality of target polynucleotides comprises a variant sequence.

In some embodiments, the variant sequence comprises a mutation, polymorphism, deletion, or insertion.

In some embodiments, the polymorphism is a single nucleotide polymorphism.

In some embodiments, one or more of the target polynucleotides is from a pathogen.

In some embodiments, the pathogen is a virus, bacteria, or fungus.

In some embodiments, the UID comprises at least 2 nucleotides.

In some embodiments, the UID comprises at least 10 nucleotides.

In some embodiments, the UID comprises at least 15 nucleotides.

In some embodiments, the UID comprises at most 50 nucleotides.

In some embodiments, the UID comprises from 10-30 nucleotides.

In some embodiments, the UID comprises a degenerate sequence.

In some embodiments, the UID comprises a full or partial degenerate sequence.

In some embodiments, the UID comprises the sequence NNNNNNNNNNNNNNN (SEQ ID NO: 1), wherein N is any nucleic acid.

In some embodiments, the UID comprises the sequence NNNNNVVNNNNNWNNNNN (SEQ ID NO: 2), wherein N is any nucleic acid and W is adenine or thymine.

In some embodiments, the attaching comprises ligating.

In some embodiments, the attaching comprises amplification.

In some embodiments, the second CS(s) are amplified an exponential amplification reaction.

In some embodiments, the second CS(s) are amplified by PCR.

In some embodiments, the second CS(s) are amplified using a primer set comprising a primer to the first PBS and a primer to the second PBS.

In some embodiments, wherein the second CS(s) are amplified using a UPS.

In some embodiments, the second CS(s) are amplified using a primer set comprising a primer to a first UPS and a primer to a second UPS.

In some embodiments, the method further comprises sequencing an amplified product from one or more second CSs or one or more pluralities of second CSs In some embodiments, the sequencing is performed simultaneously.

In some embodiments, the sequencing is high throughput sequencing.

In some embodiments, the method further comprises analyzing a sequence determined In some embodiments, the analyzing is done with a computer.

In some embodiments, the method further comprises determining an amplification error rate.

In some embodiments, the method further comprises determining a sequencing error rate.

In some embodiments, the method further comprises determining a frequency of the one or more target polynucleotides.

In some embodiments, the method further comprises determining the presence or absence of a variant in the one or more target polynucleotides.

In some embodiments, the method further comprises determining whether a subject is homozygous or heterozygous for an allele.

In some embodiments, the method further comprises diagnosing, prognosing, or treating a subject with a disease or condition.

In some embodiments, the method further comprises correcting amplification errors.

In some embodiments, the method further comprises correcting sequencing errors.

In some embodiments, the method further comprises binning or grouping sequences comprising the same UID.

In some embodiments, the method further comprises binning or grouping sequences comprising the same UID using a computer or algorithm.

In some embodiments, the method further comprises binning or grouping sequences comprising the same UID using a computer or algorithm.

In some embodiments, the method further comprises clustering sequences with at least about 90%, 95%, or 99% sequence homology.

In some embodiments, the method further comprises aligning sequences with at least about 90%, 95%, or 99% sequence homology.

In some embodiments, the clustering or aligning is performed with the aid of a computer or algorithm.

In some embodiments, the method further comprises determining the number of sequence reads containing the same UID.

In some embodiments, the method further comprises determining the number of sequence reads containing both the same UID and a target sequence with at least about 90%, 95%, or 99% sequence homology.

In some embodiments, the method further comprises determining the amount of one or more target polynucleotides in one or more of the samples.

In some embodiments, the method further comprises forming a consensus sequence from two or more sequences, sequence reads, amplicon sequences, binned sequences, aligned sequences, clustered sequences, or amplicon set sequences comprising the same UID.

In some embodiments, the method further comprises determining a target polynucleotide sequence with at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 99.99%, or 100% accuracy or confidence.

In some embodiments, the sequencing and PCR errors are minimized, eliminated, or less than 0.01%, 0.001%, 0.0001%, 0.00001%, 0.000001%, or 0.0000001%.

In some embodiments, the amplifying the first CSs or MCSs limits amplification bias.

In some embodiments, the error rate of sequencing of less than or equal to 0.00001%, 0.0001%, 0.001%, 0.01%, or 0%.

In some embodiments, the error rate of sequencing is not 0.

In some embodiments, the at least 1,000, 5,000, 10,000, 20,000, 30,000, 40,000, 50,000, 1000,000, 500,000, or, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$ polynucleotides are sequenced.

In some embodiments, the method is performed in a positive amount of time less than or equal to 4 weeks, 3 weeks, 2 weeks, 1 week, 6 days, 5 days, 5 days, 4 days, 3 days, 2 days, 1 day, 18 hours, 12 hours, 9 hours, 6 hours, or 3 hours.

In some embodiments, the number of reads used to achieve a particular confidence or base calling accuracy is at least about 1.1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 30, 40, 50, 60, 70, 80, 90, 100, 200, 300, 400, 500, 600, 700, 800, 900, or 1000 fold fewer than the number of reads used to achieve the same, similar, or higher confidence or base calling accuracy using a similar method without the use of UIDs.

In some embodiments, the number of reads used to achieve a particular confidence or base calling accuracy is at least about 1, 2, 3, 4, 5, 5.5 6, 6.5 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ reads fewer than the number of reads used to achieve the same, similar, or higher confidence or base calling accuracy using a similar method without the use of UIDs.

In one aspect, a kit comprising one or more primers, reagents, enzymes, or substrates, of any of the methods described herein is provided.

In one aspect, a panel of first primers, wherein each of the first primers in the panel comprises a target specific sequence, and a UID is provided.

In some embodiments, the panel comprises at least about 2, 3, 4, 5, 10, 50, 100, 500, 1000, 5000, 10,000, 100,000, 2500,000 or more first primers comprising different target specific sequences In one aspect, a library of polynucleotides comprising a plurality of polynucleotides, wherein each polynucleotide in the plurality comprises a UID, wherein each polynucleotide in the plurality is a product from a different non-exponentially amplified template polynucleotide is provided.

In one aspect, a library of polynucleotides comprising a plurality of polynucleotides, wherein each polynucleotide in the plurality comprises a PCR product from one or more polynucleotides of any library described herein is provided.

In one aspect, a method of generating a library of polynucleotides comprising: (a) generating a first complement sequence (CS) of a target polynucleotide from a sample using a first primer, the first primer comprising a target specific sequence; (b) attaching to the first CS an adaptor comprising a first primer binding sequence (PBS) or portion thereof, thereby forming a modified complement sequence (MCS); (c) extending a second primer hybridized to the MCS, thereby forming a second CS, wherein the second primer comprises: (i) a target specific region, and (ii) a second PBS; and (d) amplifying the second CS using primers that hybridize to the first PBS and second PBS respectively is provided.

In one aspect, a method of generating a library of polynucleotides comprising: (a) extending target specific first primer hybridized to a target polynucleotide to form a first CS; (b) attaching an adaptor to the first CS to form an MCS; (c) extending a second primer hybridized to the MCS to form a second CS; and (d) amplifying the second CS; wherein (a) or (c) do not comprise exponential amplification is provided.

In one aspect, a method of generating a library of polynucleotides comprising: (a) generating a first CS, or modified form thereof (MCS), from a target polynucleotide; (b) generating a second CS from a polynucleotide comprising the sequence of the first CS; wherein the second CS is generated by a non-exponential amplification reaction; and (c) amplifying the second CS is provided.

In one aspect, a method of accurately determining the sequence of a target polynucleotide comprising: (a) generating a second CS from a first CS, or modified form thereof (MCS), generated from a target polynucleotide; wherein the first and second CSs are each individually generated by (i) a primer extension reaction, or (ii) a linear amplification reaction; (b) amplifying the second CS; (c) sequencing at least one of the amplified second CSs; (d) aligning at least two sequences from (c) comprising at least 10% sequence identity; and (e) determining a consensus sequence based on (d), wherein the consensus sequence accurately represents the target polynucleotide sequence is provided.

In some embodiments, (a) comprises generating the first CS by hybridizing the first primer to the target polynucleotide and extending the hybridized first primer.

In some embodiments, (a) comprises generating the first CS by extending a first primer hybridized to the target polynucleotide.

In some embodiments, the first primer is hybridized to the target polynucleotide via a target specific sequence.

In some embodiments, (a) comprises performing a primer extension reaction or a reverse transcription reaction.

In some embodiments, (a) comprises a primer extension reaction.

In some embodiments, the target polynucleotide is DNA.

In some embodiments, (a) is performed using a DNA polymerase.

In some embodiments, (a) comprises a reverse transcription reaction.

In some embodiments, the target polynucleotide is RNA.

In some embodiments, (a) is performed using a reverse transcriptase.

In some embodiments, the adaptor comprises a first PBS.

In some embodiments, the MCS comprises the first PBS.

In some embodiments, the second primer comprises a target specific region.

In some embodiments, the second primer comprises a second PBS.

In some embodiments, the first CS comprises a first PBS.

In some embodiments the method further comprises attaching an adaptor to the first CS to form the MCS.

In some embodiments, the adaptor comprises a first PBS.

In some embodiments, the polynucleotide comprising the sequence of the first CS is the MCS.

In some embodiments, the MCS comprises a first PBS

In some embodiments, the MCS comprises a first PBS.

In some embodiments, the attaching is performed after (a).

In some embodiments, the attaching is performed before (b).

In some embodiments, generating the second CS comprises extending a second primer hybridized to the first CS.

In some embodiments, generating the second CS comprises extending a second primer hybridized to the MCS.

In some embodiments, the second primer comprises a target specific region.

In some embodiments, the second primer comprises a second PBS.

In some embodiments, the second CS is generated from the first CS.

In some embodiments, the first CS comprises a first PBS.

In some embodiments, the second CS is generated from the MCS.

In some embodiments, the MCS is generated via attaching an adaptor to the first CS to form the MCS.

In some embodiments, the MCS comprises a first PBS.

In some embodiments, generating the second CS comprises extending a second primer hybridized to the first CS.

In some embodiments, the generating the second CS comprises extending a second primer hybridized to the MCS.

In some embodiments, the second primer comprises a target specific region.

In some embodiments, the second primer comprises a second PBS.

In some embodiments, wherein the first primer comprises a universal ligation sequence (ULS).

In some embodiments, the adaptor comprises a single stranded region comprising a sequence complementary to the ULS.

In some embodiments, the sequence complementary to the ULS is at the 5' end of the single stranded region of the adaptor.

In some embodiments, the first primer further comprises a phosphorylated 5' end.

In some embodiments, the method further comprises generating the phosphorylated 5' end prior to attaching the adapter.

In some embodiments, the first primer further comprises a first portion of a partial primer binding site, wherein the complete primer binding site comprises two portions.

In some embodiments, the adapter comprises the second portion of the partial primer binding site.

In some embodiments, the complete primer binding site is formed by the attaching of the adapter to the first CS.

In some embodiments, the second primer further comprises a universal priming sequence (UPS).

In some embodiments, the adapter further comprises a UPS.

In some embodiments, the adapter comprises a single stranded polynucleotide.

In some embodiments, the method further comprises extending the first primer hybridized to the adaptor, wherein the extended portion of the first primer comprises a region complementary to the adaptor or a portion thereof.

In some embodiments, the adapter comprises a double stranded polynucleotide.

In some embodiments, the adapter further comprises an overhang region.

In some embodiments, the overhang region comprises a sequence complementary to a portion of the first CS.

In some embodiments, the portion of the first CS complementary to the overhang region of the adaptor is an end of the first CS.

In some embodiments, the adapter further comprises a region not complementary to the first CS.

In some embodiments, the adapter further comprises a sample barcode (SBC) sequence.

In some embodiments, the adapter further comprises an SBC sequence.

In some embodiments, the region not complementary to the first CS comprises the SBC sequence.

In some embodiments, the adapter further comprises an affinity molecule or capture sequence.

In some embodiments, the adapter comprises an affinity molecule, wherein the affinity molecule is biotin.

In some embodiments, the MCS further comprises an affinity molecule or capture sequence.

In some embodiments, the MCS comprises an affinity molecule, wherein the affinity molecule is biotin.

In some embodiments, the method further comprises binding the affinity molecule or capture sequence to a solid surface.

In some embodiments, the solid surface is a bead.

In some embodiments, the method further comprises separating the target polynucleotide or a non-target polynucleotide from the bound MCS.

In some embodiments, the sequence complementary to a portion of the first CS is 5' to the SBC.

In some embodiments, the sequence complementary to a portion of the first CS is 3' or 5' to the UPS.

In some embodiments, the MCS comprises the adapter.

In some embodiments, the MCS comprises a single strand of the double stranded adapter.

In some embodiments, the MCS comprises a UPS.

In some embodiments, the first PBS of the MCS comprises the UPS.

In some embodiments, the first PBS of the MCS does not comprise the UPS.

In some embodiments, the second primer comprises a UPS.

In some embodiments, the second PBS of the second primer comprises the UPS.

In some embodiments, the second PBS of the second primer does not comprise the UPS.

In some embodiments, the MCS comprises a first UPS and the second primer comprises a second UPS.

In some embodiments, the first PBS of the MCS comprises the first UPS.

In some embodiments, the second PBS of the second primer comprises the second UPS.

In some embodiments, the second CS comprises the first PBS, the MCS, the second PBS, the target sequence, compliments thereof, or any combination thereof.

In some embodiments, the second CS comprises a sequence complementary to the first PBS.

In some embodiments, the second CS comprises a sequence complementary to the MCS.

In some embodiments, the second CS comprises the second PBS.

In some embodiments, the second CS comprises the target sequence.

In some embodiments, the second CS comprises the UPS.

In some embodiments, the second CS comprises a sequence complementary to the first UPS.

In some embodiments, the second CS comprises the second UPS.

In some embodiments, the second CS is generated from a non-exponential amplification reaction.

In some embodiments, the second CS is generated from a single second primer.

In some embodiments, the second CS is generated from a primer extension reaction.

In some embodiments, the second CS is generated from a linear amplification reaction.

In some embodiments, the amplification reaction comprises a single round of amplification.

In some embodiments, the amplification reaction comprises two or more rounds of amplification.

In some embodiments, the amplification reaction comprises 10 or more rounds of amplification.

In some embodiments, the second CS is generated before an exponential amplification reaction is performed.

In some embodiments, the target polynucleotide comprises a plurality of target polynucleotides.

In some embodiments, each of the target polynucleotides of the plurality comprises different sequences.

In some embodiments, each of the target polynucleotides of the plurality comprises the same sequence.

In some embodiments, the first primer comprises a plurality of first primers each comprising a target specific region.

In some embodiments, the target specific region of each of the plurality of first primers is different.

In some embodiments, the target specific region of each of the plurality of first primers is the same.

In some embodiments, the second primer comprises a plurality of second primers, each comprising a sequence complementary to a target specific region.

In some embodiments, the target specific region of each of the plurality of first primers is different.

In some embodiments, the target specific region of each of the plurality of first primers is the same.

In some embodiments, the first primer hybridizes to the 3' end, the 5' end, or an internal region of the target polynucleotide.

In some embodiments, the second primer hybridizes to the 3' end, the 5' end, or an internal region of the first CS or MCS.

In some embodiments, the first CS comprises a plurality of first CSs

In some embodiments, each of the first CSs of the plurality comprises different sequences.

In some embodiments, each of the first CSs of the plurality comprises the same sequence.

In some embodiments, the adapter comprises a plurality of adapters.

In some embodiments, each of the adapters of the plurality comprises different sequences.

In some embodiments, each of the adapters of the plurality comprises the same sequence.

In some embodiments, the MCS comprises a plurality of MCSs.

In some embodiments, each of the MCSs of the plurality comprises different sequences.

In some embodiments, each of the MCSs of the plurality comprises the same sequence.

In some embodiments, the second CS comprises a plurality of second CSs.

In some embodiments, each of the second CSs of the plurality comprises different sequences.

In some embodiments, each of the second CSs of the plurality comprises the same sequence.

In some embodiments, each first primer comprises the same UPS, the same first PBS, or both.

In some embodiments, each first CS comprises the same UPS the same first PBS, or both.

In some embodiments, each adapter comprises the same UPS the same first PBS, the same SBC or a combination thereof.

In some embodiments, each MCS comprises the same UPS the same first PBS, the same SBC or a combination thereof.

In some embodiments, each second primer comprises the same UPS, the same second PBS, or both.

In some embodiments, each second CS comprises the same UPS, the same first UPS, the same second UPS, the same SBC, the same first PBS, the same second PBS, or a combination thereof.

In some embodiments, each adapter comprises a different UPS, a different first PBS, a different SBC, or a combination thereof.

In some embodiments, each MCS comprises a different UPS, a different first PBS, a different SBC, or a combination thereof.

In some embodiments, each first primer of a first plurality of first primers is extended simultaneously, is extended in the same reaction chamber, is hybridized to a target polynucleotide simultaneously, or is hybridized to a target polynucleotide in the same reaction chamber.

In some embodiments, each first CS or MCS of a first plurality of first CSs or MCSs is generated simultaneously, is generated in the same reaction chamber, is amplified simultaneously, or is amplified in the same reaction chamber.

In some embodiments, each second primer of a first plurality of second primer is extended simultaneously, is extended in the same reaction chamber, is hybridized to a first CS or MCS simultaneously, or is hybridized to a first CS or MCS in the same reaction chamber.

In some embodiments, each second CS of a first plurality of second CSs is generated simultaneously, is generated in the same reaction chamber, is amplified simultaneously, or is amplified in the same reaction chamber.

In some embodiments, the sample is a biological sample.

In some embodiments, the sample is a biological sample from a subject.

In some embodiments, the subject is a subject with a disease or condition.

In some embodiments, the subject is a subject without a disease or condition.

In some embodiments, the subject is an animal.

In some embodiments, the animal is a human.

In some embodiments, the sample is a blood sample.

In some embodiments, the target polynucleotide is isolated from the sample.

In some embodiments, the target polynucleotide is amplified directly from the sample.

In some embodiments, the sample comprises a plurality of samples comprising a first sample and a second sample.

In some embodiments, the plurality of samples comprises at least 3, 4 5, 10, 20, 30, 40, 50, 60, 70, 80, 90 or 100 or more samples.

In some embodiments, the plurality of samples comprises at least about 100, 200, 300, 400, 500, 600, 700, 800, 900 or 1000 or more samples.

In some embodiments, the plurality of samples comprises at least about 1000, 2000, 3000, 4000, 5000, 6000, 7000, 8000, 9000, 10,000, 100,000, or 1,000,000 or more samples.

In some embodiments, the plurality of samples comprises at least about 10,000 samples.

In some embodiments, the first sample is from a first subject and the second sample is from a second subject.

In some embodiments, the first subject is a subject with a disease or condition.

In some embodiments, the second subject is a subject without a disease or condition.

In some embodiments, each first primer of the first plurality of first primers is contacted to the first sample and each first primer of a second plurality of first primers is contacted to the second sample.

In some embodiments, first primer of the second plurality of first primers is extended simultaneously, is extended in the same reaction chamber, is hybridized to a target polynucleotide simultaneously, or is hybridized to a target polynucleotide in the same reaction chamber.

In some embodiments, the first plurality of first primers and the second plurality of first primers are extended simultaneously or are hybridized to a target polynucleotide simultaneously.

In some embodiments, each second primer of the first plurality of second primers is contacted to the first sample and each second primer of the second plurality of second primers is contacted to the second sample.

In some embodiments, each second primer of a second plurality of second primers is extended simultaneously, is extended in the same reaction chamber, is hybridized to a target polynucleotide simultaneously, or is hybridized to a target polynucleotide in the same reaction chamber.

In some embodiments, the first plurality of second primers and the second plurality second primers are extended simultaneously, are extended in the same reaction chamber, are hybridized to a first CS or MCS simultaneously, or are hybridized to a first CS or MCS in the same reaction chamber.

In some embodiments, each first CS or MCS of the first plurality of first CSs or MCSs generated from a target polynucleotide in the first sample and each first CS or MCS of a second plurality of first CSs or MCSs is generated from a target polynucleotide in the second sample.

In some embodiments, each first CS or MCS of the second plurality of first CSs or the second MCSs is generated simultaneously, is generated in the same reaction chamber, is amplified simultaneously, or is amplified in the same reaction chamber.

In some embodiments, the first plurality of first CSs and the second plurality of first CSs are generated simultaneously, are generated in the same reaction chamber, are amplified simultaneously, or are amplified in the same reaction chamber.

In some embodiments, each second CS of the first plurality of second CSs generated from a target polynucleotide in the first sample and each second CS of a second plurality of second CSs is generated from a target polynucleotide in the second sample.

In some embodiments, each second CS of the second plurality of second CSs is generated simultaneously, is generated in the same reaction chamber, is amplified simultaneously, or is amplified in the same reaction chamber.

In some embodiments, the first plurality of second CSs and the second plurality of second CSs are generated simultaneously, are generated in the same reaction chamber, are amplified simultaneously, or are amplified in the same reaction chamber.

In some embodiments, the method further comprises combining the first sample and the second sample.

In some embodiments, the combining is done after generating the first plurality of first CSs or MCSs.

In some embodiments, one or more of the target polynucleotides or plurality of target polynucleotides comprises a variant sequence.

In some embodiments, the variant sequence comprises a mutation, polymorphism, deletion, or insertion.

In some embodiments, the polymorphism is a single nucleotide polymorphism.

In some embodiments, one or more of the target polynucleotides is from a pathogen.

In some embodiments, the pathogen is a virus, bacteria, or fungus.

In some embodiments, the attaching comprises ligating.

In some embodiments, the attaching comprises amplification.

In some embodiments, the second CS(s) are amplified an exponential amplification reaction.

In some embodiments, the second CS(s) are amplified by PCR.

In some embodiments, the second CS(s) are amplified using a primer set comprising a primer to the first PBS and a primer to the second PBS.

In some embodiments, the second CS(s) are amplified using a UPS.

In some embodiments, the second CS(s) are amplified using a primer set comprising a primer to a first UPS and a primer to a second UPS.

In some embodiments, the method further comprises sequencing an amplified product from one or more second CSs or one or more pluralities of second CSs In some embodiments, the sequencing is performed simultaneously.

In some embodiments, the sequencing is high throughput sequencing.

In some embodiments, the method further comprises analyzing a sequence determined In some embodiments, the analyzing is done with a computer.

In some embodiments, the method further comprises determining an amplification error rate.

In some embodiments, the method further comprises determining a sequencing error rate.

In some embodiments, the method further comprises determining a frequency of the one or more target polynucleotides.

In some embodiments, the method further comprises determining the presence or absence of a variant in the one or more target polynucleotides.

In some embodiments, the method further comprises determining whether a subject is homozygous or heterozygous for an allele.

In some embodiments, the method further comprises diagnosing, prognosing, or treating a subject with a disease or condition.

In some embodiments, the method further comprises correcting amplification errors.

In some embodiments, the method further comprises correcting sequencing errors.

In some embodiments, the method further comprises binning sequences with at least about 90%, 95%, or 99% sequence homology.

In some embodiments, the method further comprises grouping sequences with at least about 90%, 95%, or 99% sequence homology.

In some embodiments, the method further comprises clustering sequences with at least about 90%, 95%, or 99% sequence homology.

In some embodiments, the method further comprises aligning sequences with at least about 90%, 95%, or 99% sequence homology.

In some embodiments, the clustering or aligning is performed with the aid of a computer or algorithm.

In some embodiments, the method further comprises determining the number of sequence reads with at least about 90%, 95%, or 99% sequence homology.

In some embodiments, the method further comprises determining the amount of one or more target polynucleotides in one or more of the samples.

In some embodiments, the method further comprises forming a consensus sequence from two or more sequences, sequence reads, amplicon sequences, binned sequences, aligned sequences, or clustered sequences.

In some embodiments, the method further comprises determining a target polynucleotide sequence with at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 99.99%, or 100% accuracy or confidence.

In some embodiments, sequencing and PCR errors are minimized, eliminated, or less than 0.01%, 0.001%, 0.0001%, 0.00001%, 0.000001%, or 0.0000001%.

In some embodiments, amplifying the first CSs or MCSs limits amplification bias.

In some embodiments, the error rate of sequencing of less than or equal to 0.00001%, 0.0001%, 0.001%, 0.01%, or 0%.

In some embodiments, the error rate of sequencing is not 0.

In some embodiments, at least 1,000, 5,000, 10,000, 20,000, 30,000, 40,000, 50,000, 1000,000, 500,000, or $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$ polynucleotides are sequenced.

In some embodiments, the method is performed in a positive amount of time less than or equal to 4 weeks, 3 weeks, 2 weeks, 1 week, 6 days, 5 days, 5 days, 4 days, 3 days, 2 days, 1 day, 18 hours, 12 hours, 9 hours, 6 hours, or 3 hours.

In some embodiments, the sample is a whole blood sample.

In some embodiments, the sample is an FFPE sample.

In some embodiments, the percentage of amplicons containing 10 or more UIDs is equal to the percentage of amplicons containing 10 or more UIDs generated from a purified polynucleotide sample.

In some embodiments, the percentage of amplicons containing 10 or more UIDs is only less than about 1%, 2%, 3%, 4%, 5%, 6%, 7%, 8%, 9%, or at most 10% less than the percentage of amplicons containing 10 or more UIDs generated from a purified polynucleotide sample.

In some embodiments, the on target specificity is equal to the on target specificity observed from a purified polynucleotide sample.

In some embodiments, the on target specificity is only less than about 1%, 2%, 3%, 4%, 5%, 6%, 7%, 8%, 9%, or at most 10% less than the on target specificity observed from a purified polynucleotide sample.

In some embodiments, the coverage uniformity is equal to the coverage uniformity observed from a purified polynucleotide sample.

In some embodiments, the coverage uniformity is only less than about 1%, 2%, 3%, 4%, 5%, 6%, 7%, 8%, 9%, or at most 10% less than the coverage uniformity observed from a purified polynucleotide sample.

In some embodiments, the method comprises slow ramping rates during linear amplification.

In some embodiments, the method comprises slow ramping rates during extension.

In some embodiments, the extension comprises maintaining a reaction at from about 90° C.-99° C. for a first time period, lowering the temperature at about 0.1° C./s to about 60° C., maintaining the reaction at from about 55° C.-60° C. for a second time period, adding a DNA polymerase, raising the temperature at about 0.1° C./s to about 65° C., maintaining the reaction at about 65° C. for a third time period, raising the temperature at about 0.1° C./s to about 80° C., and maintaining the reaction at about 80° C. for a fourth time period.

In some embodiments, the extension comprises maintaining a reaction at from about 90° C.-99° C. for a first time period, lowering the temperature at about 0.1° C./s to about 68° C., maintaining the reaction at from about 68° C. for a second time period, lowering the temperature at about 0.1° C./s to about 55° C., maintaining the reaction at from about 55° C. for a third time period, adding a DNA polymerase, raising the temperature at about 0.1° C./s to about 65° C., maintaining the reaction at about 65° C. for a fourth time period, raising the temperature at about 0.1° C./s to about 80° C., and maintaining the reaction at about 80° C. for a fifth time period.

In some embodiments, the linear amplification comprises maintaining a reaction at from about 90° C.-99° C. for a first time period, lowering the temperature at about 0.1° C./s to about 60° C., maintaining the reaction at from about 60° C. for a second time period, raising the temperature at about 0.1° C./s to about 72° C., and maintaining the reaction at about 72° C. for a third time period.

In some embodiments, the extension comprises lowering and/or raising a temperature at a rate of about 0.1° C./s.

In some embodiments, the linear amplification comprises lowering and/or raising a temperature at a rate of about 0.1° C./s.

In some embodiments, the first primers, the second primers, or both are at a fixed concentration.

In some embodiments, the extending, amplifying, or both are performed in the presence of magnesium chloride, ammonium sulfate, D-(+)-trehalose, betaine, or a combination thereof.

In some embodiments, each of the first primers, the second primers, or both comprise a melting temperature of between 60° C.-68° C.

In some embodiments, each of the first primers, the second primers, or both comprise a length of between 21 and 32 nucleotides.

In some embodiments, each of the first primers, the second primers, or both do not contain 4 or more pyrimidines in the last 5 nucleotides at their 3' end.

In some embodiments, each of the first primers, the second primers, or both are designed to produce amplicons containing between 30% and 70% GC content.

In some embodiments, each of the first primers, the second primers, or both are designed to produce amplicons with a length of between 225 and 300 base pairs.

In some embodiments, each of the first primers, the second primers, or both exclude primers from an initial primer panel with the highest number of misreads during the extension, amplification, or both.

In some embodiments, each of the first primers, the second primers, or both exclude primers from an initial primer panel that prevalently from dimers.

In some embodiments, each of the first primers, the second primers, or both exclude primers from an initial primer panel that are responsible for generating one or more of the highest number of total reads for one or more of the target polynucleotides.

In one aspect, a method of selecting primers for a primer panel comprising a plurality of first primers and a plurality of second primers is provided, comprising: a first pass, wherein primers selected comprise: a melting temperature from 60° C.-68° C., a length from 21-32 nucleotides, 3 or less pyrimidines in the last 5 nucleotides at their 3' end, primers that generate sequence reads with from 30%-70% GC, and primers that generate sequence reads with a length from 225-300 nucleotides; a second pass, wherein primers selected do not comprise: one or more primers that generate the highest number of misreads during the extension or the amplification, primers that generate a plurality of sequence reads comprising greater than 1% primer dimer sequences, and primers that generate a plurality of sequence reads comprising 1% or more misreads during the extension or the amplification and greater than 0.3% primer dimer sequences; and a third pass, wherein the primers selected do not comprise one or more of primers that generate the highest number of total sequence reads.

In one aspect, a method of excluding a primer from a primer panel comprising a plurality of first primers and a plurality of second primers is provided, comprising: a first pass, wherein primers excluded comprise: a melting temperature below 60° C. or above 68° C., a length below 21 nucleotides or above 32 nucleotides, and 4 or more pyrimidines in the last 5 nucleotides at their 3' end, primers that generate sequence reads with less than 30% GC content or greater than 70% GC content, and primers that generate sequence reads with a length below 225 nucleotides or above 300 nucleotides; a second pass, wherein primers excluded comprise: one or more primers that generate the highest number of misreads during the extension or the amplification, primers that generate a plurality of sequence reads comprising greater than 1% primer dimer sequences, and primers that generate a plurality of sequence reads comprising 1% or more misreads during the extension or the amplification and greater than 0.3% primer dimer sequences; and a third pass, wherein primers excluded comprise one or more of primers that generate the highest number of total sequence reads.

In one aspect, provided herein is primer panel comprising a plurality of primers, wherein each of the primers in the plurality of primers comprises: a melting temperature from 60° C.-68° C., a length from 21-32 nucleotides, 3 or less pyrimidines in the last 5 nucleotides at their 3' end, and generate sequence reads with from 30%-70% GC and with a length from 225-300 nucleotides In some embodiments, the primer panel does not comprise: one or more primers that generate the highest number of misreads during an extension reaction or an amplification reaction, primers that generate a plurality of sequence reads comprising greater than 1% primer dimer sequences, and primers that generate a plurality of sequence reads comprising 1% or more misreads during the extension reaction or the amplification reaction and greater than 0.3% primer dimer sequences; and one or more of primers that generate the highest number of total sequence reads.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 4 depicts a chart showing on target specificity percent using the indicated primer panels from non-improved and improved targeted sequencing methods described herein and compared to other primer panels known in the art (Other #1 and other #2). The Tex-1 panel is a carrier panel to 23 genes (all exon). CS-23 is an rsSNP focused primer panel to 18 genes.

FIG. 8 depicts the concentrations of primers and results where the per primer concentration was fixed (Group 1) and where the total primer concentration was fixed (Group 2) using the full, half, quarter, or small fraction of primers from a panel of about 350 primers under the less stringent conditions depicted in FIG. 8.

FIG. 13 depicts a chart showing the genes and associated diseases, number of exons, and number of probe sets of the exemplary primer panel CS-350. The list of primerless exons on the right indicates exons for which primer sequences were not yielded using other primer design methods than those described herein.

FIG. 15B depicts a chart showing the on target specificity, uniformity of coverage, and mean read depth per amplicon at a 100× cap of the indicated primer panel of about 350 primers and subpanels generated therefrom using the exclusion criteria shown in FIG. 14.

FIG. 25 depicts a chart summarizing settings for improved primer design for use in methods for targeted sequencing.

FIG. 26 depicts schematics of improved off-target hit calling criteria for use in methods for targeted sequencing.

Figure 27:
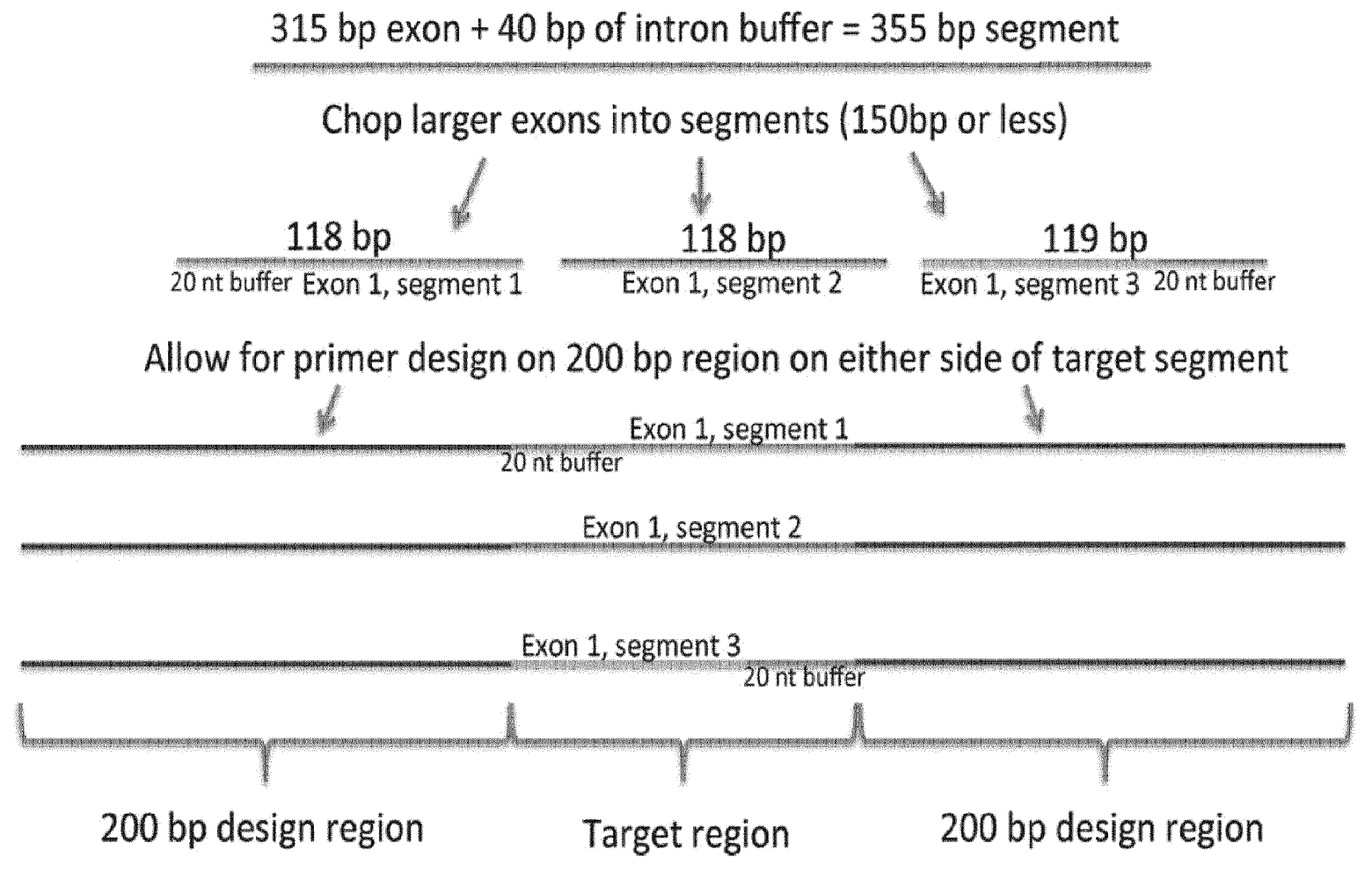

FIG. 27 depicts a schematic of improved primer design for use in methods for targeted sequencing. One improved primer design is adding an about 20 nt intron buffer sequence. One improved primer design is evenly divided exons for better coverage and enhanced flexibility

FIG. 32 depicts charts showing SNP calling differences between a whole blood sample and a sample of DNA extracted from whole blood. The top chart shows SNP calls missed using the whole blood sample. The top chart shows SNP calls missed using the sample of DNA extracted from whole blood. Figure discloses SEQ ID NOS 94-95, 94-96, and 96-97, respectively, in order of appearance.

FIG. 39 depicts a chart of the expected and actual number of sequences for each barcoded sample and percentage of the total sequence reads per barcoded sample.

FIG. 46 depicts a chart summarizing quality metrics of the methods described herein.

FIG. 50A shows graphs of sequencing read counts of DNA targeted panels using a first primer pair (BC3) without a UID (left) and with a UID (right). FIG. 50B shows graphs of sequencing read counts of DNA targeted panels using a second primer pair (BC1) without a UID (left) and with a UID (right) using a method of targeted sequencing. FIG. 50C shows a graph of sequencing read counts of DNA targeted panels using a method of targeted sequencing with post UID filtering.

FIG. 51A depicts a graph of sequencing read counts of RNA targeted panels (left) and a graph of the sequencing read frequencies (right). FIG. 51B is a log scale version of the graph shown in FIG. 51A (left) of the sequencing read frequencies. Data shown here represents read/expression count post filtering.

FIG. 57 depicts a sequence analysis of the GBA gene using a method of targeted sequencing with UID filtering.

Both alleles of the GBA gene from a patient sample were aligned using Clustal W. The patient shows heterozygocity post UID filtering. Both alleles were compared to the Ensembl human genome reference. Lack of a "*" denote a mis-pairing alignment between one of the 3 sequences. The GBA gene of the patient presented here has one allele identical to the human reference genome, and a second allele with 6 observed sequence polymorphisms/mutations. Figure discloses SEQ ID NOS 98-100, respectively, in order of appearance.

Figure 1:
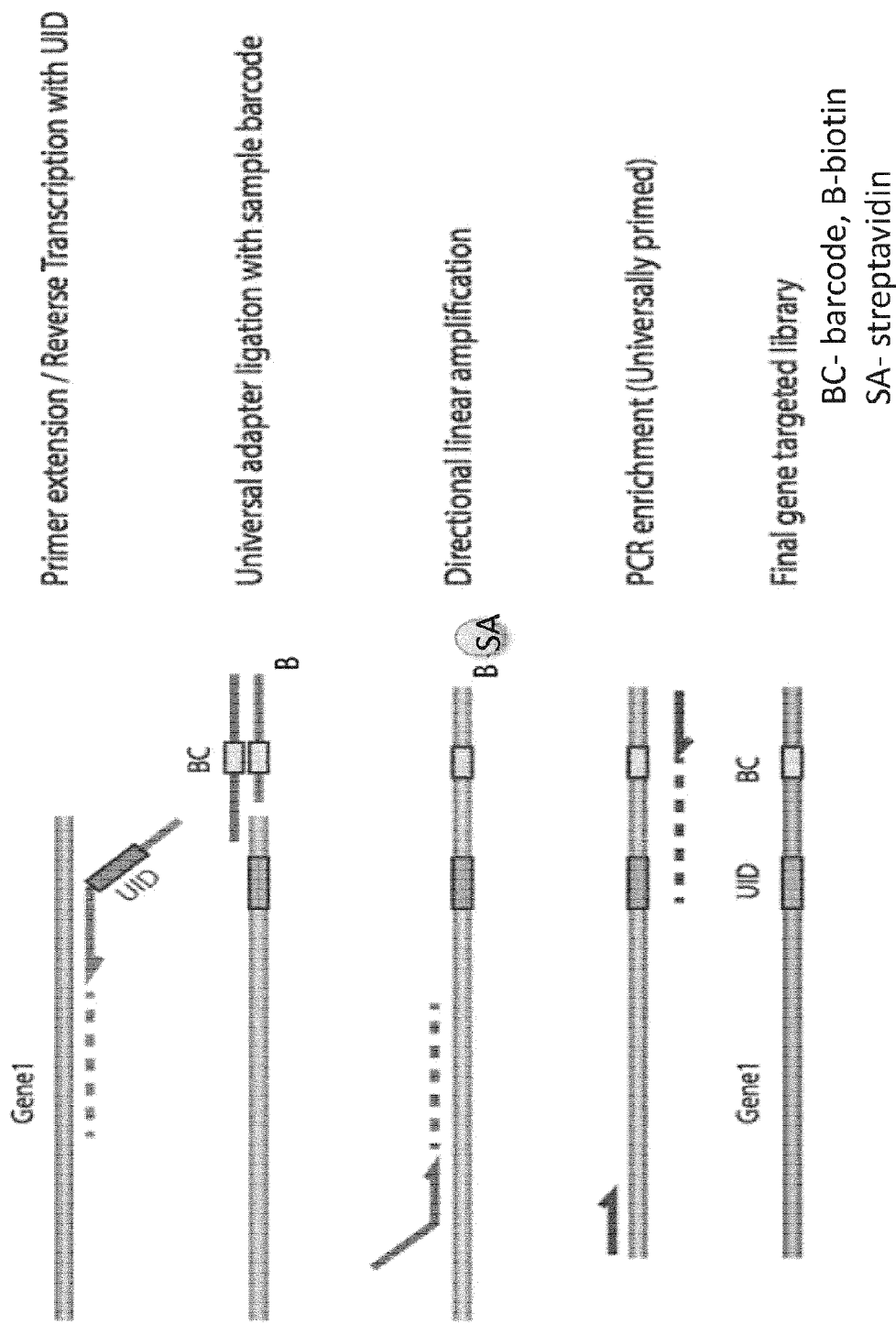
FIG. 1 depicts a schematic of an exemplary method for targeted sequencing described herein.
Figure 2:
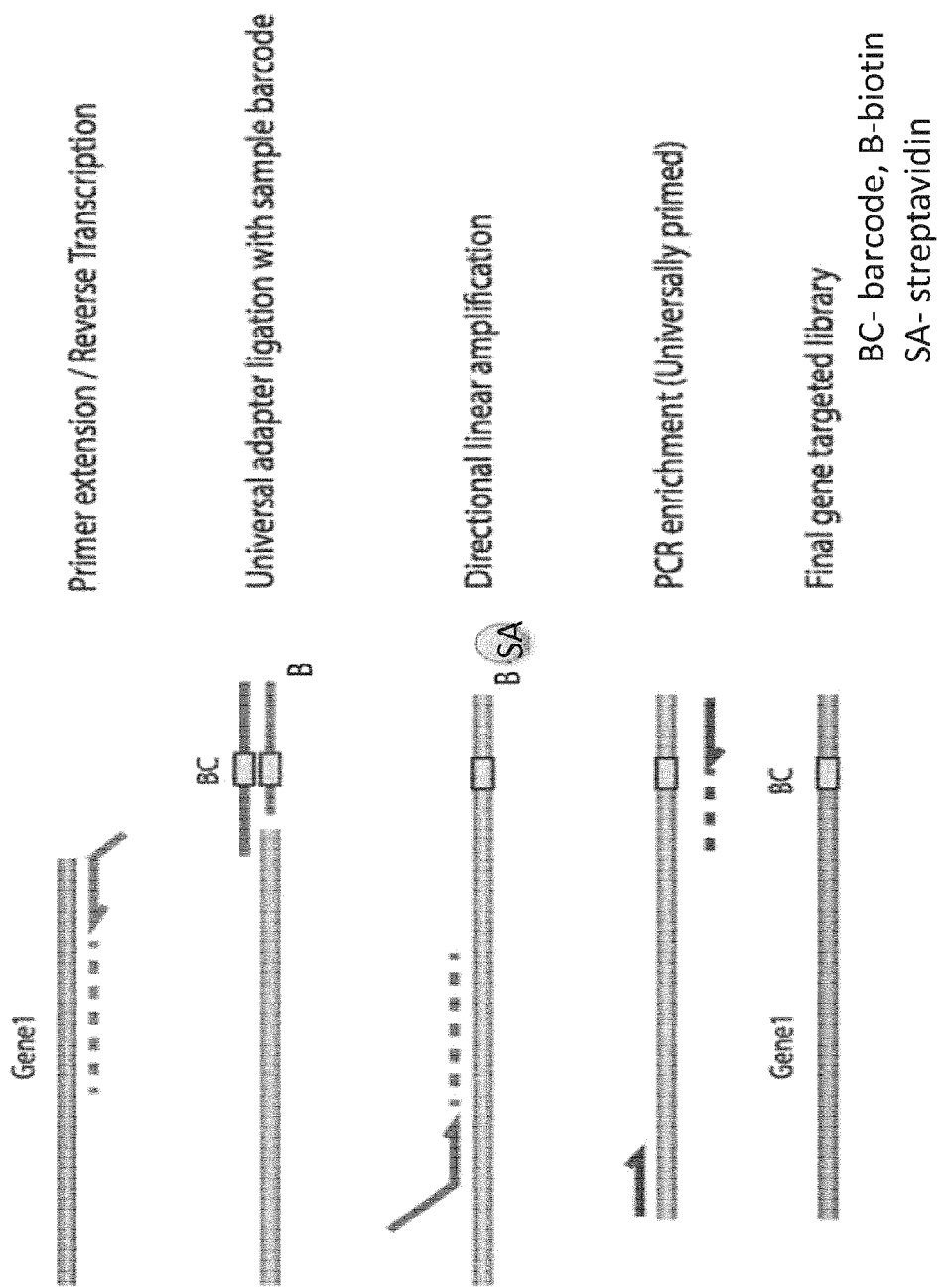
FIG. 2 depicts a schematic of an exemplary method for targeted sequencing described herein.
Figure 3:
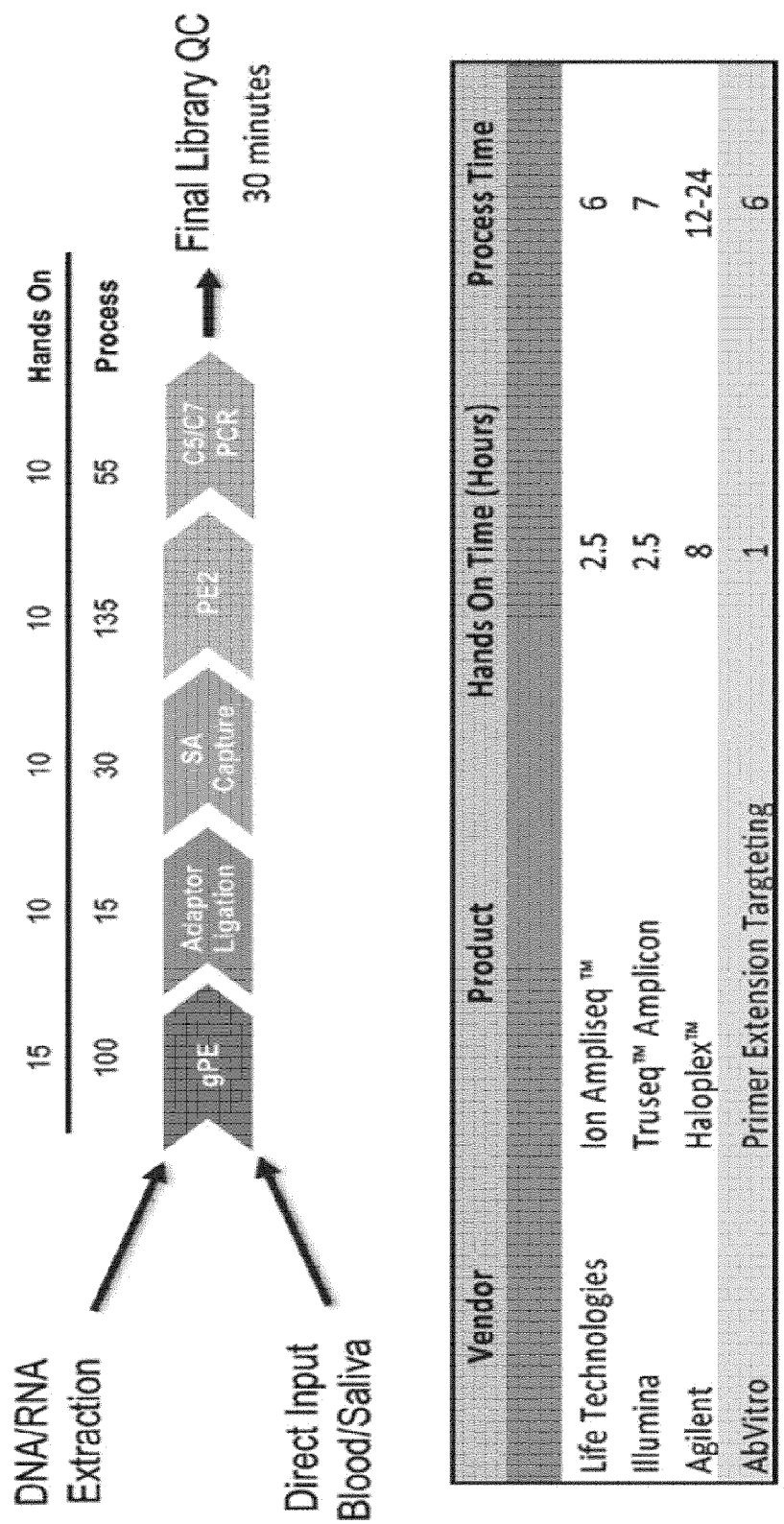
FIG. 3 depicts a schematic of an exemplary process for generating improved targeted sequencing methods. Processing times are depicted.
Figure 5:
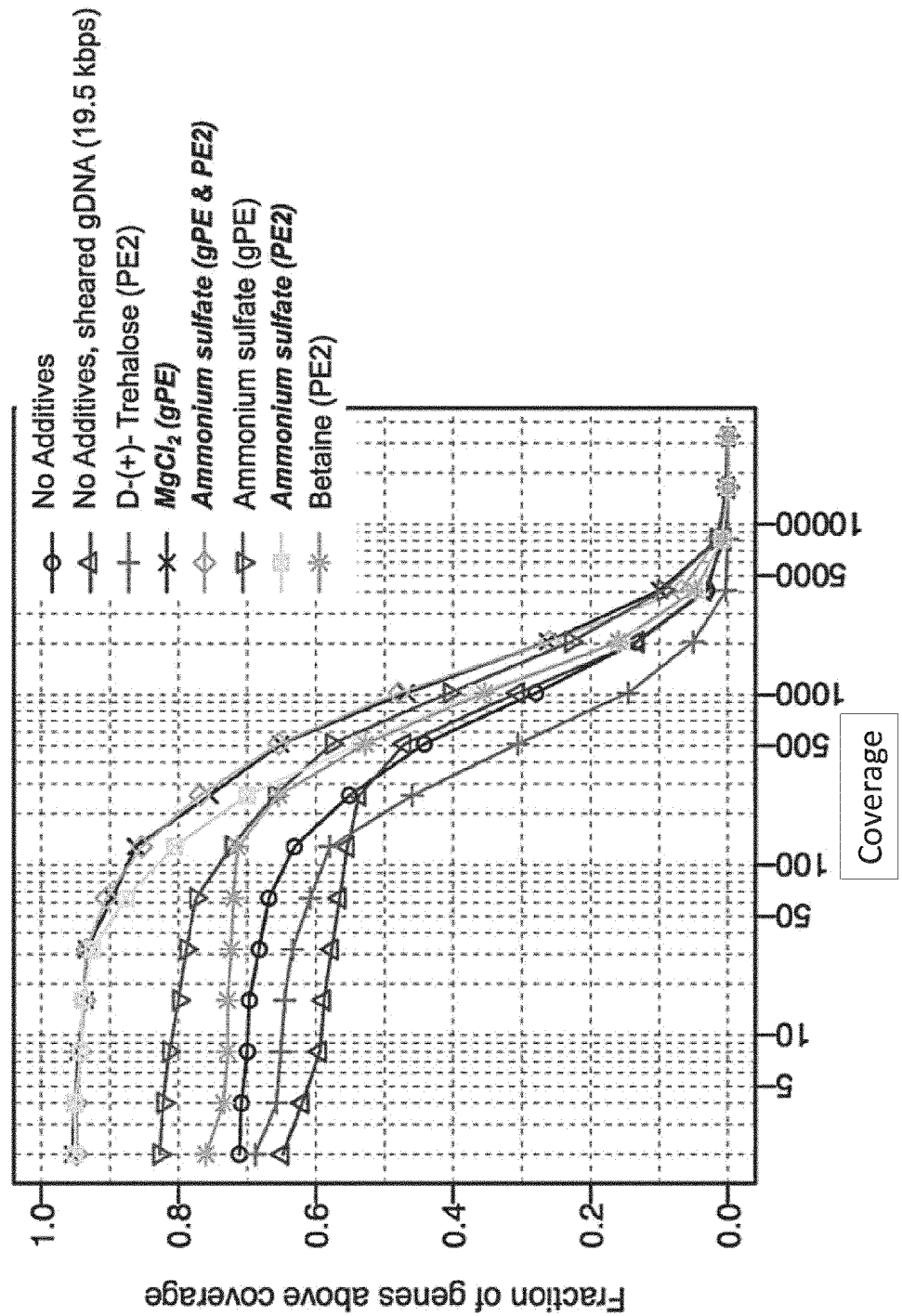
FIG. 5 depicts a graph of target read coverage with the indicated reaction conditions. The fraction of genes above coverage vs. the read depth is shown with the indicated reaction conditions. Conditions having a positive effect on sequence coverage are depicted in bold.
Figure 6:
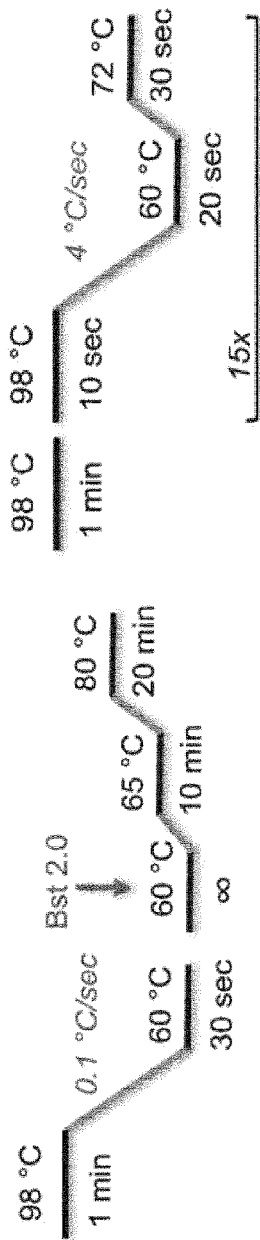
FIG. 6A depicts schematics of ramping and annealing conditions for the indicated steps of an exemplary method for targeted sequencing under less stringent conditions used for a panel of 30 primers.
FIG. 6B depicts the concentrations of primers in a panel of about 350 primers used under the ramping and annealing conditions in 6A that was insufficient to generate sufficient target production.
Figure 7:
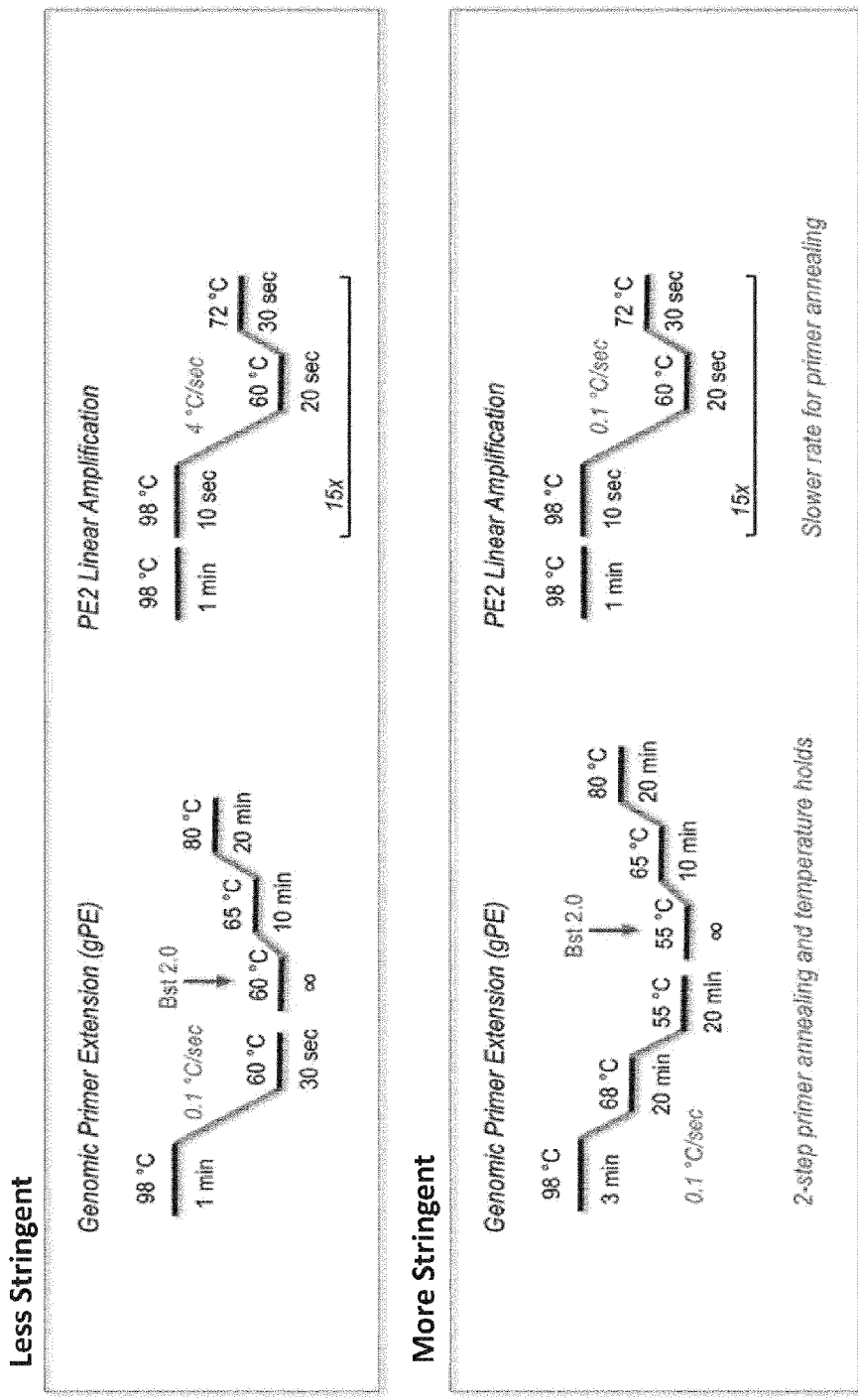
FIG. 7 depicts schematics of exemplary methods for targeted sequencing under less stringent (top) and more stringent (bottom) ramping and annealing conditions. Stringency was increased by slowing ramping rates for the second primer extension step. Stringency was increased by adding a 68° C. hold step fro the first primer extension step. Stringency was increased by lowering the minimum annealing temperature to 55° C.
Figure 9:
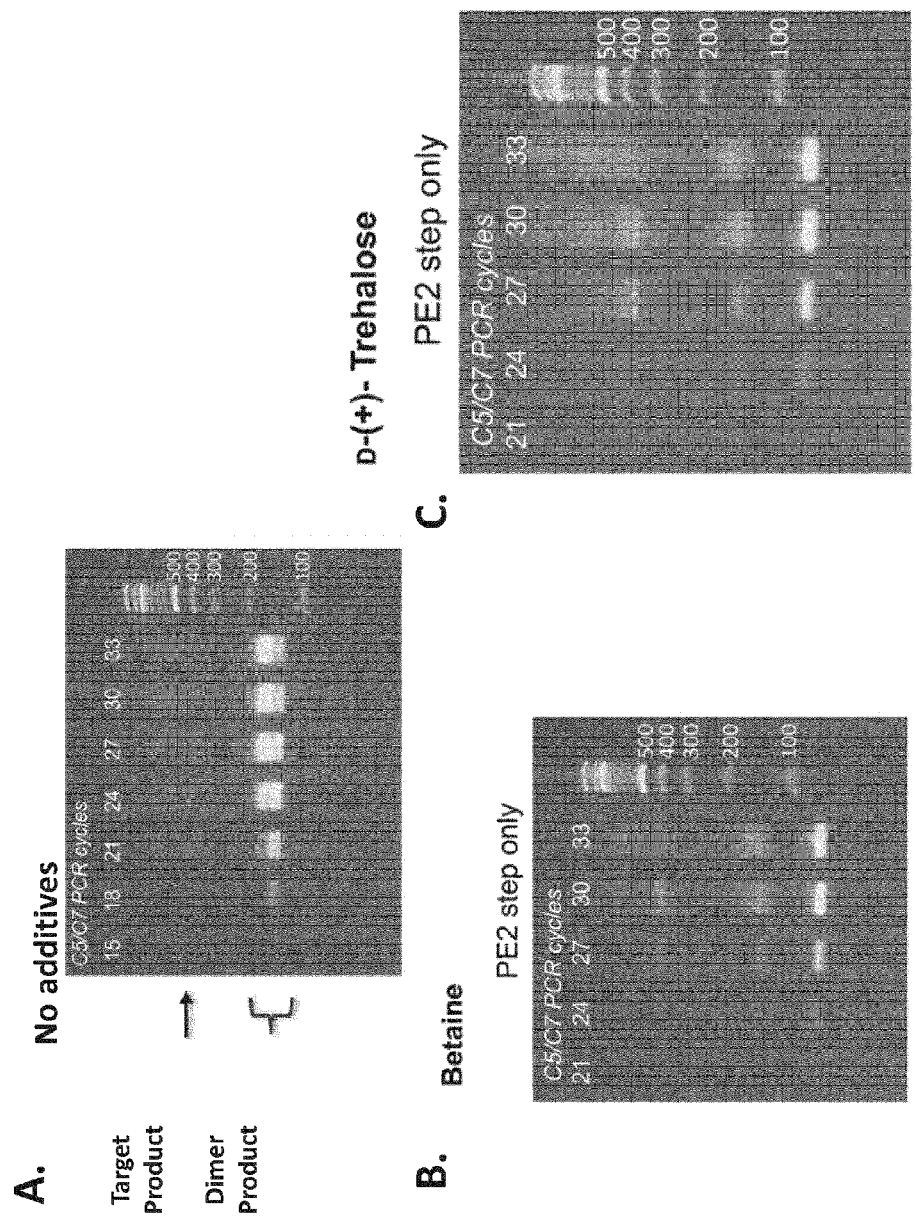
FIG. 9A depicts the products after the indicated PCR cycles of an exemplary targeted sequencing method on an agarose gel alongside a 100 base pair (bp) ladder the no additives added. Target product and dimer product are shown.
FIG. 9B depicts the products after the indicated PCR cycles of an exemplary targeted sequencing method on an agarose gel alongside a 100 base pair (bp) ladder with the additive betaine. Target product and dimer product are shown.
FIG. 9C depicts the products after the indicated PCR cycles of an exemplary targeted sequencing method on an agarose gel alongside a 100 base pair (bp) ladder with the additive trehalose. Target product and dimer product are shown.
FIG. 9D depicts the products after the indicated PCR cycles of an exemplary targeted sequencing method on an agarose gel alongside a 100 base pair (bp) ladder with the additive magnesium chloride. Target product and dimer product are shown.
FIG. 9E depicts the products after the indicated PCR cycles of an exemplary targeted sequencing method on an agarose gel alongside a 100 base pair (bp) ladder with the additive ammonium sulfate. Target product and dimer product are shown.
Figure 10:
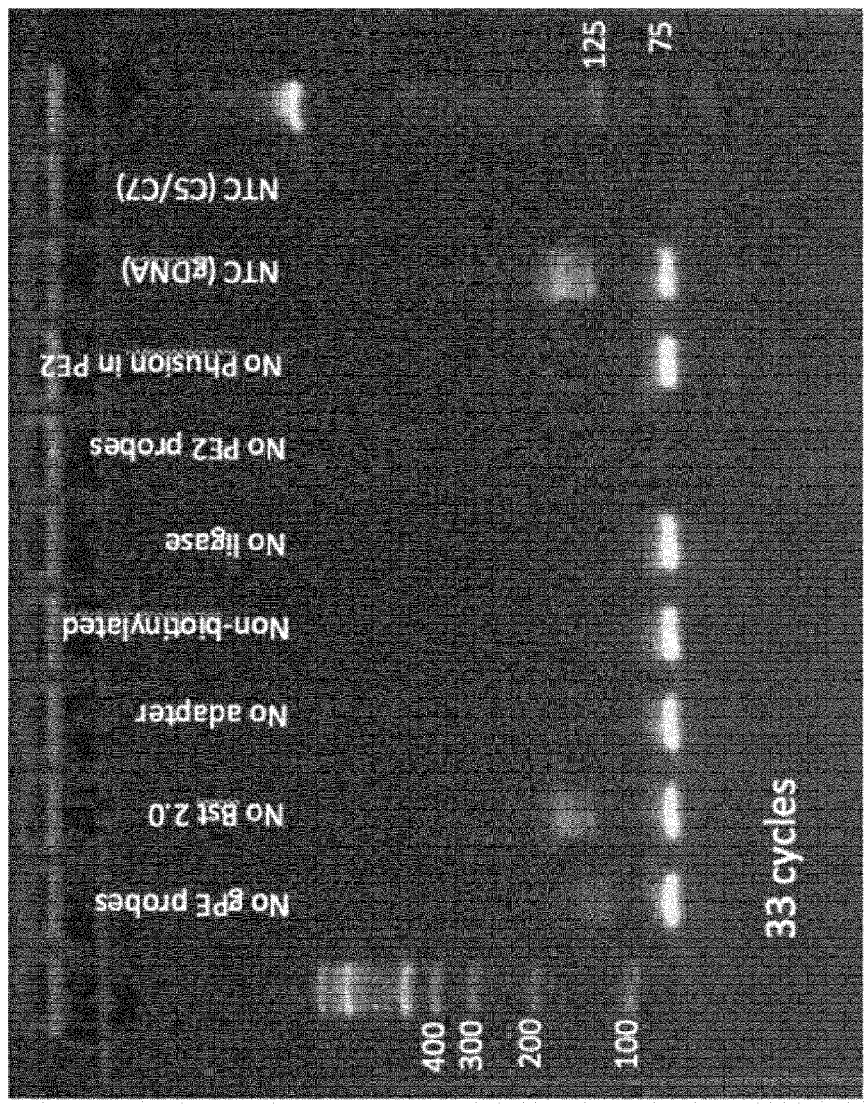
FIG. 10 depicts the products after 33 PCR cycles of an exemplary targeted sequencing method on an agarose gel alongside a 100 base pair (bp) ladder under the indicated conditions.
Figure 11:
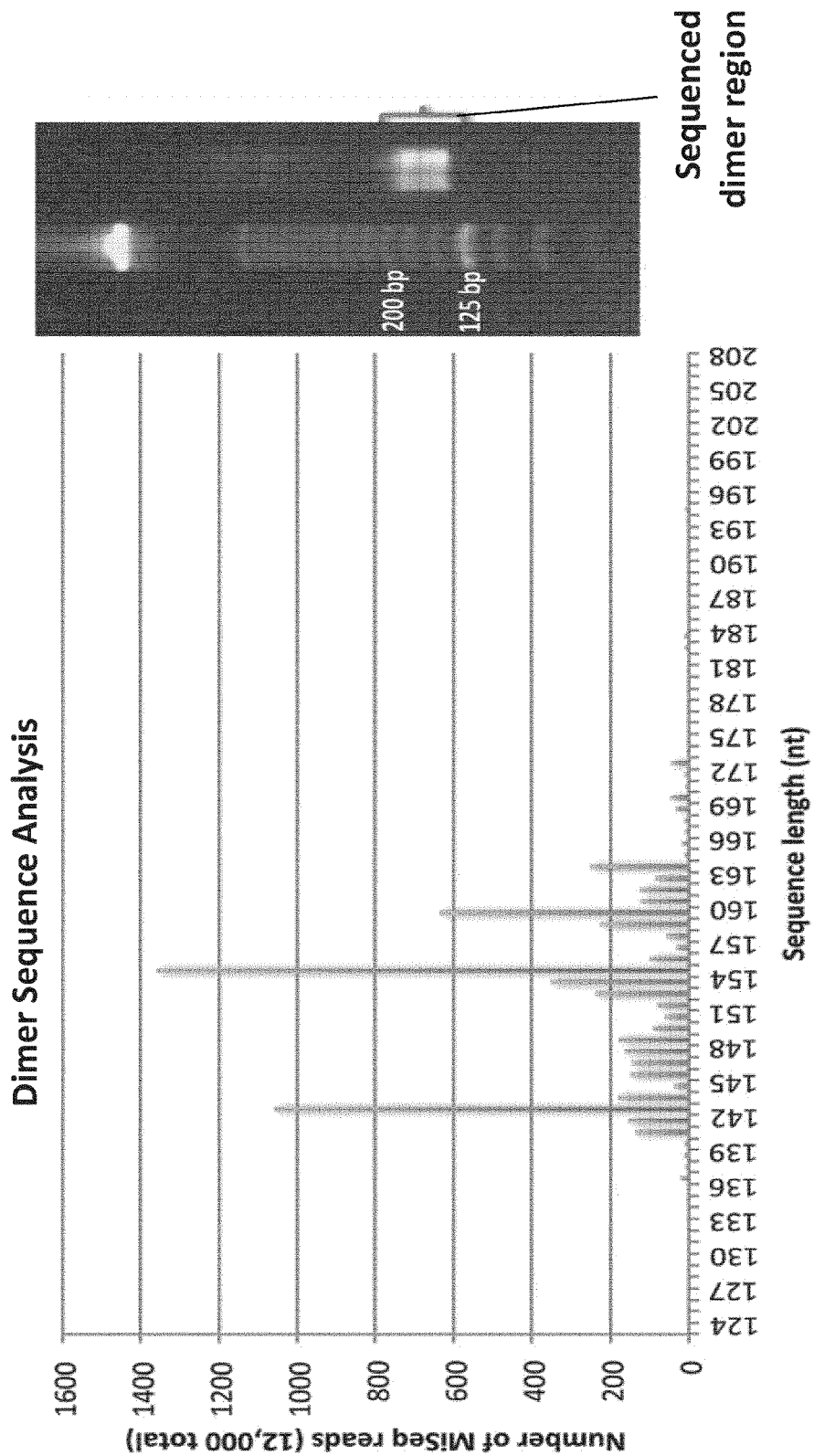
FIG. 11 depicts a graph of dimer sequence analysis of the length of the sequence vs. the sequence length. The corresponding dimer products sequenced are shown on the agarose gel to the right.
Figure 12:
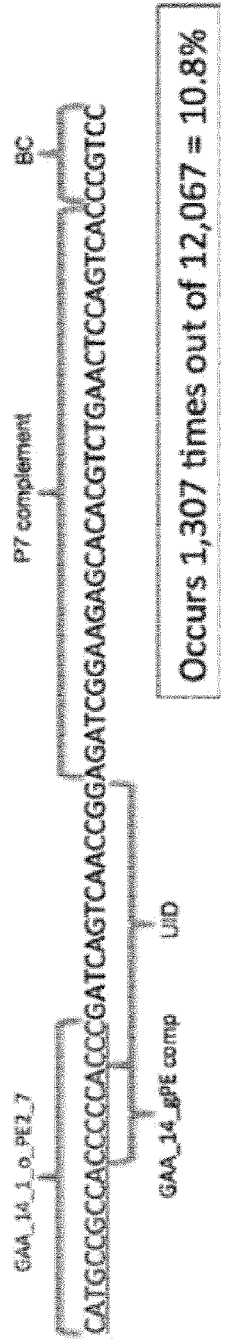
FIG. 12 depicts a diagram representing the proposed mechanism of undesired product formation during the second primer extension step as determined by dimer sequencing analysis. Dimer formation is facilitated by primers with high melting temperatures at a low annealing temperature. Dimer formation is facilitated by primers with high GC content interacting with the UID. Figure discloses SEQ ID NOS 90-91, 92, 91, and 93, respectively, in order of appearance.
Figure 14:
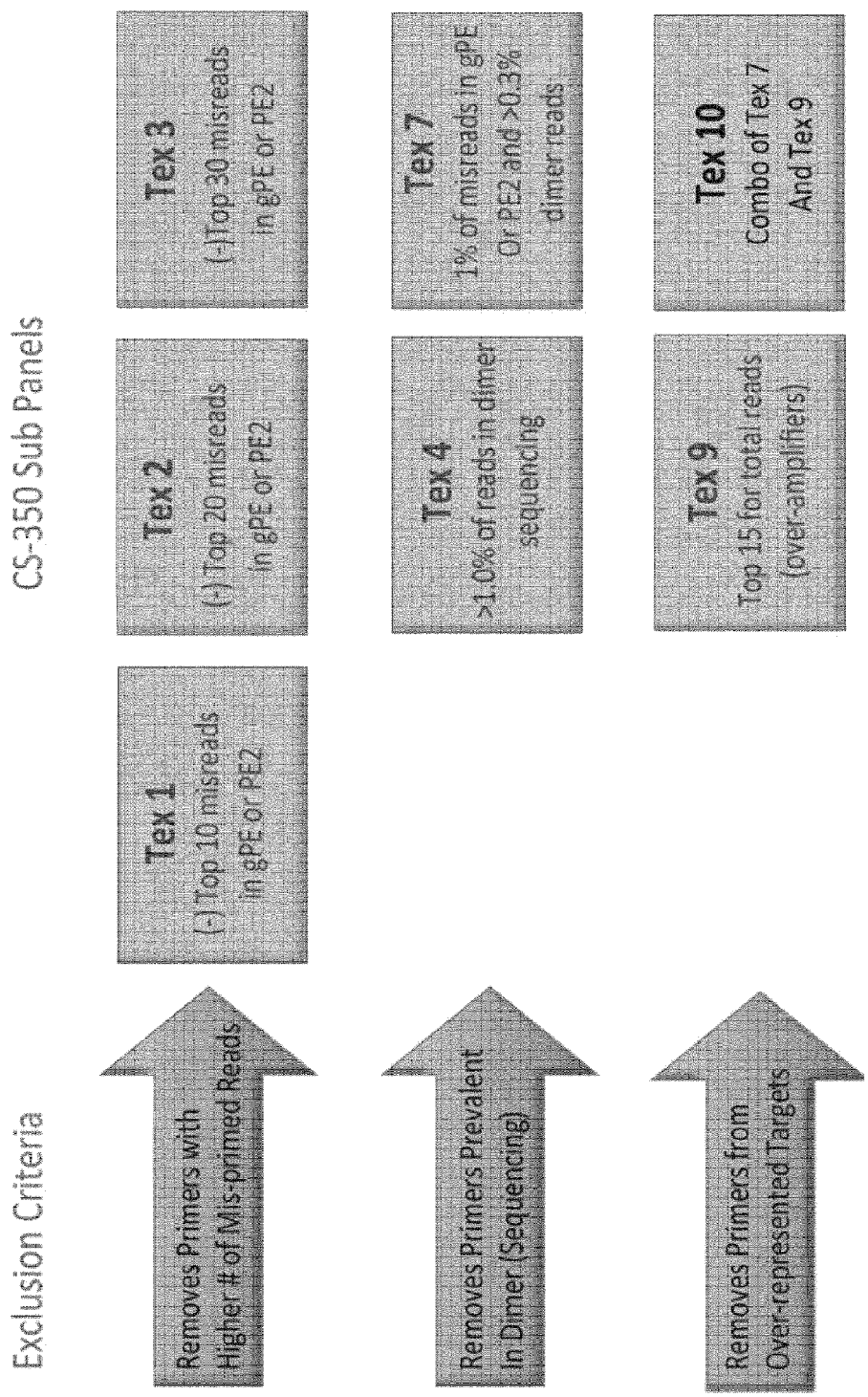
FIG. 14 depicts a diagram of exclusion criteria used to generate primer sub panels from a primer panel containing about 350 primers.
Figure 15A:
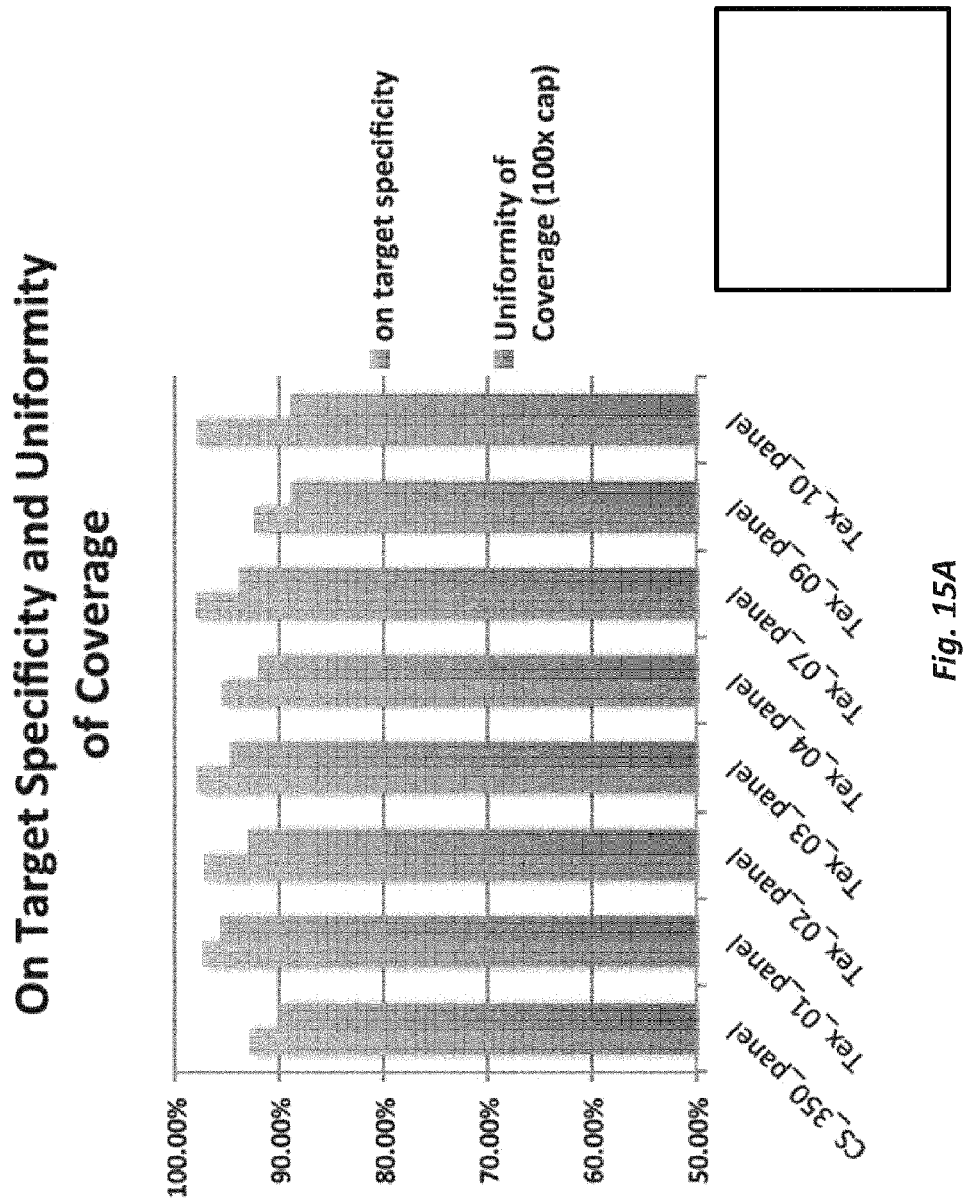
FIG. 15A depicts a plot showing the on target specificity and uniformity of coverage at a 100× cap of the indicated primer panel of about 350 primers and subpanels generated therefrom using the exclusion criteria shown in FIG. 14.
Figure 16:
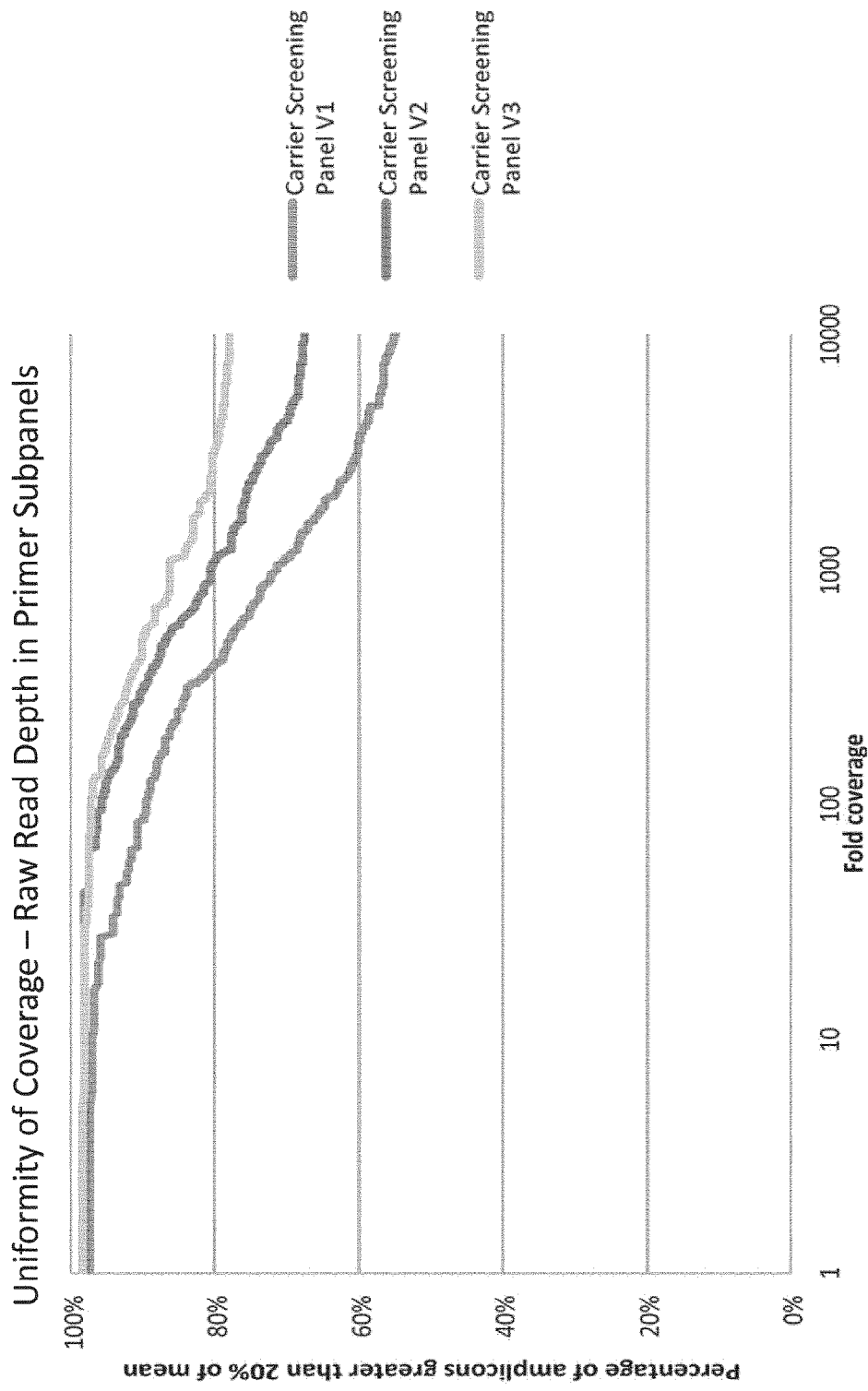
FIG. 16 depicts a plot showing the uniformity of coverage over the indicated in silico cap range of the indicated panel of about 350 primers and subpanels generated therefrom using the exclusion criteria shown in FIG. 14.
Figure 17:
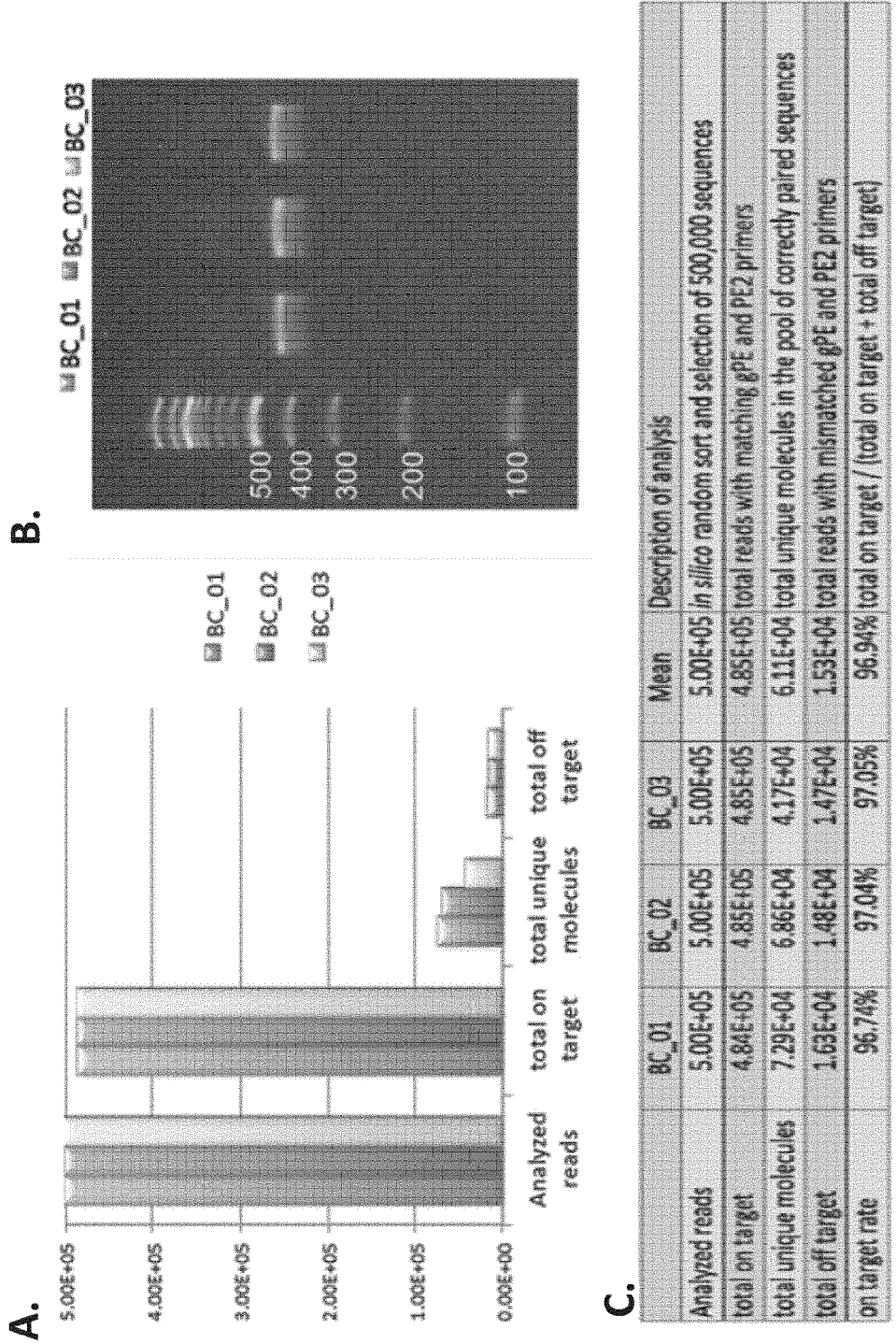
FIG. 17A depicts a graph showing the on target specificity of an exemplary method for targeted sequencing described herein using three different UIDs (BC_01, BC_02, BC_03).
FIG. 17B depicts the products after PCR of an exemplary targeted sequencing method described herein using three different UIDs.
FIG. 17C depicts a chart with the corresponding values from FIG. 17A.
Figure 18:
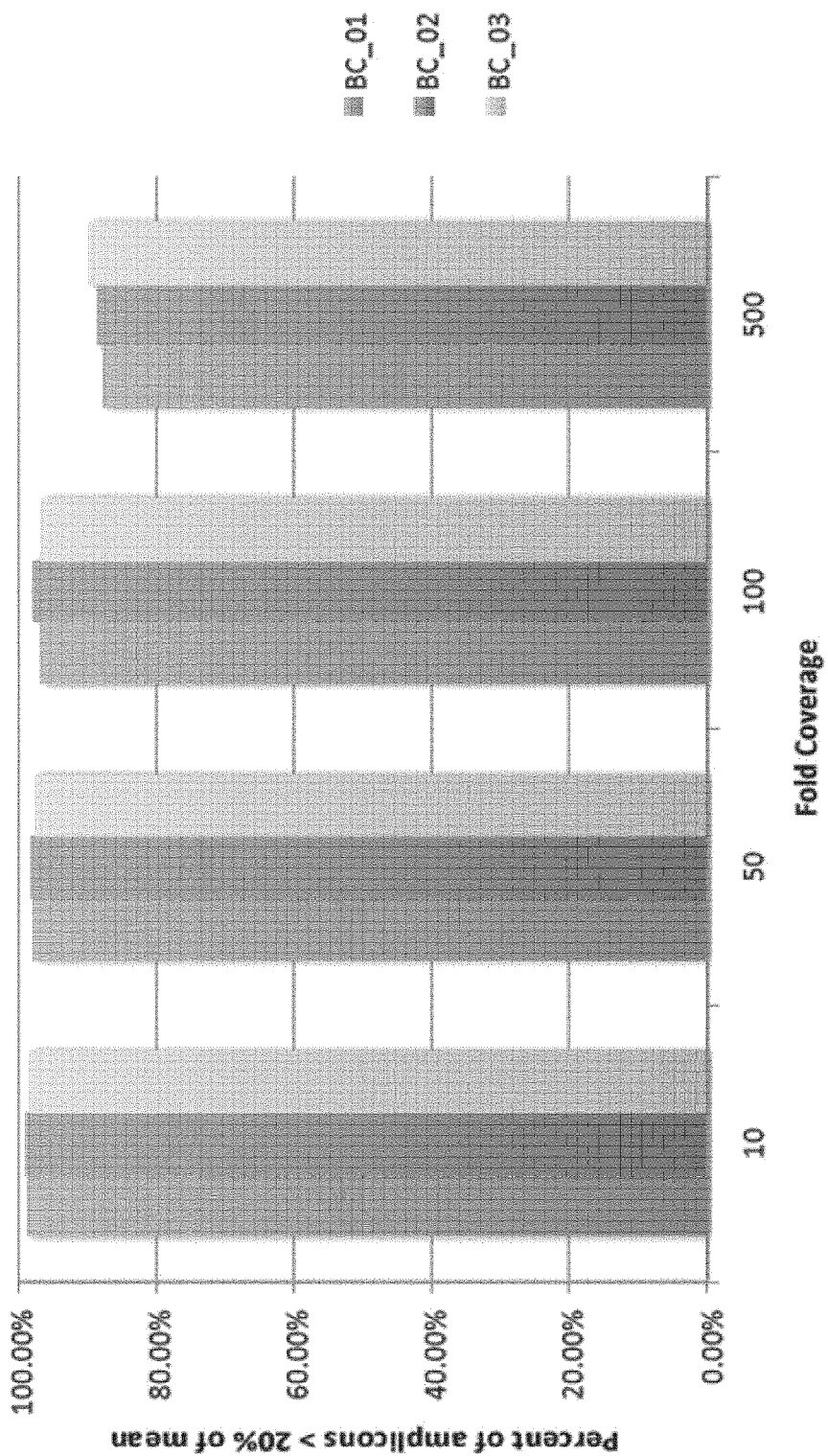
FIG. 18 depicts a plot of the percentage of amplicons greater than 20% of the mean over the indicated in silico cap range showing the uniformity of coverage of an exemplary method for targeted sequencing described herein using three different UIDs.
Figure 19:
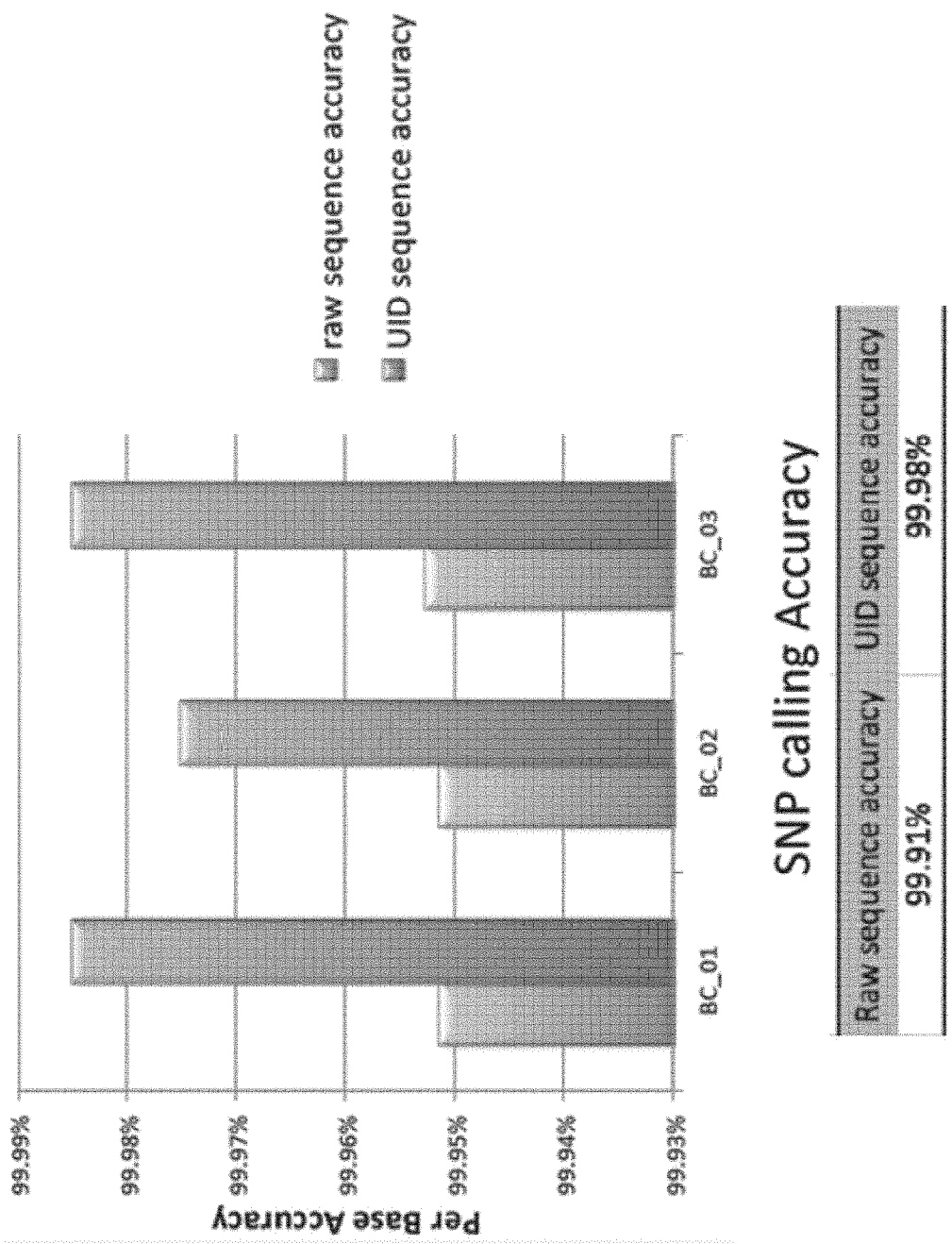
FIG. 19 depicts a plot comparing raw reads (without UID) to UID enhanced accuracy
Figure 20:
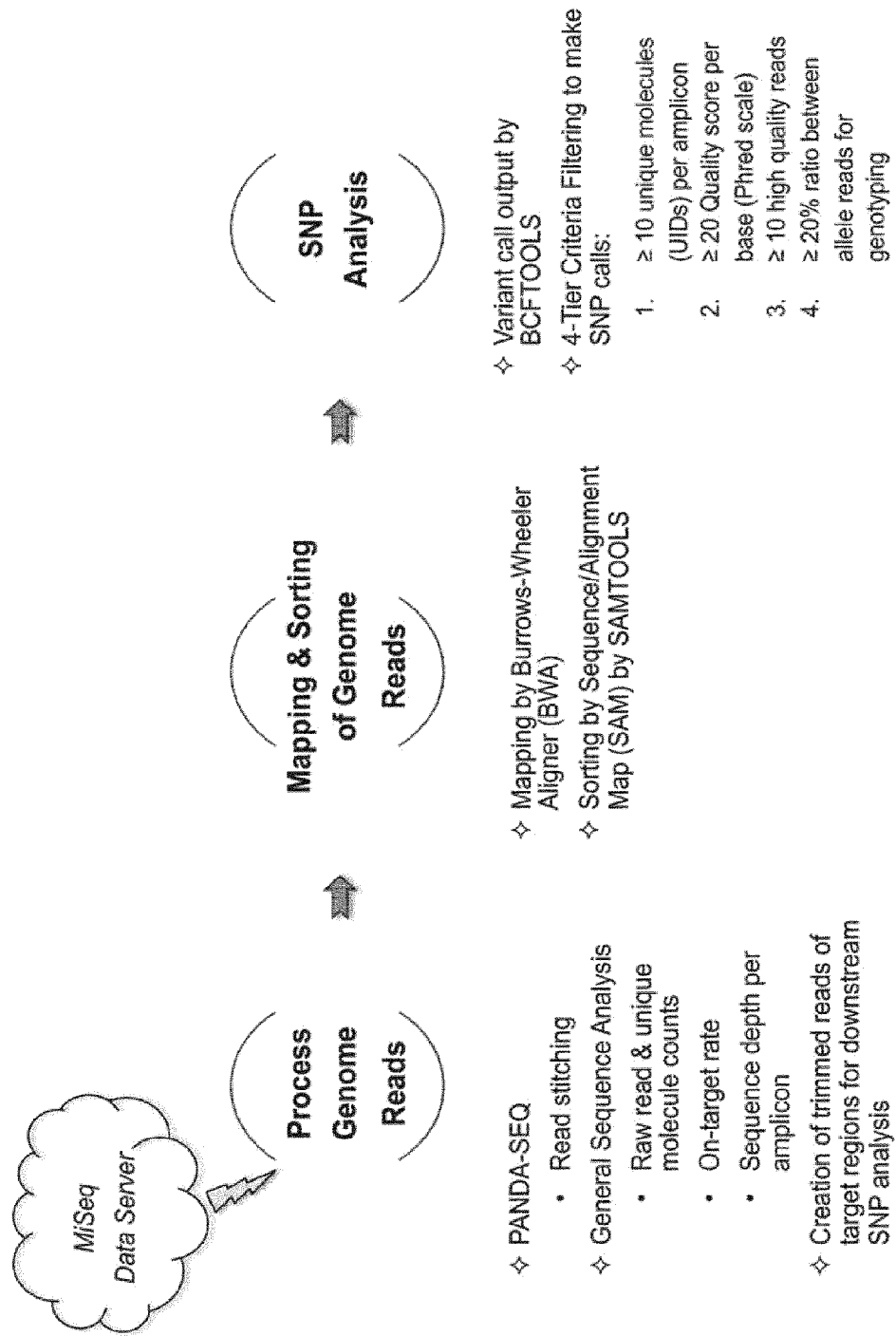
FIG. 20 depicts a schematic of SNP detection and sequence analysis workflow using an exemplary method for targeted sequencing.
Figure 21:
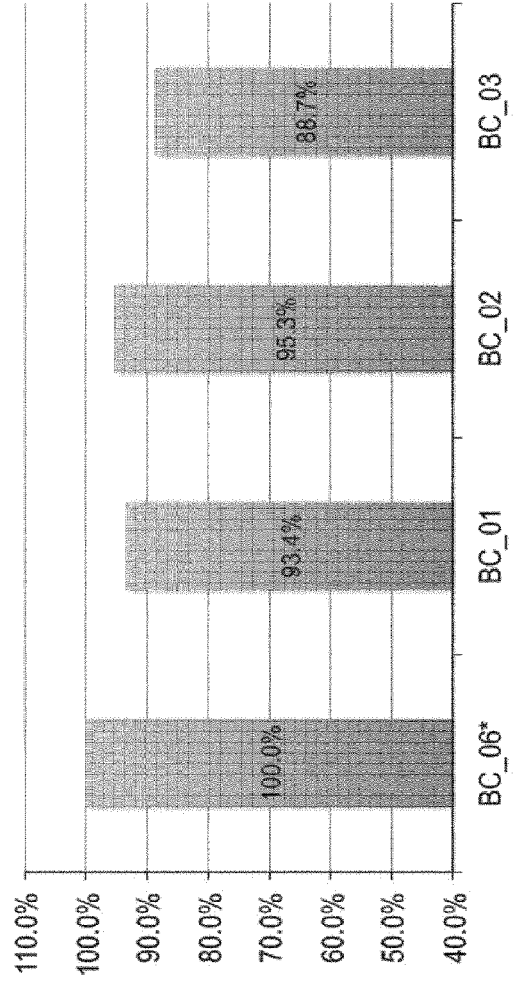
FIG. 21 depicts a plot and corresponding chart showing the relative percentage of SNP calls that match between samples using an exemplary method for targeted sequencing described herein using the indicated UIDs. Reduced cycling with BC_6 resulted in higher numbers of unique molecules.
Figure 22A:
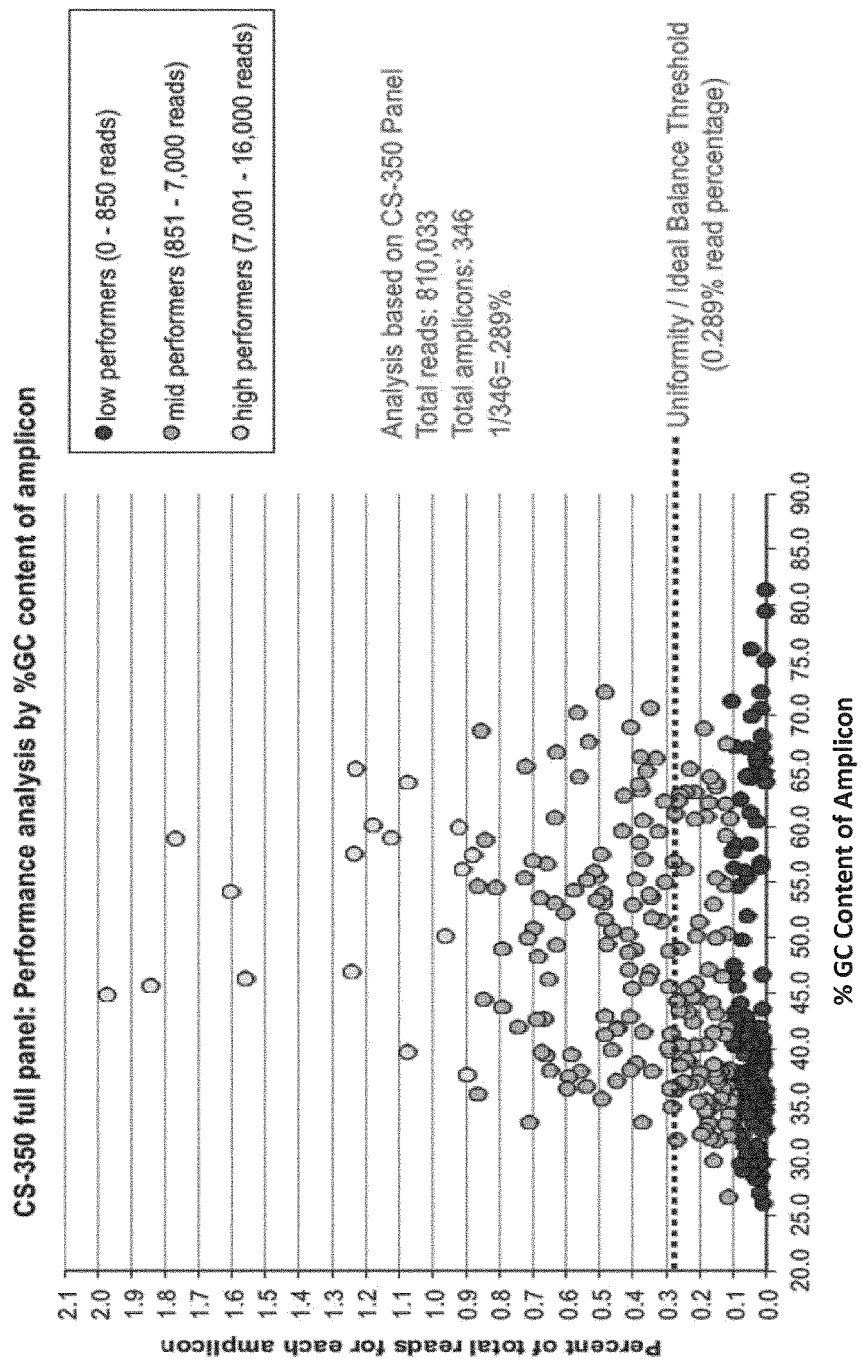
FIG. 22A depicts a plot of the read percentage of each amplicon vs. the amplicon % GC content using an exemplary method for targeted sequencing described herein. A large number of low performers are present in Group A.
Figure 22B:
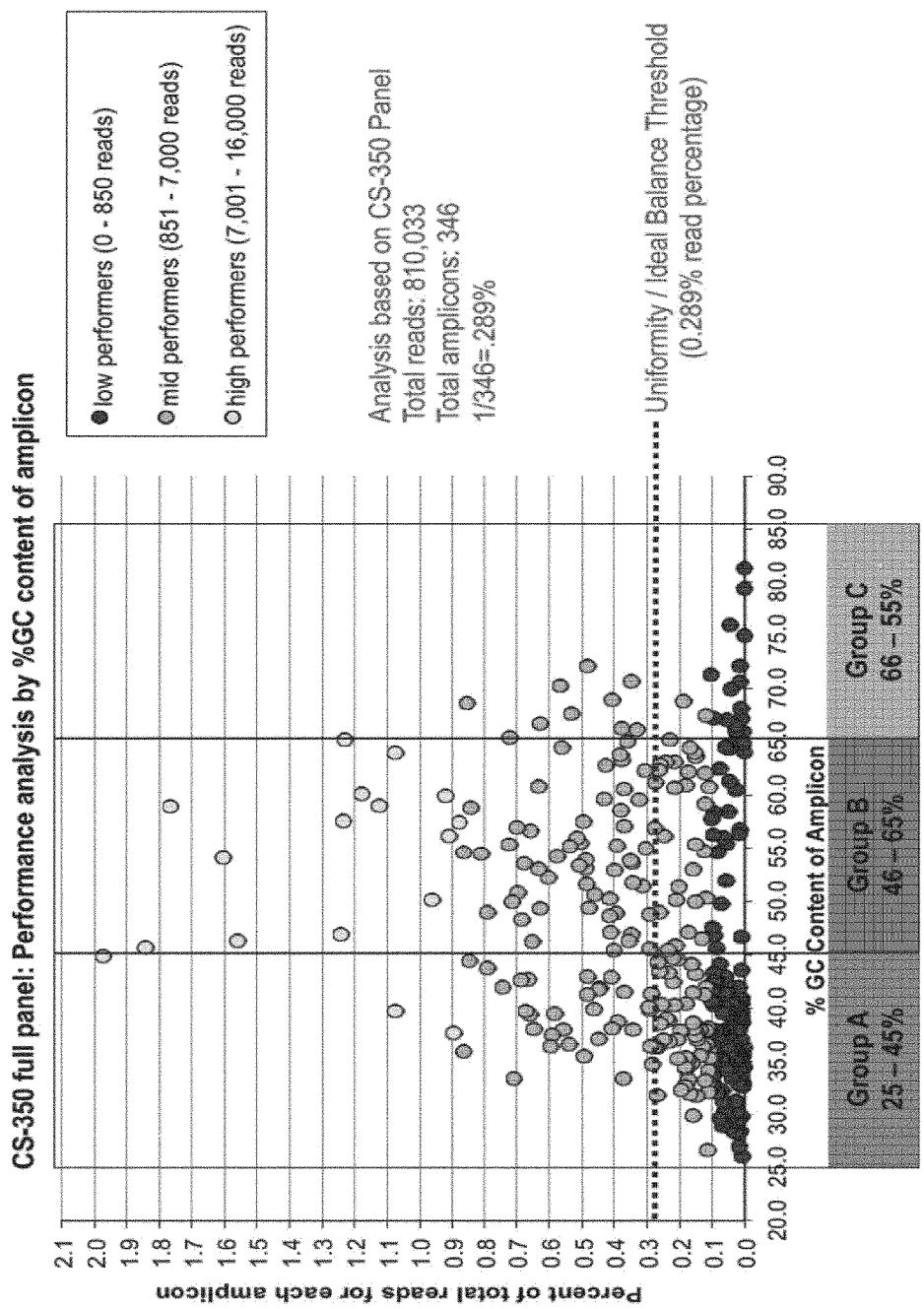
FIG. 22B depicts a plot of the read percentage of each amplicon vs. the amplicon % GC content using an exemplary method for targeted sequencing described herein.
Figure 23A:
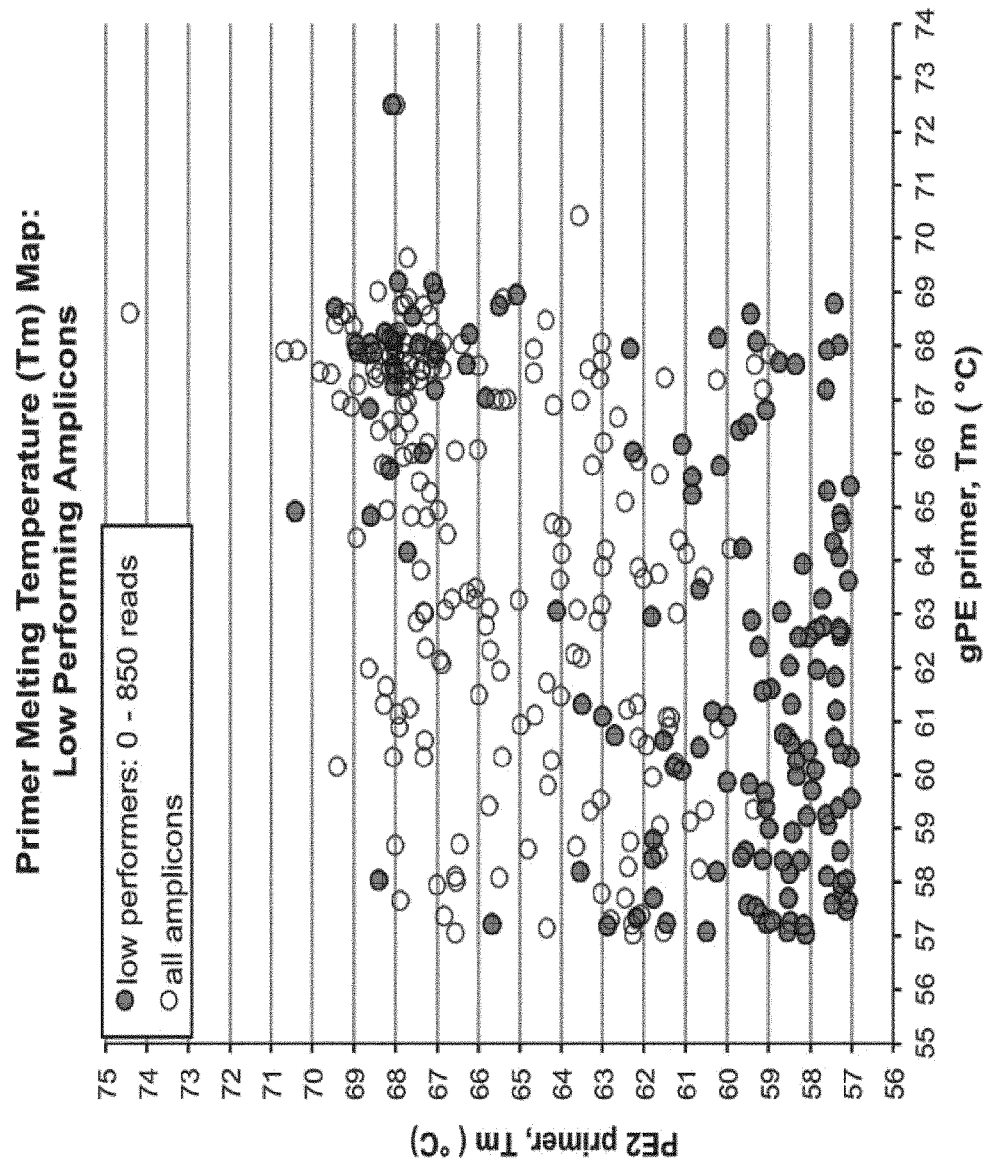
FIG. 23A depicts a plot of low performing amplicons mapped by their respective primer melting temperature.
Figure 23B:
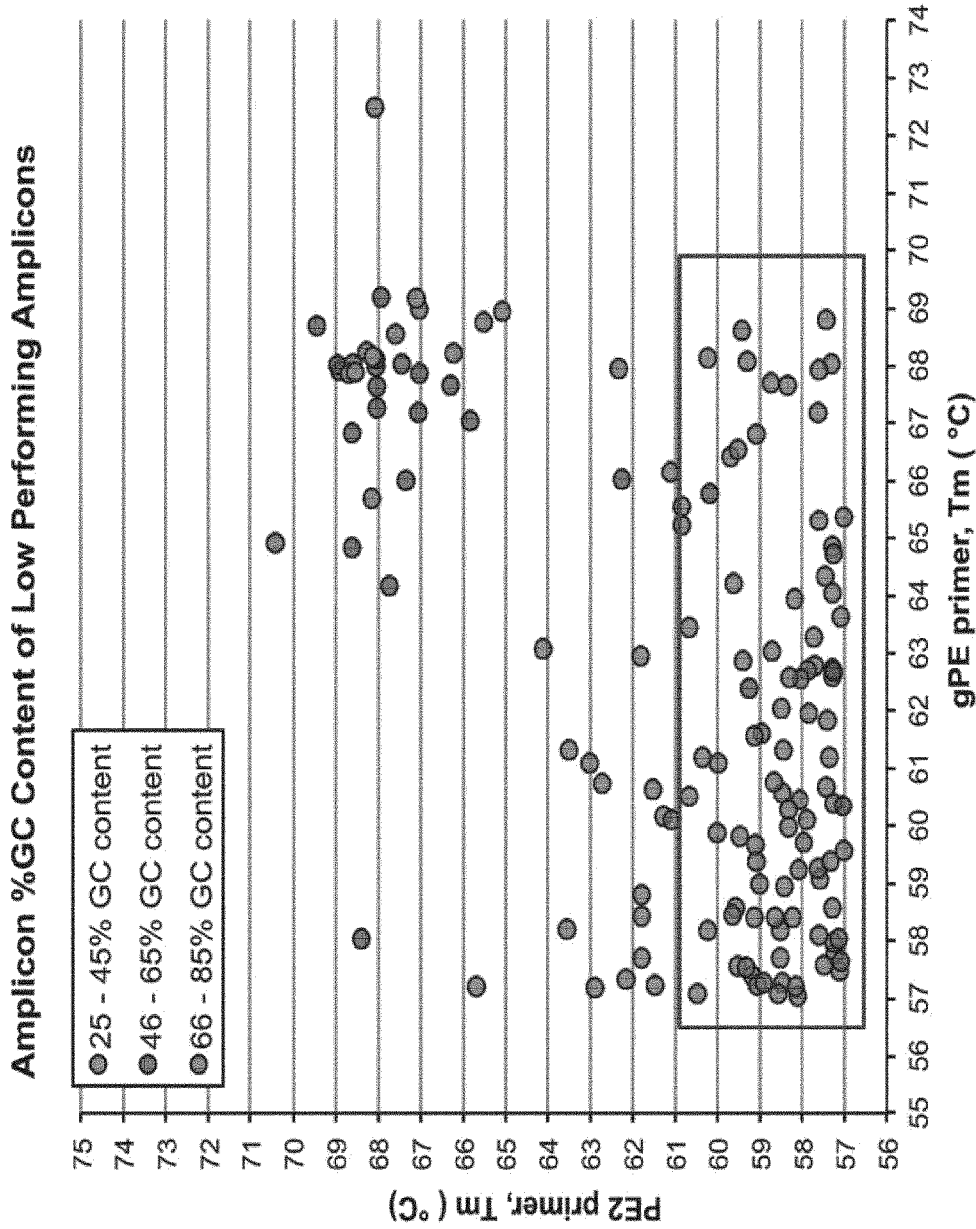
FIG. 23B depicts a plot of low performing amplicons mapped by their respective primer melting temperature.
Figure 24:
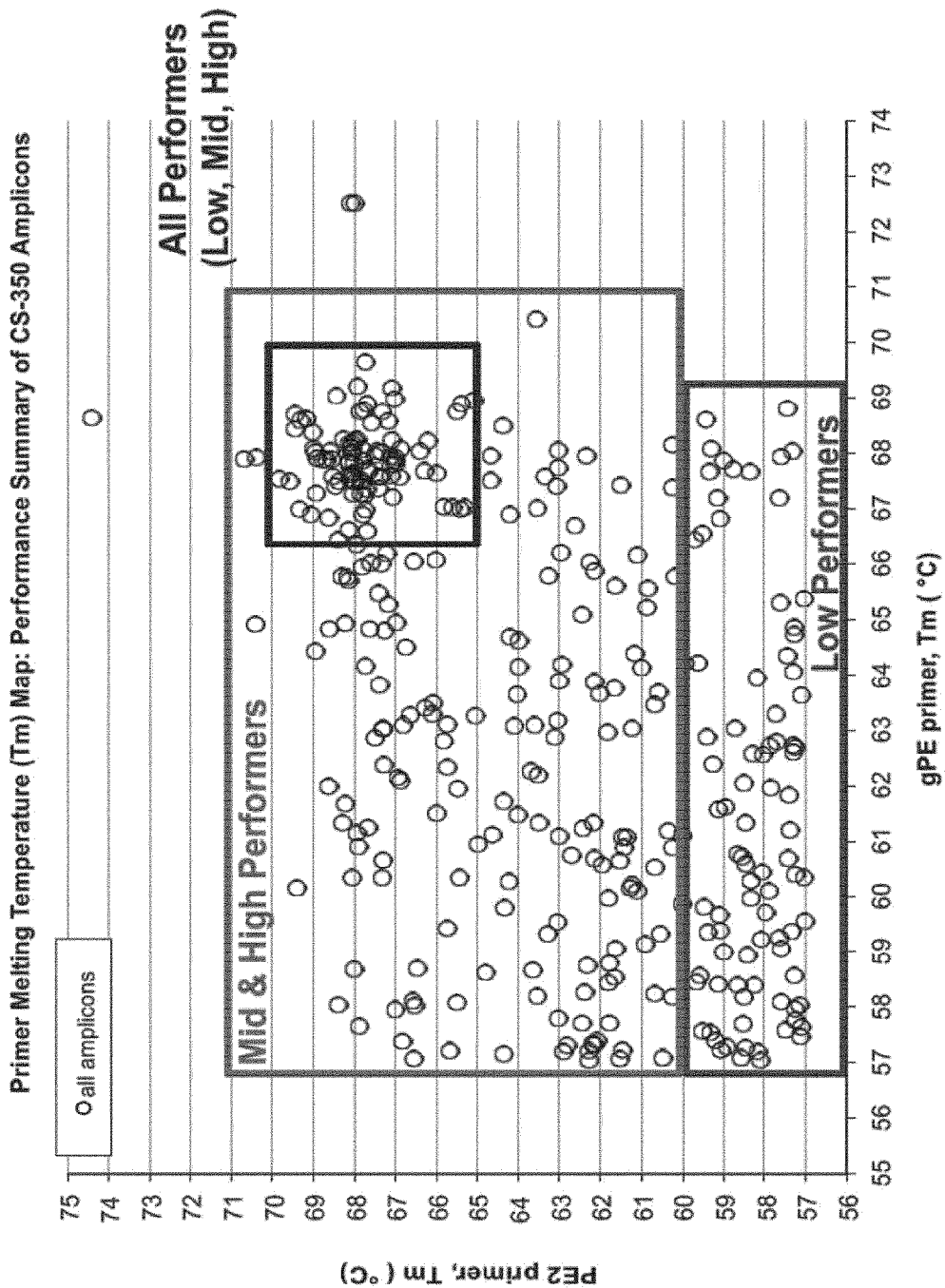
FIG. 24 depicts a plot of low, mid, and high performing amplicons mapped by their respective primer melting temperature.
Figure 28:
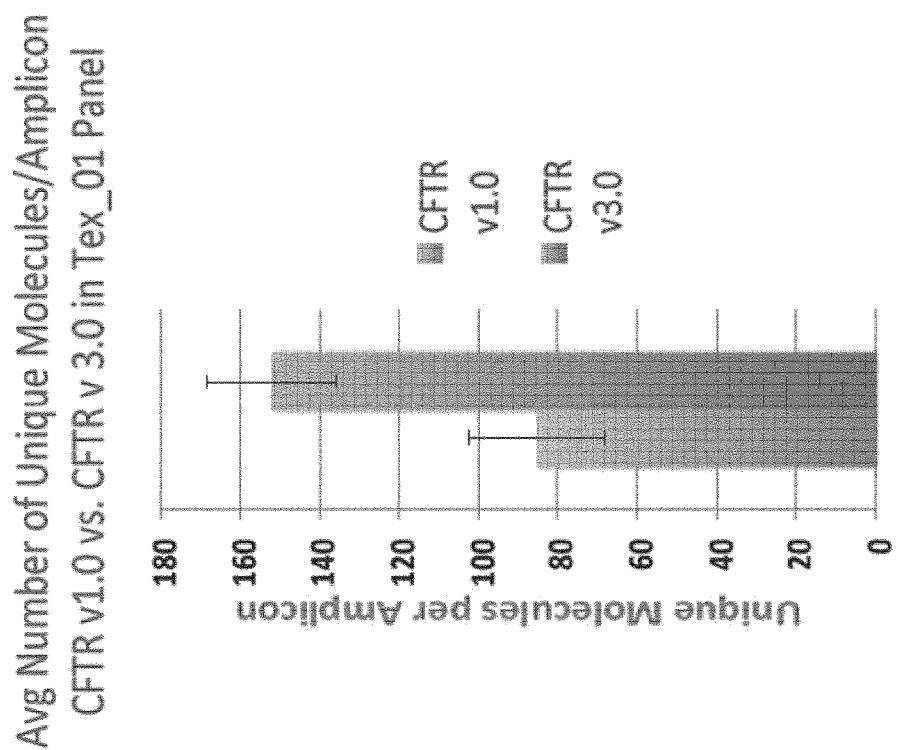
FIG. 28 depicts a graph showing an improved primer panel (v.3.0) designed using the primer design method described herein compared to the primer panel designed using a prior art method (v. 1.0). The improved panel leads to improved amplification efficiency and increased the number of unique molecules detected leading to enhanced SNP calling capabilities, a reduction in sequencing coverage requirements, and lowers sample input requirements.
Figure 29:
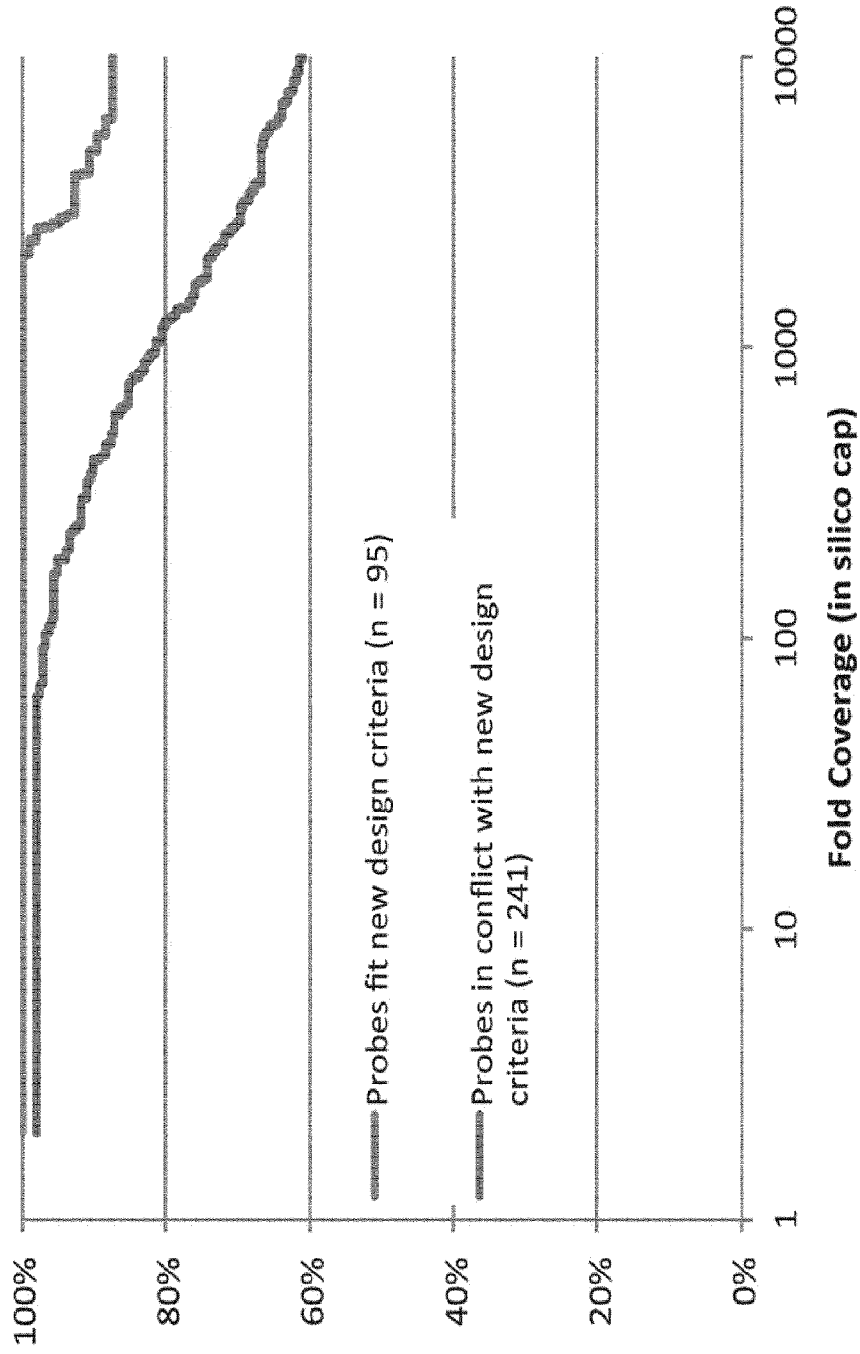
FIG. 29 depicts a plot comparing uniformity of coverage for primers in the indicated subpanel that fit improved primer design criteria vs primers in the same subpanel that do not fit improved primer design criteria. The primers in the subpanel that fit improved primer design criteria demonstrate higher uniformity of coverage, higher on target specificity, and higher read counts.
Figure 30A:
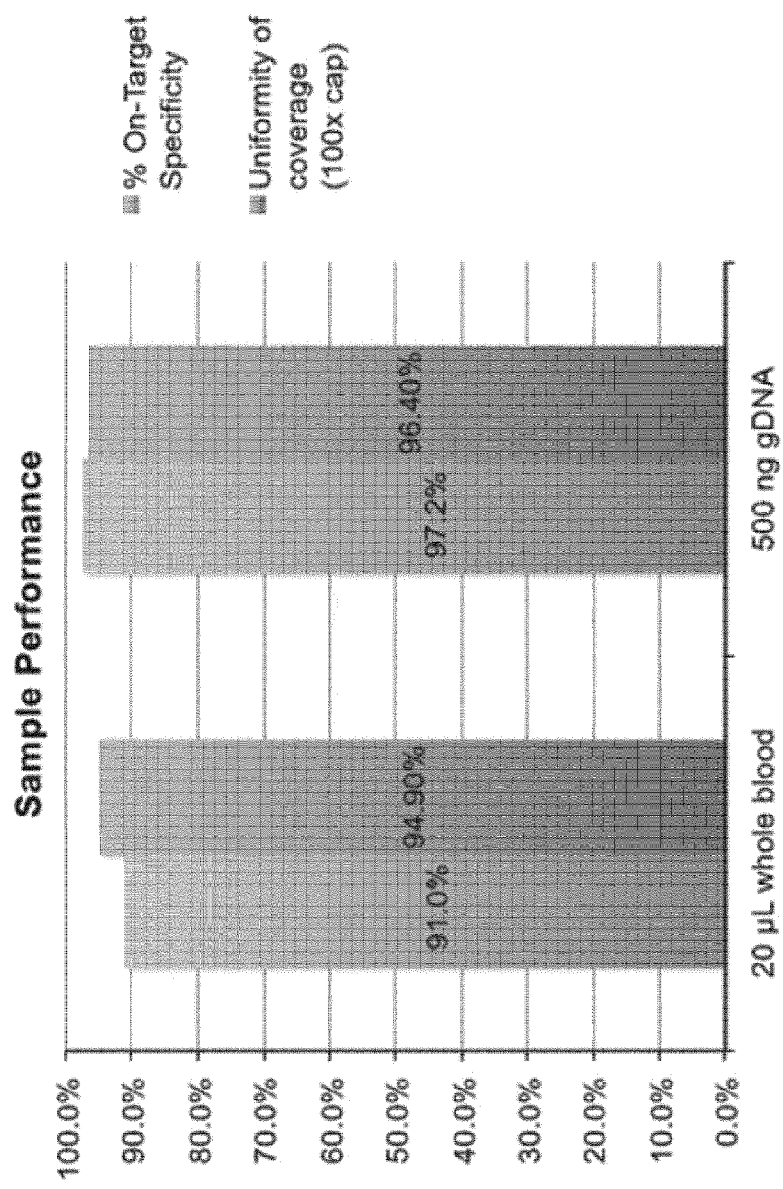
FIG. 30A depicts a graph showing whole blood sample performance with respect to uniformity and coverage and on target specificity compared to a sample of DNA extracted from whole blood.
Figure 30B:
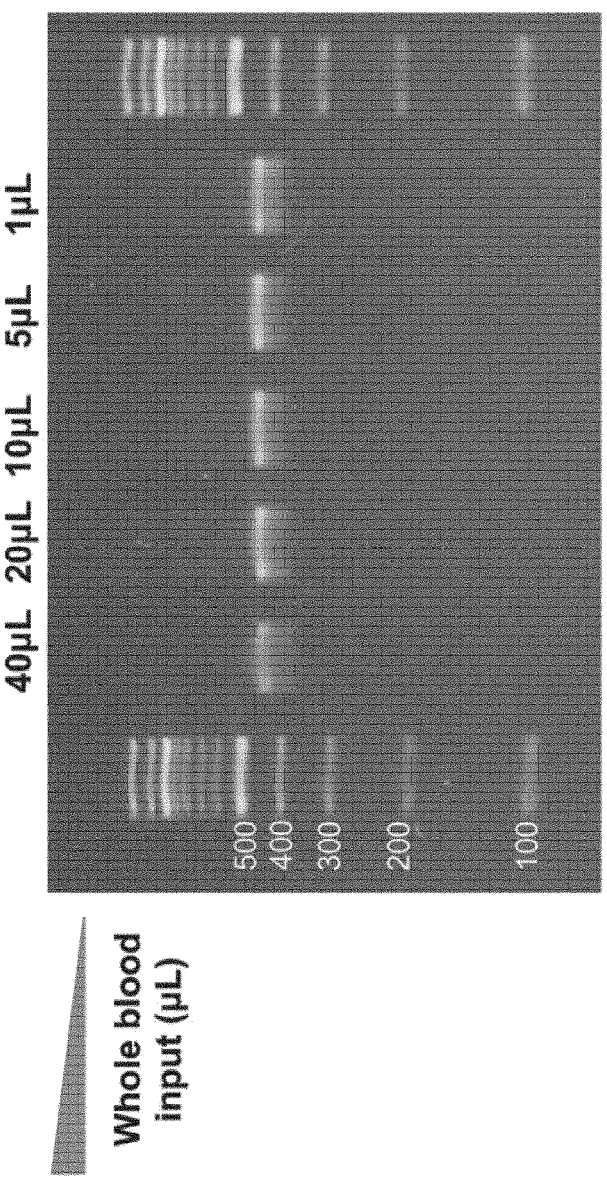
FIG. 30B depicts the products after the indicated PCR cycles of an exemplary targeted sequencing method using the indicated volumes of a sample of whole blood on an agarose gel alongside a 100 base pair (bp) ladder. As little as 1 μL of whole blood can be used.
Figure 31:
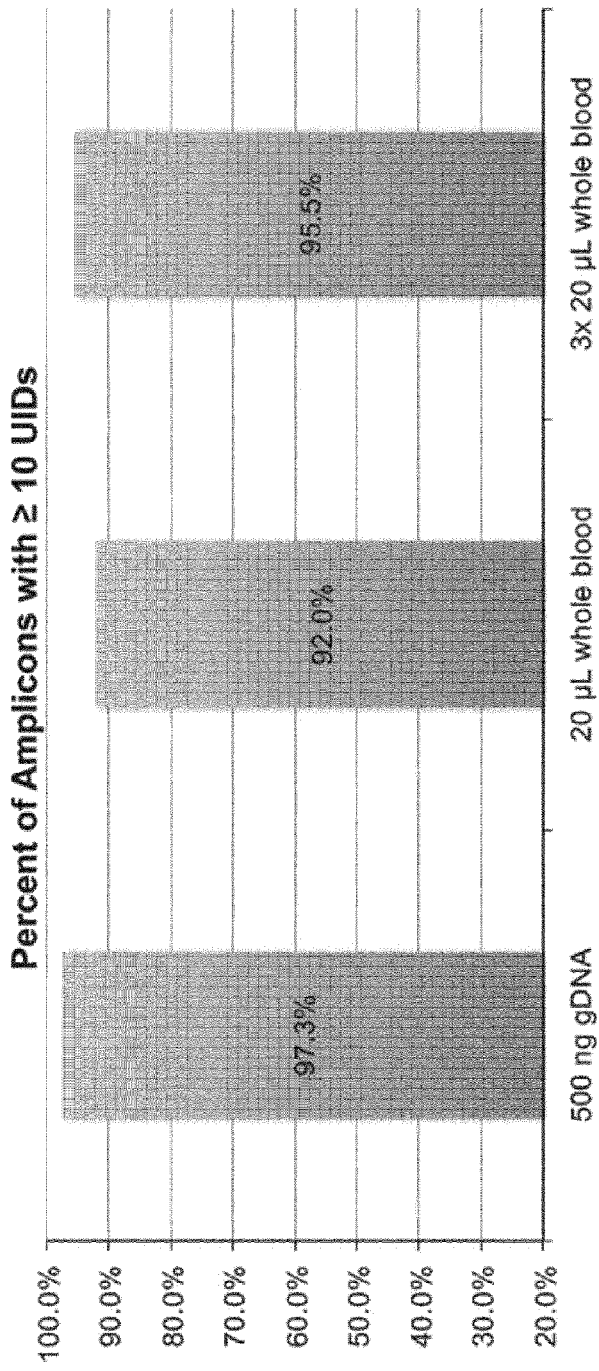
FIG. 31 depicts a graph (top) and corresponding table (bottom) of an analysis comparing the number of amplicons with greater than 10 unique molecules from a whole blood sample and a sample of DNA extracted from whole blood. The 3× whole blood sample combine three first primer extension reactions prior to adaptor ligation.
Figure 33:
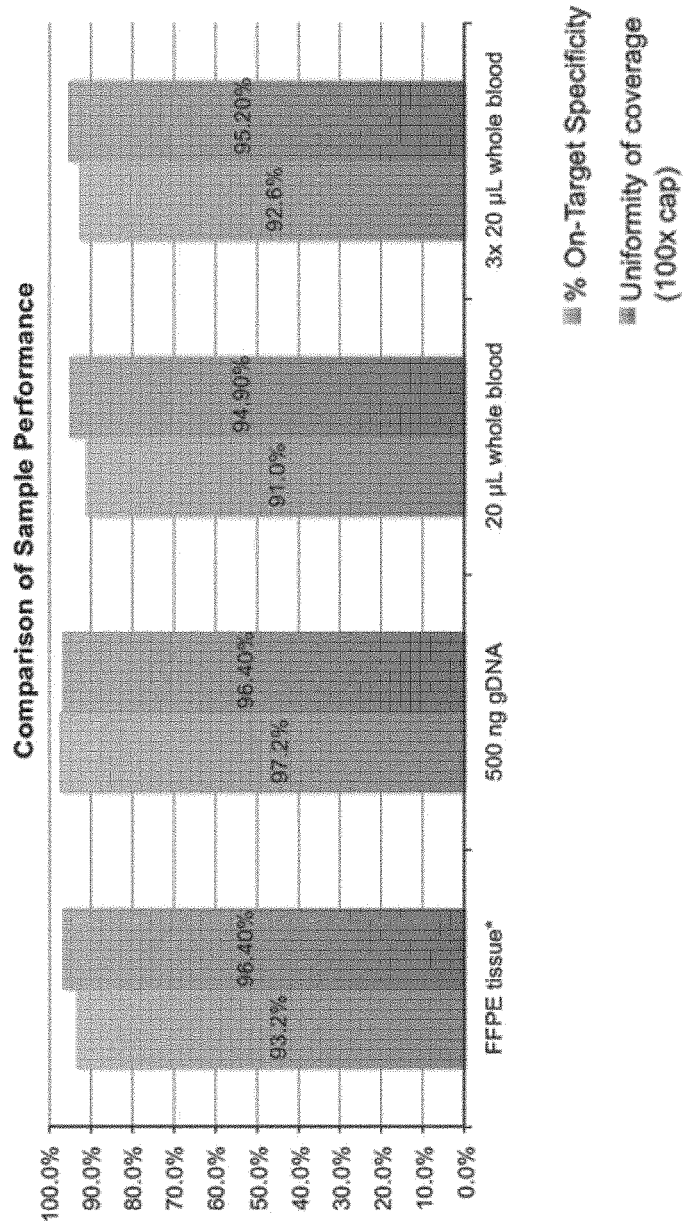
FIG. 33 depicts a graph showing FFPE prostate tissue sample performance with respect to uniformity and coverage and on target specificity compared to a whole blood sample and a sample of DNA extracted from whole blood.
Figure 34:
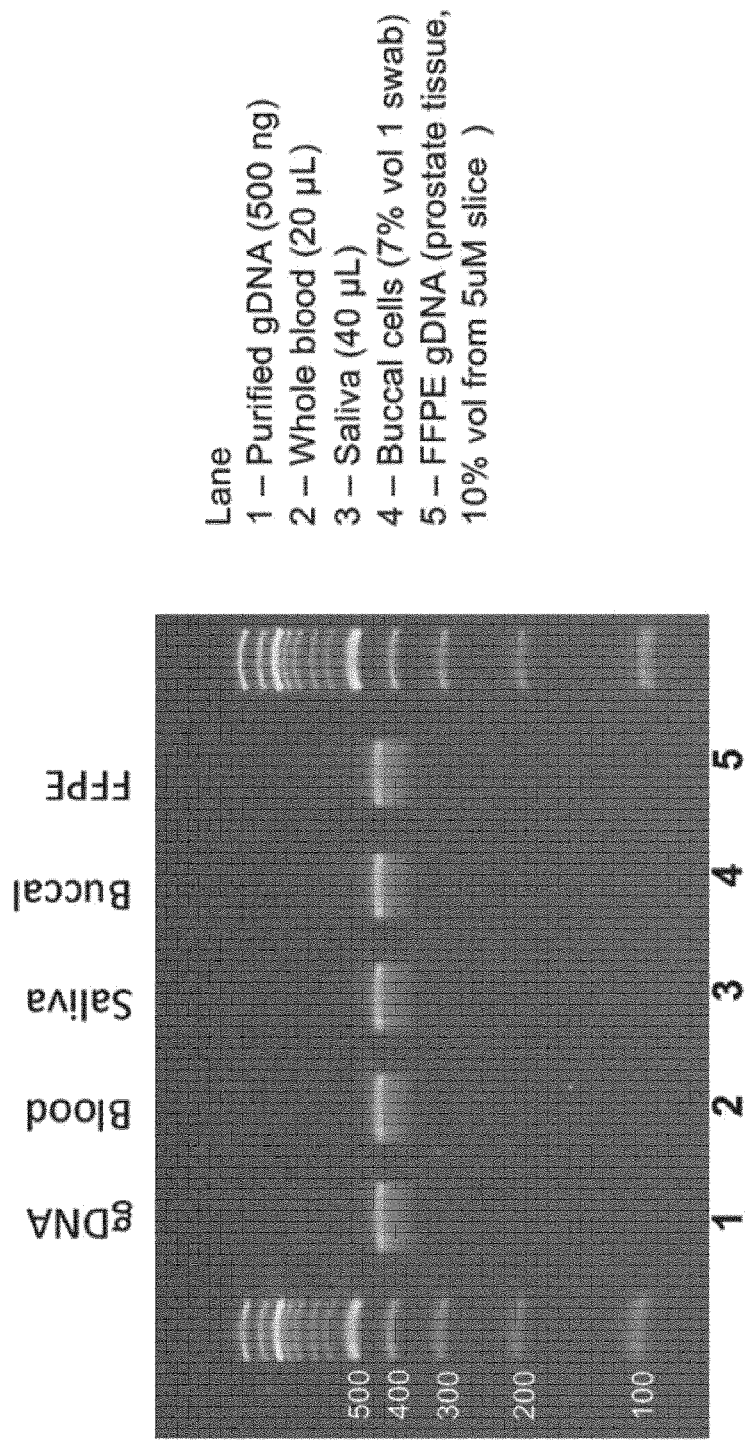
FIG. 34 depicts the products from an exemplary targeted sequencing method using a variety of samples on an agarose gel alongside a 100 base pair (bp) ladder. The methods described herein can accommodate a variety of samples including the direct input of whole blood or saliva into the first primer extension reaction without prior nucleotide extraction, buccal samples, and FFPE samples.
Figure 35:
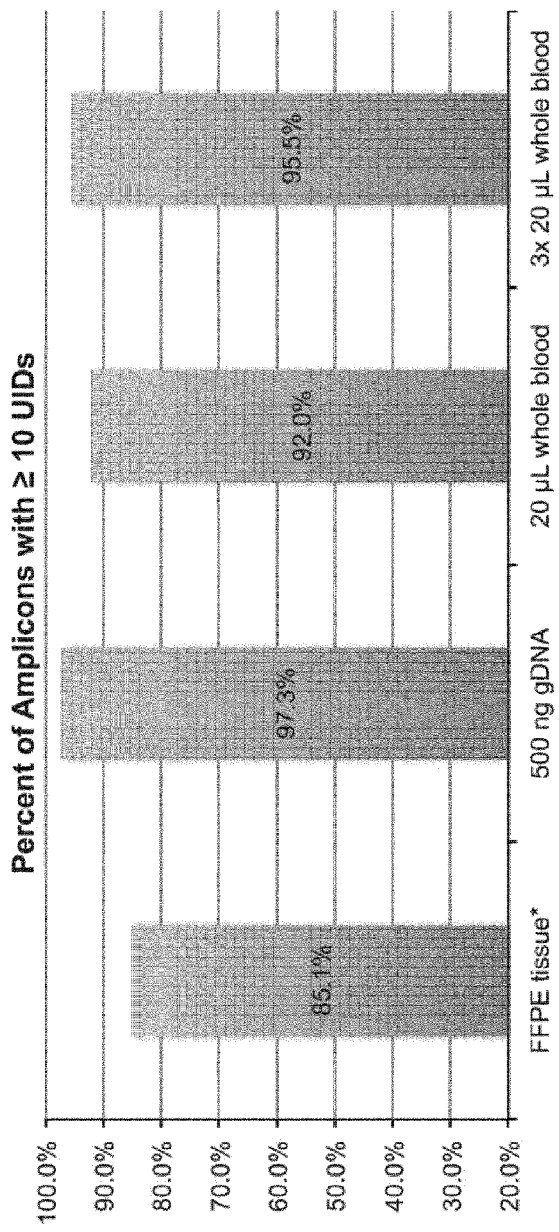
FIG. 35 depicts a graph (top) and corresponding table (bottom) of an analysis comparing the number of amplicons with greater than 10 unique molecules from an FFPE sample, a whole blood sample, and a sample of DNA extracted from whole blood. The 3× whole blood sample combine three first primer extension reactions prior to adaptor ligation.
Figure 36:
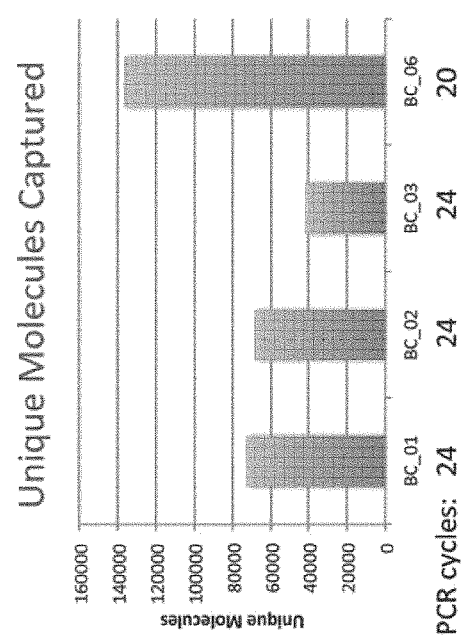
FIG. 36 depicts a graph of the number of unique molecules detected using the indicated number of PCR cycles and indicated UIDs. The graph demonstrates that reducing the number of PCR cycles prevents formation of over amplified larger products, reduces PCR duplication, may allow for reductions in required sequencing depth, may improve data for low input samples, and can leverage linear amplification to offset reduced PCR cycling.
Figure 37:
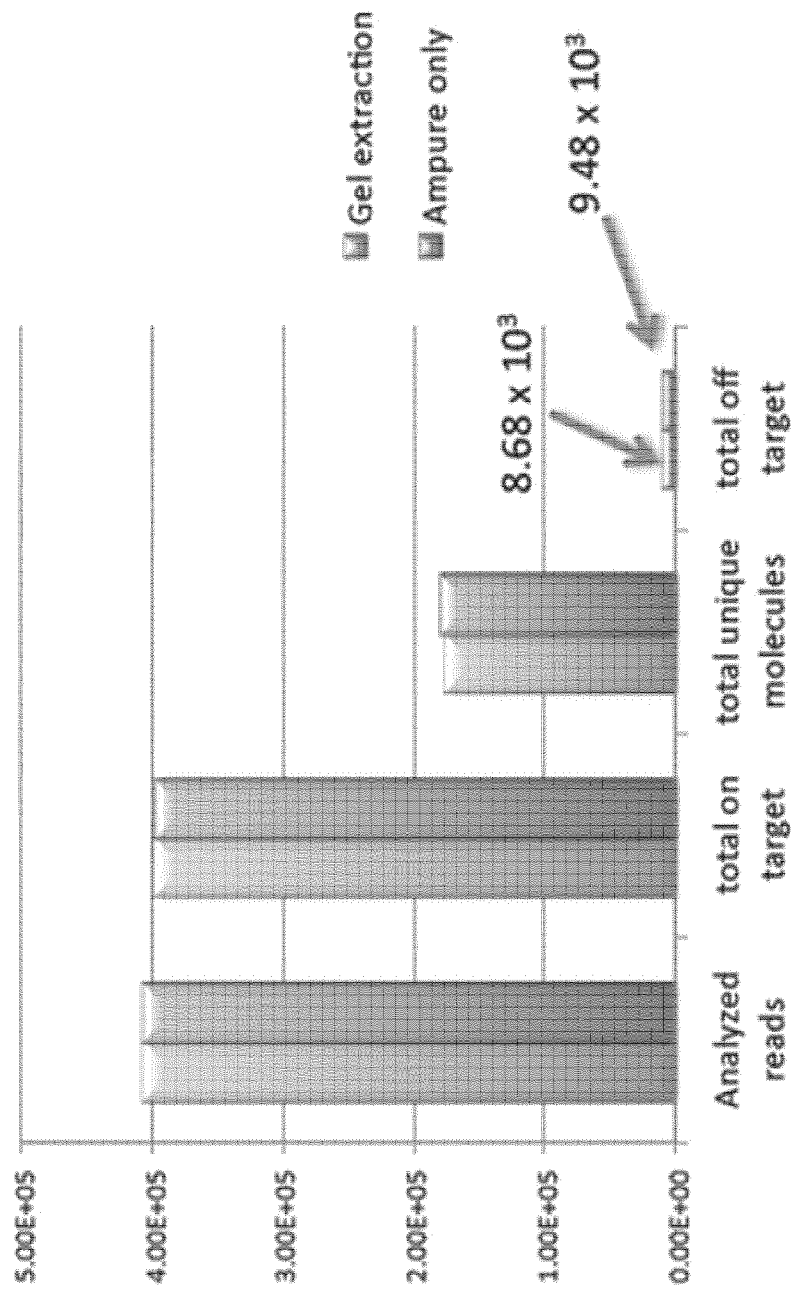
FIG. 37 depicts a graph depicting sequencing data quality using a library produced from an exemplary targeted sequencing method that has been gel purified compared to a library that has ben Ampure purified.
Figure 38:
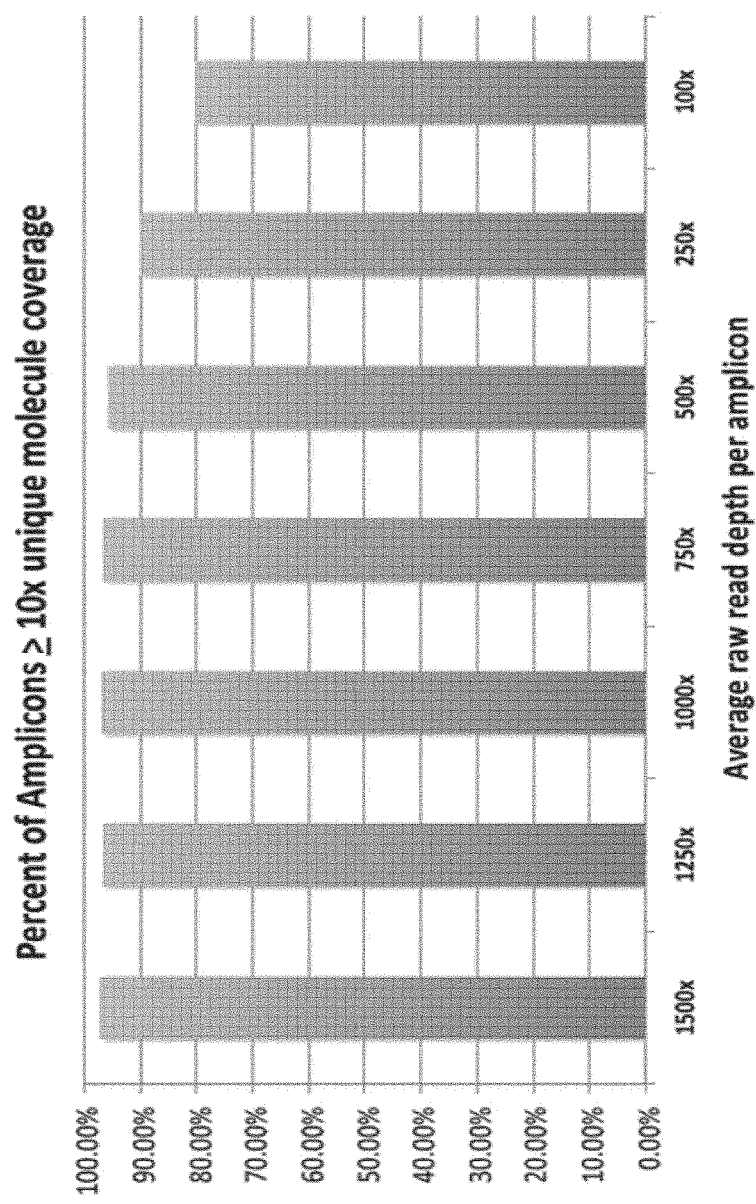
FIG. 38 depicts a graph of an in silico read titration showing the percent of amplicons with greater than or equal to 10 unique molecule coverage. Sequencing at 500× average read depth per amplicon provided adequate unique molecule coverage for 95% of amplicon in the Tex_01 primer panel (336 amplicons). This can allow for a multiplex of 90 samples per run (336×500=168,000 reads).
Figure 40:
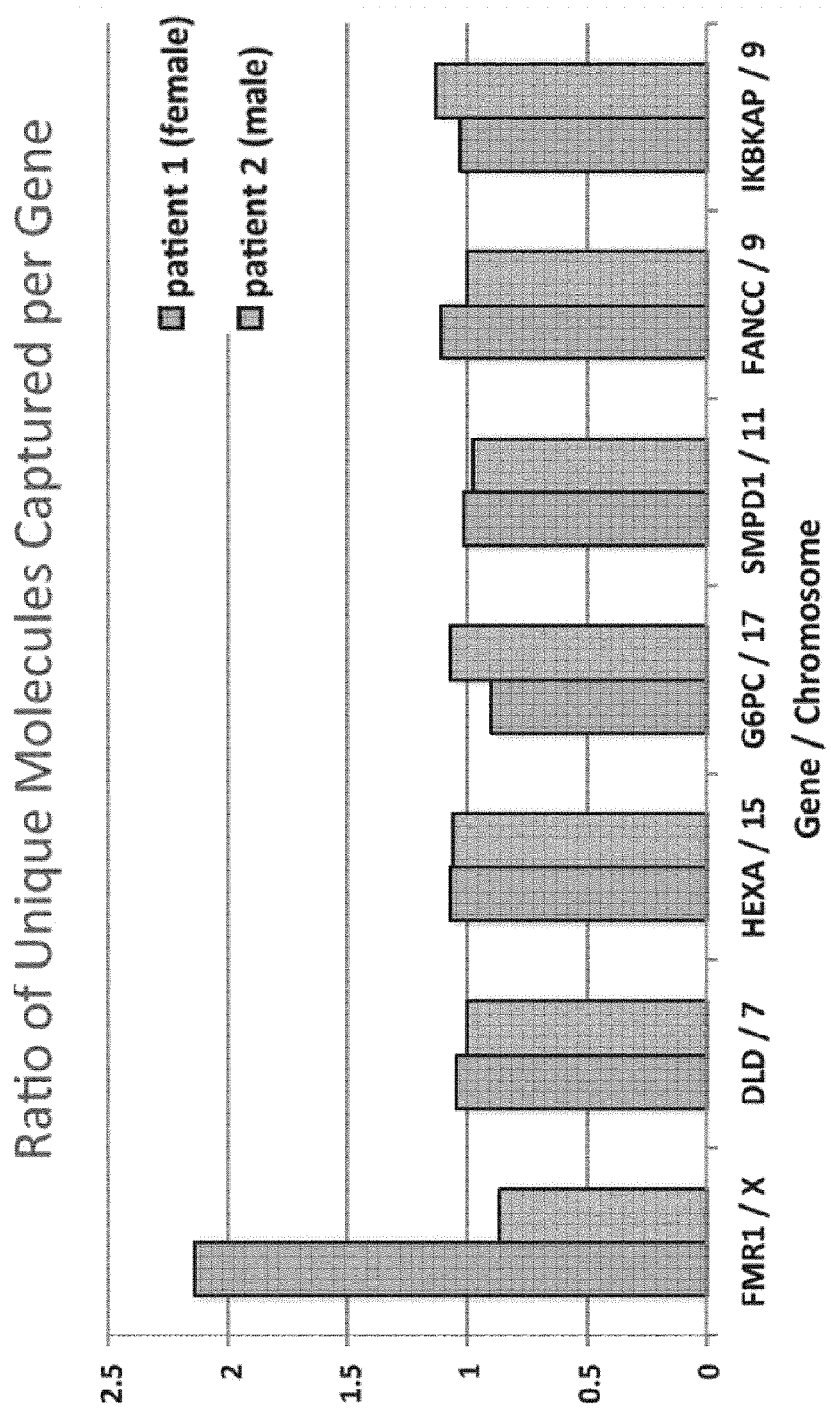
FIG. 40 depicts a graph of copy number quantitation showing the ratio of unique molecules captured per gene. The ratio of unique reads (UID filtered) for a given gene were compared for genes on autosomal chromosomes vs. the X chromosome. The ratio of reads between a male reference patient and three test patients is depicted. This demonstrates the quantitative capability of using UID analysis for targeted sequencing.
Figure 41:
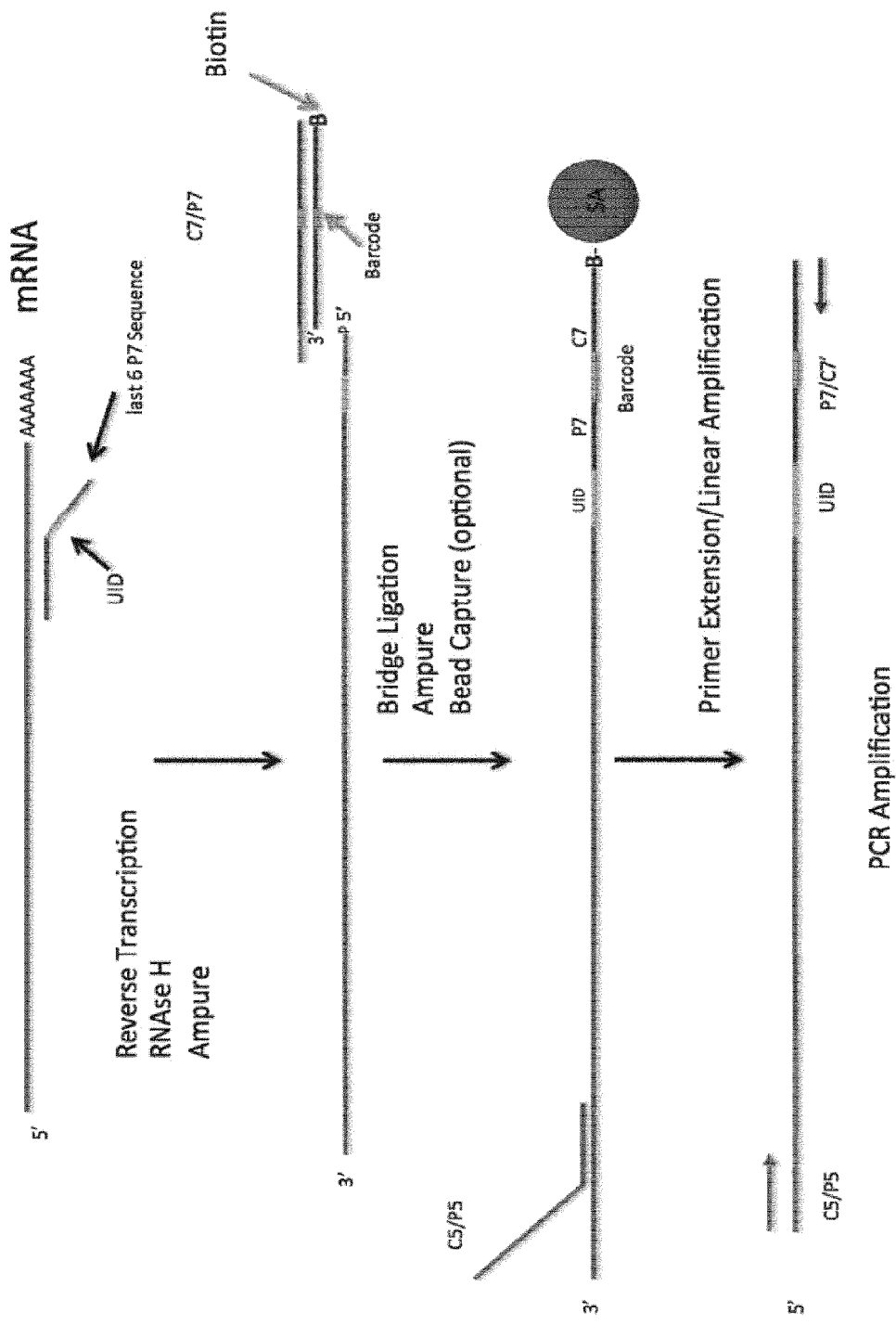
FIG. 41 depicts a schematic of an exemplary RNA-based method for primer extension targeted sequencing with a demonstrated ability to amplify products greater than 700 bps in length.
Figure 42:
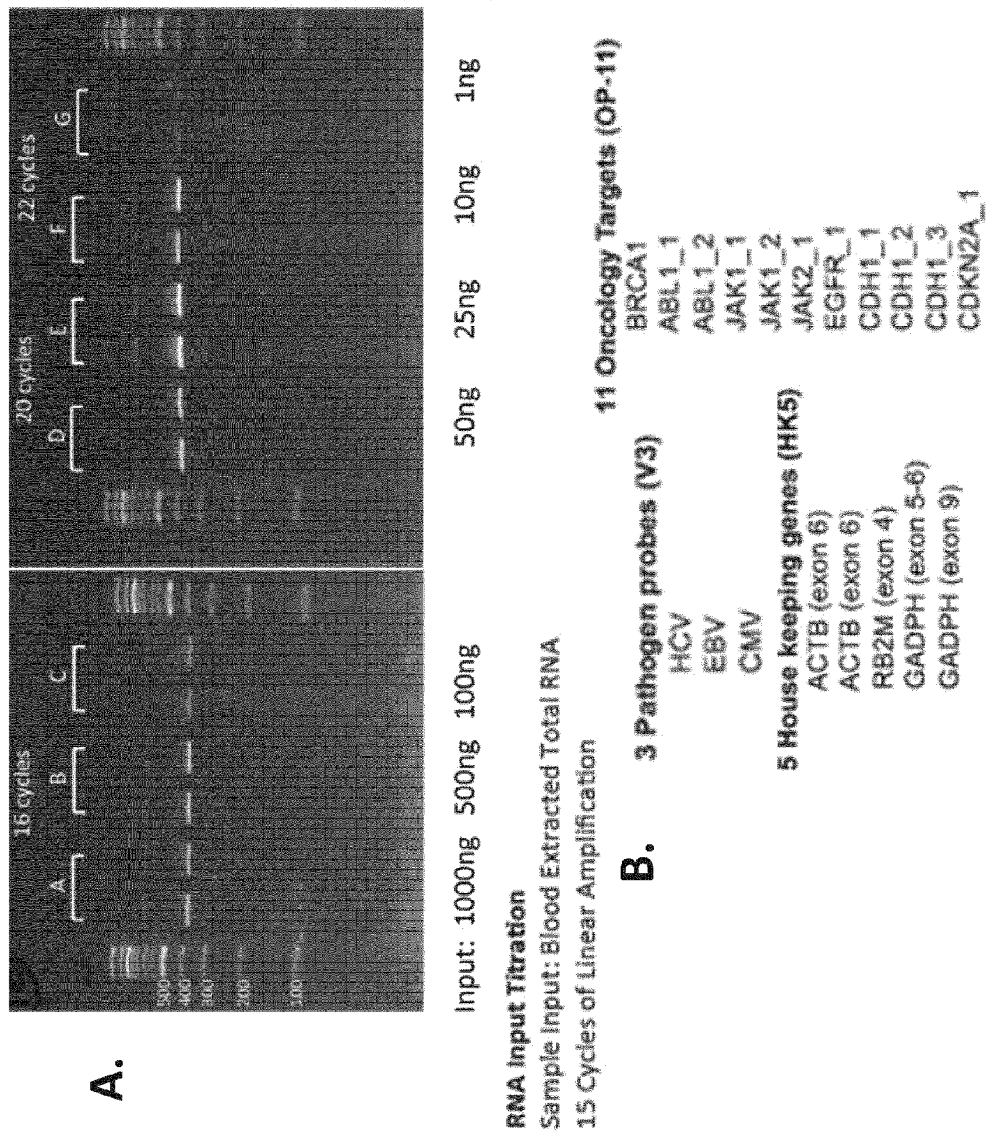
FIG. 42A depicts the products from an exemplary RNA targeted sequencing method after the indicated PCR cycles using the indicated RNA input amounts on an agarose gel alongside a 100 base pair (bp) ladder.
FIG. 42B depicts an exemplary list of targets to which exemplary RNA targeted sequencing methods described herein have been successfully applied.
Figure 43:
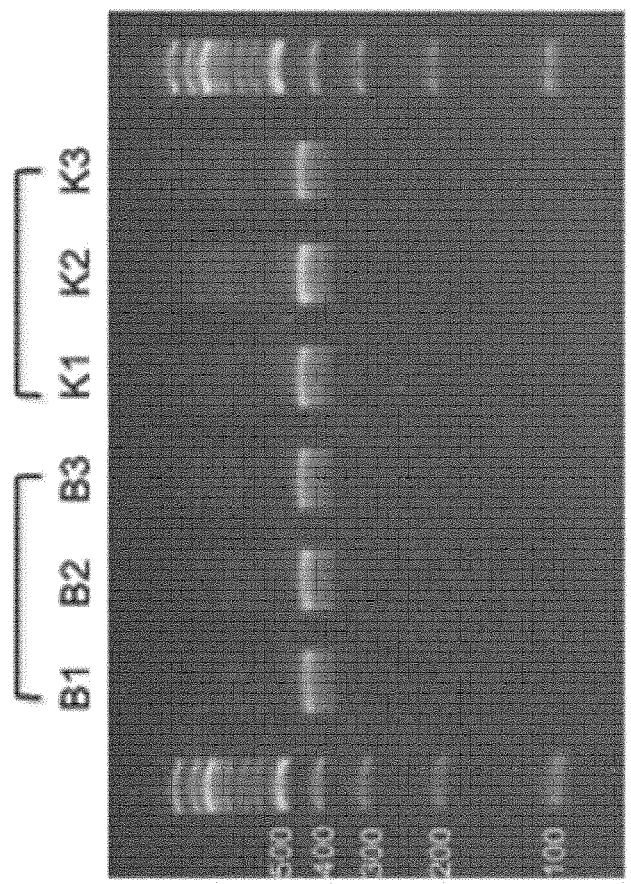
FIG. 43 depicts the products from an exemplary targeted sequencing method on an agarose gel alongside a 100 base pair (bp) ladder performed as technical repeats. This demonstrates the reproducibility of the methods described herein.
Figure 44:
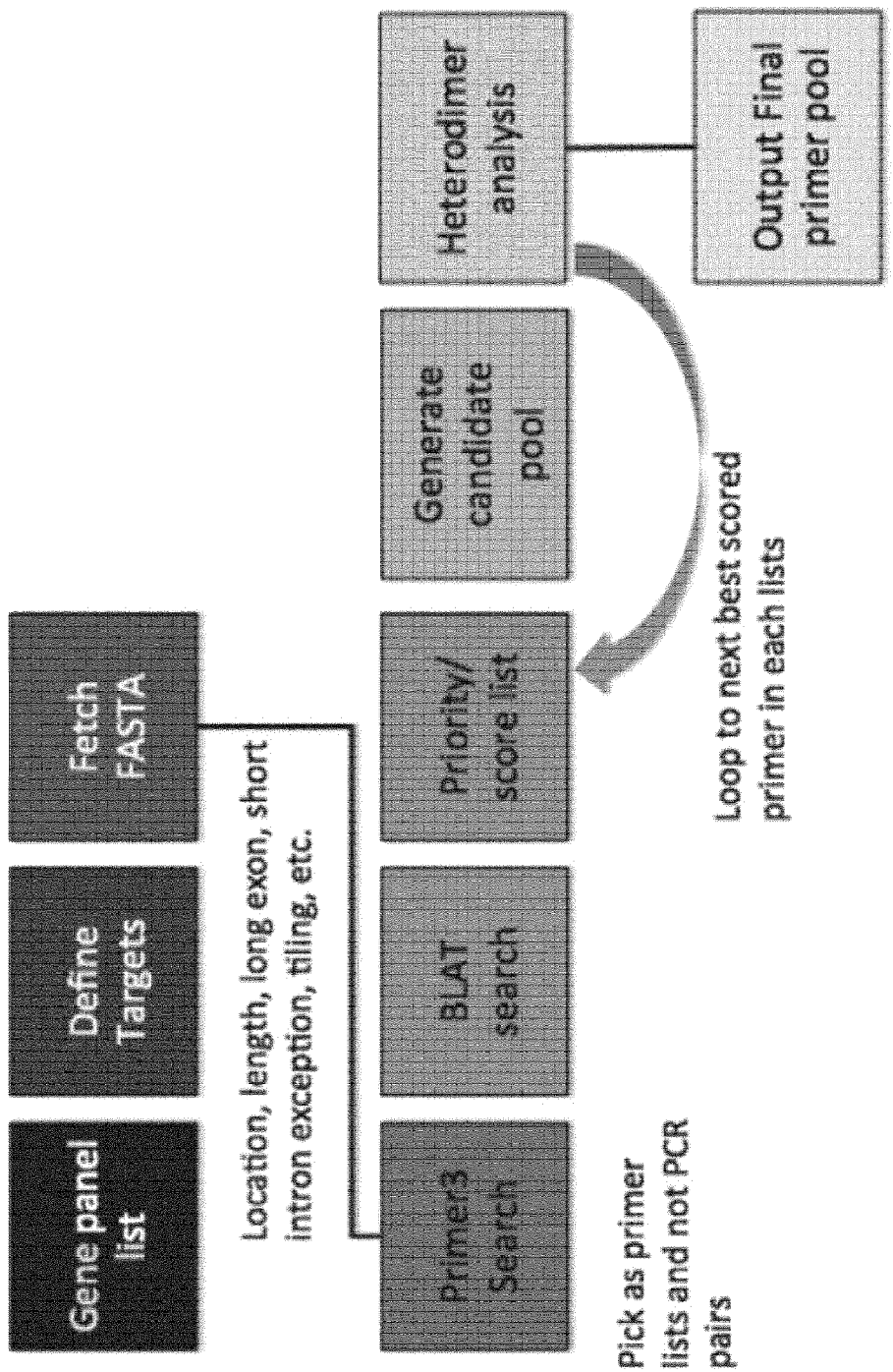
FIG. 44 depicts a schematic of exemplary primer design software developed for producing primer panels
Figure 45A:
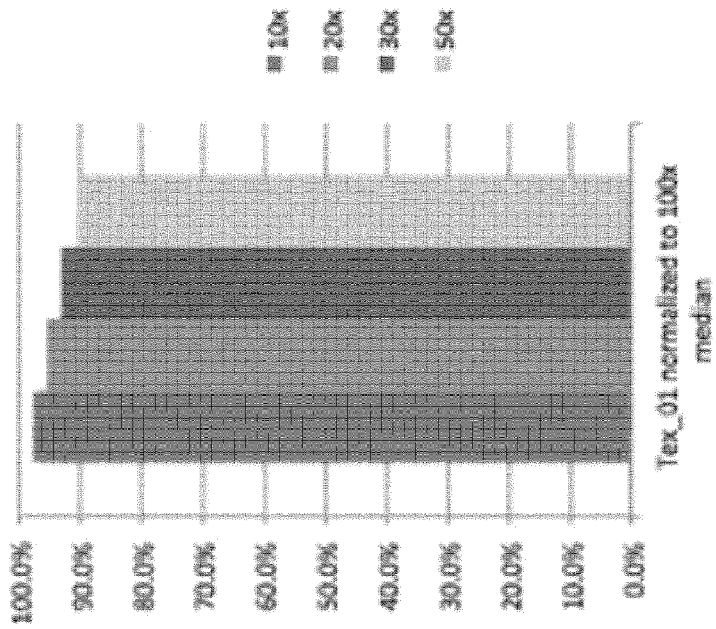
FIG. 45A depicts a plot of the percentage of amplicons greater than 20% of the mean over the indicated in silico cap range showing the uniformity of coverage of an exemplary method for targeted sequencing described herein using a primer subpanel at the indicated fold read coverages normalized to 100× median.
Figure 45B:
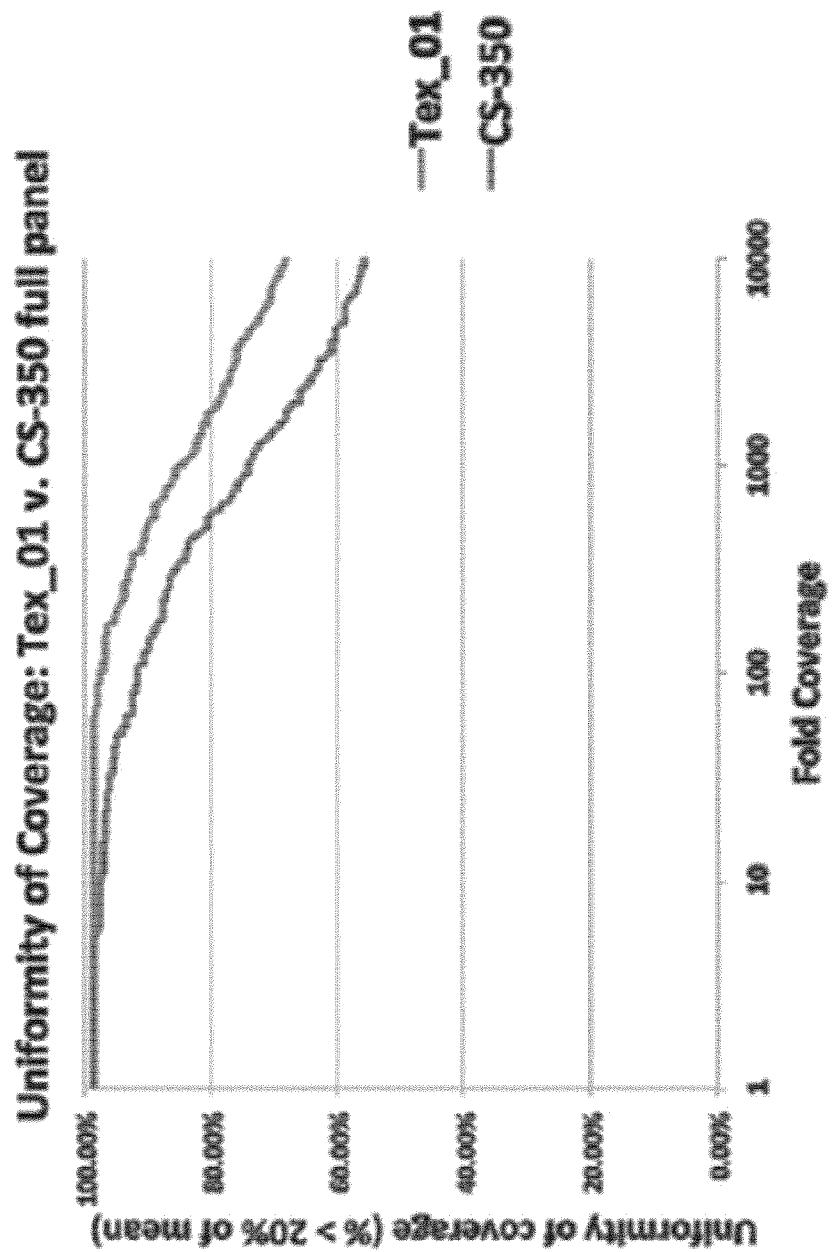
FIG. 45B depicts a graph comparing the uniformity of coverage of the indicated primer panel of about 350 primers and a subpanel generated therefrom using the exclusion criteria shown in FIG. 15 and other methods described herein.
Figure 47:
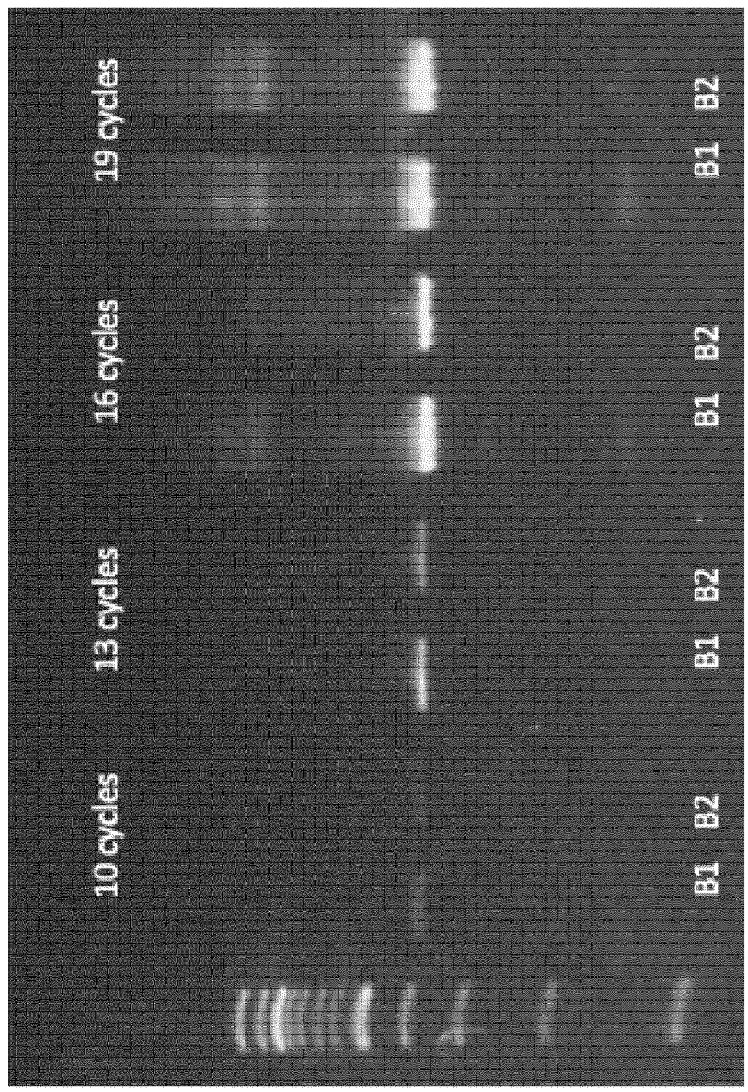
FIG. 47 depicts the products of the DNA targeted sequencing method on a 2% agarose gel alongside a 100 base pair (bp) ladder. Samples from 2 patients (B1 and B2) are shown after the indicated PCR amplification cycles.
Figure 48:
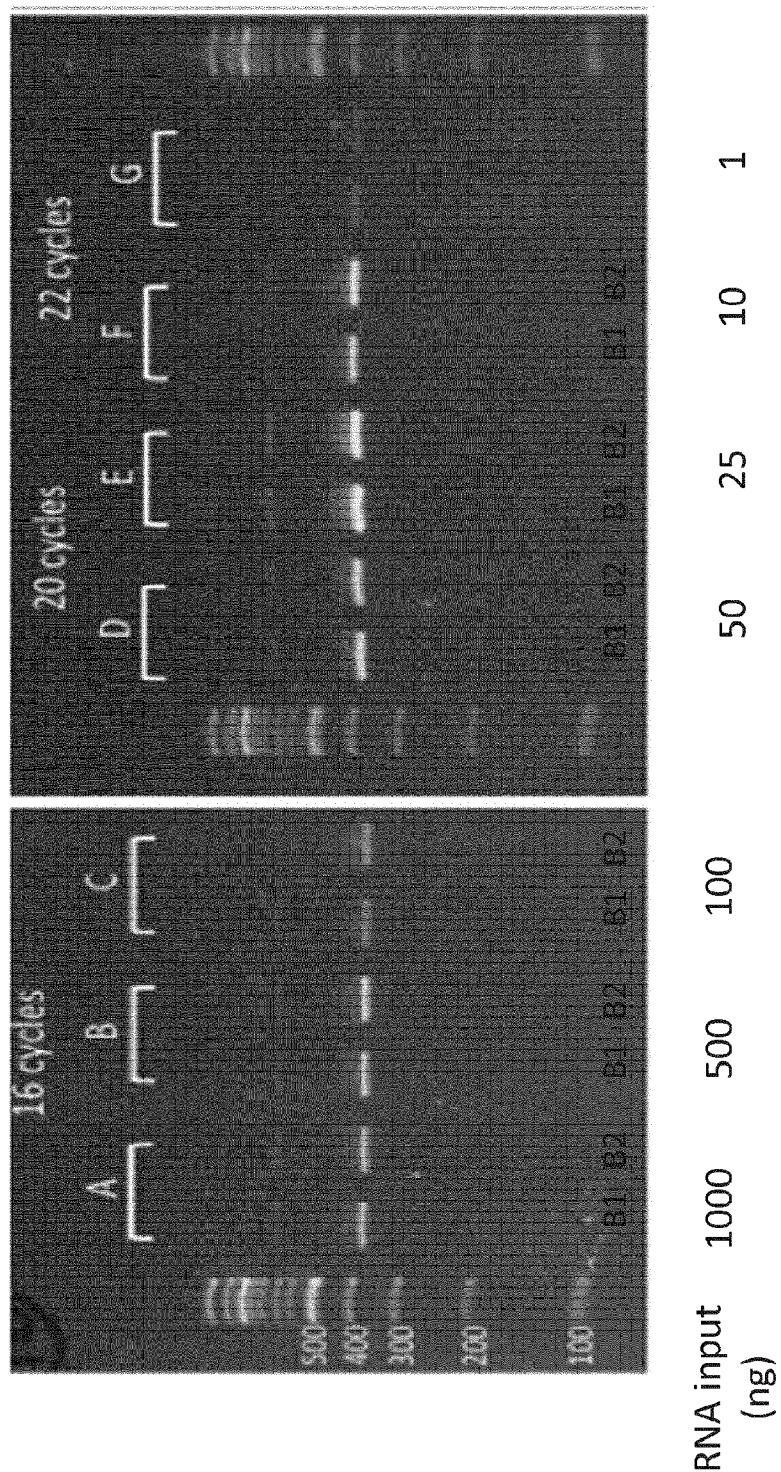
FIG. 48 depicts products of an RNA targeted sequencing method on a 2% agarose gel alongside a 100 bp ladder. Samples from 2 patients (B1 and B2) are shown at after the indicated PCR amplification cycles. For each patient, a titration of the starting RNA input material was done from 1000 ng down to 1 ng.
Figure 49:
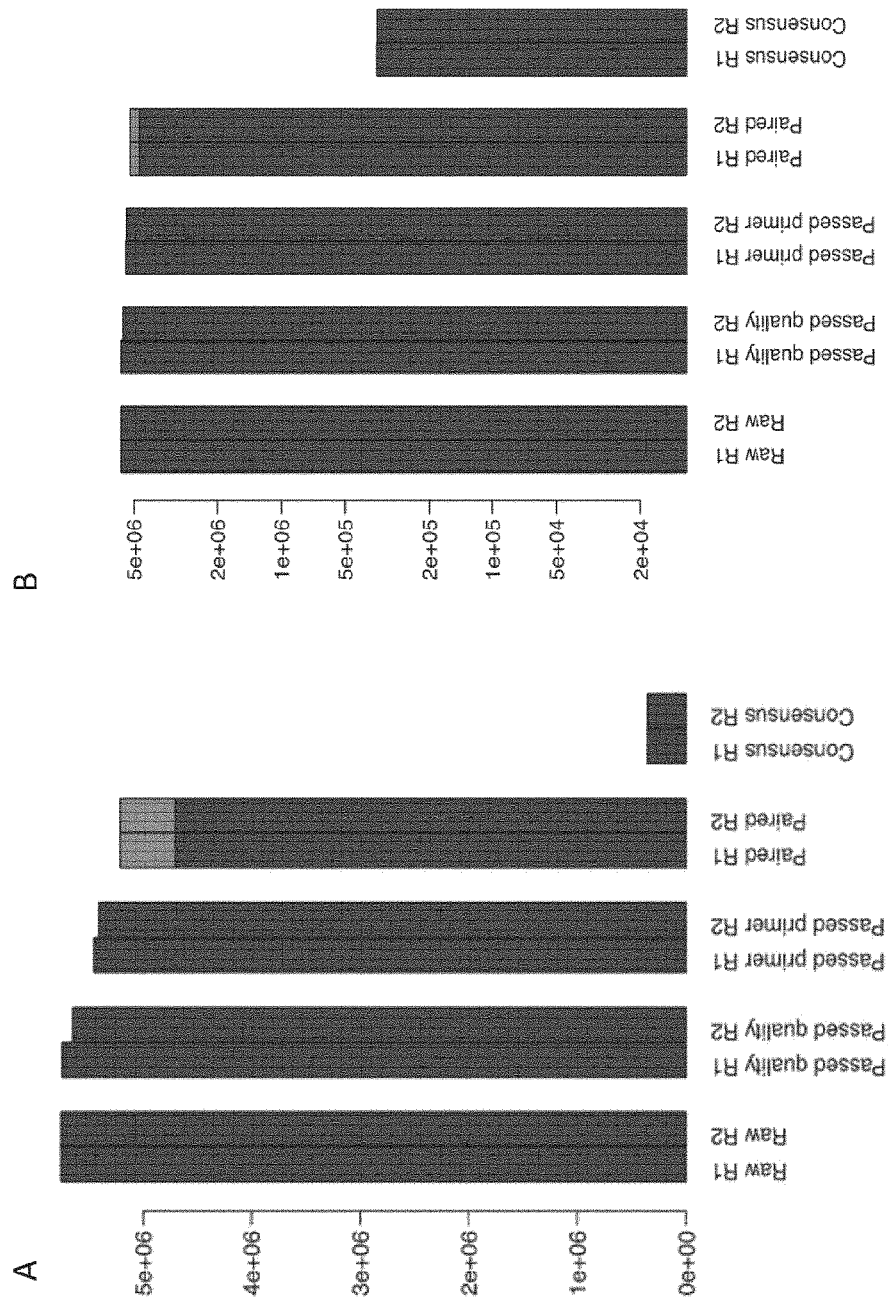
FIG. 49 depicts histograms of results using a post Next-generation sequencing (NGS) data filtering process using a method of targeted sequencing. The histogram in FIG. 49B is a log scale version of 49A. NGS was conducted using a paired-end read (R1 and R2) approach, yielding a total of ~6 million reads for the sample shown. Sequences with a phred Q score of 30 or higher were further analyzed (passed quality R1, and R2). Sequence data was then queried for the presence of an expected primer panel used in the DNA targeted library protocol (passed primer R1 and R2). Any sequencing reads not starting with one of the expected primer sequences were discarded. For each read with a known or expected primer sequence on R1, the expected primer on R2 was qualified (paired R1 and R2). Therefore, when a known R1 primer is mis-matched with a different target primer on R2 (or vice versa), it corresponds to a non-specific amplification product (shown in light grey). If a known R1 primer is not mis-matched with a different target primer on R2 (or vice versa), it corresponds to a specific amplification product (shown in dark grey).
Figure 50A:
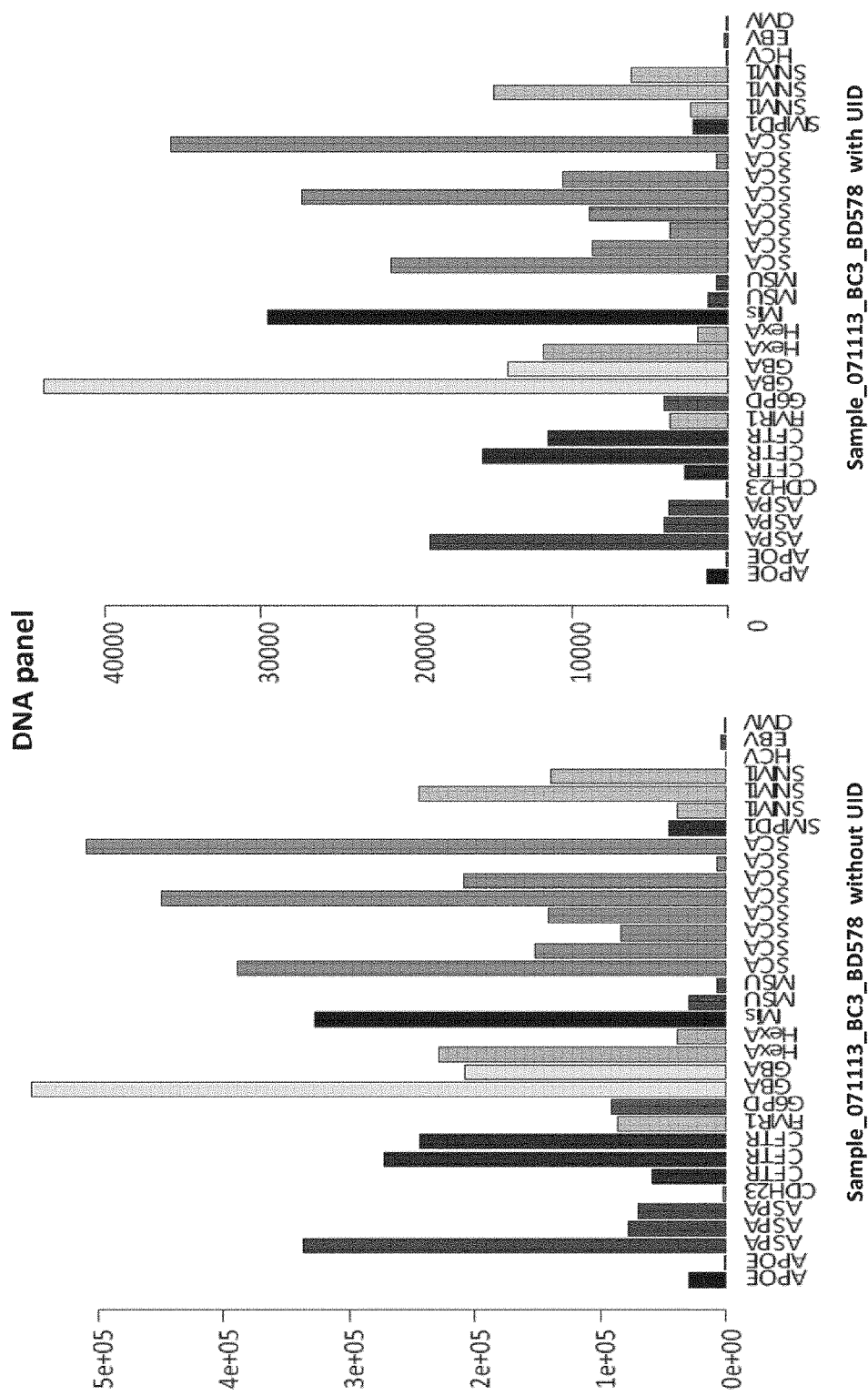
FIGS. 50A-50C depict graphs of sequencing read counts of DNA targeted panels. Each indicated gene was targeted by a specific primer pair used in the preparation of the DNA sample.
Figure 50B:
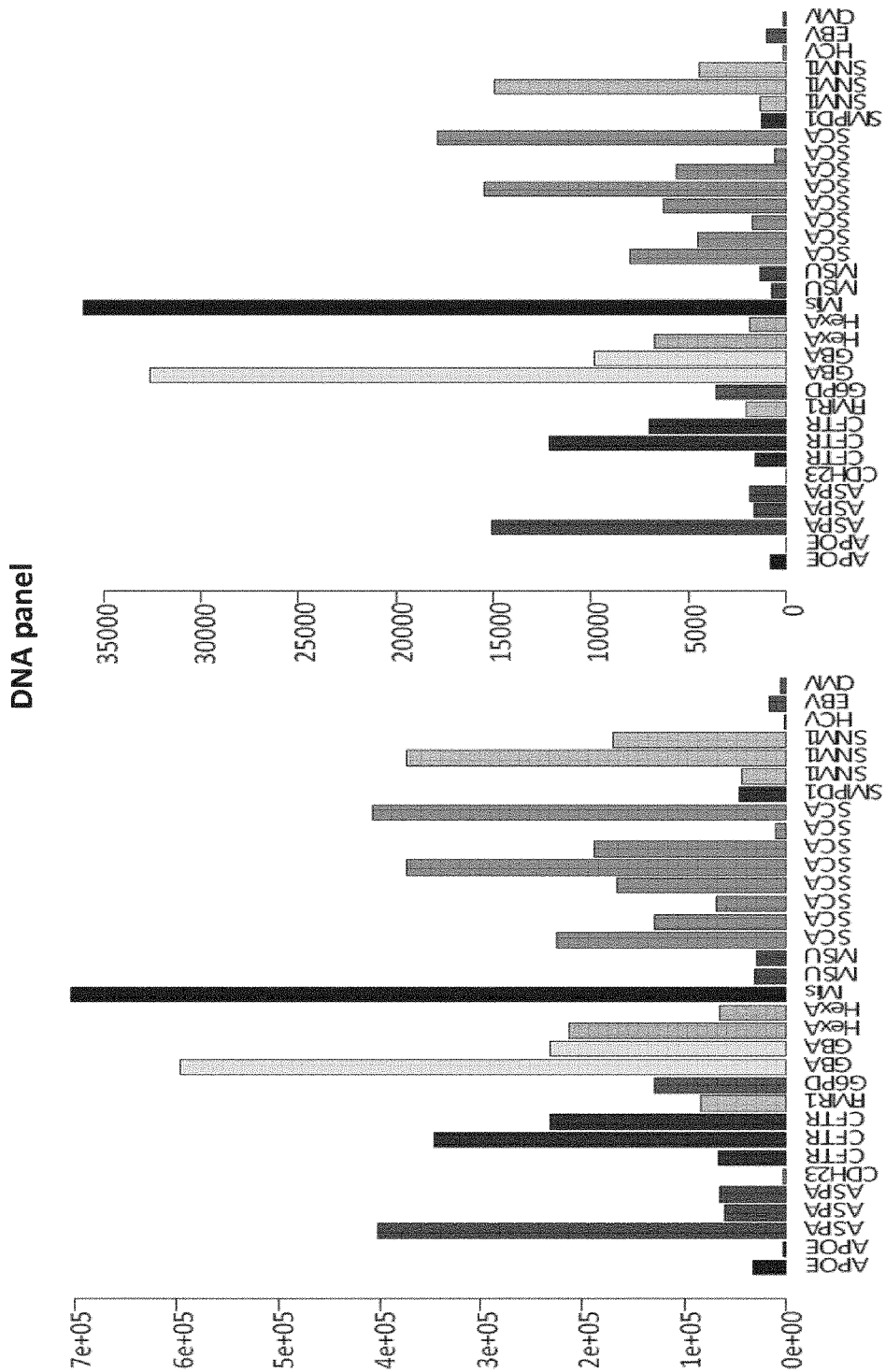
Figure 50C:
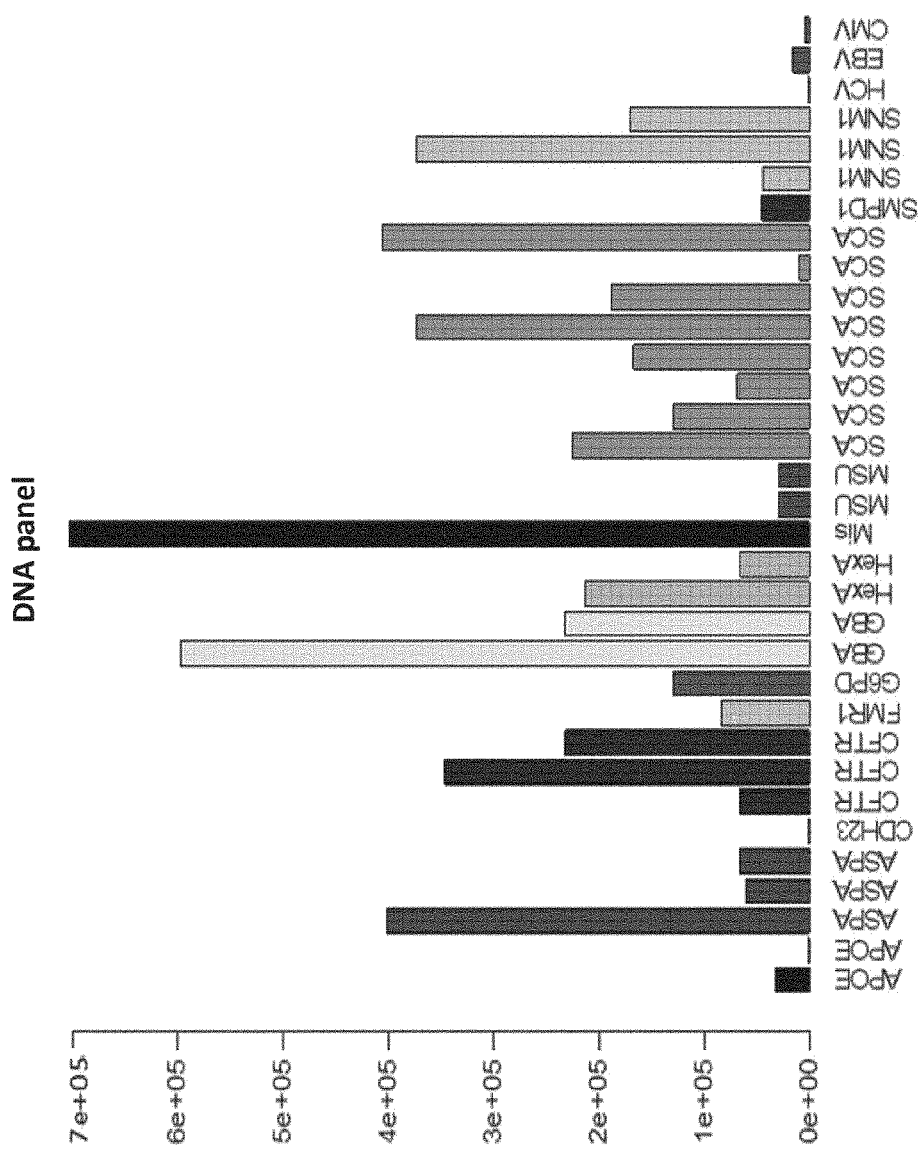
Figure 51A:
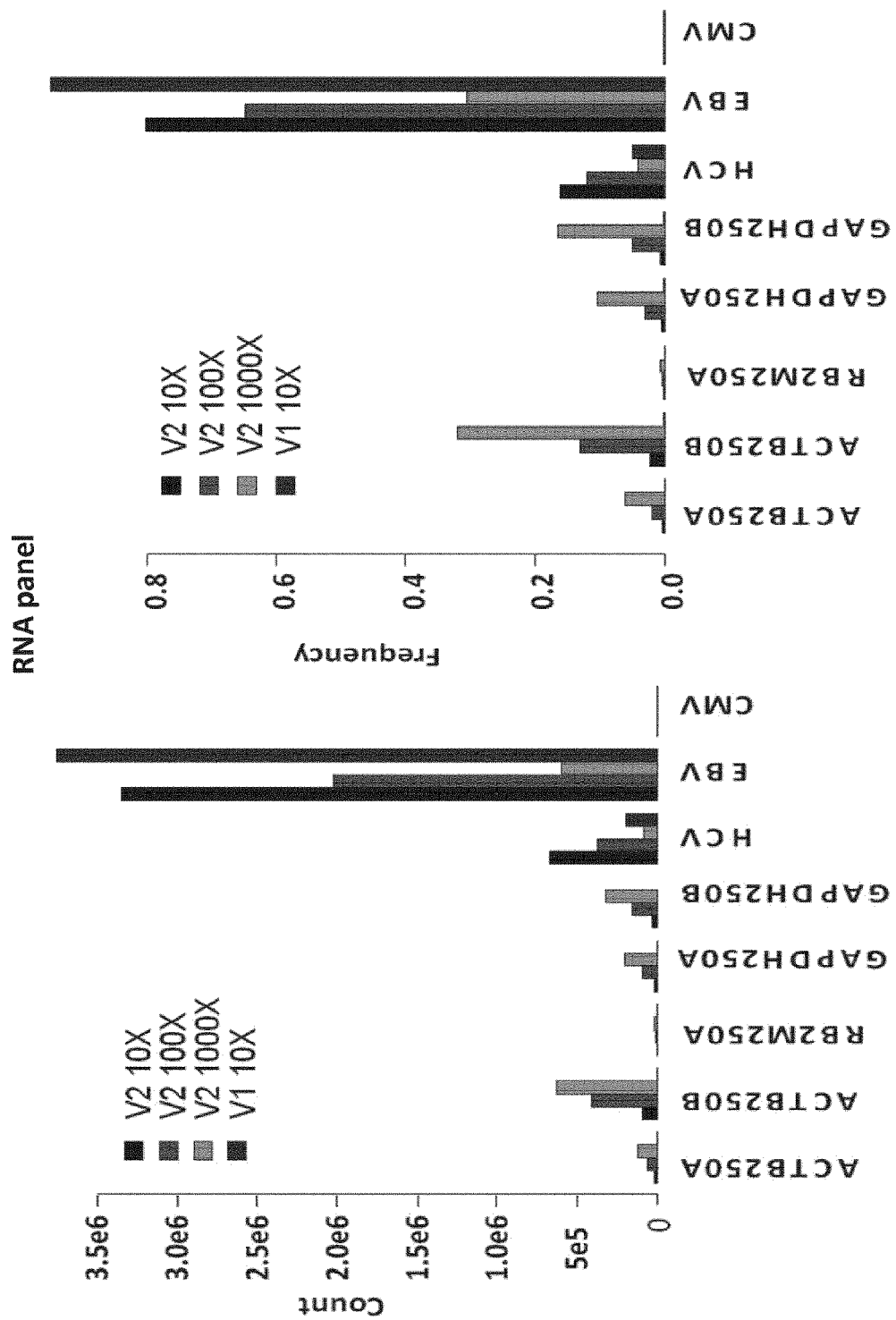
FIGS. 51A-51B depict sequencing read count of RNA targeted panels using a method of targeted sequencing with UID filtering. Each indicated gene transcript was targeted by a specific primer pair used in the preparation of the RNA sample.
Figure 51B:
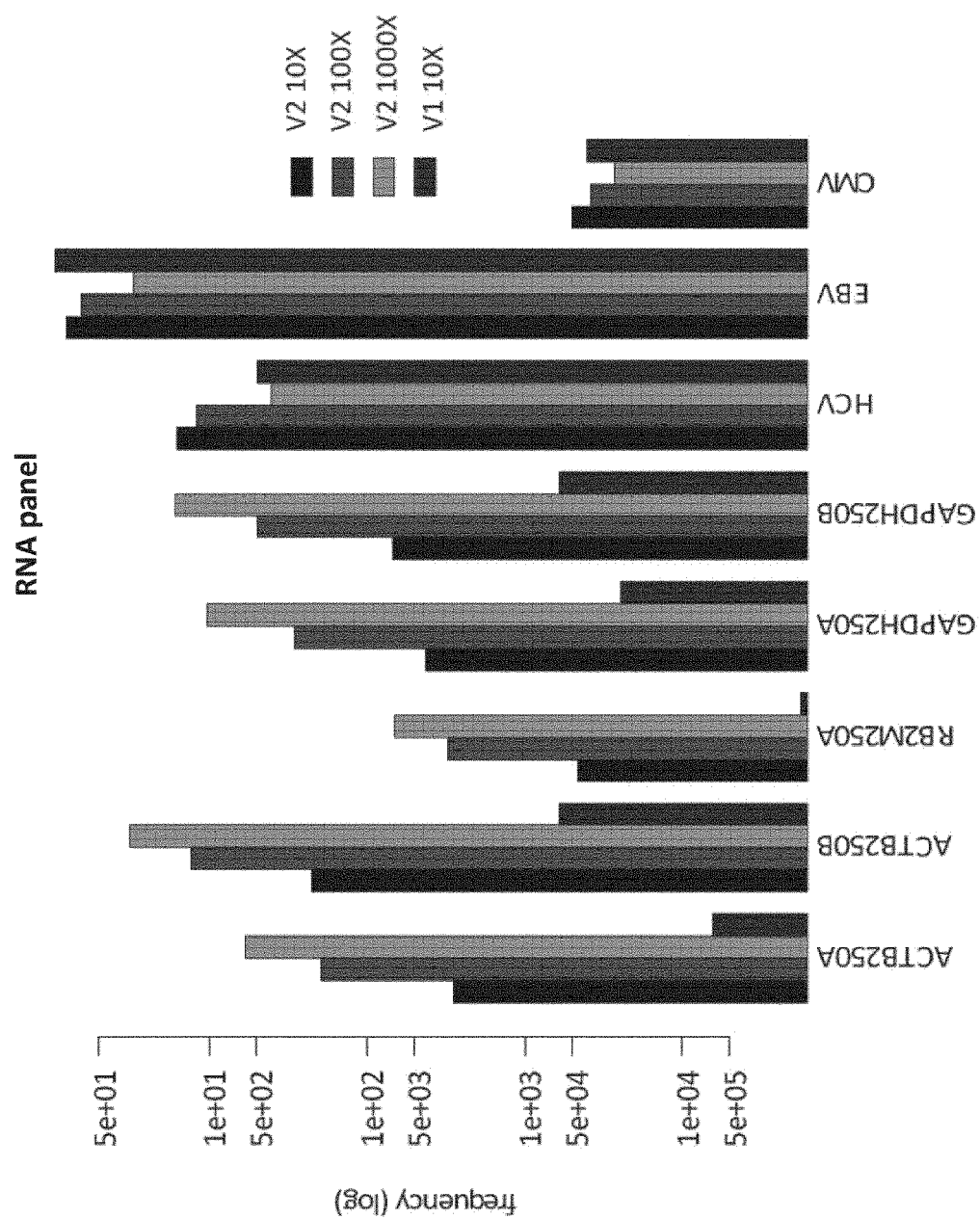
Figure 52:
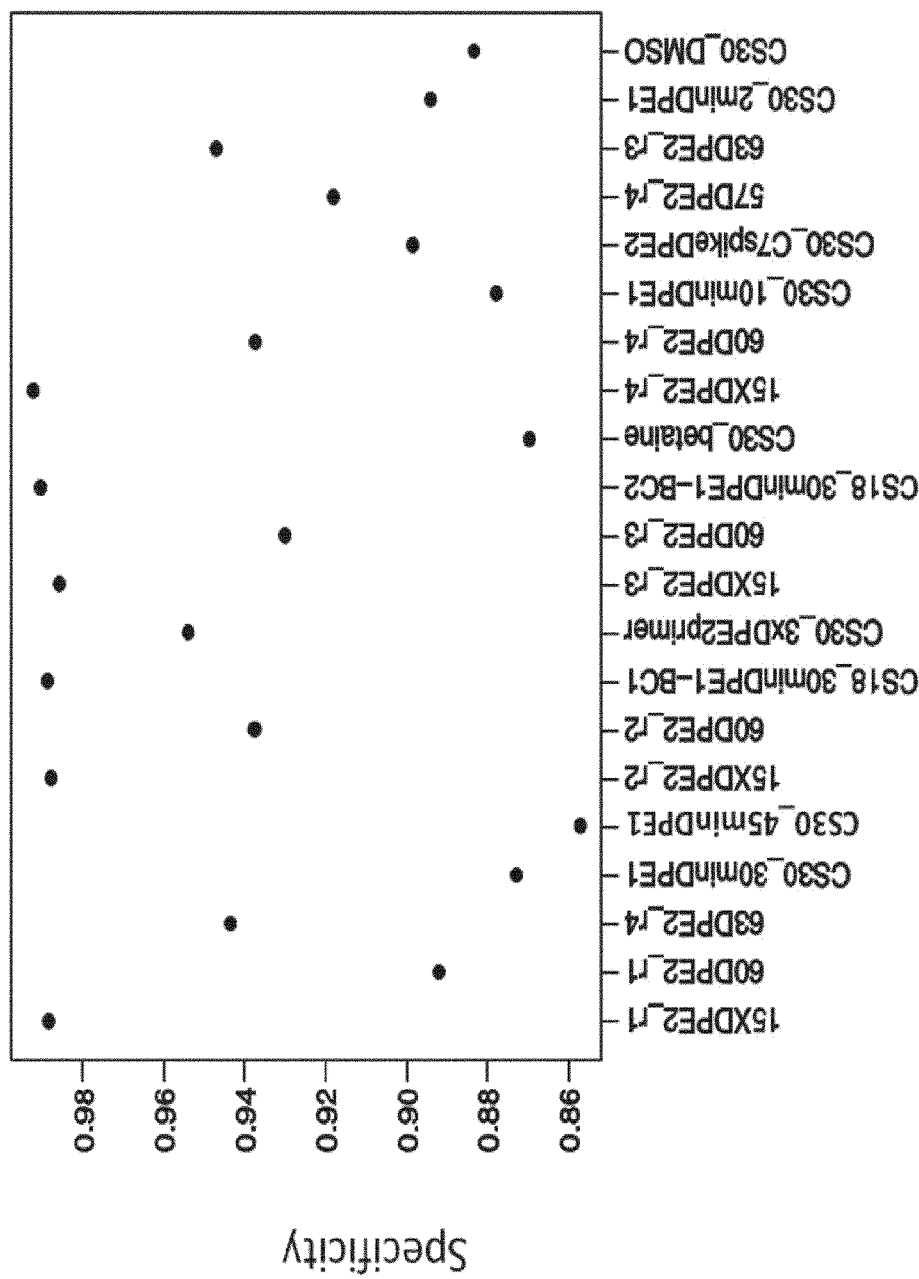
FIG. 52 depicts a plot of results from a target specificity analysis for the indicated targets and conditions using a method of targeted sequencing. Various protocol conditions were tested (number of cycles, buffers, annealing conditions, etc.). As shown, 99.2% target specificity was achieved under some conditions. (e.g., 99.2% of the sequencing reads were the desired target with minimal non-specific amplification.
Figure 53:
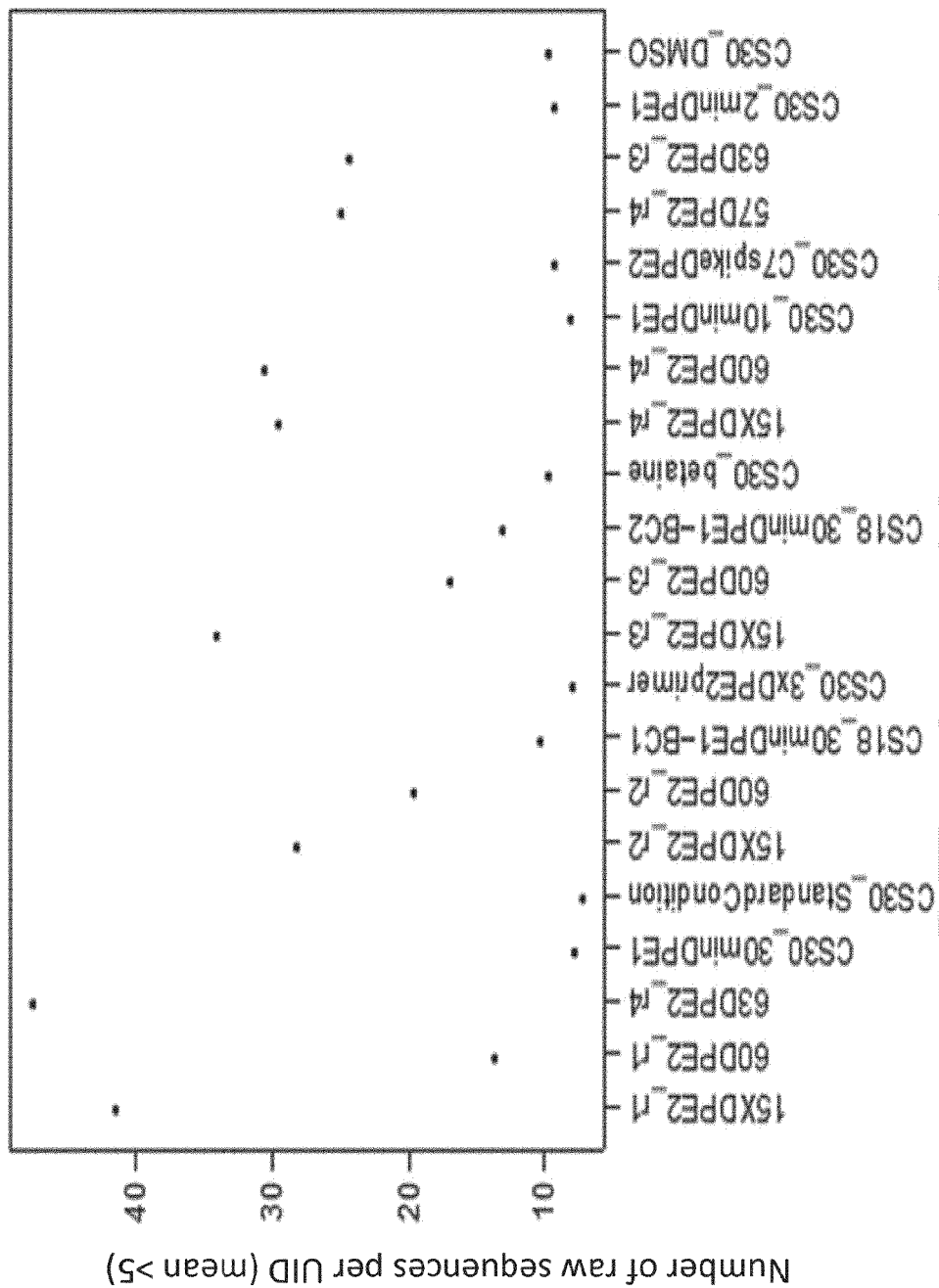
FIG. 53 depicts a plot of UID distribution for the indicated targets and conditions using a method of targeted sequencing with UID filtering. Various protocol conditions were tested (number of cycles, buffers, annealing conditions, etc.). The number of raw sequences per UID can vary depending on the conditions used.
Figure 54:
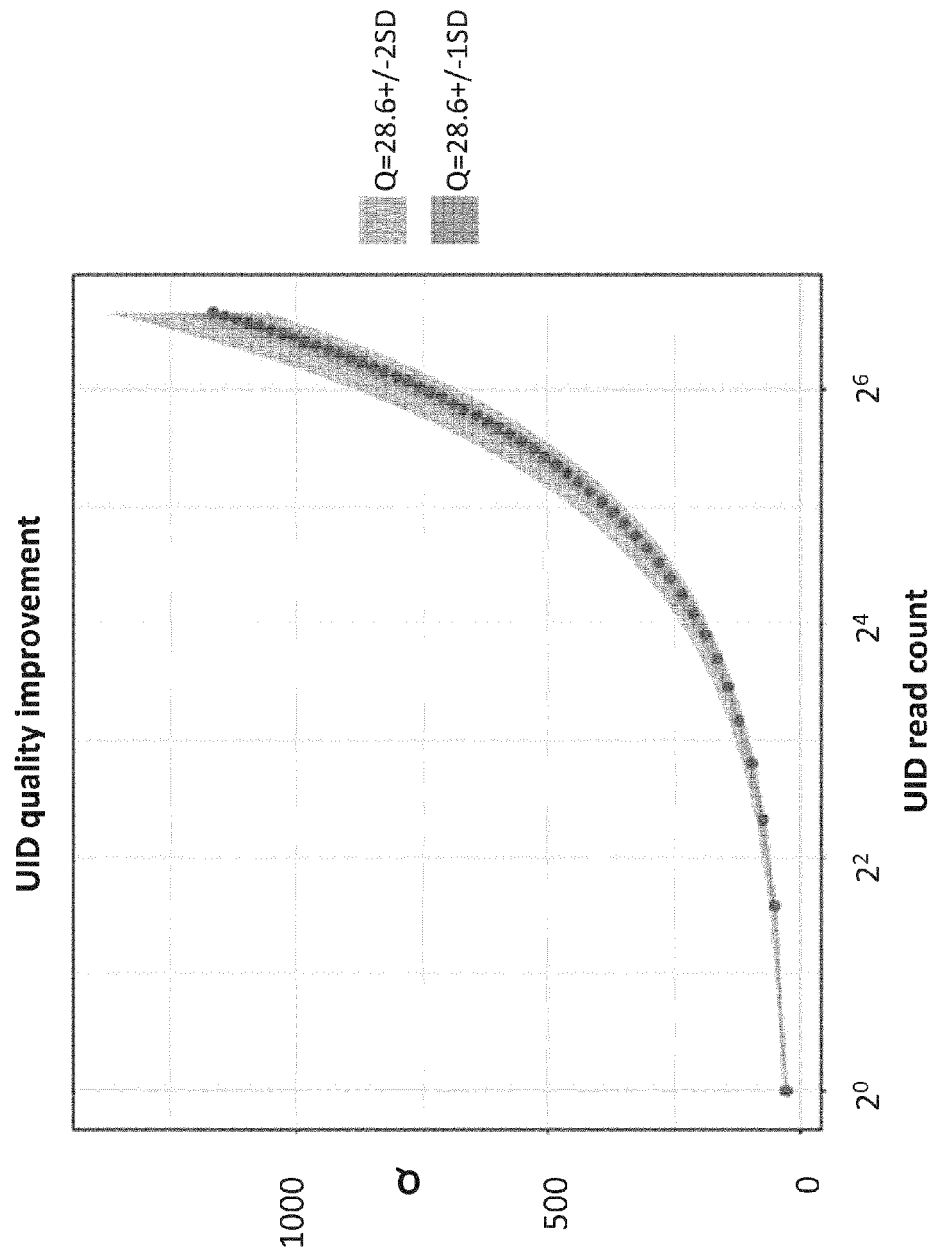
FIG. 54 depicts a plot of the putative increase in sequencing accuracy phred score (Q) in relation to the number of reads per UID sequence using a method of targeted sequencing with UID filtering.
Figure 55:
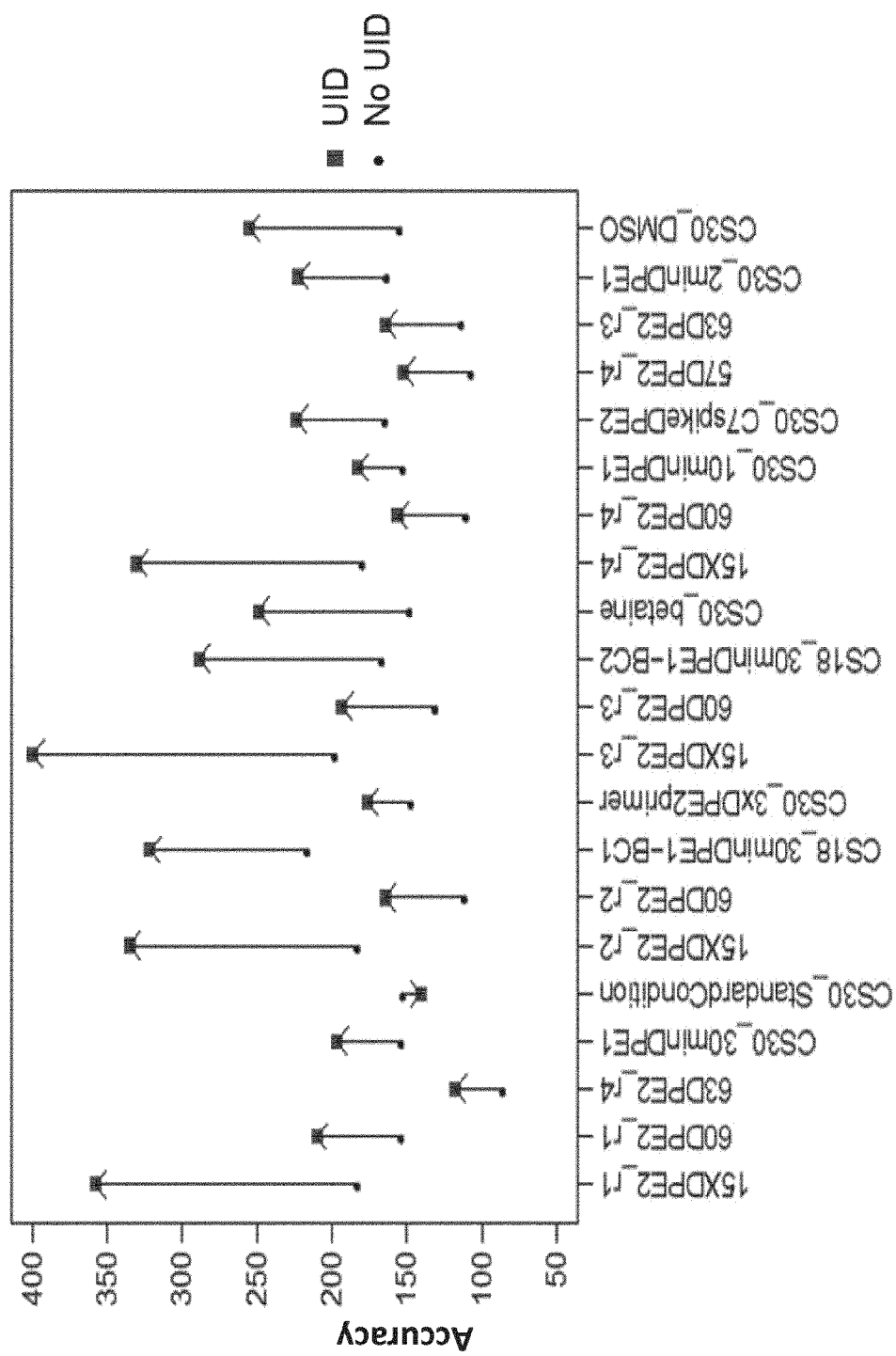
FIG. 55 depicts a plot showing accuracy improvement of each indicated target using a method of targeted sequencing when UID filtering is applied.
Figure 56:
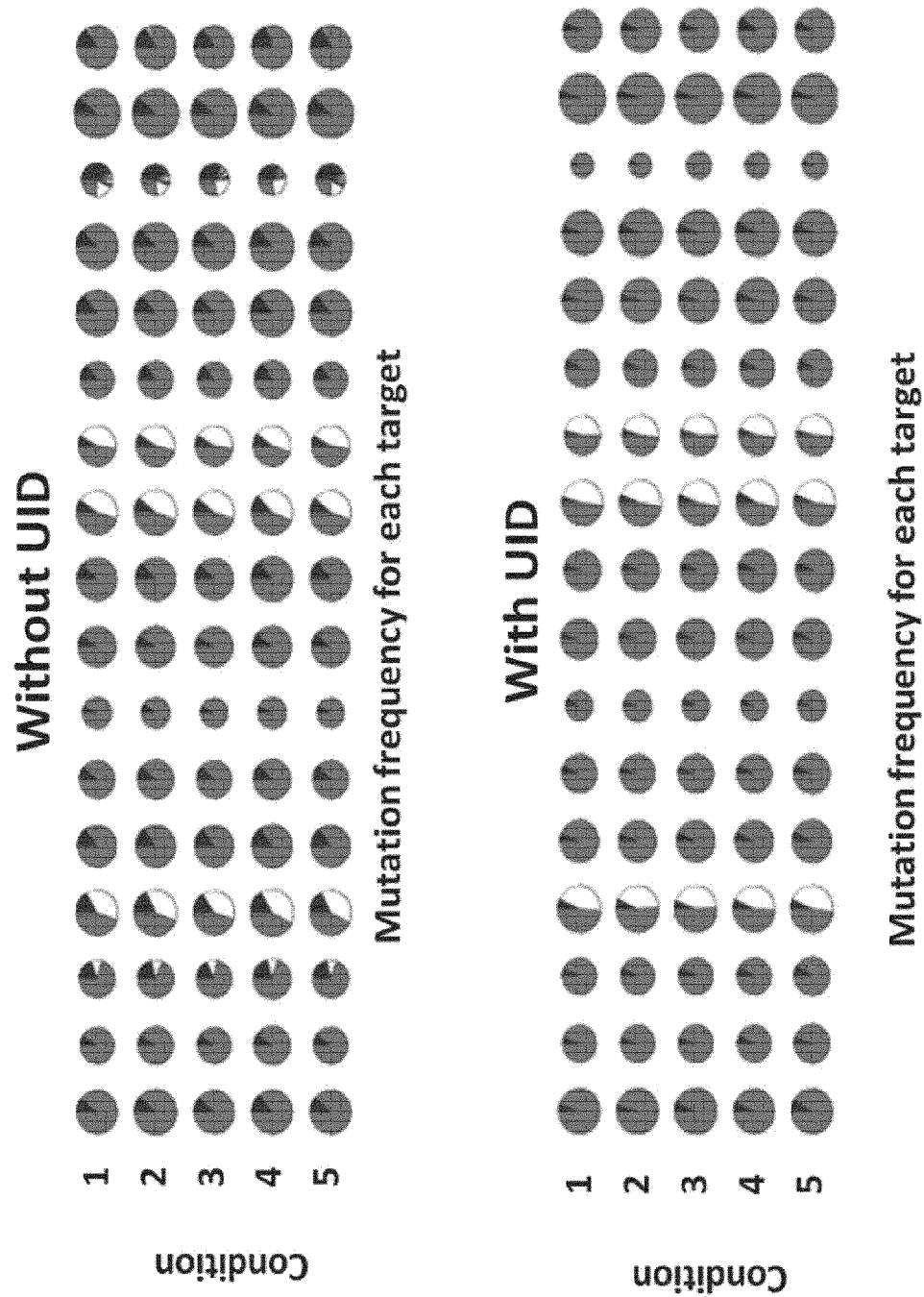
FIG. 56 depicts a chart of UID consensus analysis and accuracy of SNP genotyping analysis using a method of targeted sequencing with UID filtering. Various DNA target regions (y-axis) against various experimental conditions (x-axis) were tested. The consensus sequence for each indicated target is shown in grey, and mutation/SNPs are shown in white. Homozygous genes are dominated by grey. Heterozygous genes are indicated by about ~50% of their sequences showing a common sequence in white. Mutations and indels caused by PCR or sequencing errors are shown in black.
Figure 58:
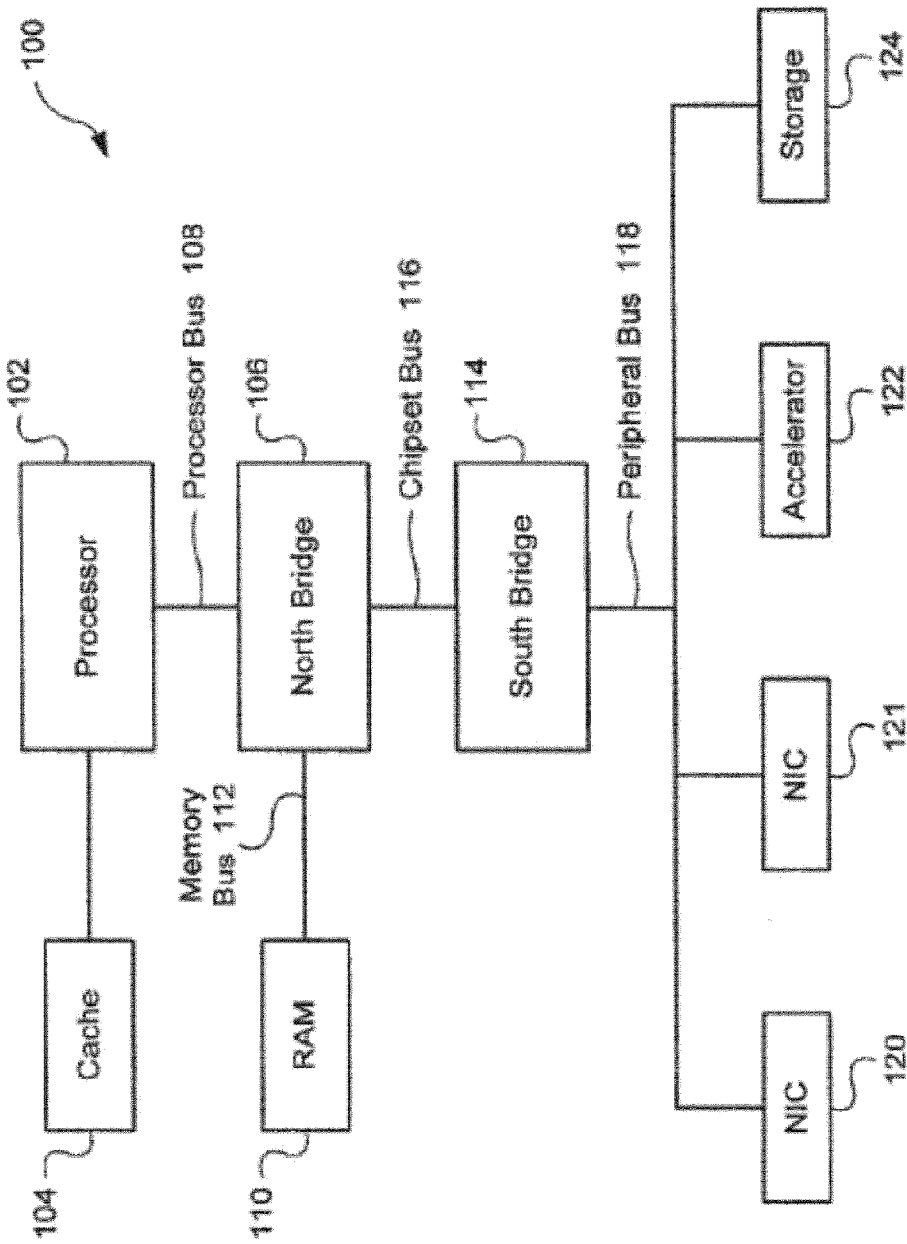

FIG. 58 is a block diagram illustrating a first example architecture of a computer system that can be used in connection with example embodiments of the present invention.

Figure 59:
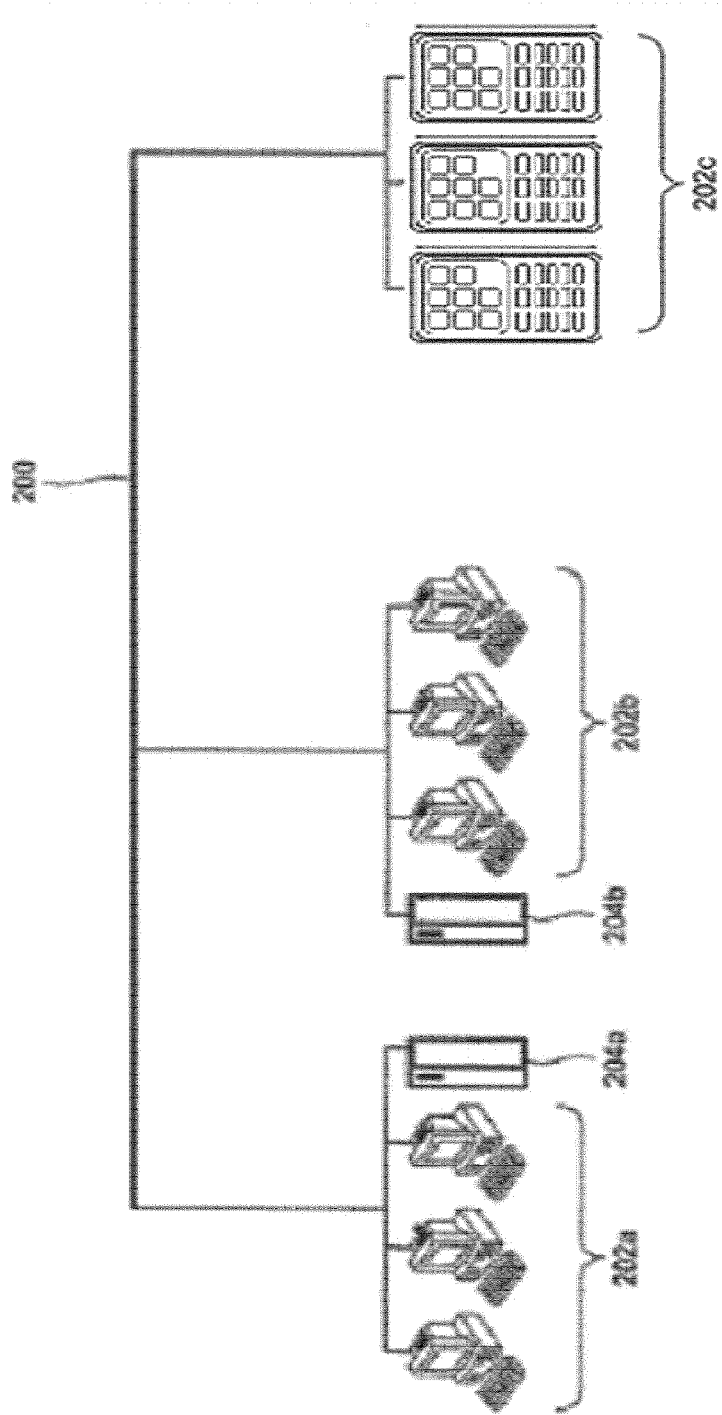

FIG. 59 is a diagram illustrating a computer network that can be used in connection with example embodiments of the present invention.

Figure 60:
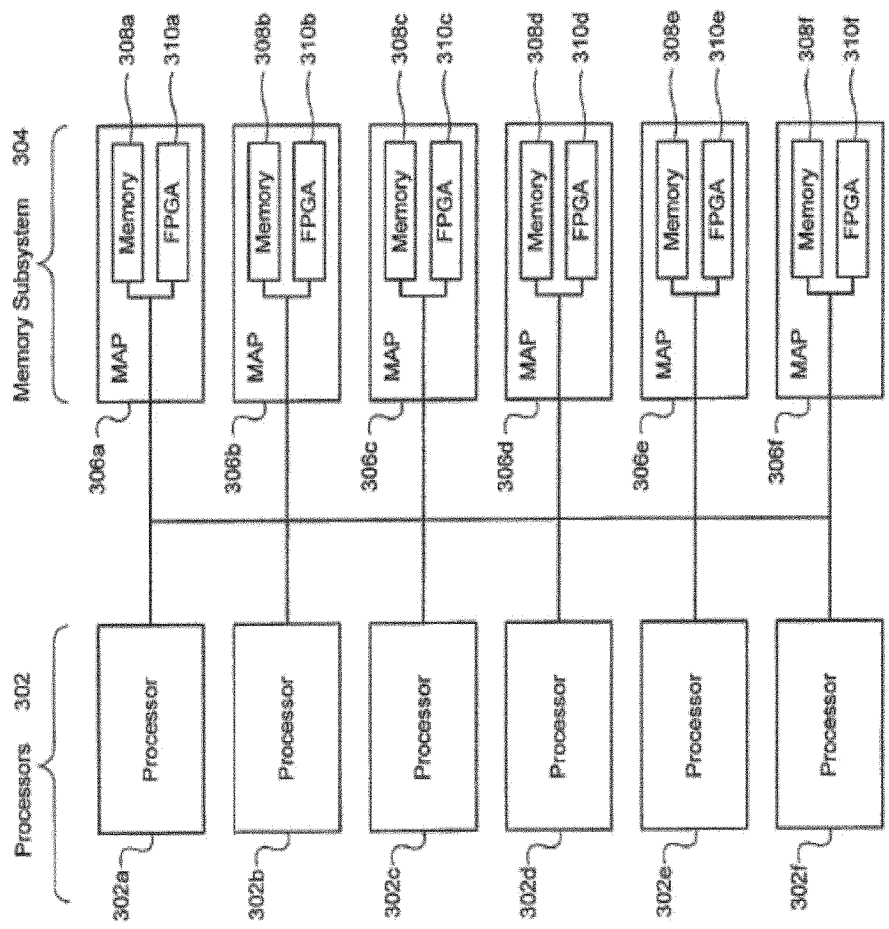

FIG. 60 is a block diagram illustrating a second example architecture of a computer system that can be used in connection with example embodiments of the present invention.

DETAILED DESCRIPTION

As used herein, amplifying comprises performing an amplification reaction. A product of a primer extension reaction can comprise the primer sequence together with the complement to the template produced during extension of the primer. In some embodiments, amplification reactions comprise extension of two primers, each hybridized to a complementary strand of a polynucleotide. Amplification of polynucleotides can be performed by any means known in the art. Polynucleotides can be amplified by polymerase chain reaction (PCR) or isothermal DNA amplification.

An amplification reaction can comprise one or more additives. In some embodiments, the one or more additives are dimethyl sulfoxide (DMSO), glycerol, betaine (mono) hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), ammonium sulfate, magnesium chloride, tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREX-CEL-Q. In some embodiments, an amplification reaction can comprise 0, 1, 2, 3, 4, 5, 6, 7, 8, 9, or 10 different additives. In other cases, an amplification reaction can comprise at least 0, 1, 2, 3, 4, 5, 6, 7, 8, 9, or 10 different additives. In some embodiments, an extension, reverse transcription or amplification reaction comprising one or more additives can be characterized by an increase As used herein, a polymerase chain reaction (PCR) comprises an in vitro amplification reaction of specific polynucleotide sequences by the simultaneous primer extension of complementary strands of a double stranded polynucleotide. PCR reactions produce copies of a template polynucleotide flanked by primer binding sites. The result, with two primers, is an exponential increase in template polynucleotide copy number of both strands with each cycle, because with each cycle both strands are replicated. The polynucleotide duplex has termini corresponding to the ends of primers used. PCR can comprise one or more repetitions of denaturing a template polynucleotide, annealing primers to primer binding sites, and extending the primers by a DNA or RNA polymerase in the presence of nucleotides. Particular temperatures, durations at each step, and rates of change between steps depend on many factors well-known to those of ordinary skill in the art. (McPherson et al., IRL Press, Oxford (1991 and 1995)). For example, in a conventional PCR using Taq DNA polymerase, a double stranded template polynucleotide can be denatured at a temperature >90° C., primers can be annealed at a temperature in the range 50-75° C., and primers can be extended at a temperature in the range 72-78° C. In some embodiments, PCR comprises Reverse transcription PCR (RT-PCR), real-time PCR, nested PCR, quantitative PCR, multiplexed PCR, or the like. In some embodiments, PCR does not comprise RT-PCR. (U.S. Pat. Nos. 5,168,038, 5,210,015, 6,174,670, 6,569,627, and 5,925,517; Mackay et al., Nucleic Acids Research, 30: 1292-1305 (2002)). RT-PCR comprises a PCR reaction preceded by a reverse transcription reaction and a resulting cDNA is amplified, Nested PCR comprises a two-stage PCR wherein an amplicon of a first PCR reaction using a first set of primers becomes the sample for a second PCR reaction using a second primer set, at least one of which binds to an interior location of an amplicon of a first PCR reaction. Multiplexed PCR comprises a PCR reaction, wherein a plurality of polynucleotide sequences is subjected to PCR in the same reaction mixture simultaneously. PCR reaction volumes can be anywhere from 0.2 nL-1000 μL. Quantitative PCR comprises a PCR reaction designed to measure an absolute or relative amount, abundance, or concentration of one or more sequences in a sample. Quantitative measurements can include comparing one or more reference sequences or standards to a polynucleotide sequence of interest. (Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989)).

As used herein, an allele can be a specific genetic sequence within a cell, individual or population that differs from other sequences of the same gene in the sequence of at least one variant site within the gene sequence. Sequences of variant sites that differ between different alleles can be variants—such as polymorphisms or mutations. Variants can comprise point mutations, polymorphisms, single nucleotide polymorphisms (SNPS), single nucleotide variations (SNVs), translocations, insertions, deletions, amplifications, inversions, interstitial deletions, copy number variations (CNVs), loss of heterozygosity, or any combination thereof. A sample is "heterozygous" at a chromosomal locus if it has two different alleles at that locus. A sample is "homozygous" at a chromosomal locus if it has two identical alleles at that locus.

In some embodiments, variants can include changes that affect a polypeptide, such as a change in expression level, sequence, function, localization, binding partners, or any combination thereof. In some embodiments, a genetic variation can be a frameshift mutation, nonsense mutation, missense mutation, neutral mutation, or silent mutation. For example, sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid, for example, if the change in the nucleic acid sequence causes a frame shift, the frame shift can result in a change in the encoded amino acids, and/or can result in the generation of a premature stop codon, causing generation of a truncated polypeptide. In some embodiments, a variant can be a synonymous change in one or more nucleotides, for example, a change that does not result in a change in the amino acid sequence. Such a polymorphism can, for example, alter splice sites, affect the stability or transport of mRNA, or otherwise affect the transcription or translation of an encoded polypeptide. In some embodiments, a synonymous mutation can result in the polypeptide product having an altered structure due to rare codon usage that impacts polypeptide folding during translation, which in some cases may alter its function and/or drug binding properties if it is a drug target. In some embodiments, the changes that can alter DNA increase the possibility that structural changes, such as amplifications or deletions, occur at the somatic level.

As used herein, a polymorphism can be an occurrence of two or more genetically determined alternative sequences or alleles in a population. A polymorphic or site comprises the locus at which divergence occurs. In some embodiments, the polymorphisms occur at a frequency of less than 0.5%, 1%, 2%, or 5%. In some embodiments, the polymorphisms occur at a frequency of greater than 1%, 5%, 10%, 20%, or 30%. In some embodiments, biomarkers have at least two alleles, each occurring at frequency of greater than 1%, 5%, 10%, or 20% in a selected population. In some embodiments, polymorphisms comprise viral or bacterial sequences and occur at a frequency of less than 0.5%, 1%, 2%, or 5% in a selected population. A polymorphism can include one or more variants including base changes, insertions, repeats, or deletions of one or more bases. Polymorphisms can include single nucleotide polymorphisms (SNPs). Copy number variants (CNVs), transversions and other rearrangements are also forms of variants. Polymorphisms include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements. The most frequent allele sequence of a selected population can be the wild type allele. Diploid organisms may be homozygous or heterozygous for alleles.

As used herein, genotyping comprises determining the genetic sequence of a subject at one or more genomic positions. For example, genotyping can include determining which allele or alleles a subject has for a single SNP or two or more SNPs. A diploid subject can be homozygous for each of the two possible alleles or heterozygous. Normal cells heterozygous at one or more loci may give rise to tumor cells homozygous at those loci. This loss of heterozygosity (LOH) can result from deletion of normal genes, loss of the chromosome carrying the normal gene, mitotic recombination, or loss of a chromosome with a normal gene and duplication of a chromosome with a deleted or inactivated gene. LOH may be copy neutral or may result from a deletion or amplification.

As used herein, a subject, individual, and patient include living organisms such as mammals Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., Xenopus), and non-mammalian invertebrates, as well as transgenic species thereof. In certain aspects, a subject refers to a single organism (e.g., human) In certain aspects, or a group of individuals composing a small cohort having either a common immune factor to study and/or disease, and/or a cohort of individuals without the disease (e.g., negative/normal control) are provided. A subject from whom samples are obtained can either be inflicted with a disease and/or disorder (e.g., one or more allergies, infections, cancers or autoimmune disorders or the like) and can be compared against a negative control subject which is not affected by the disease.

Targeted Sequencing Methods in General

The methods described here can be used for generating a library of polynucleotides for sequencing. The sequence determined for a polynucleotide in a sample can be determined with high accuracy and confidence in base calls. The methods can comprise specifically targeting, uniquely encoding, modifying, amplifying, sequencing and/or quantifying DNA or RNA sequences present in sample. These methods allow for the addition of sequences that can format a library of polynucleotide amplicons for sequencing or other molecular analyses. The sequencing library produced by these methods may incorporate a UID that can allow for binning of sequence reads derived from the same initial RNA or DNA molecule in the sample. These methods can allow a determination to be made as to whether an observed sequence variant found in a population of RNA or DNA molecules is a true polymorphism or mutation, or the observed sequence variant resulted from an amplification artifact, such as an amplification error or bias. In any of the methods described herein, it is contemplated that the UID is optional. Thus, any recitation of "UID" refers to an optional UID.

These include methods for preparing a library of polynucleotides generated using target specific primers to be sequenced on a NGS platform. Many biological targets, such as from a biological patient sample, can be analyzed from the NGS compatible library after sequencing. The methods allow for identification of target frequencies (e.g., gene expression or allelic distribution). The methods also allow for identification and mutations or SNPs in a genome or transcriptome, such as from a diseased or non-diseased subject, from which accurate sequence information can be derived. The methods also allow for determining the presence or absence of contamination or infections in a biological sample from a subject, such as by using target specific primers to foreign organisms or viruses, such as a bacteria or a fungus.

The methods described herein offer an advantageous balance of sensitivity and specificity and advantages conferred by linear primer extension reactions and/or UID-tagging. In some embodiments, the methods are designed for smaller panel sizes, such as panels of clinical interest. These methods can have very low upfront costs, can be done quickly, and are amendable to RNA or DNA targets. Furthermore, designing primers for use in these methods is not burdensome and is similar to the ease of designing primers for standard PCR reactions. The methods can be used for formatting libraries of polynucleotides for a variety of sequencing and other molecular analyses. Additionally, various applications can be performed individually or simultaneously. For example, sequencing of targets required for cancer mutation profiling, analyzing SNPs and mutations, testing for carriers, detecting infections, diagnosing diseases, and analyzing gene expression can be performed individually or simultaneously.

Initial Targeting: Forming UID-Tagged Polynucleotides Complementary to Target Polynucleotides Depending on the type of polynucleotide target to be analyzed, the methods can utilize reverse transcription (RT) or primer extension (PE). A primer extension reaction can be a single primer extension step. A primer extension reaction can comprise extending one or more individual primers once. A primer extension reaction can comprise extending one or more individual primers in one step. In some embodiments, polynucleotides complementary to DNA targets can be generated by performing primer extension reactions. For example, UID tagged polynucleotides complementary to DNA targets can be generated by performing primer extension reactions. In some embodiments, target polynucleotide complement sequences, such as UID-tagged polynucleotides complementary to RNA targets, can be generated by performing reverse transcription reactions. Target polynucleotide complement sequences, such as UID-tagged polynucleotides complementary to RNA targets can be generated by performing reverse transcription reactions. A target polynucleotide includes polynucleotides present in a sample initially.

As used herein, a "target polynucleotide complement sequence" is a polynucleotide comprising a sequence complementary to a target sequence or a complement thereof (complement of a sequence complementary to a target sequence). In some embodiments, a target polynucleotide complement sequence comprises a first complement sequence. A "first complement sequence" is a polynucleotide reverse transcribed from a target polynucleotide or formed from a primer extension reaction on a target polynucleotide. In some embodiments, a target polynucleotide complement sequence comprises a modified complement sequence. A "modified complement sequence" is a polynucleotide reverse transcribed from a target polynucleotide or formed from a primer extension reaction on a target polynucleotide, comprising an adaptor. In some embodiments, a target polynucleotide complement sequence comprises a second complement sequence. A "second complement sequence" is a polynucleotide comprising a sequence complementary to a first complement sequence or modified complement sequence. In some embodiments, a target polynucleotide complement sequence comprises a UID. For example, a first complement sequence may comprise a UID. For example, a modified complement sequence may comprise a UID. For example, a second complement sequence may comprise a UID. For example, a second complement sequence may comprise a sequence complementary to a UID from a first complement sequence or modified complement sequence. In some embodiments, a target polynucleotide complement sequence does not comprise a UID. For example, a first complement sequence may not comprise a UID. For example, a modified complement sequence may not comprise a UID. For example, a second complement sequence may not comprise a UID.

The methods can comprise an RT or PE reaction in a first step. The methods can comprise a linear primer extension reaction in a later step. A linear primer extension reaction can result in linear amplification as opposed to exponential amplification. For targeted sequencing of many polynucleotides, each individual target specific primer may have some degree of efficiency variation caused by variations in extension by various enzyme, or differences in annealing efficiency to their respective targets. This can create a bias which can be exponentially extended by PCR. The methods described herein can utilize linear primer extension to reduce or avoid this bias, resulting in a reduction or avoidance of variation frequency of the targets relative to one another and can give improved confidence and frequency or base call analysis and accuracy. The methods described herein have been found to avoid these bias issues and can maintain a true frequency representation of the starting pool of targets. In some embodiments, the only exponential amplification reaction, such as a PCR reaction, performed in the methods is at a final stage of library generation and can utilize a universal primer set. In these embodiments, all targets can be amplified uniformly during an exponential amplification step without introduction of gene specific variation or bias.

Reverse Transcription (RT of Target Polynucleotides to Form Complementary UID-Tagged Polynucleotides)

Using primers described herein, RNA polynucleotides can be reverse transcribed using suitable reagents known in the art. RNA can comprise mRNA.

In some embodiments, a method comprises reverse transcribing a target RNA polynucleotide to form cDNA using one or more primers (RT primers). In some embodiments, an RT primer comprises an oligo-dT primer or a sequence specific primer. In some embodiments, a plurality of RT primers comprises one or more oligo-dT primers or one or more sequence specific primers. In some embodiments, a reverse transcription reaction is the first step of generating a library of polynucleotides from a sample containing a target polynucleotide. In some embodiments, a target polynucleotide is not subjected to RT-PCR. In some embodiments, a target polynucleotide is not subjected to an exponential amplification. In some embodiments, exponential amplification is not performed in the next step after the reverse transcription. In some embodiments, exponential amplification is not performed in the next 2 steps after the reverse transcription. In some embodiments, exponential amplification is not performed in the next 3 steps after the reverse transcription. In some embodiments, the cDNA of the target polynucleotide produced from the reverse transcription step is not amplified further during this step. In some embodiments, the method comprises only one cycle of reverse transcription. In other embodiments, the method comprises repeatedly reverse transcribing the target RNA molecule to produce multiple cDNA molecules, such as a first complement sequence that may contain a UID.

An RT primer can further comprise a region that is not complementary to a region of the RNA. In some embodiments, the RT primers may further comprise a UID. For example, each RT primer of a plurality of RT primers can comprise a different UID. This can allow for uniquely barcoding each of the cDNAs copied from the RNA molecules being reverse transcribed. In some embodiments, the region of an RT primer that is not complementary to a region of the target RNA may comprise a UID. In some embodiments, the region of each RT primer of a plurality of RT primers that is not complementary to a region of the target RNA may comprise a UID. In some embodiments, the RT primers can further comprise a known sequence, such as a universal primer binding site or a sequence complementary to a universal priming site. In some embodiments, the RT primers can further comprise a phosphorylated 5' end. In some embodiments, the RT primers can further comprise a known sequence, such as a universal primer binding site or a sequence complementary to a universal priming site, at the 5' end. In some embodiments, the region that is not complementary to a region of the RNA is 5' to a region of the primer that is complementary to the RNA. In some embodiments, the region that is not complementary to a region of the RNA is a 5' overhang region. In some embodiments, the region that is not complementary to a region of the target RNA comprises a priming site for amplification and/or a sequencing reaction.

In some embodiments, an RT primer can comprise a universal ligation sequence. In some embodiments, the universal ligation sequence is 5' of the UID. In some embodiments, the universal ligation sequence is 5' to the target specific region. In some embodiments, the universal ligation sequence is 5' of the UID and 5' of the target specific region. In some embodiments, the universal ligation sequence is at the 5' end of the RT primer. In some embodiments, a plurality of RT primers can comprise a first RT primer with a first universal ligation sequence and one or more second RT primers comprising at least a second universal primer sequence.

Primer Extension of Single-Stranded or Double-Stranded DNA Target Polynucleotides to Form Complementary UID-Tagged Polynucleotides Using primers described herein, DNA polynucleotides can be hybridized to a primer and primer extension (gPE or PE) can be performed using suitable reagents known in the art. In some embodiments, primer extension comprises a single extension of a primer. In some embodiments, primer extension does not comprise multiple extensions of a primer. In some embodiments, primer extension does not comprise a single extension of a primer. In some embodiments, primer extension comprises multiple extensions of a primer. In some embodiments, a method comprises performing primer extension on a target DNA polynucleotide to form a target polynucleotide complement sequence, such as a first complement sequence, using one or more primers (PE primers). In some embodiments, a PE primer comprises a sequence specific primer. In some embodiments, a plurality of PE primers comprises one or more sequence specific primers. In some embodiments, a primer extension reaction is the first step of generating a library of polynucleotides from a sample containing a target polynucleotide. In some embodiments, a target polynucleotide is not subjected to PCR. In some embodiments, a target polynucleotide is not subjected to an exponential amplification. In some embodiments, exponential amplification is not performed in the next step after the primer extension. In some embodiments, exponential amplification is not performed in the next 2 steps after the primer extension. In some embodiments, exponential amplification is not performed in the next 3 steps after the primer extension. In some embodiments, the complementary polynucleotide of the target polynucleotide produced from the primer extension step is not amplified further during this step. In some embodiments, the method comprises only one cycle of primer extension. In other embodiments, the method comprises repeatedly extending or linear amplification of a primer hybridized to a target DNA molecule to produce multiple copies of the DNA molecules, such as target polynucleotide complement sequence that may contain a UID.

The one or more PE primers can comprise a region complementary to a region or sequence of a target DNA, such as a target specific region that hybridizes to a target polynucleotide, such as a biomarker. The one or more PE primers can comprise a region complementary or substantially complementary to a region of the target DNA. In some embodiments, the one or more PE primers can comprise a first PE primer with a region complementary to a sequence of a first target polynucleotide, and a second PE primer with a region complementary to sequence of a second target polynucleotide. For example the first target polynucleotide can be a first DNA molecule and the second target polynucleotide can be a second DNA molecule. In some embodiments, the one or more PE primers can comprise a first PE primer with a region complementary to a sequence of a first DNA, and one or more second PE primers each with a region complementary to a sequence of one or more second DNAs. In some embodiments, the first and second target sequences are the same. In some embodiments, the first and second target sequences are different same.

A PE primer can further comprise a region that is not complementary to a region of the DNA. The PE primers can further comprise a UID. For example, each PE primer of a plurality of PE primers can comprise a different UID. This can allow for uniquely barcoding each of the complementary DNAs copied from the DNA molecules being subjected to a primer extension reaction. In some embodiments, the region of a PE primer that is not complementary to a region of the target DNA may comprise a UID. In some embodiments, the region of each PE primer of a plurality of PE primers that is not complementary to a region of the target DNA may comprise a UID. In some embodiments, the PE primers can further comprise a known sequence, such as a universal primer binding site or a sequence complementary to a universal priming site. In some embodiments, the PE primers can further comprise a phosphorylated 5' end. In some embodiments, the PE primers can further comprise a known sequence, such as a universal primer binding site or a sequence complementary to a universal priming site, at the 5' end. In some embodiments, the region that is not complementary to a region of the DNA is 5' to a region of the primer that is complementary to the DNA. In some embodiments, the region that is not complementary to a region of the DNA is a 5' overhang region. In some embodiments, the region that is not complementary to a region of the target DNA comprises a priming site for amplification and/or a sequencing reaction.

In some embodiments, a library of PE primers can be used during the primer extension step.

In some embodiments, a PE primer can comprise a universal ligation sequence. In some embodiments, the universal ligation sequence is 5' of the UID. In some embodiments, the universal ligation sequence is 5' to the target specific region. In some embodiments, the universal ligation sequence is 5' of the UID and 5' of the target specific region. In some embodiments, the universal ligation sequence is at the 5' end of the PE primer. In some embodiments, a plurality of PE primers can comprise a first PE primer with a first universal ligation sequence and one or more second PE primers comprising at least a second universal primer sequence.

In some embodiments, an annealing temperature of 55° C. is used to accommodate lower primer melting temperatures. In some embodiments a hold step is used at 68° C. for the initial PE step. In some embodiments, the global concentration of the primers is fixed at a concentration. In some embodiments, magnesium chloride, ammonium sulfate, D-(+)-Trehalose, betaine, or a combination thereof is used during the primer extension step.

Partial Formatting of UID-Tagged Polynucleotides Complementary to Targets

After generating target polynucleotide complement sequences, for example, first complement sequences, a polynucleotide adaptor sequence can be added to the first complement sequences. A target polynucleotide complement sequence, such as first complement sequence that may contain a UID, to which an adaptor sequence has been added, can be a modified complement sequence (MCS). In some embodiments, a polynucleotide adaptor sequence can be added to target polynucleotide complement sequences, such as first complement sequences that may contain a UID, in the next step following generating target polynucleotide complement sequences. In some embodiments, a polynucleotide adaptor sequence can be added to target polynucleotide complement sequences, such as first complement sequences that may contain a UID, in the second step following generating target polynucleotide complement sequence containing UIDs. In some embodiments, a polynucleotide adaptor sequence can be added to target polynucleotide complement sequences, such as first complement sequences that may contain a UID, in the third step following generating target polynucleotide complement sequences containing UIDs. In some embodiments, a polynucleotide adaptor sequence does not contain a UID.

In some embodiments, a polynucleotide adaptor sequence can be added to target polynucleotide complement sequences, such as first complement sequences that may contain a UID, by ligation (U.S. Pat. Nos. 4,883,750, 5,476,930, 5,593,826, 5,426,180, 5,871,921; and U.S. Patent Publication No. 2004/0110213). Ligation techniques can comprise blunt-end ligation and sticky-end ligation. Ligation reactions may include DNA ligases such as DNA ligase I, DNA ligase III, DNA ligase IV, and T4 DNA ligase. Ligation reactions may include RNA ligases such as T4 RNA ligase I and T4 RNA ligase II. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3' to 5' phosphodiester bond, substrates include single-stranded RNA and DNA as well as dinucleoside pyrophosphates.

In some embodiments, a polynucleotide adaptor sequence is not added to target polynucleotide complement sequences, such as first complement sequences that may contain a UID, by ligation. In some embodiments, a polynucleotide adaptor sequence can be added to target polynucleotide complement sequences, such as first complement sequences that may contain a UID, by an amplification reaction. In some embodiments, a polynucleotide adaptor sequence can be added to target polynucleotide complement sequences, such as first complement sequences that may contain a UID, by an amplification reaction with one or more primers containing the adaptor sequence. In some embodiments, a polynucleotide adaptor sequence is not added to target polynucleotide complement sequences, such as first complement sequences that may contain a UID, by an amplification reaction. In some embodiments, a polynucleotide adaptor sequence is not added to target polynucleotide complement sequences, such as first complement sequences that may contain a UID, by an amplification reaction with one or more primers containing the adaptor sequence. In some embodiments, a polynucleotide adaptor sequence can be added to target polynucleotide complement sequences, such as second complement sequences that may contain a UID, during a PCR enrichment step as described below.

In some embodiments, a polynucleotide adaptor sequence can be added to target polynucleotide complement sequences, such as first complement sequences that may contain a UID, by ligation in the next step following generating target polynucleotide complement sequences. In some embodiments, an adaptor can be a single stranded polynucleotide. In some embodiments, an adaptor can be a double stranded polynucleotide. In some embodiments, an adaptor can be a bridge polynucleotide containing a double stranded region and a single stranded region, such as an overhang region. In some embodiments, an adaptor can be a bridge polynucleotide containing a double stranded region and a single stranded region, wherein the strand containing the single stranded region is not ligated to the target polynucleotide complement sequences, such as first complement sequences that may contain a UID. In some embodiments, an adaptor can be a bridge polynucleotide containing a double stranded region and a single stranded region, wherein the strand not containing the single stranded region is ligated to the target polynucleotide complement sequences, such as first complement sequences that may contain a UID. In some embodiments, an adaptor can be a bridge polynucleotide containing a double stranded region and a single stranded region, wherein the strand not containing a region complementary to the target polynucleotide complement sequences, such as first complement sequences that may contain a UID, is ligated to the target polynucleotide complement sequences. In some embodiments, an adaptor can be a bridge polynucleotide containing a double stranded region and a single stranded region, wherein the strand containing a region complementary to the target polynucleotide complement sequences, such as first complement sequences that may contain a UID, is not ligated to the target polynucleotide complement sequences. In some embodiments, an adaptor can be a bridge polynucleotide containing a double stranded region and a single stranded region, wherein the strand containing a region complementary to the target polynucleotide complement sequences, such as first complement sequences that may contain a UID, is hybridized to the target polynucleotide complement sequences. In some embodiments, an adaptor can be a bridge polynucleotide containing a double stranded region and a single stranded region, wherein the strand not containing a region complementary to the target polynucleotide complement sequences, such as first complement sequences that may contain a UID, is not hybridized to the target polynucleotide complement sequences.

In some embodiments, the 5' overhang region can be complementary to one or more target polynucleotide complement sequences, such as those containing UIDs. In some embodiments, the 5' overhang region can be complementary to a 5' region of one or more polynucleotide complement sequences, such as those containing UIDs. In some embodiments, the 5' overhang region can comprise a sequence complementary to a universal ligation sequence, such as a universal ligation sequence of an RT primer or a PE primer. In some embodiments, the 5' overhang region can be complementary to a 5' region of one or more target polynucleotide complement sequences, such as those containing UIDs, wherein the 5' region is 5' to the UID. In some embodiments, an adaptor can be a bridge polynucleotide containing a double stranded region and a single stranded region, such as a 5' overhang region or end. In some embodiments, an adaptor can be a bridge polynucleotide containing a double stranded region and a single stranded region, such as a 3' overhang region or end. In some embodiments, an adaptor can be a bridge polynucleotide containing a double stranded region and two single stranded regions, such as a 3' overhang region or end and a 5' overhang region or end. In some embodiments, the 5' overhang region can be complementary to a 5' region of one or more target polynucleotide complement sequences, such as those containing UIDs, wherein the adaptor can be ligated to the one or more target polynucleotide complement sequences, such as those containing UIDs when hybridized. In some embodiments, the 5' overhang region can be complementary to a 5' region of one or more target polynucleotide complement sequences, such as those containing UIDs, wherein the adaptor can be in close proximity, or next to, the 5' end one or more target polynucleotide complement sequences containing UIDs when hybridized. In some embodiments, the 5' overhang region can be complementary to a 5' region of one or more target polynucleotide complement sequences, such as those containing UIDs, wherein the adaptor can be in close proximity, or next to, the 5' phosphate end one or more target polynucleotide complement sequences, such as those containing UIDs, when hybridized. In some embodiments, the 5' overhang region can be the same length, or substantially the same length, as the sequence to which it is complementary on the one or more target polynucleotide complement sequences, such as those containing UIDs.

In some embodiments, a polynucleotide adaptor sequence comprising a primer binding site, or complement of a primer binding site, can be added to the target polynucleotide complement sequences, such as first complement sequences that may contain a UID. In some embodiments, a target polynucleotide complement sequences, such as first complement sequences that may contain a UID, containing a first primer binding site of a primer binding set, such as for exponential amplification or sequencing, can be a partially formatted target polynucleotide complement sequence, such as a modified complement sequence that may contain a UID. In some embodiments, a target polynucleotide complement sequence, such as a first complement sequence, containing a first primer binding site of a first primer set and a first primer binding site of a second primer binding set, such as for exponential amplification or sequencing, can be a fully formatted target polynucleotide complement sequence, such as a modified complement sequence that may contain a UID. In some embodiments, the primer binding site or complement thereof is added to each of a plurality of target polynucleotide complement sequences, such as first complement sequences that may contain a UID. In some embodiments, the primer binding site or complement thereof added to each of a plurality of target polynucleotide complement sequences, such as first complement sequences that may contain a UID, is the same sequence. In some embodiments, the primer binding site or complement thereof added to each of a plurality of target polynucleotide complement sequences, such as first complement sequences that may contain a UID, is a different sequence. In some embodiments, the primer binding site or complement thereof added to each of a plurality of target polynucleotide complement sequences in a first amplicon or amplicon set is the same sequence as a primer binding site or complement thereof added to each of a plurality of target polynucleotide complement sequences, in a second amplicon or amplicon set. As used herein, an amplicon comprises a polynucleotide product of an amplification reaction. An amplicon set comprises a clonal population of polynucleotides produced from an amplification reaction. In some embodiments, amplicon sets are formed by the amplification of a single starting sequence. In some embodiments, an amplicon set comprises a population of polynucleotides derived from a single polynucleotide in an amplification reaction. In some embodiments, an amplicon set comprises a population of polynucleotides derived from a single polynucleotide or amplicons of that polynucleotide in an amplification reaction. Amplicons may be produced by a variety of amplification reactions. Amplicons can comprise copies of one or more nucleic acids. In some embodiments, amplicons or amplicon sets are produced by PCR. In some embodiments, amplicons or amplicon sets are not produced by PCR.

In some embodiments, the primer binding site or complement thereof added to each of a plurality of target polynucleotide complement sequences in a first amplicon or amplicon set is a different sequence than a primer binding site or complement thereof added to each of a plurality of target polynucleotide complement sequences, in a second amplicon or amplicon set. In some embodiments, the primer binding site or complement thereof added to each of a plurality of UID-containing polynucleotides from a first sample is a different sequence than a primer binding site or complement thereof added to each of a plurality of target polynucleotide complement sequences, from a second sample. In some embodiments, the primer binding site or complement thereof added to each of a plurality of target polynucleotide complement sequences, from a first sample is the same sequence as a primer binding site or complement thereof added to each of a plurality of target polynucleotide complement sequences, from a second sample. In some embodiments, the primer binding site or complement thereof comprises a known sequence. In some embodiments, the primer binding site or complement thereof comprises a primer binding site for amplification. In some embodiments, the primer binding site or complement thereof comprises a universal priming sequence. In some embodiments, the primer binding site or complement thereof comprises a first primer binding for a first primer of a primer set. In some embodiments, the primer binding site or complement thereof comprises a first primer binding for performing an exponential amplification reaction, such as PCR, for example, to be used in a PCR enrichment step as described below. In some embodiments, the primer binding site or complement thereof comprises a first primer binding for performing a non-exponential amplification reaction. In some embodiments, the primer binding site or complement thereof comprises a primer binding site for sequencing. In some embodiments, the primer binding site or complement thereof comprises a primer binding site for analysis.

In some embodiments, a polynucleotide adaptor sequence further comprises a sample barcode sequence (SBC). In the methods described, sample barcoding on a generic adaptor sequence can eliminate the need for multiple probe sets for each UID employed. As used herein, a sample barcode (SBC) on a polynucleotide comprises a sequence that can be used to identify a source from which a polynucleotide is derived. For example, a nucleic acid sample may be a pool of polynucleotides derived from a plurality of different samples, (e.g., polynucleotides derived from different individuals, different tissues or cells, or polynucleotides isolated at different times points), where the polynucleotides from each different sample of the plurality are tagged with a unique SBC. Thus, an SBC provides a correlation between a polynucleotide and its source. (U.S. Pat. Nos. 7,537,897, 7,544,473, and 7,393,665). In some embodiments, the same SBC may be used to tag a different sample being processed in a different experiment. In some embodiments, a different SBC may be used to tag each different sample or a subset of samples being processed in an experiment. For example, samples from one or more subjects with a disease or condition can have a first SBC and samples from one or more subjects without a disease or condition can have a second, different SBC. For example, different samples derived from the same sample can be tagged with different SBCs.

In some embodiments, a polynucleotide adaptor sequence further comprises an SBC or complement thereof that is between a primer binding site sequence or complement thereof of the adaptor, and a region of the adaptor, such as a 5' overhang region that is complementary to a sequence of the one or more target polynucleotide complement sequences. In some embodiments, a polynucleotide adaptor sequence further comprises an SBC, wherein the SBC is within a duplexed region of the adaptor. In some embodiments, a polynucleotide adaptor sequence further comprises an SBC, wherein the SBC is not within a duplexed region of the adaptor. In some embodiments, a polynucleotide adaptor sequence further comprises an SBC, wherein the SBC is within a single stranded region of the adaptor. In some embodiments, a polynucleotide adaptor sequence further comprises an SBC, wherein the SBC is on a different strand than the strand containing a region of complementarity to the one or more target polynucleotide complement sequences, such as a 5' overhang region. In some embodiments, a polynucleotide adaptor sequence further comprises an SBC, wherein the SBC is on the same strand as the strand containing a region of complementarity, such as a 5' overhang region, to the one or more target polynucleotide complement sequences, such as first complement sequences. In some embodiments, a polynucleotide adaptor sequence further comprises an SBC, wherein the SBC is on the strand not containing a region of complementarity, such as a 5' overhang region, to the one or more target polynucleotide complement sequences, such as first complement sequences. In some embodiments, the primer binding site or complement thereof added to a plurality of target polynucleotide complement sequences, such as first complement sequences, is 5' to an SBC sequence of the adaptor. In some embodiments, the primer binding site or complement thereof added to a plurality of target polynucleotide complement sequences, such as first complement sequences, is 3' to an SBC sequence of the adaptor.

A method may further comprise combining a first and a second sample prior to conducting any of the one or more reactions. In some embodiments, a method further comprises combining polynucleotides generated from a first and a second sample. In some embodiments, a method further comprises combining polynucleotides generated from a first and a second sample after performing a primer extension reaction. In some embodiments, a method further comprises combining polynucleotides generated from a first and a second sample after attaching an adaptor to polynucleotides in the first or second sample. In some embodiments, a method further comprises combining polynucleotides generated from a first and a second sample after attaching an adaptor comprising a SBC to polynucleotides in the first or second sample. In some embodiments, a method further comprises combining target polynucleotide complement sequences, generated from a first and a second sample. In some embodiments, a method further comprises combining polynucleotides generated from a first and a second sample comprising one or more primer binding sites, such as one or more universal primer binding sites. In some embodiments, a method further comprises combining polynucleotides generated from a first and a second sample after performing an exponential amplification of the polynucleotides in the first and/or second samples. In some embodiments, the sample origin of the polynucleotides originating from a first sample and a second sample can be determined using an SBC. In some embodiments, the sample origin of the polynucleotides originating from a first sample and a second sample can be determined using a UID. The sample origin of the polynucleotides originating from a first sample and a second sample can be determined using a primer binding site sequence. The sample origin of the polynucleotides originating from a first sample and a second sample can be determined using a target specific sequence.

Optional Clean-Up

In some embodiments, a method further comprises optionally purifying one or more of the adaptor tagged polynucleotides, such as modified complement sequences that may contain a UID. In some embodiments, the adaptor added to a plurality of target polynucleotide complement sequences, such as first complement sequences, comprises an affinity tag. An affinity tag can be bound to a binding partner and molecules that do not bind to the binding partner (e.g., molecules without the affinity tag) can be washed away, or the affinity tagged molecules can be isolated from molecules without an affinity tag. In some embodiments, an affinity tag can be a first molecule that binds specifically to a second molecule. In some embodiments, the affinity tag can be a known nucleotide sequence. In some embodiments, the affinity tag can be a chemical moiety. In some embodiments, the affinity tag can be biotin or streptavidin. In some embodiments, the affinity tag can be a peptide or protein, such as an antibody. Thus, the adaptor can comprise a protein-nucleic acid complex. Any affinity tag known in the art can be used. In some embodiments, the affinity tag can be used to purify the adaptor modified (e.g., ligated or amplified) target polynucleotide complement sequences, such as modified complement sequences that may contain a UID, from one or more other polynucleotides. A support or surface containing one or more immobilized polynucleotide, chemical, or proteinaceous molecules that bind to an affinity tag can be used. For example, the affinity tag can be used to purify the adaptor target polynucleotide complement sequences, such as modified complement sequences that may contain a UID, from one or more other polynucleotides by binding a biotin of the adaptor modified target polynucleotide complement sequences to a surface or substrate comprising a streptavidin moiety. As used herein, immobilization comprises direct or indirect attachment to a solid support through one or more covalent or non-covalent bonds. In some embodiments, immobilization comprises direct or indirect attachment to a solid support by hybridization. In some embodiments, the affinity tag can be used to purify the adaptor target polynucleotide complement sequences, such as modified complement sequences that may contain a UID, from one or more polynucleotide sequences that are not of interest, such as a non-target polynucleotide. In some embodiments, the affinity tag can be used to purify the adaptor target polynucleotide complement sequences, such as modified complement sequences that may contain a UID, from one or more primers used in a previous reaction or method step. In some embodiments, the affinity tag can be used to purify the adaptor target polynucleotide complement sequences, such as modified complement sequences that may contain a UID, from one or more primers used in a previous reaction or method step, or from one or more polynucleotide sequences that are not of interest, such as a non-target polynucleotide. In some embodiments, an affinity tag is not used in the methods described. For example, in some embodiments, an adaptor does not comprise an affinity tag. For example, in some embodiments, an affinity tag is not used in the methods described when the target molecule is RNA.

Linear Primer Extension/Linear Amplification

A method can further comprise performing a second single round of primer extension or linear primer extension (also called linear amplification). In some embodiments, one or more primers used for the linear extension/amplification are isolated into one or more separate reactions from the one or more RT or PE primers used in the reverse transcription or primer extension step. By separating the primer pairs in this manner, unwanted primer interactions can be reduced As used herein, linear amplification or linear primer extension refers to a process of non-exponential extension of product copy number. In some embodiments, only the template strand is replicated during each cycle of a linear amplification. In some embodiments, the primer extension itself is not copied during linear amplification. When a single unpaired primer is used in place of two primers, the result is a linear growth in extension product copy number instead of an exponential growth of both strands as in PCR.

Using primers described herein, DNA polynucleotides produced from one or more of the above methods or method steps can be hybridized to a primer (LPE primer) and linear primer extension can be performed using suitable reagents known in the art. For example, one or more target polynucleotide complement sequences, such as modified complement sequences that may contain a UID, can be hybridized to an LPE primer and linear primer extension can be performed. For example, one or more target polynucleotide complement sequences, such as first complement sequences that may contain a UID, to which an adaptor has been added, such as by ligation or amplification, can be hybridized to an LPE primer and linear primer extension can be performed. In some embodiments, an LPE comprises a UID. In some embodiments, an LPE comprises a UID, and an RT or PE primer does not contain a UID. In some embodiments, an LPE comprises a UID, and an RT or PE primer comprises a UID. In some embodiments, an LPE and an RT primer comprise a UID, and a PE primer does not contain a UID. In some embodiments, an LPE and a PE primer comprise a UID, and an RT primer does not contain a UID.

In some embodiments, linear primer extension comprises multiple extensions of an LPE primer. In some embodiments, linear primer extension comprises multiple extensions of each LPE primer in a plurality of LPE primers. In some embodiments, linear primer extension comprises multiple extensions of each LPE primer in a plurality of LPE primers, wherein each LPE primer in the plurality targets a different polynucleotide. In some embodiments, linear primer extension comprises multiple extensions of each LPE primer in a plurality of LPE primers, wherein each LPE primer in the plurality targets the same polynucleotide. In some embodiments, a second round of primer extension comprises a single extension of an LPE primer. In some embodiments, linear primer extension does not comprise multiple extensions of a primer. In some embodiments, a method comprises performing linear primer extension on one or more target polynucleotide complement sequences, such as modified complement sequences that may contain a UID, comprising an adaptor, to form a complementary polynucleotide, such as DNA, using one or more primers (LPE primers). In some embodiments, a method comprises performing linear primer extension on one or more target polynucleotide complement sequences, wherein the one or more target polynucleotide complement sequences do not comprise an adaptor, such as first complement sequences that may contain a UID. In some embodiments, a LPE primer comprises a sequence specific primer. In some embodiments, a plurality of LPE primers comprises one or more sequence specific primers. In some embodiments, a linear primer extension reaction is the first, second, third, or fourth step of generating a library of polynucleotides from a sample containing a target polynucleotide. In some embodiments, a linear primer extension reaction is the third step of generating a library of polynucleotides from a sample containing a target polynucleotide. In some embodiments, a linear primer extension reaction is the fourth step of generating a library of polynucleotides from a sample containing a target polynucleotide. In some embodiments, a linear primer extension reaction is performed after an RT or PE reaction. In some embodiments, a linear primer extension reaction is performed after a reaction that adds an adaptor to a target polynucleotide complement sequence, such as a first complement sequence that may contain a UID. In some embodiments, a linear primer extension reaction is performed after an RT or PE reaction and after a reaction that adds an adaptor to a target polynucleotide complement sequence, such as a first complement sequence that may contain a UID. In some embodiments, a linear primer extension reaction is performed prior to performing an exponential amplification reaction, such as PCR. In some embodiments, exponential amplification is performed in the next step after the linear primer extension. In some embodiments, exponential amplification is not performed in the next step after the linear primer extension. In some embodiments, exponential amplification is not performed in the next 2 steps after the linear primer extension. In some embodiments, exponential amplification is not performed in the next 3 steps after the linear primer extension. In some embodiments, a complementary polynucleotide of the target polynucleotide complement sequence, such as a second complement sequence that may contain a UID, produced from the linear primer extension step is not amplified further after this step. In some embodiments, the method comprises only one cycle of linear primer extension. In other embodiments, the method comprises repeatedly extending a primer hybridized to a target polynucleotide complement sequence to produce multiple copies of the target polynucleotide complement sequences, such as second complement sequences that may contain a UID. The methods can comprise conducting at least about 1, 2, 3, 4, 5, 6, 7, 8, 9, 10, 11, 12, 13, 14, 15, 16, 17, 18, 19, or 20 linear primer extension reactions or linear primer extension cycles. In some embodiments, less sample input can be used in the methods using linear amplification/extension as described herein than a similar method employing a non-linear amplification step. In some embodiments, fewer PCR cycles can be used in the methods using linear amplification/extension as described herein than a similar method employing a non-linear amplification step. For example, 20 PCR cycles can be sufficient for the methods using linear amplification/extension, while 24 PCR cycles may be required for a similar method employing a non-linear amplification step.

The one or more LPE primers can comprise a sequence complementary to a sequence, or complement sequence of a target polynucleotide complement sequence, such as a first complement sequence or modified complement sequence. For example, the one or more LPE primers can comprise a sequence complementary to a sequence, or complement sequence of a target polynucleotide complement sequence, such as a first complement sequence or modified complement sequence or a target polynucleotide in an initial sample. For example, the one or more LPE primers can comprise a sequence complementary to a sequence or complement sequence of a target polynucleotide complement sequence, such as a first complement sequence or modified complement sequence that is a product of an amplification reaction, ligation reaction, primer extension, or combinations thereof.

In some embodiments, the one or more LPE primers comprise a sequence complementary to a complement sequence of a target polynucleotide. In some embodiments, the one or more LPE primers comprise a sequence complementary to a sequence of a target polynucleotide complement sequence, such as a first complement sequence or modified complement sequence. In some embodiments, the one or more LPE primers comprise a first sequence complementary to a complement sequence of a target polynucleotide and second sequence complementary to a sequence of a target polynucleotide complement sequence, such as a first complement sequence or modified complement sequence. In some embodiments, the first and second sequences are the same sequence. In some embodiments, the first and second sequences are different sequences. In some embodiments, the sequence complementary to a target polynucleotide complement sequence, such as a first complement sequence or modified complement sequence, of one or more LPE primers is not complementary to a target sequence. In some embodiments, the sequence complementary to a UID containing polynucleotide of one or more LPE primers is not complementary to any polynucleotide that does not contain an UID. In some embodiments, the sequences complementary to a target polynucleotide complement sequence, such as a first complement sequence or modified complement sequence, of one or more LPE primers are not complementary to any other polynucleotide in a sample.

In some embodiments, the target polynucleotide complement sequence is a single stranded polynucleotide. In some embodiments, the target polynucleotide complement sequence is a double stranded polynucleotide. In some embodiments, the target polynucleotide complement sequence, such as a first complement sequence is an extension product from a PE or RT reaction. In some embodiments, the target polynucleotide complement sequence further comprises an adaptor sequence, such as a ligated adaptor sequence or modified complement sequence. In some embodiments, the target polynucleotide complement sequence, is an extension product from a PE or RT reaction further comprising an adaptor sequence, such as a modified complement sequence. In some embodiments, the target polynucleotide complement sequence is an extension product from a PE or RT reaction further comprising a first primer site, such as a PCR, sequencing, or universal priming site. In some embodiments, the target polynucleotide complement sequence, such as a first, second, or modified complement sequence is immobilized on a substrate or surface. In some embodiments, the target polynucleotide complement sequence, such as a first or modified complement sequence, comprises a SBC.

In some embodiments, the sequence complementary to a target polynucleotide complement sequence, such as a first or modified complement sequence of one or more LPE primers is not a sequence complementary to a first strand of any target polynucleotide. In some embodiments, the sequence complementary to a target polynucleotide complement sequence, such as a first or modified complement sequence, of one or more LPE primers is complementary to a sequence generated during an RT or PE reaction. In some embodiments, the sequence complementary to a target polynucleotide complement sequence, such as a first or modified complement sequence, of one or more LPE primers is complementary to a complement sequence of a target polynucleotide that can hybridize to a sequence of the target polynucleotide that is 5' to the sequence of the target polynucleotide complementary to an RT or PE primer. In some embodiments, the sequence complementary to a target polynucleotide complement sequence one or more LPE primers is complementary to a complement sequence of a target polynucleotide that hybridizes to a sequence of the target 3' to the sequence of the target polynucleotide complementary to an RT or PE primer. In some embodiments, a sequence of a target polynucleotide containing a variant or a region for analysis by any of the methods described herein can be between the sequence of the target polynucleotide complementary to one or more RT or PE primers and the sequence of the target polynucleotide whose complement is complementary to one or more LPE primers.

In some embodiments, the sequence complementary to a target polynucleotide complement sequence, such as a first or modified complement sequence, of one or more LPE primers is not a sequence complementary to a sequence of one or more PE or RT primers. In some embodiments, the sequence complementary to a target polynucleotide complement sequence, a first or modified complement sequence, of one or more LPE primers is not a sequence complementary to a target specific sequence of one or more PE or RT primers.

In some embodiments, the one or more LPE primers comprise a first LPE primer with a region complementary to a sequence of a first template polynucleotide, and a second LPE primer with a region complementary to a sequence of a second template polynucleotide. For example, the first template polynucleotide can be a first DNA molecule and the second first template polynucleotide can be a second DNA molecule. For example, the first template polynucleotide can be a first DNA molecule derived from a first target polynucleotide in a sample and the second first template polynucleotide can be a second DNA molecule derived from a second target polynucleotide in a sample. In some embodiments, the one or more LPE primers comprise a first LPE primer with a region complementary to a sequence of a first DNA, and one or more second LPE primers each with a region complementary to a sequence of one or more second DNAs. In some embodiments, the sequences of the first and second DNAs are the same. In some embodiments, the sequences of the first and second DNAs are different. In some embodiments, the first and second template sequences are the same. In some embodiments, the first and second template sequences are different. In some embodiments, the first and second target sequences are the same. In some embodiments, the first and second target sequences are different.

A LPE primer can further comprise a region that is not complementary to a region of the template. In some embodiments, the LPE primers can further comprise a known sequence, such as a universal primer binding site or a sequence complementary to a universal priming site. In some embodiments, the LPE primers can further comprise a known sequence, such as a universal primer binding site or a sequence complementary to a universal priming site, at the 5' end. In some embodiments, the region that is not complementary to a region of the template is 5' to a region of the primer that is complementary to the template. In some embodiments, the region that is not complementary to a region of the template is a 5' overhang region or a 3' overhang region. In some embodiments, the region that is not complementary to a region of the template comprises a priming site for amplification and/or a sequencing reaction. In some embodiments, the region that is not complementary to a region of the template comprises a priming site for a second primer of a primer set for amplification and/or a sequencing reaction, such as a PCR reaction or PCR enrichment step. Optionally, the region that is not complementary to a region of the template comprises a universal sequence for clustering on a high-throughput sequencing platform. In some embodiments, the region that is not complementary to a region of the template comprises a priming site for a second primer of a primer set for amplification and/or a sequencing reaction, wherein the priming site for a first primer of the primer set is contained within the LPE template. In some embodiments, the priming site for a first primer of the primer set contained within the LPE template is added in a previous RT, PE, LPE, or adaptor addition (e.g., ligation) reaction. In some embodiments, an LPE reaction is performed using a DNA polymerase.

In some embodiments, the LPE primers can further comprise a second UID. For example, each LPE primer of a plurality of LPE primers can comprise a different second UID. This can allow for barcoding each of the DNAs copied from the DNA molecules being subjected to a linear primer extension reaction with a second UID. In some embodiments, the second UID is the same as the UID on the DNA molecules being subjected to a linear primer extension reaction. In some embodiments, the second UID is different from the UID on the DNA molecules being subjected to a linear primer extension reaction. In some embodiments, the region of an LPE primer that is not complementary to a region of the template comprises a second UID. In some embodiments, the region of each LPE primer of a plurality of LPE primers that is not complementary to a region of the target DNA comprises a second UID.

In some embodiments slow ramping rates are used for the linear extension/amplification step. In some embodiments, the linear extension/amplification primers are used at a fixed global concentration. In some embodiments, magnesium chloride, ammonium sulfate, D-(+)-Trehalose, betaine, or a combination thereof is used during the linear amplification/extension step.

PCR Enrichment

A method can further comprise performing an exponential amplification reaction. In some embodiments, a method can further comprise performing PCR. For example, an exponential amplification reaction can utilize a plurality of forward/reverse primers and a reverse primer. In some embodiments, an exponential amplification reaction can comprise two or more exponential amplifications. In some embodiments, a first and/or second PCR reaction can utilize a plurality of forward/reverse primers and a plurality of reverse primers. A first and/or second primer of a plurality of forward/reverse primers can be a forward/reverse primer containing a region complementary to template polynucleotides, such as DNA or cDNA molecules. In some embodiments, a plurality of forward/reverse primers comprises one or more forward/reverse primers wherein each of the forward/reverse primers in the plurality of forward/reverse primers comprises a region complementary to one or more upstream or downstream primer binding sites, such as universal primer binding sites.

In some embodiments, an exponential amplification reaction is not performed before a primer extension or a reverse transcription reaction. In some embodiments, an exponential amplification reaction is not performed before, or is performed after, generating a target polynucleotide complement sequence, such as a first complement sequence.

In some embodiments, an exponential amplification reaction is not performed before, or is performed after, attaching an adaptor to a template polynucleotide. In some embodiments, an exponential amplification reaction is not performed before, or is performed after, attaching an adaptor by ligation to a template polynucleotide. In some embodiments, an exponential amplification reaction is not performed before, or is performed after, attaching an adaptor to a target polynucleotide complement sequence, such as a first complement sequence. In some embodiments, an exponential amplification reaction is not performed before, or is performed after, attaching an adaptor by ligation to a target polynucleotide complement sequence, such as a first complement sequence.

In some embodiments, an exponential amplification reaction is not performed before, or is performed after, attaching a first priming site to a template sequence or complement thereof, for the exponential amplification. For example, an exponential amplification reaction may not be performed before, or may be performed after, attaching a priming site for a first primer of a primer set to a template sequence or complement thereof. In some embodiments, an exponential amplification reaction is not performed before, or is performed after, attaching a first priming site to a target polynucleotide complement sequence, such as a first complement sequence. In some embodiments, an exponential amplification reaction is not performed before, or is performed after, attaching a first priming site by ligation to a polynucleotide comprising a target polynucleotide complement sequence, such as a first complement sequence.

In some embodiments, an exponential amplification reaction is not performed before, or is performed after, attaching a SBC to a template sequence or complement thereof. In some embodiments, an exponential amplification reaction is not performed before, or is performed after, attaching a SBC to a target polynucleotide complement sequence, such as a first complement sequence. In some embodiments, an exponential amplification reaction is performed while introducing a SBC by amplification to a template sequence or complement thereof. In some embodiments, an exponential amplification reaction is performed while introducing a SBC by amplification to a target polynucleotide complement sequence, such as a second complement sequence.

In some embodiments, an exponential amplification reaction is not performed before, or is performed after, attaching a universal priming sequence to a template sequence or complement thereof. In some embodiments, an exponential amplification reaction is not performed before, or is performed after, attaching a universal priming sequence to a target polynucleotide complement sequence. In some embodiments, an exponential amplification reaction is not performed before, or is performed after, attaching a universal priming sequence by ligation to a template sequence or complement thereof. In some embodiments, an exponential amplification reaction is not performed before, or is performed after, attaching a universal priming sequence by ligation to a target polynucleotide complement sequence.

In some embodiments, an exponential amplification is not performed before, or is performed after, a linear amplification reaction. In some embodiments, an exponential amplification reaction is not performed before, or is performed after, attaching an adaptor to a linear amplification template sequence. In some embodiments, an exponential amplification reaction is not performed before, or is performed after, attaching an adaptor by ligation to a linear amplification template sequence. In some embodiments, an exponential amplification reaction is not performed before, or is performed after, attaching a first priming site to a linear amplification template sequence. In some embodiments, an exponential amplification reaction is not performed before, or is performed after, attaching an SBC to a linear amplification template sequence. In some embodiments, an exponential amplification reaction is not performed before, or is performed after, attaching a universal priming sequence to a linear amplification template sequence.

For example, an exponential amplification reaction may not be performed before a linear primer extension reaction. For example, an exponential amplification reaction may be performed after a linear primer extension reaction. In some embodiments, an exponential amplification reaction is not performed before, or is performed after, generating one or more copies of a target polynucleotide complement sequence, such as a second complement sequence. In some embodiments, an exponential amplification reaction is not performed before, or is performed after, generating one or more copies of a target polynucleotide complement sequence, such as a second complement sequence, using an LPE primer. In some embodiments, an exponential amplification reaction is not performed before, or is performed after, generating one or more copies of a plurality of target polynucleotide complement sequences, such as second complement sequences, using a plurality of LPE primers. In some embodiments, an exponential amplification reaction is not performed before, or is performed after, attaching a first and a second priming site for the exponential amplification. For example, an exponential amplification reaction may not be performed before, or may be performed after, attaching a first priming site for a first primer of a primer set and a second priming site for a second primer of the primer set. In some embodiments, an exponential amplification reaction is not performed before, or is performed after, attaching a first priming site by ligation and a second priming site for the exponential amplification. In some embodiments, an exponential amplification reaction is not performed before, or is performed after, attaching a first priming site and a second priming site by a linear primer extension reaction for the exponential amplification. In some embodiments, an exponential amplification reaction is not performed before, or is performed after, attaching a first priming site or complement thereof by ligation and a second priming site by a linear primer extension reaction for the exponential amplification. For example, the first and second priming sites can be priming sites for a pair of primers used for the exponential amplification reaction. For example, the first and second priming sites can be universal priming sites. For example, the first and second priming sites can be priming sites for sequencing.

In some embodiments, an exponential amplification reaction is not performed before, or is performed after, immobilizing a polynucleotide to a surface or support. In some embodiments, an exponential amplification reaction is performed on a copy of a polynucleotide immobilized to a surface or support. In some embodiments, an exponential amplification reaction is performed on a copy of a polynucleotide immobilized to a surface or support generated from a linear primer extension reaction.

In some embodiments, an exponential amplification reaction is not performed before, or is performed after, immobilizing one or more a target polynucleotide complement sequences to a surface or support. In some embodiments, an exponential amplification reaction is not performed before, or is performed after, a linear primer reaction is performed on one or more immobilized target polynucleotide complement sequences. In some embodiments, an exponential amplification reaction is performed on a polynucleotide copied from a polynucleotide bound to a surface or solid support. In some embodiments, an exponential amplification reaction is performed on a polynucleotide complement sequence, such as a second complement sequence, copied from a target polynucleotide complement sequence, such as a first complement sequence or modified complement sequence that may contain a UID, bound to a surface or solid support.

In some embodiments, an exponential amplification reaction is performed on a SBC containing polynucleotide copied from a UID containing polynucleotide bound to a surface or solid support. In some embodiments, an exponential amplification reaction is performed on a polynucleotide containing a first primer binding site, a second primer binding site, or both that was copied from a UID containing polynucleotide bound to a surface or solid support. In some embodiments, an exponential amplification reaction is performed on a polynucleotide containing a first primer binding site, a second primer binding site, a first universal priming site, a second universal priming site, or any combination thereof, that was copied from a UID containing polynucleotide, bound to a surface or solid support.

In some embodiments, an exponential amplification reaction is performed on a SBC containing polynucleotide copied from a SBC containing polynucleotide bound to a surface or solid support. In some embodiments, an exponential amplification reaction is performed on a UID containing polynucleotide copied from an SBC containing polynucleotide bound to a surface or solid support. In some embodiments, an exponential amplification reaction is performed on a polynucleotide containing a first primer binding site, a second primer binding site, or both that was copied from an SBC containing polynucleotide bound to a surface or solid support. In some embodiments, an exponential amplification reaction is performed on a polynucleotide containing a first primer binding site, a second primer binding site, a first universal priming site, a second universal priming site, or any combination thereof, that was copied from an SBC containing polynucleotide bound to a surface or solid support.

In some embodiments, an exponential amplification reaction is performed on a first and/or second primer site containing polynucleotide copied from a first and/or second primer site containing polynucleotide bound to a surface or solid support. In some embodiments, an exponential amplification reaction is performed on a SBC containing polynucleotide copied from a first and/or second primer site containing polynucleotide bound to a surface or solid support. In some embodiments, an exponential amplification reaction is performed on a UID containing polynucleotide copied from a first and/or second primer site containing polynucleotide bound to a surface or solid support. In some embodiments, an exponential amplification reaction is performed on a polynucleotide containing a first universal primer binding site, a second universal primer binding site, or both that was copied from a first and/or second primer site containing polynucleotide bound to a surface or solid support. In some embodiments, an exponential amplification reaction is performed on a polynucleotide containing a first primer binding site, a second primer binding site, a first universal priming site, a second universal priming site, or any combination thereof, that was copied from an first and/or second primer site containing polynucleotide bound to a surface or solid support.

Using primers described herein, DNA polynucleotides produced from one or more of the above methods or method steps can be hybridized to a primer set (e.g., a PCR primer set or an exponential amplification primer set) and exponential amplification can be performed using suitable reagents known in the art. For example, one or more second complement sequences can be hybridized to first primer of a primer set (such as a reverse primer) and primer extension can be performed; a second primer of a primer set (such as a forward primer) can then be hybridized to a product of the extension reaction and primer extension can be performed.

In some embodiments, exponential amplification comprises multiple cycles. In some embodiments, the same first and second primers of a primer set are used for the exponential amplification reaction of multiple template polynucleotides. In some embodiments, one or more of the exponential amplification primers are not target specific primers. In some embodiments, both primers of an exponential amplification primer set are not target specific primers. In some embodiments, the same first and second primers of a primer set are used for the exponential amplification reaction of multiple template polynucleotides in the same reaction vessel. In some embodiments, the same first and second primers of a primer set are used for the exponential amplification reaction of multiple template polynucleotides in the same reaction. In some embodiments, the same first and second primers of a primer set are used for the exponential amplification reaction of multiple template polynucleotides simultaneously. For example, the same first and second primers of a primer set can be used to exponentially amplify a plurality of target polynucleotide complement sequences, such as a plurality of second complement sequences derived from a different target sequence. For example, the same first and second primers of a primer set can be used to exponentially amplify a plurality of target polynucleotide complement sequences, such as a plurality of second complement sequences derived from a different target sequence. For example, the same first and second primers of a primer set can be used to exponentially amplify a plurality of target polynucleotide complement sequences, such as a plurality of second complement sequences, comprising the same target sequence or complement thereof. For example, the same first and second primers of a primer set can be used to exponentially amplify a plurality of target polynucleotide complement sequences of an amplicon. For example, the same first and second primers of a primer set can be used to exponentially amplify a plurality of target polynucleotide complement sequences, such as a plurality of second complement sequences of an amplicon set. For example, the same first and second primers of a primer set can be used to exponentially amplify each of a plurality of target polynucleotide complement sequences generated using any of the methods described herein. For example, the same first and second primers of a primer set can be used to exponentially amplify each of a plurality of target polynucleotide complement sequences containing an adaptor sequence. For example, the same first and second primers of a primer set can be used to exponentially amplify each of a plurality of target polynucleotide complement sequences containing an SBC. For example, the same first and second primers of a primer set can be used to exponentially amplify each of a plurality of target polynucleotide complement sequences containing a first and a second universal priming site.

In some embodiments, the first and second primers of a primer set can be used to exponentially amplify a UID, a SBC, a target region, any complement thereof, or any combination thereof. For example, the first and second primer binding sites can be hybridize 5' and 3', respectively, to a UID, a SBC, a target region, any complement thereof, or any combination thereof.

In some embodiments an exponential amplification reaction is the, second, third, fourth, or fifth step of generating a library of polynucleotides from a sample containing a target polynucleotide. In some embodiments, an exponential amplification reaction is not the second step of generating a library of polynucleotides from a sample containing a target polynucleotide. In some embodiments, an exponential amplification reaction is not the first amplification reaction performed in a method of generating a library of polynucleotides from a sample containing a target polynucleotide. In some embodiments, an exponential amplification reaction is the third step of generating a library of polynucleotides from a sample containing a target polynucleotide. In some embodiments, an exponential amplification reaction is the fourth step of generating a library of polynucleotides from a sample containing a target polynucleotide. In some embodiments, an exponential amplification reaction is the fifth step of generating a library of polynucleotides from a sample containing a target polynucleotide. In some embodiments, an exponential amplification reaction is performed after an RT or PE reaction. In some embodiments, an exponential amplification reaction is performed after a reaction that adds an adaptor to a target polynucleotide complement sequence, such as a first complement sequence. In some embodiments, an exponential amplification reaction is performed after an RT or PE reaction and after a reaction that adds an adaptor to a target polynucleotide complement sequence, such as a first complement sequence. In some embodiments, an exponential amplification reaction is performed prior to performing a second exponential amplification reaction, such as PCR. In some embodiments, exponential amplification is performed in the next step after the linear primer extension. In some embodiments, exponential amplification is not performed in the next step after the linear primer extension. In some embodiments, exponential amplification is not performed in the next step after an RT or PE reaction. In some embodiments, exponential amplification is not performed in the next 2 steps after an RT or PE reaction. In some embodiments, exponential amplification is not performed in the next 3 steps after an RT or PE reaction. In some embodiments, a library of polynucleotide sequences, that may contain a UID, produced from an exponential amplification step, is not amplified further after this step. In some embodiments, the method comprises only one cycle of exponential amplification. In some embodiments, the method comprises repeatedly extending both primers of a primer set to produce multiple copies of the polynucleotide sequences that may contain a UID The exponential amplification primers can comprise a sequence complementary to a sequence, or complement sequence of a target polynucleotide complement sequence. For example, the one or more exponential amplification primers can comprise a sequence complementary to a sequence, or complement sequence of a target polynucleotide complement sequence or a target polynucleotide in an initial sample. For example, the one or more exponential amplification primers can comprise a sequence complementary to a sequence or complement sequence of a target polynucleotide complement sequence that is a product of an amplification reaction, ligation reaction, primer extension, linear primer extension, or combinations thereof. For example, the one or more exponential amplification primers can comprise a sequence complementary to a sequence or complement sequence of a first, second, or modified sequence.

In some embodiments, the one or more exponential amplification primers do not comprise a sequence complementary to a sequence or complement sequence of a target polynucleotide. In some embodiments, the one or more exponential amplification primers do not comprise a sequence complementary to a sequence or complement sequence of a target polynucleotide complement sequence. In some embodiments, the one or more exponential amplification primers do not comprise a sequence that is complementary to a sequence or complement sequence of a target polynucleotide and do not comprise a sequence that is complementary to a sequence or complement sequence of a target polynucleotide complement sequence.

In some embodiments, the one or more exponential amplification primers comprise a sequence complementary to a sequence or complement sequence of a target polynucleotide. In some embodiments, the one or more exponential amplification primers comprise a sequence complementary to a sequence or complement sequence of a UID containing polynucleotide. In some embodiments, the one or more exponential amplification primers comprise a sequence that is complementary to a sequence or complement sequence of a target polynucleotide and comprise a sequence that is complementary to a sequence or complement sequence of a UID containing polynucleotide.

In some embodiments, the sequence complementary to a UID containing polynucleotide of one or more exponential amplification primers is not complementary to a target sequence. In some embodiments, the sequence complementary to a UID containing polynucleotide of one or more exponential amplification primers is not complementary to any polynucleotide that does not contain an UID. In some embodiments, the sequences complementary to a UID containing polynucleotide of one or more exponential amplification primers are not complementary to any other polynucleotide in a sample.

In some embodiments, the target polynucleotide complement sequence amplified exponentially is a single stranded polynucleotide. In some embodiments, the target polynucleotide complement sequence amplified exponentially is a double stranded polynucleotide. In some embodiments, the target polynucleotide complement sequence amplified exponentially is a copy of an extension product from a PE or RT reaction. In some embodiments, the target polynucleotide complement sequence amplified exponentially further comprises an adaptor sequence, such as a ligated adaptor sequence. In some embodiments, the target polynucleotide complement sequence amplified exponentially is a complement of an extension product from a PE or RT reaction further comprising an adaptor sequence. In some embodiments, the target polynucleotide complement sequence amplified exponentially is a complement of a complement sequence of an extension product from a PE or RT reaction further comprising a first and/or second primer binding site, such as a PCR, sequencing, or universal priming site. In some embodiments, the target polynucleotide complement sequence amplified exponentially is immobilized on a substrate or surface. In some embodiments, the target polynucleotide complement sequence amplified exponentially comprises a SBC.

In some embodiments, the sequence complementary to a target polynucleotide complement sequence amplified exponentially of one or more exponential amplification primers is not a sequence in a target polynucleotide. In some embodiments, the sequence complementary to a target polynucleotide complement sequence amplified exponentially of one or more exponential amplification primers is complementary to a complement sequence of a sequence generated during an RT or PE reaction. In some embodiments, the sequence complementary to a target polynucleotide complement sequence amplified exponentially of one or more exponential amplification primers is complementary to a sequence of a target polynucleotide that hybridizes to a sequence of the target 5' to the sequence of the target polynucleotide complementary to an RT or PE primer. In some embodiments, the sequence complementary to a target polynucleotide complement sequence amplified exponentially of one or more exponential amplification primers is complementary to a sequence of a target polynucleotide that hybridizes to a sequence of the target 3' to the sequence of the target polynucleotide complementary to an RT or PE primer. In some embodiments, a sequence of a target polynucleotide containing a variant or a region for analysis by any of the methods described herein can be between the sequence of the target polynucleotide complementary to one or more RT or PE primers and the sequence of the target polynucleotide complementary to one or more exponential amplification primers.

In some embodiments, the sequence complementary to a target polynucleotide complement sequence amplified exponentially of one or more exponential amplification primers is not a sequence complementary to a sequence of one or more PE or RT primers. In some embodiments, the sequence complementary to a target polynucleotide complement sequence amplified exponentially of one or more exponential amplification primers is not a sequence complementary to a target specific sequence of one or more PE or RT primers.

In some embodiments, the one or more exponential amplification primers comprise a first exponential amplification primer with a region complementary to a sequence of a first template polynucleotide, and a second exponential amplification primer with a region complementary to a sequence of a second template polynucleotide. For example, the first template polynucleotide can be a first DNA molecule and the second first template polynucleotide can be a second DNA molecule. For example, the first template polynucleotide can be a first DNA molecule derived from a first target polynucleotide in a sample and the second first template polynucleotide can be a second DNA molecule derived from a second target polynucleotide in a sample. In some embodiments, the one or more exponential amplification primers comprise a first exponential amplification primer with a region complementary to a sequence of a first DNA, and one or more second exponential amplification primers each with a region complementary to a sequence of one or more second DNAs. In some embodiments, the sequences of the first and second DNAs are the same. In some embodiments, the sequences of the first and second DNAs are different. In some embodiments, the first and second template sequences are the same. In some embodiments, the first and second template sequences are different. In some embodiments, the first and second target sequences are the same. In some embodiments, the first and second target sequences are different.

Sequencing

After performing one or more of the methods or method steps described herein, a library of polynucleotides generated can be sequenced.

Sequencing can be performed by any sequencing method known in the art. In some embodiments, sequencing can be performed in high throughput. Suitable next generation sequencing technologies include the 454 Life Sciences platform (Roche, Branford, Conn.) (Margulies et al., Nature, 437, 376-380 (2005)); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., Genome Res. 16, 383-393 (2006); and U.S. Pat. Nos. 6,306,597, 7,598,035, 7,232,656), or DNA Sequencing by Ligation, SOLiD System (Applied Biosystems/Life Technologies; U.S. Pat. Nos. 6,797,470, 7,083, 917, 7,166,434, 7,320,865, 7,332,285, 7,364,858, and 7,429, 453); or the Helicos True Single Molecule DNA sequencing technology (Harris et al., Science, 320, 106-109 (2008); and U.S. Pat. Nos. 7,037,687, 7,645,596, 7,169,560, and 7,769, 400), the single molecule, real-time (SMRTTm) technology of Pacific Biosciences, and sequencing (Soni et al., Clin. Chem. 53, 1996-2001 (2007)). A method can further comprise sequencing one or more polynucleotides in the library. A method can further comprise aligning one or more polynucleotide sequences, sequence reads, amplicon sequences, or amplicon set sequences in the library to each other.

As used herein, aligning comprises comparing a test sequence, such as a sequence read, to one or more other test sequences, reference sequences, or a combination thereof. In some embodiments, aligning can be used to determine a consensus sequence from a plurality of sequences or aligned sequences. In some embodiments, aligning comprises determining a consensus sequence from a plurality of sequences that each has an identical UID. In some embodiments, the length of a sequence aligned for comparison purposes is at least 30%, at least 40%, at least 50%, at least 60%, at least 70%, at least 80%, at least 90%, or at least 95%, of the length of a reference sequence. The actual comparison of the two or more sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

In some aspects, determining the number of polynucleotides, amplicons, or amplicons sets with different sequences can comprise determining the sequences of the polynucleotides, amplicons, or amplicons sets. In some aspects, determining the number of different UID-containing polynucleotides, amplicons, or amplicons sets can comprise determining the sequence of the UID-containing polynucleotides, amplicons, or amplicons sets. Determining the sequence of a polynucleotide may comprise conducting a sequencing reaction to determine the sequence of at least a portion of the target region, UID, SBC, at least a portion of the polynucleotide, a complement thereof, a reverse complement thereof, or any combination thereof. In some embodiments only the UID or a portion of the UID is sequenced. In some embodiments only the SBC or a portion of the SBC is sequenced. In some embodiments only target region or a portion of the target region is sequenced. In some embodiments, a sequencing reaction can occur on a support as described herein, in a continuous follow, in a dilution, or in one or more physically separate volumes.

Sequencing can comprise at least about 200, 300, 400, 500, 600, 700, 800, 900, 1000 or more sequencing reads per run. As used herein, a sequence read comprises a sequence of nucleotides determined from a sequence or stream of data generated by a sequencing technique. In some embodiments, sequencing comprises sequencing at least about 1500, 2000, 3000, 4000, 5000, 6000, 7000, 8000, 9000, 10,000, or more sequencing reads per run. Sequencing can comprise more than, less than, or equal to about 1,000,000,000 sequencing reads per run. Sequencing can comprise more than, less than, or equal to about 200,000,000 reads per run.

A method can comprise determining a sequence of a target polynucleotide by determining a consensus sequence from two or more sequence reads. In some embodiments, an average of 5-50 or 20-30 raw reads per UID provides a desired balance of consensus sequence accuracy and sufficient sequencing depth (higher raw read counts can need greater sequencing depth). In some embodiments, accuracy (e.g., aggregate normal distribution) can be improved when aligning and collapsing sequence reads into consensus sequences using UID information. A feature of UID consensus accuracy is the enhanced capability to accurately determining the presence or absence of a mutation or SNP on a second allele resulting in an accurate call of heterozygocity of a patient with a detected SNP.

A method can comprise generating a consensus sequence from one or more alignments, such as one or more alignments of one or more polynucleotide sequences, sequence reads, amplicon sequences, or amplicon set sequences in the library to each other. A consensus sequence determined using the methods and libraries produced, as described herein, can improve base call accuracy. For example, a determined consensus sequence can have an improved quality score compared to other methods in the art. As used herein, a quality score comprises a measure of the probability that a base assignment at a particular sequence location is correct. Thus, a quality score value can be related to a probability of correct base calling. The methods described herein can be used to determine a target polynucleotide sequence with a quality score of about, or at least about 10. The methods described herein can lower or use a low number of sequence reads to achieve the same or higher confidence in sequence accuracy. In some embodiments, fewer sequence reads are used in a method described herein employing use of UIDs than a similar method without the use of UIDs to determine a sequence with a similar or the same confidence or base calling accuracy.

In some embodiments, sequence reads without both exponential amplification priming sites or compliments thereof, an adaptor sequence, an SBC, an optional UID, two universal priming sequences, or any combination thereof, can be mis-reads. A method can comprise sequencing mis-reads. A method can comprise determining the number of mis-reads, such as for determining a reaction condition or designing primer sequences. Comparing the number of mis-reads generated under one or more first conditions or sets of conditions can be used to determine a preferred condition or condition set. For example, a first method can be carried out at a high salt concentration during a PCR reaction, and a second method can be carried out at a low salt concentration during a PCR reaction, wherein the first and second method are carried out substantially the same aside from the salt concentration difference. If the first method results in a higher number of mis-reads, such as a higher number of mis-reads for a particular target polynucleotide sequence or primer, a lower salt reaction condition can be determined to be preferred for that particular target polynucleotide sequence or primer.

In some embodiments, only sequence reads with both exponential amplification priming sites or compliments thereof, an adaptor sequence, an SBC, an optional UID, two universal priming sequences, or any combination thereof, are used for aligning or determining a consensus sequence. In some embodiments, one or more sequence reads without both exponential amplification priming sites or compliments thereof, an adaptor sequence, an SBC, an optional UID, two universal priming sequences, or any combination thereof, are not used for aligning or determining a consensus sequence.

In some embodiments, one or more sequence reads without both exponential amplification priming sites or compliments thereof are not used for aligning or determining a consensus sequence. In some embodiments, one or more sequence reads without a single exponential amplification priming site (e.g., PCR priming site) or complement thereof are not used for aligning or determining a consensus sequence. In some embodiments, one or more sequence reads comprising two exponential amplification priming sites or compliments thereof are not used for aligning or determining a consensus sequence, when the two exponential amplification priming sites are not corresponding exponential amplification priming sites for a primer pair used, such as a primer pair used in a PCR reaction.

In some embodiments, only sequence reads with both exponential amplification priming sites or compliments thereof are used for aligning or determining a consensus sequence. In some embodiments, only sequence reads with two exponential amplification priming sites or compliments thereof that correspond to exponential amplification priming sites for a primer pair used, such as a primer pair used in a PCR reaction, are used for aligning or determining a consensus sequence. In some embodiments, one or more sequence reads without an SBC are not used for aligning or determining a consensus sequence. In some embodiments, only sequence reads with an SBC are used for aligning or determining a consensus sequence. In most embodiments, one or more sequence reads without a UID are not used for aligning or determining a consensus sequence. In most embodiments, only sequence reads with a UID are used for aligning or determining a consensus sequence. In some embodiments, one or more sequence reads without an adaptor sequence are not used for aligning or determining a consensus sequence. In some embodiments, only sequence reads with an adaptor sequence are used for aligning or determining a consensus sequence. In some embodiments, one or more sequence reads without two universal priming sequences are not used for aligning or determining a consensus sequence. In some embodiments, only sequence reads with two universal priming sequences are used for aligning or determining a consensus sequence.

In some embodiments, a sequence can be determined as accurate when at least 5% of the sequences containing the same UID, the sequences in an amplicon or the sequences in an amplicon set are present. For example, a sequence can be determined as accurate when at least 10%, 15%, 20%, 25%, 30%, 35%, 40%, 45%, 50%, 55%, 60%, 65%, 70%, 75%, 80%, 85%, 90%, 92%, 95%, 97%, 98%, 99% or more of the sequences containing the same UID, the sequences in an amplicon or the sequences in an amplicon set are present. For example, a sequence can be determined as accurate when at least about 75% to about 99% of the sequences containing the same UID, the sequences in an amplicon or the sequences in an amplicon set are present. For example, a sequence can be determined as accurate when at least about 85% to about 99% of the sequences containing the same UID, the sequences in an amplicon or the sequences in an amplicon set are present. For example, a sequence can be determined as accurate when at least about 92% to about 99% of the sequences containing the same UID, the sequences in an amplicon or the sequences in an amplicon set are present.

In some embodiments, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

Target Polynucleotides

The methods described herein can be used to generate a library of polynucleotides from one or more target polynucleotides for sequencing. Target polynucleotides include any polynucleotides of interest that are not products of an amplification reaction. For example, a target polynucleotide can include a polynucleotide in a biological sample. For example, target polynucleotides do not include products of a PCR reaction. For example, target polynucleotides may include a polynucleotide template used to generate products of an amplification reaction, but do not include the amplification products themselves. For example, target polynucleotides include polynucleotides of interest that can be subjected to a reverse transcription reaction or a primer extension reaction. For example, target polynucleotides include RNA or DNA. In some embodiments, target RNA polynucleotides are mRNA. In some embodiments, target RNA polynucleotides are polyadenylated. In some embodiments, the RNA polynucleotides are not polyadenylated. In some embodiments, the target polynucleotides are DNA polynucleotides. The DNA polynucleotides may be genomic DNA. The DNA polynucleotides may comprise exons, introns, untranslated regions, or any combination thereof.

In some embodiments, libraries can be generated from two or more regions of a target polynucleotide. In some embodiments, methods libraries can be generated from two or more target polynucleotides. In some embodiments, target polynucleotides are genomic nucleic acids or DNA derived from chromosomes. In some embodiments, target polynucleotides include sequences comprising a variant, such as a polymorphism or mutation. In some embodiments, target polynucleotides include DNA and not RNA. In some embodiments, target polynucleotides include RNA and not DNA. In some embodiments, target polynucleotides include DNA and RNA. In some embodiments, a target polynucleotide is an mRNA molecule. In some embodiments, a target polynucleotide is a DNA molecule. In some embodiments, a target polynucleotide is a single stranded polynucleotide. In some embodiments, a target polynucleotide is a double stranded polynucleotide. In some embodiments, a target polynucleotide is a single strand of a double stranded polynucleotide.

Target polynucleotides can be obtained from any biological sample and prepared using methods known in the art. In some embodiments, target polynucleotides are directly isolated without amplification. Methods for direct isolation are known in the art. Non-limiting examples include extracting genomic DNA or mRNA from a biological sample, organism or, cell.

In some embodiments, one or more target polynucleotides are purified from a biological sample. In some embodiments, a target polynucleotide is not purified from the biological sample in which it is contained. In some embodiments, a target polynucleotide is isolated from a biological sample. In some embodiments, a target polynucleotide is not isolated from the biological sample in which it is contained. For example, in some embodiments, a target polynucleotide is not extracted or purified from the sample. For example, in some embodiments, a target mRNA is not purified from a sample, such as through a poly-A purification method. In some embodiments, a target polynucleotide can be a cell-free nucleic acid. In some embodiments, a target polynucleotide can be a fragmented nucleic acid. In some embodiments, a target polynucleotide can be a transcribed nucleic acid. In some embodiments, a target polynucleotide is a modified polynucleotide. In some embodiments, a target polynucleotide is a non-modified polynucleotide.

In some embodiments, a target polynucleotide is polynucleotide from a single cell. In some embodiments, target polynucleotides are from individual cells. In some embodiments, a target polynucleotide is polynucleotide from a sample containing a plurality of cells.

In some embodiments, a target polynucleotide encodes a biomarker sequence. In some embodiments, a target polynucleotide encodes 2 or more biomarker sequences. In some embodiments, a plurality of target polynucleotides encodes a biomarker sequence. In some embodiments, a plurality of target polynucleotides encodes 2 or more biomarker sequences.

Diagnostics

In some embodiments, a method can further comprise diagnosing, prognosing, monitoring, treating, ameliorating and/or preventing in a subject a disease, disorder, symptom and/or condition. In some embodiments, a method can further comprise diagnosing, prognosing, monitoring, treating, ameliorating and/or preventing in a subject a disease, disorder, symptom and/or condition, based on a presence, absence, or level of a target polynucleotide. In some embodiments, a method can further comprise diagnosing, prognosing, monitoring, treating, ameliorating and/or preventing in a subject a disease, disorder, symptom and/or condition, based on a presence, absence, or level of one or more target polynucleotides.

In some embodiments, a method can further comprise diagnosing, prognosing, monitoring, treating, ameliorating and/or preventing in a subject a disease, disorder, symptom and/or condition based on a presence, absence, level, or sequence of one or more of the sequences obtained using the methods described herein. For example, a diagnosis of a disease can be made based on a presence, absence, level, or sequence of a variant sequence obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence, one or more of the sequence reads obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence of one or more of the consensus sequences obtained using the methods described herein. In some embodiments, a method can further comprise diagnosing, prognosing, monitoring, treating, ameliorating and/or preventing in a subject a disease, disorder, symptom and/or condition based on a determination of a level (e.g., an amount or concentration) of a target polynucleotide in a sample. A level of a target polynucleotide in a sample can be determined based on one or more sequence reads, sequences, consensus sequences, or any combination thereof. A level of each of a plurality of target polynucleotides in a sample can be determined using the methods described herein. A level of each of a plurality of target polynucleotide in a sample can be determined based on a number of sequence reads, sequences, consensus sequences, or any combination thereof of each target polynucleotide in the plurality. For example, a level of a first target polynucleotide and a level of a second target polynucleotide can be determined using the methods described herein.

In some embodiments, first and second target polynucleotides of a plurality of target polynucleotides are the same. For example, a first target polynucleotide can comprise a first copy of an mRNA molecule and a second target polynucleotide can comprise a second copy of an mRNA molecule. In some embodiments, the first and second target polynucleotides are different. For example, a first target polynucleotide can comprise a first mRNA molecule and a second target polynucleotide can comprise a second mRNA molecule transcribed from a different gene than the first mRNA molecule. For example, a first target polynucleotide can comprise a first allele and a second target polynucleotide can comprise a second allele. For example, a first target polynucleotide can comprise a wild-type sequence and a second target polynucleotide can comprise a variant sequence.

A panel of target polynucleotides can comprise a plurality of biomarkers. A panel of biomarkers can comprise a plurality of target polynucleotides. In some embodiments, a panel of biomarkers comprises a sequence from each of plurality of different target polynucleotides. For example, a panel of biomarkers can comprise a sequence of a first and a second target polynucleotide that are different. For example, a panel of target polynucleotides can comprise a plurality of biomarkers, such as variant sequences, known to be associated with a disease or known to not be associated with a disease. For example, a panel of target polynucleotides can comprise at least one biomarker for each of a plurality of genetic loci. In some embodiments, the types of two or more target polynucleotides in a panel of target polynucleotide are different. For example, a panel of target polynucleotides can comprise a plurality of target polynucleotides comprising a first target mRNA molecule and a second target DNA molecule. For example, a panel of target polynucleotides can comprise a plurality of target polynucleotides comprising a first target that is RNA and a second target that is DNA. For example, a panel of target polynucleotides can comprise a plurality of target polynucleotides comprising a first target that is mRNA and a second target that is genomic DNA. In some embodiments, the types of two or more target polynucleotides in a panel of target polynucleotide are the same. For example, a panel of target polynucleotides can comprise a plurality of target polynucleotides comprising a first target that is RNA and a second target that is RNA. For example, a panel of target polynucleotides can comprise a plurality of target polynucleotides comprising a first target that is mRNA and a second target that is mRNA. For example, a panel of target polynucleotides can comprise a plurality of target polynucleotides comprising a first target that is mRNA and a second target that is miRNA. For example, a panel of target polynucleotides can comprise a plurality of target polynucleotides comprising a first target that is DNA and a second target that is DNA. For example, a panel of target polynucleotides can comprise a plurality of target polynucleotides comprising a first target that is genomic DNA and a second target that is genomic DNA. For example, a panel of target polynucleotides can comprise a plurality of target polynucleotides comprising a first target that is cellular DNA and a second target that is circulating DNA.

In some embodiments, the types of biomarkers of two or more target polynucleotides in a panel of target polynucleotide are different. For example, a panel of target polynucleotides can comprise a plurality of biomarkers comprising a first biomarker to a genetic locus, a second biomarker for a variant sequence. For example, a panel of target polynucleotides can comprise a plurality of biomarkers comprising a first biomarker for a SNP and a second biomarker for a mutation. In some embodiments, the types of biomarkers of two or more target polynucleotides in a panel of target polynucleotide are the same. For example, a panel of target polynucleotides can comprise a plurality of biomarkers comprising a first biomarker to a genetic locus, a second biomarker for another genetic locus. For example, a panel of target polynucleotides can comprise a plurality of biomarkers comprising a first biomarker for a SNP, a second biomarker for a SNP.

In some embodiments, a method can further comprise diagnosing or prognosing a subject with a disease, disorder, symptom and/or condition with at least 50% confidence. In some embodiments, the presence, absence, level, sequence, or any combination thereof, of a target polynucleotide in the subject, such as a biomarker, can be determined with at least 50% confidence. In some embodiments, the presence, absence, level, sequence, or any combination thereof, of a target polynucleotide in the subject can be determined with a 50%-100% confidence.

Samples

As used herein, a sample comprises a biological, environmental, medical, or patient source or sample containing a polynucleotide, such as a target polynucleotide. Any biological sample containing polynucleotides can be used in the methods described herein. For example, a sample can be a biological sample from a subject containing RNA or DNA. The polynucleotides can be extracted from the biological sample, or the sample can be directly subjected to the methods without extraction of the polynucleotides. The sample can be extracted or isolated DNA or RNA. A sample can also be total RNA or DNA extracted from a biological specimen, a cDNA library, viral, or genomic DNA. In one embodiment, polynucleotides are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the polynucleotides are obtained from a single cell. Polynucleotides can be obtained directly from an organism or from a biological sample obtained from an organism. Any tissue or body fluid specimen may be used as a source for nucleic acid for use in the invention. Polynucleotides can also be isolated from cultured cells, such as a primary cell culture or a cell line. The cells or tissues from which template nucleic acids are obtained can be infected with a virus or other intracellular pathogen.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, 211d Ed., Cold Spring Harbour Laboratory Press: New York) and several kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

One or more samples can be from one or more sources. One or more of samples may be from two or more sources. One or more of samples may be from one or more subjects. One or more of samples may be from two or more subjects. One or more of samples may be from the same subject. One or more subjects may be from the same species. One or more subjects may be from different species. One or more subjects may be healthy. One or more subjects may be affected by a disease, disorder or condition.

In some embodiments, a sample is a fluid, such as blood, saliva, lymph, urine, cerebrospinal fluid, seminal fluid, sputum, stool, or tissue homogenates.

A sample can be taken from a subject with a condition. In some embodiments, the subject from whom a sample is taken can be a patient, for example, a cancer patient or a patient suspected of having cancer. The subject can be a mammal, e.g., a human, and can be male or female. In some embodiments, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some embodiments, the disease or condition is a pathogenic infection. The target polynucleotides can be from a pathogen. The pathogen can be a virus, bacterium, fungi, or protozoan. In some embodiments, the pathogen can be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*),

*Giardia* (e.g., *G. lamblia*), *Isospora* (e.g., *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T anthropophthera, T. hominis*), and *Vittaforma* (e.g., *V. corneae*). The pathogen can be a fungus, such as, *Candida, Aspergillus, Cryptococcus, Histoplasma, Pneumocystis*, and *Stachybotrys*. The pathogen can be a bacterium. Exemplary bacteria include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*. The virus can be a reverse transcribing virus. Examples of reverse transcribing viruses include, but are not limited to, single stranded RNA-RT (ssRNA-RT) virus and double-stranded DNA-RT (dsDNA-RT) virus. Non-limiting examples of ssRNA-RT viruses include retroviruses, alpharetrovirus, betaretrovirus, gammaretrovirus, deltaretrovirus, epsilonretrovirus, lentivirus, spuma virus, metavirirus, and pseudoviruses. Non-limiting examples of dsDNA-RT viruses include hepadenovirus and caulimovirus. The virus can be a DNA virus. The virus can be a RNA virus. The DNA virus can be a double-stranded DNA (dsDNA) virus. In some embodiments, the dsDNA virus is an adenovirus, herpes virus, or pox virus. Examples of adenoviruses include, but are not limited to, adenovirus and infectious canine hepatitis virus. Examples of herpes viruses include, but are not limited to, herpes simplex virus, varicella-zoster virus, cytomegalovirus, and Epstein-Barr virus. A non-limiting list of pox viruses includes smallpox virus, cow pox virus, sheep pox virus, monkey pox virus, and vaccinia virus. The DNA virus can be a single-stranded DNA (ssDNA) virus. The ssDNA virus can be a parvovirus. Examples of parvoviruses include, but are not limited to, parvovirus B19, canine parvovirus, mouse parvovirus, porcine parvovirus, feline panleukopenia, and Mink enteritis virus.

The virus can be a RNA virus. The RNA virus can be a double-stranded RNA (dsRNA) virus, (+) sense single-stranded RNA virus ((+)ssRNA) virus, or (−) sense single-stranded ((−)ssRNA) virus. A non-limiting list of dsRNA viruses include reovirus, orthoreovirus, cypovirus, rotavirus, bluetongue virus, and phytoreovirus. Examples of (+) ssRNA viruses include, but are not limited to, picornavirus and togavirus. Examples of picornaviruses include, but are not limited to, enterovirus, rhinovirus, hepatovirus, cardiovirus, aphthovirus, poliovirus, parechovirus, erbovirus, kobuvirus, teschovirus, and coxsackie. In some embodiments, the togavirus is a rubella virus, Sindbis virus, Eastern equine encephalitis virus, Western equine encephalitis virus, Venezuelan equine encephalitis virus, Ross River virus, O'nyong'nyong virus, Chikungunya, or Semliki Forest virus. A non-limiting list of (−) ssRNA viruses include orthomyxovirus and rhabdovirus. Examples of orthomyxoviruses include, but are not limited to, influenzavirus a, influenzavirus B, influenzavirus C, isavirus, and thogotovirus. Examples of rhabdoviruses include, but are not limited to, cytorhabdovirus, dichorhabdovirus, ephemerovirus, lyssavirus, novirhabdovirus, and vesiculovirus.

A sample can be a biological sample from any organism or virus. Samples for use in the present invention include viral particles or preparations. In some embodiments, the starting material can be a sample containing nucleic acids, from any organism, from which genetic material can be obtained. One or more of samples can be from a mammal, bacteria, virus, fungus or plant. One or more samples can be from a human, horse, cow, chicken, pig, rat, mouse, monkey, rabbit, guinea pig, sheep, goat, dog, cat, bird, fish, frog and fruit fly.

In some embodiments, the polynucleotides are bound as to other target molecules such as proteins, enzymes, substrates, antibodies, binding agents, beads, small molecules, peptides, or any other molecule Generally, nucleic acid can be extracted from a biological sample by a variety of techniques (Sambrook et al., Molecular Cloning: A Laboratory Manual, Third Edition, Cold Spring Harbor, N.Y. (2001)).

In some embodiments, the sample is saliva. In some embodiments, the sample is whole blood. In some embodiments, in order to obtain sufficient amount of polynucleotides for testing, a blood volume of at least about 0.001, 0.005, 0.01, 0.05, 0.1, 0.5, 1, 2, 3, 4, 5, 10, 20, 25, 30, 35, 40, 45, or 50 mL is drawn. In some embodiments, blood can be collected into an apparatus containing a magnesium chelator including but not limited to EDTA, and is stored at 4° C. Optionally, a calcium chelator, including but not limited to EGTA, can be added.

In some embodiments, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers. In some embodiments, non-nucleic acid materials can be removed from the starting material using enzymatic treatments (such as protease digestion).

In some embodiments, the starting material can be a tissue sample comprising a tissue, with non-limiting examples including brain, liver, lung, kidney, prostate, ovary, spleen, lymph node (including tonsil), thyroid, pancreas, heart, skeletal muscle, intestine, larynx, esophagus, stomach, bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye or brain. In other cases, the starting material can be cells containing nucleic acids. The tissue may comprise an infected tissue, diseased tissue, malignant tissue, calcified tissue or healthy tissue. A sample can comprise at least one cell from one or more biological tissues. For example, a sample can comprise one or more malignant cells.

The one or more malignant cells may be derived from a tumor, carcinoma, sarcoma, or leukemia. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma). Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some embodiments, the cancer is a skin cancer, such as a basal cell carcinoma, squamous cell carcinoma, melanoma, nonmelanoma, or actinic (solar) keratosis. In some embodiments, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma. In some embodiments, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some embodiments, the cancer is a meningioma. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

A plurality of samples may comprise at least 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

The one or more polynucleotides in a first sample may be different from one or more polynucleotides in a second sample. The one or more polynucleotides in a first sample may be different from one or more polynucleotides in a plurality of samples. One or more polynucleotides in a sample can comprise at least about 80%, 85%, 90%, 95%, 96%, 97%, 98%, 99%, or 100% sequence identity. In some embodiments, one or more polynucleotides in a sample can differ by less than about 100, 90, 80, 70, 60, 50, 40, 30, 25, 20, 25, 10, 9, 8, 7, 6, 5, 4, 3, 2, or 1 nucleotide or base pair. A plurality of polynucleotides in one or more samples of the plurality of samples can comprise two or more identical sequences. At least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the total polynucleotides in one or more of the plurality of samples can comprise the same sequence. A plurality of polynucleotides in one or more samples of the plurality of samples may comprise at least two different sequences. At least about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 100% of the total polynucleotides in one or more of the plurality of samples may comprise at least two different sequences. In some embodiments, one or more polynucleotides are variants of each other. For example, one or more polynucleotides may contain single nucleotide polymorphisms or other types of mutations. In another example, one or more polynucleotides are splice variants.

A first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples.

The plurality of samples may be obtained concurrently. A plurality of samples can be obtained at the same time. The plurality of samples can be obtained sequentially. A plurality of samples can be obtained over a course of years, 100 years, 10 years, 5 years, 4 years, 3 years, 2 years, or 1 year of obtaining one or more different samples. One or more samples can be obtained within about one year of obtaining one or more different samples.

One or more samples can be obtained within 12 months, 11 months, 10 months, 9 months, 8 months, 7 months, 6 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or one day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 sec, 45 sec, 30 sec, 20 sec, 10 sec, 5 sec, 2 sec or 1 sec of obtaining one or more different samples. One or more samples can be obtained within less than one second of obtaining one or more different samples.

The different polynucleotides of a sample can be present in the sample at different concentrations or amounts. For example, the concentration or amount of one polynucleotide can be greater than the concentration or amount of another polynucleotide in the sample. In some embodiments, the concentration or amount of at least one polynucleotide in the sample is at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of at least one other polynucleotide in the sample. In another example, the concentration or amount of one polynucleotide is less than the concentration or amount of another polynucleotide in the sample. The concentration or amount of at least one polynucleotide in the sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least one other polynucleotide in the sample.

In some embodiments, two or more samples may contain different amounts or concentrations of the polynucleotides. In some embodiments, the concentration or amount of one polynucleotide in one sample may be greater than the concentration or amount of the same polynucleotide in a different sample. For example, a blood sample might contain a higher amount of a particular polynucleotide than a urine sample. Alternatively, a single sample can divided into two or more subsamples. The subsamples may contain different amounts or concentrations of the same polynucleotide. The concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of the same polynucleotide in another sample. Alternatively, the concentration or amount of one polynucleotide in one sample may be less than the concentration or amount of the same polynucleotide in a different sample. For example, the concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of the same polynucleotide in another sample.

Whole Blood Samples

In some embodiments, the sample is whole blood. In some embodiments, the percentage of amplicons containing 10 or more UIDs generated from a whole blood sample is equal to the percentage of amplicons containing 10 or more UIDs generated from a purified polynucleotide sample. In some embodiments, the percentage of amplicons containing 10 or more UIDs generated from a whole blood sample is only less than about 1%, 2%, 3%, 4%, 5%, 6%, 7%, 8%, 9%, or at most 10% less than the percentage of amplicons containing 10 or more UIDs generated from a purified polynucleotide sample. In some embodiments, the on target specificity observed from a whole blood sample is equal to the on target specificity observed from a purified polynucleotide sample. In some embodiments, the on target specificity observed from a whole blood sample is only less than about 1%, 2%, 3%, 4%, 5%, 6%, 7%, 8%, 9%, or at most 10% less than the on target specificity observed from a purified polynucleotide sample. In some embodiments, the coverage uniformity observed from a whole blood sample is equal to the coverage uniformity observed from a purified polynucleotide sample. In some embodiments, the coverage uniformity observed from a whole blood sample is only less than about 1%, 2%, 3%, 4%, 5%, 6%, 7%, 8%, 9%, or at most 10% less than the coverage uniformity observed from a purified polynucleotide sample.

FFPE Samples

In some embodiments, the sample is a formalin-fixed, paraffin-embedded (FFPE) sample. In some embodiments, the percentage of amplicons containing 10 or more UIDs generated from a FFPE sample is equal to the percentage of amplicons containing 10 or more UIDs generated from a purified polynucleotide sample. In some embodiments, the percentage of amplicons containing 10 or more UIDs generated from a FFPE sample is only less than about 1%, 2%, 3%, 4%, 5%, 6%, 7%, 8%, 9%, or at most 10% less than the percentage of amplicons containing 10 or more UIDs generated from a purified polynucleotide sample. In some embodiments, the on target specificity observed from a FFPE sample is equal to the on target specificity observed from a purified polynucleotide sample. In some embodiments, the on target specificity observed from a FFPE sample is only less than about 1%, 2%, 3%, 4%, 5%, 6%, 7%, 8%, 9%, or at most 10% less than the on target specificity observed from a purified polynucleotide sample. In some embodiments, the coverage uniformity observed from a FFPE sample is equal to the coverage uniformity observed from a purified polynucleotide sample. In some embodiments, the coverage uniformity observed from a FFPE sample is only less than about 1%, 2%, 3%, 4%, 5%, 6%, 7%, 8%, 9%, or at most 10% less than the coverage uniformity observed from a purified polynucleotide sample.

Libraries

The libraries disclosed herein may be used in a variety of applications. As used herein, a library comprises a plurality of molecules. In some embodiments, a library comprises a plurality of polynucleotides. In some embodiments, a library comprises a plurality of primers. In some embodiments, a library comprises a plurality of RT primers. In some embodiments, a library comprises a plurality of PE primers. In some embodiments, a library comprises a plurality of linear primer extension (LPE) primers. In some embodiments, a library comprises a plurality of adaptors. In some embodiments, a library comprises a plurality of primers for non-exponential amplification, such as linear amplification. In some embodiments, a library comprises a plurality of primers for exponential amplification, such as PCR. In some embodiments, a library comprises a plurality of polynucleotides for sequencing. For example, the library could be used for sequencing applications. In some embodiments, a library comprises a plurality of sequence reads from one or more polynucleotides, amplicons, or amplicon sets. A library can be stored and used multiple times to generate samples for analysis. Some applications include, for example, genotyping polymorphisms, studying RNA processing, and selecting clonal representatives to do sequencing according to the methods provided herein. Libraries comprising a plurality of polynucleotides, such as primers or libraries for sequencing or amplification, can be generated, wherein a plurality of polynucleotides comprises at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, or 900 UIDs or unique polynucleotides. In some embodiments, libraries of polynucleotides comprise a plurality of at least about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more unique polynucleotides, wherein each unique polynucleotide comprises a UID. In some embodiments, libraries of polynucleotides comprise a plurality of amplicon sets, wherein each amplicon set comprises a plurality of polynucleotides with the same UID. In some embodiments, libraries of polynucleotides comprise a plurality of at least about 1, 2, 3, 4, 5, 6, 7, 8, 9, 10, 20, 30, 40, 50, 60, 70, 80, 90, 100, 100, 200, 300, 40, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000 or more amplicons, wherein each polynucleotide in the one or more amplicons comprises a plurality of polynucleotides with the same UID. In some embodiments, libraries of polynucleotides comprise a plurality of at least about 1, 2, 3, 4, 5, 6, 7, 8, 9, 10, 20, 30, 40, 50, 60, 70, 80, 90, 100, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000 or more amplicon sets, wherein each amplicon set comprises a plurality of polynucleotides or amplicons with the same UID. In some embodiments, libraries of polynucleotides comprise a plurality of at least about 1, 2, 3, 4, 5, 6, 7, 8, 9, 10, 20, 30, 40, 50, 60, 70, 80, 90, 100, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000 or more polynucleotides, amplicons or amplicon sets, wherein each polynucleotide, amplicon or amplicon set comprises a plurality of polynucleotides, amplicons or amplicon sets with the same template sequence or portion thereof. In some embodiments, libraries of polynucleotides comprise a plurality of at least about 1, 2, 3, 4, 5, 6, 7, 8, 9, 10, 20, 30, 40, 50, 60, 70, 80, 90, 100, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000 or more polynucleotides, amplicons or amplicon sets, wherein each polynucleotide, amplicon or amplicon set comprises a plurality of polynucleotides, amplicons or amplicon sets with a template sequence or portion thereof that differs from one or more other polynucleotides, amplicons or amplicon sets by one more bases caused by amplification or sequencing error or bias.

Primers

Conducting the one or more reactions of the methods disclosed herein can comprise the use of one or more primers. As used herein, a primer comprises a double-stranded, single-stranded, or partially single-stranded oligonucleotide that is sufficiently complementary to hybridize to a template polynucleotide. A primer can be a single-stranded DNA prior to binding a template polynucleotide. In some embodiments, the primer initially comprises double-stranded sequence. A primer site includes the area of the template to which a primer hybridizes. In some embodiments, primers are capable of acting as a point of initiation for template-directed nucleic acid synthesis. For example, primers can initiate template-directed nucleic acid synthesis when four different nucleotides and a polymerization agent or enzyme, such as DNA or RNA polymerase or reverse transcriptase. A primer pair includes 2 primers: a first primer with a 5' upstream region that hybridizes with a 5' end of a template sequence, and a second primer with a 3' downstream region that hybridizes with the complement of the 3' end of the template sequence. In some embodiments, a primer comprises a target specific sequence and UID sequence. In some embodiments, a primer comprises a barcode sequence. In some embodiments, a primer comprises a UID sequence. In some embodiments, a primer comprises a sample barcode sequence. In some embodiments, a primer comprises a universal priming sequence. In some embodiments, a primer comprises a PCR priming sequence. In some embodiments, a primer comprises a PCR priming sequence used to initiate amplification of a polynucleotide. (Dieffenbach, PCR Primer: A Laboratory Manual, 2nd Edition (Cold Spring Harbor Press, New York (2003)). The universal primer binding site or sequence allows the attachment of a universal primer to a polynucleotide and/or amplicon. Universal primers are well known in the art and include, but are not limited to, −47F (M13F), alfaMF, AOX3', AOX5', BGHr, CMV-30, CMV-50, CVMf, LACrmt, lambda gt10F, lambda gt10R, lambda gt11F, lambda gt11R, M13 rev, M13Forward(−20), M13Reverse, male, p10SEQPpQE, pA-120, pet4, pGAP Forward, pGL-RVpr3, pGLpr2R, pKLAC14, pQEFS, pQERS, pucU1, pucU2, reversA, seqIREStam, seqIRESzpet, seqori, seqPCR, seqpIRES−, seqpIRES+, seqpSecTag, seqpSecTag+, seqretro+PSI, SP6, T3-prom, T7-prom, and T7-termInv. As used herein, attach can refer to both or either covalent interactions and noncovalent interactions. Attachment of the universal primer to the universal primer binding site may be used for amplification, detection, and/or sequencing of the polynucleotide and/or amplicon. The universal primer binding site may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some embodiments, the universal primer binding site comprises 1-10, 10-20, 10-30 or 10-100 nucleotides or base pairs. In some embodiments, the universal primer binding site comprises from about 1-90, 1-80, 1-70, 1-60, 1-50, 1-40, 1-30, 1-20, 1-10, 2-90, 2-80, 2-70, 2-60, 2-50, 2-40, 2-30, 2-20, 2-10, 1-900, 1-800, 1-700, 1-600, 1-500, 1-400, 1-300, 1-200, 1-100, 2-900, 2-800, 2-700, 2-600, 2-500, 2-400, 2-300, 2-200, 2-100, 5-90, 5-80, 5-70, 5-60, 5-50, 5-40, 5-30, 5-20, 5-10, 10-90, 10-80, 10-70, 10-60, 10-50, 10-40, 10-30, 10-20, 10-10, 5-900, 5-800, 5-700, 5-600, 5-500, 5-400, 5-300, 5-200, 5-100, 10-900, 10-800, 10-700, 10-600, 10-500, 10-400, 10-300, 10-200, 10-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can have a length compatible with its use in synthesis of primer extension products. A primer can be a polynucleotide that is 8 to 200 nucleotides in length. The length of a primer can depend on the sequence of the template polynucleotide and the template locus. For example, the length and/or melting temperature (Tm) of a primer or primer set can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, primers are about 8-100 nucleotides in length, for example, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, or 20-60 nucleotides in length and any length there between. In some embodiments, primers are at most about 10, 12, 15, 20, 21, 22, 23, 24, 25, 26, 27, 28, 29, 30, 35, 40, 45, 50, 55, 60, 65, 70, 75, 80, 85, 90, 95 or 100 nucleotides in length.

Generally, one or more pairs of primers can be used in an exponential amplification reaction; one primer of a primer pair can be a forward primer and one primer of a primer pair can be a reverse primer. In some embodiments, a first pair of primers can be used in the exponential amplification reaction; one primer of the first pair can be a forward primer complementary to a sequence of a first template polynucleotide molecule and one primer of the first pair can be a reverse primer complementary to a second sequence of the first template polynucleotide molecule, and a first template locus can reside between the first sequence and the second sequence. In some embodiments, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence. In some embodiments, a third pair of primers can be used in the amplification reaction; one primer of the third pair can be a forward primer complementary to a first sequence of a third template polynucleotide molecule and one primer of the third pair can be a reverse primer complementary to a second sequence of the third template polynucleotide molecule, and a third template locus can reside between the first sequence and the second sequence. In some embodiments, a first, second, or third template locus comprises a barcode, such as a UID.

The one or more primers can anneal to at least a portion of a plurality of template polynucleotides. The one or more primers can anneal to the 3' end and/or 5' end of the plurality of template polynucleotides. The one or more primers can anneal to an internal region of the plurality of template polynucleotides. The internal region can be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends or 5' ends the plurality of template polynucleotides. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. In some embodiments, the one or more custom primers do not anneal to a UID. In some embodiments, the one or more custom primers anneal to an SBC, a target specific region, compliments thereof, or any combination thereof. The one or more primers can comprise a universal primer and a UID containing primer. The one or more primers primer can be designed to amplify or perform primer extension, reverse transcription, linear extension, non-exponential amplification, exponential amplification, PCR, or any other amplification method of one or more target or template polynucleotides The target specific region can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. in some embodiments, the target specific region comprises from about 5-10, 10-15, 10-20, 10-30, 15-30, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, 20-60, 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can be designed according to known parameters for avoiding secondary structures and self-hybridization. In some embodiments, different primer pairs can anneal and melt at about the same temperatures, for example, within 1, 2, 3, 4, 5, 6, 7, 8, 9 or 10° C. of another primer pair. In some embodiments, one or more primers in a plurality of primers can anneal and melt at about the same temperatures, for example, within 1, 2, 3, 4, 5, 6, 7, 8, 9 or 10° C. of another primer in the plurality of primers. In some embodiments, one or more primers in a plurality of primers can anneal and melt at different temperatures than another primer in the plurality of primers.

A plurality of primers for one or more steps of the methods described herein can comprise a plurality of primers comprising about, at most about, or at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1,000,000, 50,000,000, 100,000,000 different primers. For example, each primer in a plurality of primers can comprise a UID. For example, each primer in a plurality of primers can comprise a different target or template specific region or sequence. For example, each primer in a plurality of primers can comprise a different UID and a different target or template specific region or sequence. For example, each primer in a plurality of primers can comprise a different UID and the same target or template specific region or sequence.

Primer Panels

In some embodiments, the primer panels used for the methods described herein comprise or consist of primers with a melting temperature range of between 60° C.-68° C. In some embodiments, the primer panels used for the methods described herein comprise or consist of primers with a length of between 21 and 32 nucleotides. In some embodiments, the primer panels used for the methods described herein comprise or consist of primers that do not contain 4 or more pyrimidines in the last 5 nucleotides at the 3' end. In some embodiments, the primer panels used for the methods described herein comprise or consist of primers designed to produce an amplicon containing between 30% and 70% GC content. In some embodiments, the primer panels used for the methods described herein comprise or consist of primers designed to produce amplicons with a length of between 225 and 300 base pairs. In some embodiments, the primer panels used for the methods described herein comprise or consist of primers from an initial panel that excludes primers with the highest number of misreads (caused by mispriming) during the initial RT/PE step or the linear extension/amplification step. In some embodiments, the primer panels used for the methods described herein comprise or consist of primers from an initial panel that excludes primers prevalent in dimers. In some embodiments, the primer panels used for the methods described herein comprise or consist of primers from an initial panel that excludes primers that are responsible for generating one or more of the highest number of total reads for a target (over-amplifiers). Any one or combination of the above metrics can be used in generating primer panels for use in the methods described.

UIDs

In some embodiments, barcodes, such as an SBC or UID, can each have a length within a range of from 4 to 36 nucleotides, or from 6 to 30 nucleotides, or from 8 to 20 nucleotides. In certain aspects, the melting temperatures of barcodes within a set are within 10° C. of one another, within 5° C. of one another, or within 2° C. of one another. In other aspects, barcodes are members of a minimally cross-hybridizing set. For example, the nucleotide sequence of each member of such a set can be sufficiently different from that of every other member of the set that no member can form a stable duplex with the complement of any other member under stringent hybridization conditions. In some embodiments, the nucleotide sequence of each member of a minimally cross-hybridizing set differs from those of every other member by at least two nucleotides. Barcode technologies are described in Winzeler et al. (1999) Science 285:901; Brenner (2000) Genome Biol.1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

As used herein, a Unique Identification tag (UID) comprises information that is unique to a single molecule, or two or more molecules of a plurality or library of molecules. A barcode can be a UID. In some embodiments the unique information comprises a unique sequence of nucleotides. For example, the sequence of the UID can be determined by determining the identity and order of the unique or random sequence of nucleotides comprising the UID. In some embodiments the unique information cannot be used to identify the sequence of a target polynucleotide. In some embodiments the unique information is not a known sequence linked to the identity of the sequence of a target polynucleotide. For example, a UID may be attached to one or more target polynucleotides, but the UID cannot be used to determine which of the one or more target polynucleotides to which it is attached. In some embodiments the unique information comprises a random sequence of nucleotides. In some embodiments the unique information comprises one or more unique sequences of nucleotides on a polynucleotide. In some embodiments the unique information comprises a degenerate nucleotide sequence or degenerate barcode. A degenerate barcode can comprise a variable nucleotide base composition or sequence. For example, a degenerate barcode can be a random sequence. In some embodiments, a complement sequence of a UID is also a UID sequence.

A UID can comprise any length of nucleotides. For example a UID can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. For example a UID can comprise at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. In some embodiments, a UID has a particular length of nucleotides. For example, a UID can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

In some embodiments, each UID in a plurality of UIDs has at least about 2 nucleotides. For example, each UID in a plurality of UIDs can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each UID in a plurality of UIDs has at most about 1000 nucleotides. For example, each UID in a plurality of UIDs can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each UID in a plurality of UIDs has the same length of nucleotides. For example, each UID in a plurality of UIDs can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, one or more UIDs in a plurality of UIDs have a different length of nucleotides. For example one or more first UIDs in a plurality of UIDs can have about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides and one or more second UIDs in a plurality of UIDs can have about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides, wherein the number of nucleotides of the one or more first UIDs is different than the one or more second UIDs.

The number of UIDs can be in excess of the number of molecules to be labeled. In some embodiments, the number of UIDs is at least about 2, 3, 4, 5, 6, 7, 8, 9, 10, 15, 20, 30, 40, 50, 60, 70, 80, 90, or 100 times greater than the number of molecules to be labeled.

The number of different UIDs can be in excess of the number of different molecules to be labeled. In some embodiments, the number of different UIDs is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different UIDs have the same concentration. in some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different UIDs have a different concentration.

The UIDs in a population of UIDs can have at least 10, 15, 20, 25, 30, 35, 40, 45, 50, 60, 70, 80, 90, 100, 200, 300, 400, 500, 600, 700, 800, 900, 1000 or more different sequences. For example, the UIDs in a population can have at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800, 000, 900,000, 1,000,000 or more different sequences. Thus, a plurality of UIDs can be used to generate at least 10, 15, 20, 25, 30, 35, 40, 45, 50, 60, 70, 80, 90, 100, 200, 300, 400, 500, 600, 700, 800, 900, 1000 or more different sequences from one or more polynucleotides, such as target polynucleotides. For example, a plurality of UIDs can be used to generate at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600, 000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from one or more polynucleotides, such as target polynucleotides. For example, a plurality of UIDs can be used to generate at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600, 000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more target polynucleotides.

In some embodiments, one or more UIDs are used to group or bin sequences. In some embodiments, one or more UIDs are used to group or bin sequences, wherein the sequences in each bin contain the same UID. In some embodiments, one or more UIDs are used to group or bin sequences, wherein the sequences in each bin comprise an amplicon set. In some embodiments, one or more UIDs are used to group or bin sequences, wherein the sequences in each bin comprise a plurality of sequences wherein the polynucleotides from which the plurality of sequences were generated were derived from the same polynucleotide in an amplification reaction. For example, one or more UIDs can be used to group or bin sequences in an amplicon or an amplicon set, or both. In some embodiments, one or more UIDs are not used to align sequences.

In some embodiments, one or more UIDs are not used to align sequences. In some embodiments, one or more UIDs are not used to align sequences and are used to group or bin sequences. In some embodiments, one or more UIDs are not used to align sequences and a target specific region is used to align sequences. In some embodiments, one or more UIDs are used to group or bin sequences and a target specific region is used to align sequences. In some embodiments, one or more UIDs are not used to align sequences, one or more UIDs are used to group or bin sequences, and a target specific region is used to align sequences.

In some embodiments, one or more UIDs are used to align sequences. In some embodiments, one or more UIDs are used to align sequences, wherein the aligned sequences contain the same UID. In some embodiments, one or more UIDs are used align sequences, wherein the aligned sequences comprise two or more sequences from an amplicon set. In some embodiments, one or more UIDs are used to align sequences, wherein the aligned sequences comprise a plurality of sequences wherein the polynucleotides from which the plurality of sequences were generated were derived from the same polynucleotide in an amplification reaction.

Enzymes

The methods and kits disclosed herein may comprise one or more enzymes.

Examples of enzymes include, but are not limited to ligases, reverse transcriptases, polymerases, and restriction nucleases.

In some embodiments, attachment of an adaptor to polynucleotides comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein may further comprise the use of one or more reverse transcriptases. In some embodiments, the reverse transcriptase is a HIV-1 reverse transcriptase, M-MLV reverse transcriptase, AMV reverse transcriptase, and telomerase reverse transcriptase. In some embodiments, the reverse transcriptase is M-MLV reverse transcriptase.

In some embodiments, the methods and kits disclosed herein comprise the use of one or more polymerases. Examples of polymerases include, but are not limited to, DNA polymerases and RNA polymerases. In some embodiments, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, *Sulfolobus* DNA Polymerase IV, Taq DNA Polymerase, 9° NTMm DNA Polymerase, Deep VentR™ (exo-) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

In some embodiments, the polymerase is an RNA polymerases such as RNA polymerase I, RNA polymerase II, RNA polymerase III, *E. coli* Poly(A) polymerase, phi6 RNA polymerase (RdRP), Poly(U) polymerase, SP6 RNA polymerase, and T7 RNA polymerase.

Additional Reagents

The methods and kits disclosed herein may comprise the use of one or more reagents. Examples of reagents include, but are not limited to, PCR reagents, ligation reagents, reverse transcription reagents, enzyme reagents, hybridization reagents, sample preparation reagents, affinity capture reagents, solid supports such as beads, and reagents for nucleic acid purification and/or isolation.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)) and the like. Examples of beads for use according to the embodiments can include an affinity moiety that allows the bead to interact with a nucleic acid molecule. A solid phase (e.g. a bead) can comprise a member of a binding pair (e.g. avidin, streptavidin or derivative thereof). For instance, the bead may be a streptavidin-coated bead and a nucleic acid molecule for immobilization on the bead can include a biotin moiety. In some cases, each polynucleotide molecule can include two affinity moieties, such as biotin, to further stabilize the polynucleotide. Beads can include additional features for use in immobilizing nucleic acids or that can be used in a downstream screening or selection processes. For example, the bead may include a binding moiety, a fluorescent label or a fluorescent quencher. In some cases, the bead can be magnetic. In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluoro chrome microbead, and BcMag™ Carboxy-Terminated Magnetic Beads. Beads or particles may be swellable (e.g., polymeric beads such as Wang resin) or non-swellable (e.g., CPG). In some embodiments a solid phase is substantially hydrophilic. In some embodiments a solid phase (e.g. a bead) is substantially hydrophobic. In some embodiments a solid phase comprises a member of a binding pair (e.g. avidin, streptavidin or derivative thereof) and is substantially hydrophobic or substantially hydrophilic. In some embodiments, a solid phase comprises a member of a binding pair (e.g. avidin, streptavidin or derivative thereof) and has a binding capacity greater than about 1350 pmoles of free capture agent (e.g. free biotin) per mg solid support. In some embodiments the binding capacity of solid phase comprising a member of a binding pair is greater than 800, 900, 1000, 1100, 1200, 1250, 1300, 1350, 1400, 1450, 1500, 1600, 1800, 2000 pmoles of free capture agent per mg solid support. Other examples of beads that are suitable for the invention are gold colloids or beads such as polystyrene beads or silica beads. Substantially any bead radii may be used. Examples of beads may include beads having a radius ranging from 150 nanometers to 10 microns. Other sizes may also be used.

The methods and kits disclosed herein may comprise the use of one or more buffers. Examples of buffers include, but are not limited to, wash buffers, ligation buffers, hybridization buffers, amplification buffers, and reverse transcription buffers. In some embodiments, the hybridization buffer is a commercially available buffer, such as TMAC Hyb solution, SSPE hybridization solution, and ECONOTM hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., a polynucleotide and/or amplicon). For example, the carrier may decrease non-specific loss of a polynucleotide through absorption to surfaces. The carrier may decrease the affinity of a polynucleotide to a surface or substrate (e.g., container, Eppendorf tube, pipet tip). Alternatively, the carrier may increase the affinity of a polynucleotide to a surface or substrate (e.g., bead, array, glass, slide, or chip). Carriers may protect the polynucleotide from degradation. For example, carriers may protect an RNA molecule from ribonucleases. Alternatively, carriers may protect a DNA molecule from a DNase. Examples of carriers include, but are not limited to, polynucleotides such as DNA and/or RNA, or polypeptides. Examples of DNA carriers include plasmids, vectors, polyadenylated DNA, and DNA oligonucleotides. Examples of RNA carriers include polyadenylated RNA, phage RNA, phage MS2 RNA, *E. Coli* RNA, yeast RNA, yeast tRNA, mammalian RNA, mammalian tRNA, short polyadenylated synthetic ribonucleotides and RNA oligonucleotides. The RNA carrier may be a polyadenylated RNA. Alternatively, the RNA carrier may be a non-polyadenylated RNA. In some embodiments, the carrier is from a bacteria, yeast, or virus. For example, the carrier may be a polynucleotide or a polypeptide derived from a bacteria, yeast or virus. For example, the carrier is a protein from *Bacillus subtilis*. In another example, the carrier is a polynucleotide from *Escherichia coli*. Alternatively, the carrier is a polynucleotide or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control polynucleotides, inactive enzymes, and non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some embodiments, the spike-in template is added to an amplification reaction after cycle number 2, 3, 4, 5, 6, 7, 8, 9, 10, 11, 12, 13, 14, 15, 20, 25, 30, 35, 40, 45, or 50. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Computer-Implemented Aspects

As understood by those of ordinary skill in the art, the methods and information described herein can be implemented, in all or in part, as computer executable instructions on known computer readable media. For example, the methods described herein can be implemented in hardware. Alternatively, the methods can be implemented in software stored in, for example, one or more memories or other computer readable medium and implemented on one or more processors. As is known, the processors can be associated with one or more controllers, calculation units and/or other units of a computer system, or implanted in firmware as desired. If implemented in software, the routines can be stored in any computer readable memory such as in RAM, ROM, flash memory, a magnetic disk, a laser disk, or other storage medium, as is also known. Likewise, this software can be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above can be implemented as various blocks, operations, tools, modules and techniques which, in turn, can be implemented in hardware, firmware, software, or any combination of hardware, firmware, and/or software. When implemented in hardware, some or all of the blocks, operations, techniques, etc. can be implemented in, for example, a custom integrated circuit (IC), an application specific integrated circuit (ASIC), a field programmable logic array (FPGA), a programmable logic array (PLA), etc.

Results from sequencing data can be stored in a data storage unit, such as a data carrier, including computer databases, data storage disks, or by other convenient data storage means. In certain embodiments, the computer database is an object database, a relational database or a post-relational database. Data can be retrieved from the data storage unit using any convenient data query method.

When implemented in software, the software can be stored in any known computer readable medium such as on a magnetic disk, an optical disk, or other storage medium, in a RAM or ROM or flash memory of a computer, processor, hard disk drive, optical disk drive, tape drive, etc. Likewise, the software can be delivered to a user or a computing system via any known delivery method including, for example, on a computer readable disk or other transportable computer storage mechanism.

The steps of the claimed methods can be operational with numerous other general purpose or special purpose computing system environments or configurations. Examples of well known computing systems, environments, and/or configurations that can be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed methods can be described in the general context of computer-executable instructions, such as program modules, being executed by a computer. Generally, program modules include routines, programs, objects, components, and/or data structures that perform particular tasks or implement particular abstract data types. The methods can also be practiced in distributed computing environments where tasks are performed by remote processing devices that are linked through a communications network. In both integrated and distributed computing environments, program modules can be located in both local and remote computer storage media including memory storage devices. Numerous alternative embodiments could be implemented, using either current technology or technology developed after the filing date of this application, which would still fall within the scope of the claims defining the disclosure.

While the methods, and other elements, have been described as preferably being implemented in software, they can be implemented in hardware, firmware, etc., and can be implemented by any other processor. Thus, the elements described herein can be implemented in a standard multi-purpose CPU or on specifically designed hardware or firmware such as an application-specific integrated circuit (ASIC) or other hard-wired device as desired. When implemented in software, the software routine can be stored in any computer readable memory such as on a magnetic disk, a laser disk, or other storage medium, in a RAM or ROM of a computer or processor, in any database, etc. Likewise, this software can be delivered to a user or a screening system via any known or desired delivery method including, for example, on a computer readable disk or other transportable computer storage mechanism or over a communication channel, for example, a telephone line, the internet, or wireless communication. Modifications and variations can be made in the techniques and structures described and illustrated herein without departing from the spirit and scope of the present disclosure.

FIG. 58 is a block diagram illustrating a first example architecture of a computer system 100 that can be used in connection with example embodiments of the present invention. As depicted in FIG. 58, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 59, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 100 also includes network interface cards (NICs) 120 and 121 connected to the peripheral bus for providing network interfaces to external storage, such as Network Attached Storage (NAS) and other computer systems that can be used for distributed parallel processing.

FIG. 59 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 59 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

FIG. 60 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the data management and optimization system can be implemented in software or hardware and that any variety of data storage media can be used in connection with example embodiments, including random access memory, hard drives, flash memory, tape drives, disk arrays, Network Attached Storage (NAS) and other local or distributed data storage devices and systems.

In example embodiments, the data management and optimization system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 60, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 58.

One of skill in the art will appreciate that although only one of each of the components identified above is depicted in the figures, any number of any of these components may be provided. Furthermore, one of ordinary skill in the art will recognize that one or more components of any of the disclosed systems may be combined or incorporated into another component shown in the figures. One or more of the components depicted in the figures may be implemented in software on one or more computing systems. For example, they may comprise one or more applications, which may comprise one or more computer units of computer-readable instructions which, when executed by a processor, cause a computer to perform steps of a method. Computer-readable instructions may be stored on a computer readable medium, such as a memory or disk. Such media typically provide nontransitory storage. Alternatively, one or more of the components depicted in the figures may be hardware components or combinations of hardware and software such as, for example, special purpose computers or general purpose computers. A computer or computer system may also comprise an internal or external database. The components of a computer or computer system may connect through a local bus interface.

One of skill in the art will appreciate that the above-described stages may be embodied in distinct software modules. Although the disclosed components have been described above as being separate units, one of ordinary skill in the art will recognize that functionalities provided by one or more units may be combined. As one of ordinary skill in the art will appreciate, one or more of units may be optional and may be omitted from implementations in certain embodiments.

Kits

Kits useful in the methods of the disclosure comprise components useful in any of the methods described herein, including for example, primers for nucleic acid amplification, hybridization probes for detecting genetic variation, or other marker detection, restriction enzymes, nucleic acid probes, optionally labeled with suitable labels, allele-specific oligonucleotides, antibodies that bind to an altered polypeptide encoded by a nucleic acid of the disclosure as described herein or to a wild type polypeptide encoded by a nucleic acid of the disclosure as described herein, means for amplification of genetic variations or fragments thereof, means for analyzing the nucleic acid sequence of nucleic acids comprising genetic variations as described herein, means for analyzing the amino acid sequence of a polypeptide encoded by a genetic variation, or a nucleic acid associated with a genetic variation, etc. The kits can for example, include necessary buffers, nucleic acid primers for amplifying nucleic acids, solid supports, and reagents for allele-specific detection of the fragments amplified using such primers and necessary enzymes (e.g., DNA polymerase), such as any of those described herein. Additionally, kits can provide reagents for assays to be used in combination with the methods of the present disclosure, for example, reagents for use with other screening assays for a disease or condition.

In some embodiments, the disclosure pertains to a kit for assaying a nucleic acid sample from a subject to detect the presence of a genetic variation, wherein the kit comprises reagents necessary for selectively detecting at least one particular genetic variation in the genome of the individual. In some embodiments, the disclosure pertains to a kit for assaying a nucleic acid sample from a subject to detect the presence of at least particular allele of at least one polymorphism associated with a genetic variation in the genome of the subject. In some embodiments, the reagents comprise at least one contiguous oligonucleotide that hybridizes to a fragment of the genome of the individual comprising at least genetic variation. In some embodiments, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one genetic variation, or a fragment of a genetic variation. Such oligonucleotides or nucleic acids can be designed using the methods described herein. In some embodiments, the kit comprises one or more labeled nucleic acids capable of allele-specific detection of one or more specific polymorphic markers or haplotypes with a genetic variation, and reagents for detection of the label. In some embodiments, a kit for detecting SNP markers can comprise a detection oligonucleotide probe, that hybridizes to a segment of template DNA containing a SNP polymorphisms to be detected, an enhancer oligonucleotide probe, detection probe, primer and/or an endonuclease, for example, as described by Kutyavin et al. (Nucleic Acid Res. 34:e128 (2006)).

In some embodiments, the DNA template is amplified by any means of the present disclosure, prior to assessment for the presence of specific genetic variations as described herein. Standard methods well known to the skilled person for performing these methods can be utilized, and are within scope of the disclosure. In one such embodiment, reagents for performing these methods can be included in the reagent kit.

In a further aspect of the present disclosure, a pharmaceutical pack (kit) is provided, the pack comprising a therapeutic agent and a set of instructions for administration of the therapeutic agent to humans screened for one or more variants of the present disclosure, as disclosed herein. The therapeutic agent can be a small molecule drug, an antibody, a peptide, an antisense or RNAi molecule, or other therapeutic molecules as described herein. In some embodiments, an individual identified as a carrier of at least one variant of the present disclosure is instructed to take a prescribed dose of the therapeutic agent. In one such embodiment, an individual identified as a carrier of at least one variant of the present disclosure is instructed to take a prescribed dose of the therapeutic agent. In some embodiments, an individual identified as a non-carrier of at least one variant of the present disclosure is instructed to take a prescribed dose of the therapeutic agent.

Also provided herein are articles of manufacture, comprising a probe that hybridizes with a region of human chromosome as described herein and can be used to detect a polymorphism described herein. For example, any of the probes for detecting polymorphisms described herein can be combined with packaging material to generate articles of manufacture or kits. The kit can include one or more other elements including: instructions for use; and other reagents such as a label or an agent useful for attaching a label to the probe. Instructions for use can include instructions for screening applications of the probe for making a diagnosis, prognosis, or theranosis to a disease or condition in a method described herein. Other instructions can include instructions for attaching a label to the probe, instructions for performing in situ analysis with the probe, and/or instructions for obtaining a nucleic acid sample to be analyzed from a subject. In some cases, the kit can include a labeled probe that hybridizes to a region of human chromosome as described herein.

The kit can also include one or more additional reference or control probes that hybridize to the same chromosome or another chromosome or portion thereof that can have an abnormality associated with a particular endophenotype. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes. Kits for use in self-testing can also be provided. Such test kits can include devices and instructions that a subject can use to obtain a nucleic acid sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the nucleic acid sample for analysis, e.g., to a laboratory. The kit can include one or more containers for the nucleic acid sample, or the nucleic acid sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the nucleic acid sample can be coded, for example, with a barcode for identifying the subject who provided the nucleic acid sample.

In some embodiments, an in vitro screening test can comprise one or more devices, tools, and equipment configured to collect a nucleic acid sample from an individual. In some embodiments of an in vitro screening test, tools to collect a nucleic acid sample can include one or more of a swab, a scalpel, a syringe, a scraper, a container, and other devices and reagents designed to facilitate the collection, storage, and transport of a nucleic acid sample. In some embodiments, an in vitro screening test can include reagents or solutions for collecting, stabilizing, storing, and processing a nucleic acid sample.

Such reagents and solutions for nucleotide collecting, stabilizing, storing, and processing are well known by those of skill in the art and can be indicated by specific methods used by an in vitro screening test as described herein. In some embodiments, an in vitro screening test as disclosed herein, can comprise a microarray apparatus and reagents, a flow cell apparatus and reagents, a multiplex nucleotide sequencer and reagents, and additional hardware and software necessary to assay a nucleic acid sample for certain genetic markers and to detect and visualize certain genetic markers.

EXAMPLES

Example 1

RNA Targeted Sequencing Protocol cDNA Synthesis 1 ng up to 1000 ng of RNA was combined with 5 µl of the following primer mix containing 5 pmols of each primer (SEQ ID NOS 3-7, respectively, in order of appearance):

```
ACTB250A RT6p7_UID
/5Phos/CGATCTNNNNWNNNNAACCGACTGCTGTCACCTTC

ACTB250B RT6p7_UID
/5Phos/CGATCTNNNNWNNNNCCAGGGAGACCAAAAGCCTT

RB2M250A RT6p7_UID
/5Phos/CGATCTNNNNWNNNNACCAGATTAACCACAACCATGC

GAPDH250A RT6p7_UID
/5Phos/CGATCTNNNNWNNNNATGGTTCACACCCATGACGAAC

GAPDH250B RT6p7_UID
/5Phos/CGATCTNNNNWNNNNGTTTTTCTAGACGGCAGGTCAG
```

The 12 µl reaction was heated for 1 min at 95° C, followed by 65° C for 1 min and a hold at 4° C. 4 µl of 5× First strand buffer (Life Technologies, Carlsbad, Calif.), 1 µl of 10 mM dNTPs, 1 µl of 0.1 M DTT, 1 µl RNAse Inhibitor (Enzymatics, Beverly, Mass.) and 1 µl of Superscript III (Life Technologies, Carlsbad, Calif.) was then added to the reaction. This reaction was incubated for 45 mins at 55° C. followed by an additional 5 mins at 85° C. The reaction was then incubated at 37° C. following the addition of 1 µl of RNAse H (Enzymatics, Beverly, Mass.) The reaction was purified with Ampure (Beckman Coulter Genomics, Danvers, Mass.).

Adaptor Ligation

3 µl of cDNA was combined with 2 µl of 10 µM P7/C7 adaptor, 1 µl T4 DNA Ligase (Enzymatics, MA), 2 µl of rapid ligase buffer, and 2 µl of nuclease free dH$_2$O. Reactions were incubated for 1 hr. at room temperature. The reaction was then heat inactivated by incubating for 10 mins at 65° C., and then purified with Ampure XP (Beckman Coulter Genomics, Danvers, Mass.).

```
Adaptor Sequences (SEQ ID NOS 8-19, respectively,
in order of appearance)
P7 Top strand BC-1
5'-AGATCGGAAGAGCACACGTCTGAACTCCAGTCACATCACGATCTCGT
ATGCCGTCTTCTGCTTG P7 Top strand BC-2
5'-AGATCGGAAGAGCACACGTCTGAACTCCAGTCACCGATGTATCTCGT
ATGCCGTCTTCTGCTTG P7 Top strand BC-3
5'-AGATCGGAAGAGCACACGTCTGAACTCCAGTCACTTAGGCATCTCGT
ATGCCGTCTTCTGCTTG P7 Top strand BC-4
5'-AGATCGGAAGAGCACACGTCTGAACTCCAGTCACTGACCAATCTCGT
ATGCCGTCTTCTGCTTG P7 Top strand BC-5
5'-AGATCGGAAGAGCACACGTCTGAACTCCAGTCACACAGTGATCTCGT
ATGCCGTCTTCTGCTTG P7 Top strand BC-6
5'-AGATCGGAAGAGCACACGTCTGAACTCCAGTCACGCCAATATCTCGT
ATGCCGTCTTCTGCTTG C7/P7 Bottom strand BC-1
/5BiotinTEG/CAAGCAGAAGACGGCATACGAGATCGTGATGTGACTGG
AGTTCAGACGTGTGCTCTTC C7/P7 Bottom strand BC-2
/5BiotinTEG/CAAGCAGAAGACGGCATACGAGATACATCGGTGACTGG
AGTTCAGACGTGTGCTCTTC C7/P7 Bottom strand BC-3
/5BiotinTEG/CAAGCAGAAGACGGCATACGAGATGCCTAAGTGACTGG
AGTTCAGACGTGTGCTCTTC C7/P7 Bottom strand BC-4
/5BiotinTEG/CAAGCAGAAGACGGCATACGAGATTGGTCAGTGACTGG
AGTTCAGACGTGTGCTCTTC C7/P7 Bottom strand BC-5
/5BiotinTEG/CAAGCAGAAGACGGCATACGAGATCACTGTGTGACTGG
AGTTCAGACGTGTGCTCTTC C7/P7 Bottom strand BC-6
/5BiotinTEG/CAAGCAGAAGACGGCATACGAGATATTGGCGTGACTGG
AGTTCAGACGTGTGCTCTTC
```

Primer Extension Reaction

10 µl of adaptor ligated DNA was added to 8.4 µl of dH$_2$O, 0.3 µl of 10 mM dNTP's, 5 µl of Phusion HF buffer, 0.3 µl Phusion Hotstart II polymerase (Thermo Fischer, Chicago, Ill.) and 0.5 pmols of each of the following primers in a 1 µl volume:

Pathogen control primers (SEQ ID NOS 20-22,
respectively, in order of appearance)
HCV-1 A 250
C5/P5/PEAATGATACGGCGACCACCGAGATCTACACTCTTTCCCTACAC
GACGCTCTTCCGATCTCTTCCGAGCGGTCGCAAC EBV A 250
C5/P5/PEAATGATACGGCGACCACCGAGATCTACACTCTTTCCCTACAC
GACGCTCTTCCGATCTCCTGCGCTCCATGAACATG CMV A
C5/P5/PEAATGATACGGCGACCACCGAGATCTACACTCTTTCCCTACAC
GACGCTCTTCCGATCTTAGAAAAGTGACACACACGGATC Target primers (SEQ ID NOS 23-27, respectively,
in order of appearance)
ACTB250A
C5/P5/PEAATGATACGGCGACCACCGAGATCTACACTCTTTCCCTACAC
GACGCTCTTCCGATCTTCCAGCAGATGTGGATCAGCA ACTB250B
C5/P5/PEAATGATACGGCGACCACCGAGATCTACACTCTTTCCCTACAC
GACGCTCTTCCGATCTACAGGAAGTCCCTTGCCATC RB2M250A
C5/P5/PEAATGATACGGCGACCACCGAGATCTACACTCTTTCCCTACAC
GACGCTCTTCCGATCTTCCAACATCAACATCTTGGTCAG GAPDH250A
C5/P5/PEAATGATACGGCGACCACCGAGATCTACACTCTTTCCCTACAC
GACGCTCTTCCGATCTCAAATTCCATGGCACCGTCAAG GAPDH250B
C5/P5/PEAATGATACGGCGACCACCGAGATCTACACTCTTTCCCTACAC
GACGCTCTTCCGATCTGGTATCGTGGAAGGACTCATG The reaction was incubated for 1 minute at 98° C., followed by 5 cycles of 98° C., 20 sec at 60° C., 30 sec at 72° C. followed by a hold at 4° C. The reaction was then purified with Ampure.

PCR Amplification

5 µl of Purified primer extension product was combined with 10 µl of 5× Phusion Hotstart buffer, 0.6 µl of 10 mM dNTP, 2 µl of 12.5 µM C5 PCR Primer (AATGATACGGC-GACCACCGAGATCT) (SEQ ID NO: 28), 2 µl of 12.5 µM C7 PCR Primer (CAAGCAGAAGACGGCATACGAGAT) (SEQ ID NO: 29) 29.8 µl of dH$_2$O, and 0.6 u µl of Phusion Hotstart II polymerase. The reaction was incubated for 1 min at 98° C. followed by 25 cycles of 98° C. for 10 sec, 60° C. for 20 seconds and 72° C. for 30 sec.

Pooled Reactions

PCR products were separated on an agarose gel. Gel bands were excised and purified with the Qiagen Minelute Gel Purification Kit. Purified samples were analyzed via Agilent Tapestation analysis, diluted, and pooled by library band quants prior to sequencing on the Illumina MiSeq platform.

Example 2

DNA Targeted Sequencing Prep

Genomic Primer Extension

4 µg of human genomic DNA, extracted from patient blood, was combined with 0.6 µl 10 mM dNTP, 1 µl of BST 2.0 polymerase (New England Biolabs, Ipswich, Mass.), 5 µl of 10× isothermal amplification buffer (NEB), and 1 µl of 0.5 µM CS-30 primer containing the sequences below.

CS_30 PE-1 (SEQ ID NOS 30-59, respectively, in
order of appearance)
SCA_1_UID_DPE1
/5Phos/CGATCTNNNNNWNNNNNWNNNNNACCTGTCTTGTAACCTTGA
TACC SCA_2_UID_DPE1
/5Phos/CGATCTNNNNNWNNNNNWNNNNNGGGTATAAGTCTCTCTCGT
ATGTGATG SCA_3_UID_DPE1
/5Phos/CGATCTNNNNNWNNNNNWNNNNNTCCCAAACAGCAATC
ACTTTG SCA_4_UID_DPE1
/5Phos/CGATCTNNNNNWNNNNNWNNNNNTCCCAAAGTGC
GATTACTGG SCA5_UID_DPE1
/5Phos/CGATCTNNNNNWNNNNNWNNNNNCATTTGCCATT
CAGAAGCCAAA SCA_6_UID_DPE1
/5Phos/CGATCTNNNNNWNNNNNWNNNNNAGCAGGCTGGTAAG
AAATGG SCA_7_UID_DPE1
/5Phos/CGATCTNNNNNWNNNNNWNNNNNGATCGCGCCACTGT
ACTC SCA_8_UID_DPE1
/5Phos/CGATCTNNNNNWNNNNNWNNNNNGGAGAACACAGGAA
TGGGATG MSU_1_UID_DPE1
/5Phos/CGATCTNNNNNWNNNNNWNNNNNCAGGGTTTGATTGTC
CCTAATG MSU_2_UID_DPE1
/5Phos/CGATCTNNNNNWNNNNNWNNNNNTGATTCCTGGGCAA
TGGG SNM1_1_DPE1_UID
/5Phos/CGATCTNNNNNWNNNNNWNNNNNATACTTAGGGACAA
TGCAAGAGT SNM1_2_DPE1_UID
/5Phos/CGATCTNNNNNWNNNNNWNNNNNTTATACTTAGGGACAATGC
AAGAG SNM1_3_DPE1_UID
/5Phos/CGATCTNNNNNWNNNNNWNNNNNTTGCTCCTCTCTATT
TCCATATCC SNM1_4_DPE1_UID
/5Phos/CGATCTNNNNNWNNNNNWNNNNNACCTTAAATGAAGC
CACAGC CFTR_1_DPE1_UID
/5Phos/CGATCTNNNNNWNNNNNWNNNNNTCCTTGGCTTGAGA
GAAACC CFTR_2_DPE1_UID
/5Phos/CGATCTNNNNNWNNNNNWNNNNNTGTTCCCACTGTGCT
ATTAAG APOE_1_DPE1_UID
/5Phos/CGATCTNNNNNWNNNNNWNNNNNCCTGCACCTGCTCA
GAC FMR1_1_DPE1_UID
/5Phos/CGATCTNNNNNWNNNNNWNNNNNTGCCATGGGACATC
AACAC G6PD_1_DPE1_UID
/5Phos/CGATCTNNNNNWNNNNNWNNNNNACCACCCACCTTGA
AGAAG APOE_2_DPE1_UID
/5Phos/CGATCTNNNNNWNNNNNWNNNNNGCTTCTGCAGGTCAT
CGG HexA_1_DPE1_UID
/5Phos/CGATCTNNNNNWNNNNNWNNNNNGGGATATGCCACTTCCATG
AG -continued HexA_2_DPE1_UID
/5Phos/CGATCTNNNNNWNNNNNWNNNNNCCCAAAGTGTTGGGATTAC
AG SMPD1_1_DPE1_UID
/5Phos/CGATCTNNNNNWNNNNNWNNNNNGGTCCTGACGAGTCTGGTG CFTR_3_DPE1_UID
/5Phos/CGATCTNNNNNWNNNNNWNNNNNTAGTTTCTTACCTCTTCTA
GTTGGC ASPA_1_DPE1_UID
/5Phos/CGATCTNNNNNWNNNNNWNNNNNAGAAATTTGCTTAG
ATGCCTACC ASPA_2_DPE1_UID
/5Phos/CGATCTNNNNNWNNNNNWNNNNNTGTAAGACACCGTGTAAGA
TGTAAG ASPA_3_DPE1_UID
/5Phos/CGATCTNNNNNWNNNNNWNNNNNGTACAGTCTCCGCC
CAGTG CDH23_1_DPE1_UID
/5Phos/CGATCTNNNNNWNNNNNWNNNNNCATGATCACGTCGC
GAAGTTTG GBA_1_DPE1_UID
/5Phos/CGATCTNNNNNWNNNNNWNNNNNAGGCCAGTCCTGAT
CCC GBA_2_DPE1_UID
/5Phos/CGATCTNNNNNWNNNNNWNNNNNACAGGGCAAGGATG
TTGAG Adaptor Ligation 20 µl of the eluted primer extension reaction was combined with 1.5 µl of 5 µM P7/C7 adaptor (annealed duplex of 1 top strand and 1 bottom strand oligo previously described above with correct barcode pairing), 1 µl of T4 DNA ligase, 6 µl of 5× rapid ligase buffer (New England Biolabs, Ipswich, Mass.), and 1.5 µl of Nuclease Free dH$_2$O. Reactions were incubated for 1 hr at room temperature. The reaction was then heat inactivated by incubating for 10 mins at 68° C. The reaction was then purified with Ampure XP (Beckman).

Bead Capture

180 µl of my One C1 SA beads (Dynal, Lifetech) were washed with 1 ml of 1× B&W. Beads were washed with 2 additional 1×B&W washes at 200 µl each. The total elution volume of the Ampure purified adaptor ligation was 65 ul. An equal volume, (65 µl) of 2×B&W was added and an additional 100 u µl of 1×B&W for a total volume of 230 µl per binding. Reaction was placed on the incubator shaker for 20 mins After sample binding the beads were washed with 200 µl of NSX and the liquid was removed.

Samples were then re-suspended in 200 µl of 0.1N NaOH and rotated for 20 mins at room temperature. NaOH was removed and a second wash was performed with an additional 200 µl of 0.1N NaOH. Beads were washed 2× with 600 µl of TE following NaOH removal. Beads were then washed 2× with NSX. Beads were placed in 100 µl of Tex (TE with 0.01% Triton X) and stored overnight at 4 C. Prior to the primer extension the beads were washed 2× with 200 µl of 1× Phusion HF (w/0.01 triton X) and once with 1×HF without Triton X.

Primer Extension Reaction

The bead mixture was re-suspended in 21.1 µl of dH$_2$O, 0.6 µl of 10 mM dNTP's, 6 µl of Phusion HF buffer, 0.3 µl Phusion Hotstart II polymerase (Thermo Fischer, Chicago, Ill.), and 0.5 pmols each of the following primers in a 2 µl volume:

Primer Extension 2 Primers (SEQ ID NOS 60-89, respectively, in order of appearance)

HexA_1_DPE2_P5/C5
AATGATACGGCGACCACCGAGATCTACACTCTTTCCCTACACGACGCTCT
TCCGATCTAACCTGAAGGGTGTCTTGTG

HexA_2_DPE2_P5/C5
AATGATACGGCGACCACCGAGATCTACACTCTTTCCCTACACGACGCTCT
TCCGATCTATCAACAAGACTGAGATTGAGG

SMPD1_1_DPE2_P5/C5
AATGATACGGCGACCACCGAGATCTACACTCTTTCCCTACACGACGCTCT
TCCGATCTCTGGGATCATGACTACCTGGAG

CFTR_3_DPE2_P5/C5
AATGATACGGCGACCACCGAGATCTACACTCTTTCCCTACACGACGCTCT
TCCGATCTCTGAGCGTGATTTGATAATGACC

ASPA_1_DPE2_P5/C5
AATGATACGGCGACCACCGAGATCTACACTCTTTCCCTACACGACGCTCT
TCCGATCTCCCGTGTTTGTGAATGAGG

ASPA_2_DPE2_P5/C5
AATGATACGGCGACCACCGAGATCTACACTCTTTCCCTACACGACGCTCT
TCCGATCTTTGTTTCCTGAGAGGATCAAGAC

ASPA_3_DPE2_P5/C5
AATGATACGGCGACCACCGAGATCTACACTCTTTCCCTACACGACGCTCT
TCCGATCTATGTCAGCGCAGTCAGATCAC

CDH23_1_DPE2_P5/C5
AATGATACGGCGACCACCGAGATCTACACTCTTTCCCTACACGACGCTCT
TCCGATCTAGGGTAGCCTGCGCTTC

GBA_1_DPE2_P5/C5
AATGATACGGCGACCACCGAGATCTACACTCTTTCCCTACACGACGCTCT
TCCGATCTACTCTGGGTGCTTCTCTCTTC

GBA_2_DPE2_P5/C5
AATGATACGGCGACCACCGAGATCTACACTCTTTCCCTACACGACGCTCT
TCCGATCTCCCATCCAGGCTAATCACAC

SCA1_C5/P5_DPE2
AATGATACGGCGACCACCGAGATCTACACTCTTTCCCTACACGACGCTCT
TCCGATCTGGGTTGGCCAATCTACTCC

SCA_2_C5/P5_DPE2
AATGATACGGCGACCACCGAGATCTACACTCTTTCCCTACACGACGCTCT
TCCGATCTAATGACAGGGAGCTTATAATTTAGCC

SCA_3_C5/P5_DPE2
AATGATACGGCGACCACCGAGATCTACACTCTTTCCCTACACGACGCTCT
TCCGATCTACATATTCAGCTGGCACAGTTA

SCA_4_C5/P5_DPE2
AATGATACGGCGACCACCGAGATCTACACTCTTTCCCTACACGACGCTCT
TCCGATCTTGAAACACACCTGAATACCTACAG

SCA_5_C5/P5_DPE2
AATGATACGGCGACCACCGAGATCTACACTCTTTCCCTACACGACGCTCT
TCCGATCTACAGGGCAGGCATGTTATC

SCA_6_C5/P5_DPE2
AATGATACGGCGACCACCGAGATCTACACTCTTTCCCTACACGACGCTCT
TCCGATCTGTGGTTTGGATCGACGTCTC

SCA_7_C5/P5_DPE2
AATGATACGGCGACCACCGAGATCTACACTCTTTCCCTACACGACGCTCT
TCCGATCTGGCCTTCAAAGAGCACCTG

SCA_8_C5/P5_DPE2
AATGATACGGCGACCACCGAGATCTACACTCTTTCCCTACACGACGCTCT
TCCGATCTCTACCCAGCTGCTCATGC

MSU1_C5/P5_DPE2
AATGATACGGCGACCACCGAGATCTACACTCTTTCCCTACACGACGCTCT
TCCGATCTCAGGGAACAAATGCCAAGTG

MSU2_C5/P5_DPE2
AATGATACGGCGACCACCGAGATCTACACTCTTTCCCTACACGACGCTCT
TCCGATCTGAAGGGAAGGAAGGAAGGG

-continued

SNM1_1
AATGATACGGCGACCACCGAGATCTACACTCTTTCCCTACACGACGCTCT
TCCGATCTGATTCTCTTGATGATGCTGATGC

SNM1_2
AATGATACGGCGACCACCGAGATCTACACTCTTTCCCTACACGACGCTCT
TCCGATCTTTCTCTTGATGATGCTGATGC

SNM1_3
AATGATACGGCGACCACCGAGATCTACACTCTTTCCCTACACGACGCTCT
TCCGATCTCCTTCCAAATCTCTACCCTCTATC

SNM1_4
AATGATACGGCGACCACCGAGATCTACACTCTTTCCCTACACGACGCTCT
TCCGATCTAGTAAAGTCACATAACCTCTAACC

CFTR_1
AATGATACGGCGACCACCGAGATCTACACTCTTTCCCTACACGACGCTCT
TCCGATCTAGAGTTGGTAAGGAGGAGAATG

CFTR_2
AATGATACGGCGACCACCGAGATCTACACTCTTTCCCTACACGACGCTCT
TCCGATCTCTGTGGTATCTGAACTATCTTCTC

APOE_1
AATGATACGGCGACCACCGAGATCTACACTCTTTCCCTACACGACGCTCT
TCCGATCTCATTTGTGGAGCACCTTCTG

FMR1_1
AATGATACGGCGACCACCGAGATCTACACTCTTTCCCTACACGACGCTCT
TCCGATCTAAGGATAGTTTGGAACTGAGAGAC

G6PD_1
AATGATACGGCGACCACCGAGATCTACACTCTTTCCCTACACGACGCTCT
TCCGATCTTGACCTGGCCAAGAAGAAG

APOE_2
AATGATACGGCGACCACCGAGATCTACACTCTTTCCCTACACGACGCTCT
TCCGATCTAATCGGAACTGGAGGAACAAC

The reaction was incubated for 1 minute at 98° C., followed by 5 cycles of 98° C., 20 sec at 60° C., 30 sec at 72° C. followed by a hold at 4° C. The reaction was then purified with Ampure.

PCR Amplification

5 µl of purified primer extension product was combined with 10 µl of 5× Phusion Hotstart buffer (HF), 0.6 µl of 10 mM dNTP, 2 µl of 12.5 µM C5 PCR Primer (AATGATACG-GCGACCACCGAGATCT) (SEQ ID NO: 28), 2 µl of 12.5 µM C7 PCR Primer (CAAGCAGAAGACGGCATACGA-GAT) (SEQ ID NO: 29) 29.8 µl of dH₂O, and 0.6 µl of Phusion Hotstart II polymerase. The reaction was incubated for 1 min at 98° C. followed by 25 cycles of 98° C. for 10 sec, 60° C. for 20 seconds and 72° C. for 30 sec.

Gel Bands were excised and purified with the Qiagen Minelute Gel Purification Kit as per the manufacturer's instruction. Purified samples were analyzed via Agilent Tapestation analysis and diluted and pooled by library band quants prior to sequencing on the Illumina MiSeq.

Example 3

Improved Primer Panel Creation—Analysis of Primer Dimer Formation

To create primer panels for use in the targeted sequencing methods described, the stability and robustness of amplified targets was assessed. Additionally, uniformity of coverage and sequence accuracy was assessed to create the primer panels and improve assay performance.

To improve these parameters a number of metrics were assessed including the quality of the final amplified targets, amplification cycling requirements, cleanliness of amplified products and the yield of the amplified products. Sequence analysis of amplified products was also performed to improve on target specificity, coverage uniformity, sequencing depth, and SNP calling accuracy. Iterative cycles of protocol modification, analysis of product formation, and sequence quality were used to improve assay performance.

Utilizing sequence analysis an undesired 75 bp product was determined to be related to the primers used during the linear extension/amplification step. A larger doublet or triplet 125-200 bp product was determined to be related to the C7/P7 adaptor and primers used during the linear extension/amplification step. Larger dimer products >150 bp were determined to be related to the primers used during the initial RT/PE step.

The major dimer product lengths detected with sequence analysis were 143, 155, and 160 and corresponded to dimer products. Sequence analysis revealed that the 143 bp product was associated with the MCOLN1_11_1_f_PE2_5 primer, which occurred 132 times, and the GAA_14_1_o_PE2_7 primer, which occurred 660 times. Sequence analysis revealed that the 155 bp product was associated with the GAA_14_1_o_PE2_7 primer, which occurred 1146 times. Sequence analysis revealed that the 160 bp product was associated with the IKBKAP_32_1_f_PE2_6 primer, which occurred 464 times. As a result of this analysis, these primers were removed from the primer panel.

From these analyses, unwanted dimer formation was found to be facilitated by primers with high melting temperatures (e.g., 70° C. $T_M$) and low annealing temperatures (e.g., 60° C.), primers with high GC content through interacting with primer/UID regions, and the 3' exo activity of some DNA polymerases (e.g., Phusion). As a result of these analyses and conclusions, primer panels have been created with primers that do not have a high GC % on their last 5 nucleotides on their 3' end. As a result of these analyses and conclusions, dimer product formation has been greatly reduced compared to using initial primer panels and the improvements have obviated a need for gel purification of target product.

A number of primer exclusion criteria were created from the above experiments and used to generate subpanels from the CS-350 panel. The subpanels were created using one or a combination of these exclusion parameters. First, primers with the highest number of misreads (caused by mispriming) during the initial RT/PE step or the linear extension/amplification step. Second, primers prevalent in dimers as elucidated by sequence analysis were excluded from subpanels. Third, primers that were responsible for generating one or more of the highest number of total reads for a target (over-amplifiers) were excluded from subpanels.

Example 4

Improved Primer Panels—Analysis of Amplicon % GC Content and Primer Melting Temperatures To create primer panels for use in the targeted sequencing methods described, the stability and robustness of amplified targets was assessed in comparison to the % GC content of the amplicons and melting temperatures of the primers used. The number of reads generated for a particular primer was used a metric for primer performance. Additionally, uniformity of coverage and sequence accuracy was assessed to create the primer panels and improve assay performance.

A majority of the poor performers (fewest number of reads) had a linear extension/amplification primer with a $T_M<60°$ C. and were derived from AT rich amplicons. A second cluster of poor performers were composed of amplicons with higher GC percentages and primers with high melting temperatures. As a result of these experiments and analysis, a number of criteria were created for the amplicons and primers. First, the melting temperature range of the primers to be used should be between 60° C.-68° C. Second, the primers can have a length of between 21 and 32 nucleotides. Third, primers should not contain 4 or more pyrimidines in the last 5 nucleotides at the 3' end. Fourth, the amplicon should contain between 30% and 70% GC content. Finally, the length of the amplicon should be between 225 and 300 base pairs in length.

Example 5

Improved Reaction Conditions

To improve reaction conditions for use in the targeted sequencing methods described, the stability and robustness of amplified targets was assessed. Additionally, uniformity of coverage and sequence accuracy was assessed to improve reaction conditions and improve assay performance.

To improve these parameters a number of metrics were assessed including the quality of the final amplified targets, amplification cycling requirements, cleanliness of amplified products and the yield of the amplified products. Iterative cycles of protocol modification, analysis of product formation, and sequence quality were used to improve assay performance.

Initial primer titration experiments were not sufficient to allow target production with existing amplification ramping and annealing conditions. For highly complex primer pools more stringent ramping conditions were hypothesized to be required based on assessment of the above parameters and metrics.

Using original ramping conditions for the CS-30 primer panel, 30 targets did not work with more complex primer panels. Stringency was increased by slowing ramping rates for the linear extension/amplification step (PE2), and adding a hold at 68° C. for the initial RT/PE step. The minimum annealing temperature hold was lowered to 55° C. to accommodate lower primer melting temperatures. Fixing the global concentration of the primer pools showed better product formation with panel sizes ranging from 24 to 346 amplicons. A combination of the stringent RT/PE and linear extension/amplification ramping conditions with the fixed global primer pools showed improvements over the same methods employing different conditions.

Additionally, other experiments employing various additives during the RT/PE and linear extension/amplification steps were performed to improve product formation. Several additive conditions were tested, and their impact on product formation was assessed. The data showed improvements in read coverage with optimized reaction conditions Ammonium sulfate and additional $MgCl_2$ had the most significant impact on read depth. These experiments were performed with the full CS-350 panel prior to panel optimization. These experiments were performed to help elucidate the mechanism of dimer formation and identify the primers involved.

Example 5

Targeted Sequencing Protocol

The methods described here have been used for specifically targeting, amplifying, sequencing and/or quantifying DNA or RNA sequences present in a sample. These methods have allowed for the addition of additional sequences that will format the targeted sequences for sequencing or other molecular analyses. The methods have been used to add a Unique Identifier sequence (UID) that allowed for binning of reads derived from the same RNA or DNA molecule, allowing a determination to be made as to whether certain sequence polymorphisms were found in a population of RNA or DNA molecules, or were resulting from an amplification artifact. RNA or DNA has been used as the template/starting material. The sample can be from any organism or virus. The methods have be used for formatting targeted molecules for a variety of sequencing devices and other molecular analysis devices.

A library preparation protocol was used for the purpose of targeted sequencing to be sequenced on NGS platform. In this assay, many specific biological targets (from one to many thousands), from a patient biological sample were converted into NGS compatible library, and sequenced. This allowed for identification of target frequencies (gene expression), and of mutations or SNPs in the genome or transcriptome of the patient, from which clinical information has been derived. This assay was also used to identify the presence or absence and frequency of various infections by targeting RNA or DNA of virus, bacteria or fungus in patient samples.

Various applications have been performed individually or simultaneously by sequencing targets required for cancer mutation profiling, SNPs and mutation analysis, carrier testing, infectious diagnostics, and gene expression analysis, for example.

For RNA, reverse transcription (RT) was performed using reverse transcriptase enzyme, to generate a cDNA complement to the targets or interest. For DNA, primer extension (PE) was performed, using DNA polymerase to generate DNA a complement to the targets or interest. In both cases the oligo used to performed such RT or PE was composed of a gene specific primer directed against the target of interest, a unique identifier (UID) tag (a long fully or partially degenerate barcode composed of 15 or more degenerate based; NNNNNNNNNNNNNNN (SEQ ID NO: 1), or NNNNNWNNNNNWNNNNN (SEQ ID NO: 2)), and universal tag of a known sequence (termed P7 forward primer: P7f), with a phosphorylated 5' end. The UID was used to single molecule barcode any RNA or DNA molecule and has been used at the sequence analysis stage to identify absolute starting molecule number at in the biological samples, deconvolute consensus sequences of the target, and remove all PCR or sequencing errors, therefore increasing sequencing accuracy. In order to capture many different genes, a pool composed of many of such oligo was used, where the corresponding gene specific parts of the oligo was a complement to each target to capture.

Formatting/Adapter Ligation—In this step an additional sequence required for amplification/analysis was added to the newly synthesized nucleic acid. This additional sequence can be added by ligation (preferred approach), either single stranded, or using a bridge oligo. This sequence has been added via amplification at later steps. This sequence has been used as a generic priming sequence for amplification of a large population of formatted sequences. This sequence has contained a barcode for sample identification. This sequence has also contained a purification tag such as Biotin. In on approach an adapter used for ligation was composed of an upper strand that served as a bridge oligo complementary to the P7f region, and a bottom strand oligo that was ligated to the product generated during RT or PE step. The resulting product added the rest of the P7 region (for sequencing) as well as a sample barcode (SBC), required if many patient samples are processed in parallel, and optionally, the C7 region, for clustering on an NGS platform.

Bead Capture (Optional)—In this step a partially formatted nucleic acid was captured via an affinity tag or sequence added above. This capture was used to separate target sequences from template/sample sequences that are not of interest.

Primer Extension/Linear Amplification—Linear amplification (or linear primer extension (LPE) was performed using a DNA polymerase and using a pool of oligos composed of a gene specific region for each of the targets to capture, a sequencing primer tag (P5), and a universal tag (C5) for clustering on an NGS platform. A pool of oligos was used to perform LPE of many targets at once in a single reaction. This extension occurred in solution or with the template attached to a bead or an array. The LPE has been performed as a single cycle or many cycles (up to hundreds), avoiding PCR amplification bias that would be generated in standard PCR.

PCR Enrichment—The targets of interest were amplified simultaneously by PCR using the following oligos: a forward primer composed of any parts of the LPE oligo, preferably composed of C5 (or optionally P5C5, or just P5), and a reverse primer complementary to any part of the universal adapter but preferably complementary to C7 (or optionally P7-BC-C7 or just P7).

Final Library—The final library was composed of a pool of all targets captured with the tags It is intended that the following claims define the scope of the methods, compositions, and kits described herein and that methods and compositions within the scope of these claims and their equivalents be covered thereby. The claims may be drafted to exclude any optional element. As such, this statement is intended to serve as antecedent basis for use of such exclusive terminology as "solely", "only" and the like in connection with the recitation of claim elements, or the use of a "negative" limitation.

The invention claimed is:

1. A method of accurately determining the sequence of multiple target polynucleotides while maintaining a true frequency representation of the target polynucleotides in a sample, the method comprising:
   (a) generating a first complement sequence CS from each target polynucleotide by extending a first gene-specific primer comprising a UID and a universal ligation sequence (ULS);
   (b) ligating an adaptor comprising a first primer binding sequence (PBS) to the first CS wherein the adaptor is a bridge polynucleotide comprising a double-stranded region and a single-stranded overhang region;
   (c) generating a second CS from the first CS, by extending a second gene-specific primer comprising a second primer binding sequence (PBS);
   (d) amplifying the second CS using primers that hybridize to the first and second PBS without amplification bias;
   (e) sequencing the amplified second CSs;
   (f) aligning at least two sequences containing the same UID; and
   (g) determining a consensus sequence based on (f), wherein the consensus sequence accurately represents the sequence of target polynucleotides.

2. The method of claim 1, wherein the adapter further comprises a sample barcode (SBC) sequence.

3. The method of claim 1, wherein the first CS further comprises an affinity molecule or capture sequence.

4. The method of claim 1, wherein the UID comprises the sequence NNNNNNNNNNNNNN (SEQ ID NO: 1), wherein N is any nucleic acid residue.

5. The method of claim 1, wherein the UID comprises the sequence NNNNNWNNNNNWNNNNN (SEQ ID NO: 2), wherein N is any nucleic acid residue and W is adenine or thymine.

6. The method of claim 1 wherein amplifying the second CS in step (d) is by linear amplification.

7. The method of claim 1, wherein the frequency of consensus sequences determined in step (g) accurately represents the frequency of target polynucleotides in the sample.

* * * * *

SEQUENCE LISTING

```
<160> NUMBER OF SEQ ID NOS: 100

<210> SEQ ID NO 1
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(15)
<223> OTHER INFORMATION: a, c, t, g, unknown or other

<400> SEQUENCE: 1
nnnnnnnnnn nnnnn                                                        15

<210> SEQ ID NO 2
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other

<400> SEQUENCE: 2
nnnnnwnnnn nwnnnnn                                                      17

<210> SEQ ID NO 3
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(10)
<223> OTHER INFORMATION: a, c, t, g, unknown or other
<220> FEATURE:
<221> NAME/KEY: modified_base
<222> LOCATION: (12)..(15)
<223> OTHER INFORMATION: a, c, t, g, unknown or other

<400> SEQUENCE: 3
cgatctnnnn wnnnnaaccg actgctgtca ccttc                              35

<210> SEQ ID NO 4
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(10)
<223> OTHER INFORMATION: a, c, t, g, unknown or other
<220> FEATURE:
<221> NAME/KEY: modified_base
<222> LOCATION: (12)..(15)
<223> OTHER INFORMATION: a, c, t, g, unknown or other

<400> SEQUENCE: 4
cgatctnnnn wnnnnccagg gagaccaaaa gcctt                              35

<210> SEQ ID NO 5
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(10)
<223> OTHER INFORMATION: a, c, t, g, unknown or other
<220> FEATURE:
<221> NAME/KEY: modified_base
<222> LOCATION: (12)..(15)
<223> OTHER INFORMATION: a, c, t, g, unknown or other

<400> SEQUENCE: 5
cgatctnnnn wnnnnaccag attaaccaca accatgc                            37

<210> SEQ ID NO 6
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
```

```
<220> FEATURE:
<221> NAME/KEY: modified_base
<222> LOCATION: (7)..(10)
<223> OTHER INFORMATION: a, c, t, g, unknown or other
<220> FEATURE:
<221> NAME/KEY: modified_base
<222> LOCATION: (12)..(15)
<223> OTHER INFORMATION: a, c, t, g, unknown or other

<400> SEQUENCE: 6
cgatctnnnn wnnnnatggt tcacacccat gacgaac                              37

<210> SEQ ID NO 7
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(10)
<223> OTHER INFORMATION: a, c, t, g, unknown or other
<220> FEATURE:
<221> NAME/KEY: modified_base
<222> LOCATION: (12)..(15)
<223> OTHER INFORMATION: a, c, t, g, unknown or other

<400> SEQUENCE: 7
cgatctnnnn wnnnngtttt tctagacggc aggtcag                              37

<210> SEQ ID NO 8
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
agatcggaag agcacacgtc tgaactccag tcacatcacg atctcgtatg ccgtcttctg     60
cttg                                                                 64

<210> SEQ ID NO 9
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
agatcggaag agcacacgtc tgaactccag tcaccgatgt atctcgtatg ccgtcttctg     60
cttg                                                                 64

<210> SEQ ID NO 10
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 10
agatcggaag agcacacgtc tgaactccag tcacttaggc atctcgtatg ccgtcttctg    60
cttg                                                                64

<210> SEQ ID NO 11
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
agatcggaag agcacacgtc tgaactccag tcactgacca atctcgtatg ccgtcttctg    60
cttg                                                                64

<210> SEQ ID NO 12
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
agatcggaag agcacacgtc tgaactccag tcacacagtg atctcgtatg ccgtcttctg    60
cttg                                                                64

<210> SEQ ID NO 13
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
agatcggaag agcacacgtc tgaactccag tcacgccaat atctcgtatg ccgtcttctg    60
cttg                                                                64

<210> SEQ ID NO 14
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-BiotinTEG modified"

<400> SEQUENCE: 14
caagcagaag acggcatacg agatcgtgat gtgactggag ttcagacgtg tgctcttc     58

<210> SEQ ID NO 15
<211> LENGTH: 58
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-BiotinTEG modified"

<400> SEQUENCE: 15
caagcagaag acggcatacg agatacatcg gtgactggag ttcagacgtg tgctcttc        58

<210> SEQ ID NO 16
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-BiotinTEG modified"

<400> SEQUENCE: 16
caagcagaag acggcatacg agatgcctaa gtgactggag ttcagacgtg tgctcttc        58

<210> SEQ ID NO 17
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-BiotinTEG modified"

<400> SEQUENCE: 17
caagcagaag acggcatacg agattggtca gtgactggag ttcagacgtg tgctcttc        58

<210> SEQ ID NO 18
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-BiotinTEG modified"

<400> SEQUENCE: 18
caagcagaag acggcatacg agatcactgt gtgactggag ttcagacgtg tgctcttc        58

<210> SEQ ID NO 19
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-BiotinTEG modified"

<400> SEQUENCE: 19
caagcagaag acggcatacg agatattggc gtgactggag ttcagacgtg tgctcttc        58
```

```
<210> SEQ ID NO 20
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
aatgatacgg cgaccaccga gatctacact ctttccctac acgacgctct tccgatctct    60
tccgagcggt cgcaac                                                    76

<210> SEQ ID NO 21
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
aatgatacgg cgaccaccga gatctacact ctttccctac acgacgctct tccgatctcc    60
tgcgctccat gaacatg                                                   77

<210> SEQ ID NO 22
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
aatgatacgg cgaccaccga gatctacact ctttccctac acgacgctct tccgatctta    60
gaaaagtgac acacggat c                                                81

<210> SEQ ID NO 23
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
aatgatacgg cgaccaccga gatctacact ctttccctac acgacgctct tccgatcttc    60
cagcagatgt ggatcagca                                                 79

<210> SEQ ID NO 24
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
aatgatacgg cgaccaccga gatctacact ctttccctac acgacgctct tccgatctac    60
aggaagtccc ttgccatc                                                  78
```

-continued

```
<210> SEQ ID NO 25
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
aatgatacgg cgaccaccga gatctacact ctttccctac acgacgctct tccgatcttc    60
caacatcaac atcttggtca g                                              81

<210> SEQ ID NO 26
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
aatgatacgg cgaccaccga gatctacact ctttccctac acgacgctct tccgatctca    60
aattccatgg caccgtcaag                                                80

<210> SEQ ID NO 27
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
aatgatacgg cgaccaccga gatctacact ctttccctac acgacgctct tccgatctgg    60
tatcgtggaa ggactcatg                                                 79

<210> SEQ ID NO 28
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
aatgatacgg cgaccaccga gatct                                          25

<210> SEQ ID NO 29
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
caagcagaag acggcatacg agat                                           24
```

<210> SEQ ID NO 30
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 30
cgatctnnnn nwnnnnnwnn nnnacctgtc ttgtaacctt gatacc           46

<210> SEQ ID NO 31
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 31
cgatctnnnn nwnnnnnwnn nnngggtata agtctctctc gtatgtgatg           50

<210> SEQ ID NO 32
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other

```
<220> FEATURE:
<221> NAME/KEY: modified_base
<222> LOCATION: (19)..(23)
<223> OTHER INFORMATION: a, c, t, g, unknown or other

<400> SEQUENCE: 32
cgatctnnnn nwnnnnnwnn nnntcccaaa cagcttgaat cact        44

<210> SEQ ID NO 33
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 33
cgatctnnnn nwnnnnnwnn nnntcccaaa gtgctgggat tac         43

<210> SEQ ID NO 34
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 34
cgatctnnnn nwnnnnnwnn nnncatttgc cattcaaaca gaagc       45

<210> SEQ ID NO 35
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 35
cgatctnnnn nwnnnnnwnn nnnagcaggc tggtaagaaa tgg                          43

<210> SEQ ID NO 36
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 36
cgatctnnnn nwnnnnnwnn nnngatcgcg ccactgtact c                            41

<210> SEQ ID NO 37
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 37
cgatctnnnn nwnnnnnwnn nnnggagaac acaggaatgg gatg                         44
```

-continued

```
<210> SEQ ID NO 38
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 38
cgatctnnnn nwnnnnnwnn nnncagggtt tgattgtccc taatg            45

<210> SEQ ID NO 39
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 39
cgatctnnnn nwnnnnnwnn nnntgattcc tgggcaatgg g                41

<210> SEQ ID NO 40
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
```

-continued

```
<220> FEATURE:
<221> NAME/KEY: modified_base
<222> LOCATION: (19)..(23)
<223> OTHER INFORMATION: a, c, t, g, unknown or other

<400> SEQUENCE: 40
cgatctnnnn nwnnnnnwnn nnnatactta gggacaatgc aagagt                46

<210> SEQ ID NO 41
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 41
cgatctnnnn nwnnnnnwnn nnnttatact tagggacaat gcaagag               47

<210> SEQ ID NO 42
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 42
cgatctnnnn nwnnnnnwnn nnnttgctcc tctctatttc catatcc               47

<210> SEQ ID NO 43
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 43
cgatctnnnn nwnnnnnwnn nnnaccttaa atgaagccac agc                43

<210> SEQ ID NO 44
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 44
cgatctnnnn nwnnnnnwnn nnntccttgg cttgagagaa acc                43

<210> SEQ ID NO 45
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 45
cgatctnnnn nwnnnnnwnn nnntgttccc actgtgctat taag               44
```

```
<210> SEQ ID NO 46
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 46
cgatctnnnn nwnnnnnwnn nnncctgcac ctgctcagac                              40

<210> SEQ ID NO 47
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 47
cgatctnnnn nwnnnnnwnn nnntgccatg ggacatcaac ac                           42

<210> SEQ ID NO 48
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
```

<220> FEATURE:
<221> NAME/KEY: modified_base
<222> LOCATION: (19)..(23)
<223> OTHER INFORMATION: a, c, t, g, unknown or other

<400> SEQUENCE: 48
cgatctnnnn nwnnnnnwnn nnnaccaccc accttgaaga ag        42

<210> SEQ ID NO 49
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 49
cgatctnnnn nwnnnnnwnn nnngcttctg caggtcatcg g        41

<210> SEQ ID NO 50
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 50
cgatctnnnn nwnnnnnwnn nnngggatat gccacttcca tgag        44

<210> SEQ ID NO 51
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

```
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 51
cgatctnnnn nwnnnnnwnn nnncccaaag tgttgggatt acag                    44

<210> SEQ ID NO 52
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 52
cgatctnnnn nwnnnnnwnn nnnggtcctg acgagtctgg tg                      42

<210> SEQ ID NO 53
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 53
cgatctnnnn nwnnnnnwnn nnntagtttc ttacctcttc tagttggc                48
```

```
<210> SEQ ID NO 54
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 54
cgatctnnnn nwnnnnnwnn nnnagaaatt tgcttagatg cctacc                46

<210> SEQ ID NO 55
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 55
cgatctnnnn nwnnnnnwnn nnntgtaaga caccgtgtaa gatgtaag              48

<210> SEQ ID NO 56
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
```

```
<220> FEATURE:
<221> NAME/KEY: modified_base
<222> LOCATION: (19)..(23)
<223> OTHER INFORMATION: a, c, t, g, unknown or other

<400> SEQUENCE: 56
cgatctnnnn nwnnnnnwnn nnngtacagt ctccgcccag tg                          42

<210> SEQ ID NO 57
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 57
cgatctnnnn nwnnnnnwnn nnncatgatc acgtcgcgaa gtttg                       45

<210> SEQ ID NO 58
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 58
cgatctnnnn nwnnnnnwnn nnnaggccag tcctgatccc                             40

<210> SEQ ID NO 59
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="5'-Phos modified"
```

```
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other
<220> FEATURE:
<221> NAME/KEY: modified_base
<222> LOCATION: (19)..(23)
<223> OTHER INFORMATION: a, c, t, g, unknown or other

<400> SEQUENCE: 59
cgatctnnnn nwnnnnnwnn nnnacagggc aaggatgttg ag                          42

<210> SEQ ID NO 60
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
aatgatacgg cgaccaccga gatctacact ctttccctac acgacgctct tccgatctaa       60
cctgaagggt gtcttgtg                                                     78

<210> SEQ ID NO 61
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
aatgatacgg cgaccaccga gatctacact ctttccctac acgacgctct tccgatctat       60
caacaagact gagattgagg                                                   80

<210> SEQ ID NO 62
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
aatgatacgg cgaccaccga gatctacact ctttccctac acgacgctct tccgatctct       60
gggatcatga ctacctggag                                                   80

<210> SEQ ID NO 63
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 63
aatgatacgg cgaccaccga gatctacact ctttccctac acgacgctct tccgatctct    60
gagcgtgatt tgataatgac c    81

<210> SEQ ID NO 64
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
aatgatacgg cgaccaccga gatctacact ctttccctac acgacgctct tccgatctcc    60
cgtgtttgtg aatgagg    77

<210> SEQ ID NO 65
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
aatgatacgg cgaccaccga gatctacact ctttccctac acgacgctct tccgatcttt    60
gtttcctgag aggatcaaga c    81

<210> SEQ ID NO 66
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
aatgatacgg cgaccaccga gatctacact ctttccctac acgacgctct tccgatctat    60
gtcagcgcag tcagatcac    79

<210> SEQ ID NO 67
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
aatgatacgg cgaccaccga gatctacact ctttccctac acgacgctct tccgatctag    60
ggtagcctgc gcttc    75

<210> SEQ ID NO 68
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

```
<400> SEQUENCE: 68
aatgatacgg cgaccaccga gatctacact ctttccctac acgacgctct tccgatctac    60
tctgggtgct tctctcttc                                                 79

<210> SEQ ID NO 69
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
aatgatacgg cgaccaccga gatctacact ctttccctac acgacgctct tccgatctcc    60
catccaggct aatcacac                                                  78

<210> SEQ ID NO 70
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
aatgatacgg cgaccaccga gatctacact ctttccctac acgacgctct tccgatctgg    60
gttggccaat ctactcc                                                   77

<210> SEQ ID NO 71
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
aatgatacgg cgaccaccga gatctacact ctttccctac acgacgctct tccgatctaa    60
tgacagggag cttataattt agcc                                           84

<210> SEQ ID NO 72
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
aatgatacgg cgaccaccga gatctacact ctttccctac acgacgctct tccgatctac    60
atattcagct ggcacagtta                                                80

<210> SEQ ID NO 73
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 73
aatgatacgg cgaccaccga gatctacact ctttccctac acgacgctct tccgatcttg    60
aaacacacct gaatacctac ag    82

<210> SEQ ID NO 74
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 74
aatgatacgg cgaccaccga gatctacact ctttccctac acgacgctct tccgatctac    60
agggcaggca tgttatc    77

<210> SEQ ID NO 75
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 75
aatgatacgg cgaccaccga gatctacact ctttccctac acgacgctct tccgatctgt    60
ggtttggatc gacgtctc    78

<210> SEQ ID NO 76
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 76
aatgatacgg cgaccaccga gatctacact ctttccctac acgacgctct tccgatctgg    60
ccttcaaaga gcacctg    77

<210> SEQ ID NO 77
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 77
aatgatacgg cgaccaccga gatctacact ctttccctac acgacgctct tccgatctct    60
acccagctgc tcatgc    76

<210> SEQ ID NO 78
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 78
aatgatacgg cgaccaccga gatctacact ctttccctac acgacgctct tccgatctca    60
gggaacaaat gccaagtg                                                  78

<210> SEQ ID NO 79
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
aatgatacgg cgaccaccga gatctacact ctttccctac acgacgctct tccgatctga    60
agggaaggaa ggaaggg                                                   77

<210> SEQ ID NO 80
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
aatgatacgg cgaccaccga gatctacact ctttccctac acgacgctct tccgatctga    60
ttctcttgat gatgctgatg c                                              81

<210> SEQ ID NO 81
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
aatgatacgg cgaccaccga gatctacact ctttccctac acgacgctct tccgatcttt    60
ctcttgatga tgctgatgc                                                 79

<210> SEQ ID NO 82
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
aatgatacgg cgaccaccga gatctacact ctttccctac acgacgctct tccgatctcc    60
ttccaaatct ctaccctcta tc                                             82

<210> SEQ ID NO 83
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
aatgatacgg cgaccaccga gatctacact ctttccctac acgacgctct tccgatctag    60
taaagtcaca taacctctaa cc                                              82

<210> SEQ ID NO 84
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
aatgatacgg cgaccaccga gatctacact ctttccctac acgacgctct tccgatctag    60
agttggtaag gaggagaatg                                                 80

<210> SEQ ID NO 85
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
aatgatacgg cgaccaccga gatctacact ctttccctac acgacgctct tccgatctct    60
gtggtatctg aactatcttc tc                                              82

<210> SEQ ID NO 86
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
aatgatacgg cgaccaccga gatctacact ctttccctac acgacgctct tccgatctca    60
tttgtggagc accttctg                                                   78

<210> SEQ ID NO 87
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
aatgatacgg cgaccaccga gatctacact ctttccctac acgacgctct tccgatctaa    60
ggatagtttg gaactgagag ac                                              82

<210> SEQ ID NO 88
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

<400> SEQUENCE: 88
aatgatacgg cgaccaccga gatctacact ctttccctac acgacgctct tccgatcttg    60
acctggccaa gaagaag                                                    77

<210> SEQ ID NO 89
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
aatgatacgg cgaccaccga gatctacact ctttccctac acgacgctct tccgatctaa    60
tcggaactgg aggaacaac                                                  79

<210> SEQ ID NO 90
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
catgccgcca cccccaccct a                                               21

<210> SEQ ID NO 91
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (13)..(17)
<223> OTHER INFORMATION: a, c, t, g, unknown or other

<400> SEQUENCE: 91
nnnnnwnnnn nwnnnnntgg gggtggctcc aggaaaattg g                         41

<210> SEQ ID NO 92
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(27)
<223> OTHER INFORMATION: a, c, t, g, unknown or other

```
<220> FEATURE:
<221> NAME/KEY: modified_base
<222> LOCATION: (29)..(33)
<223> OTHER INFORMATION: a, c, t, g, unknown or other

<400> SEQUENCE: 92
catgccgcca cccccacccn nwnnnnnwnn nnn                           33

<210> SEQ ID NO 93
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
catgccgcca cccccacccg atcagtcaac cggagatcgg aagagcacac gtctgaactc   60
cagtcacccg tcc                                                     73

<210> SEQ ID NO 94
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
cccgcccgcc gcccgccgc                                          19

<210> SEQ ID NO 95
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
cccgcccgcc gcccgccgcc cgccgc                                  26

<210> SEQ ID NO 96
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
atgtgtgtgt gtgtgtgtgt gtgt                                    24

<210> SEQ ID NO 97
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 97
gccagcacca g                                                          11

<210> SEQ ID NO 98
<211> LENGTH: 211
<212> TYPE: DNA
<213> ORGANISM: Homo sapiens

<400> SEQUENCE: 98
actacctttg tctctagata ccnctgattc accgagccct gcagttggcc cagcgtcccg      60
tttcactcct tgccagcccc tggacatcac ccacttggct caagaccaat ggagcggtga     120
atgggaaggg gtcactcaag ggacagcccg gagacatcta ccaccagacc tgggccagat     180
actttgtgaa gtaagggatc agcaaggatg t                                   211

<210> SEQ ID NO 99
<211> LENGTH: 211
<212> TYPE: DNA
<213> ORGANISM: Homo sapiens

<400> SEQUENCE: 99
actacctttg tctctagata ccnctgattc accgagccct gcagttggcc cagcgtcccg      60
tttcactcct tgccagcccc tggacatcac ccacttggct caagaccaat ggagcggtga     120
atgggaaggg gtcactcaag ggacagcccg gagacatcta ccaccagacc tgggccagat     180
actttgtgaa gtaagggatc agcaaggatg t                                   211

<210> SEQ ID NO 100
<211> LENGTH: 211
<212> TYPE: DNA
<213> ORGANISM: Homo sapiens

<400> SEQUENCE: 100
actacctttg tctctagata ccnctgattc accgagccct gcagttggcc cagcgtcccg      60
tttcactcct tgccagcccc tggacatcac ccactcggct caagaccaag ggagcgggga     120
atgggaaggg gccactcaag ggacagccca gagacatcta ccaccagacc tgggccagat     180
acattgtgaa gtaagggatc agcaaggatg t                                   211
```